(12) United States Patent
Alvarez et al.

(10) Patent No.: US 12,264,187 B2
(45) Date of Patent: Apr. 1, 2025

(54) COMPOSITIONS AND METHODS FOR TARGETED THERAPEUTIC DELIVERY TO BONE

(71) Applicant: Theradaptive, Inc., Frederick, MD (US)

(72) Inventors: Luis Alvarez, Lexington, MA (US); David Stewart, Monrovia, MD (US); Hyeon Park, Clarksburg, MD (US); Todd Heil, Mt. Airy, MD (US)

(73) Assignee: Theradaptive, Inc., Frederick, MD (US)

( * ) Notice: Subject to any disclaimer, the term of this patent is extended or adjusted under 35 U.S.C. 154(b) by 98 days.

(21) Appl. No.: 18/046,810

(22) Filed: Oct. 14, 2022

(65) Prior Publication Data

US 2023/0235002 A1    Jul. 27, 2023

Related U.S. Application Data

(63) Continuation of application No. PCT/US2021/027230, filed on Apr. 14, 2021.

(60) Provisional application No. 63/010,639, filed on Apr. 15, 2020.

(51) Int. Cl.
| A61K 38/18 | (2006.01) |
| A61P 19/00 | (2006.01) |
| C07K 14/475 | (2006.01) |
| C07K 14/51 | (2006.01) |
| C12N 15/62 | (2006.01) |
| C12N 15/63 | (2006.01) |

(52) U.S. Cl.
CPC ............. *C07K 14/51* (2013.01); *A61K 38/18* (2013.01); *A61P 19/00* (2018.01); *C07K 14/475* (2013.01); *C12N 15/62* (2013.01); *C12N 15/63* (2013.01)

(58) Field of Classification Search
CPC .... A61K 38/16; A61K 38/1875; C07K 14/51; C12N 15/62
See application file for complete search history.

(56) References Cited

U.S. PATENT DOCUMENTS

| 5,122,458 A | 6/1992 | Post et al. |
| 5,152,791 A | 10/1992 | Hakamatsuka et al. |
| 5,219,740 A | 6/1993 | Miller et al. |
| 5,491,082 A | 2/1996 | Suzuki et al. |
| 5,820,632 A | 10/1998 | Constantz et al. |
| 5,906,828 A | 5/1999 | Cima et al. |
| 6,207,453 B1 | 3/2001 | Maass et al. |
| 6,455,495 B1 | 9/2002 | Orgel et al. |
| 6,949,251 B2 | 9/2005 | Dalal et al. |
| 7,172,629 B2 | 2/2007 | McKay |
| 7,323,542 B2 | 1/2008 | Balian |
| 7,572,766 B2 | 8/2009 | Beyer, Jr. et al. |
| 7,871,978 B2 | 1/2011 | Balian |
| 7,977,313 B2 | 7/2011 | Gron et al. |
| 8,022,040 B2 | 9/2011 | Bertozzi et al. |
| 8,075,562 B2 | 12/2011 | Murphy et al. |
| 8,137,664 B2 | 3/2012 | Nycz et al. |
| 8,383,769 B2 | 2/2013 | Peled et al. |
| 8,420,774 B2 | 4/2013 | Murphy et al. |
| 8,778,869 B2 | 7/2014 | Murphy et al. |
| 8,846,860 B2 | 9/2014 | Murphy et al. |
| 9,295,755 B2 | 3/2016 | Murphy |
| 9,809,635 B2 | 11/2017 | Qin et al. |
| 10,329,327 B2 | 6/2019 | Alvarez et al. |
| 10,675,330 B2 | 6/2020 | Li |
| 11,066,444 B2 | 7/2021 | Stupp et al. |
| 11,192,923 B2 | 12/2021 | Alvarez |
| 11,773,138 B2 | 10/2023 | Alvarez |
| 2004/0171552 A1 | 9/2004 | Peled et al. |
| 2004/0197892 A1 | 10/2004 | Moore et al. |
| 2005/0084962 A1 | 4/2005 | Simon |
| 2005/0085623 A1 | 4/2005 | Balian |
| 2006/0040354 A1 | 2/2006 | O'Keefe |
| 2006/0193916 A1 | 8/2006 | Lazarova et al. |
| 2006/0292198 A1 | 12/2006 | Dalal et al. |
| 2008/0095817 A1 | 4/2008 | Murphy |
| 2008/0214468 A1 | 9/2008 | Balian |
| 2008/0279908 A1 | 11/2008 | Bertozzi et al. |
| 2009/0087472 A1 | 4/2009 | Murphy et al. |
| 2009/0305352 A1 | 12/2009 | Dai et al. |
| 2010/0049322 A1 | 2/2010 | McKay |
| 2010/0080850 A1 | 4/2010 | Hubbell et al. |
| 2010/0092955 A1 | 4/2010 | Harriman |
| 2010/0260673 A1 | 10/2010 | Cao et al. |
| 2011/0129611 A1 | 6/2011 | Murphy et al. |
| 2011/0165132 A1 | 7/2011 | Cool et al. |
| 2011/0305760 A1 | 12/2011 | Murphy et al. |
| 2012/0028913 A1 | 2/2012 | Peled et al. |
| 2013/0149457 A1 | 6/2013 | Murphy et al. |

(Continued)

FOREIGN PATENT DOCUMENTS

| CN | 102532272 A | 7/2012 |
| CN | 104193803 A | 12/2014 |

(Continued)

OTHER PUBLICATIONS

Bang et al., Scientific Reports, 2020, vol. 10: 10576.*
Karoulias et al., Bone Reports, 2021, vol. 14: 101092.*
Osta et al., Front. Immunol., 2014, vol. 5, Article 48.*
Peng et al., Comp. Biochem. Physiol., Part A, 2009, vol. 153(1):83-87.*
Qu et al., J. Biol. Chem., 2019, vol. 294(52):19877-19888.*
Alonso-Camino et al.: CARbodies: Human Antibodies Against Cell Surface Tumor Antigens Selected From Repertoires Displayed on T Cell Chimeric Antigen Receptors. Mol. Ther. Nucleic Acids. 2(5):e93 (2013).

(Continued)

*Primary Examiner* — Xiaozhen Xie
(74) *Attorney, Agent, or Firm* — Wilson Sonsini Goodrich & Rosati

(57) ABSTRACT

Provided herein are polypeptides comprising a therapeutic targeted for delivery to an organ or tissue, and uses thereof.

19 Claims, 21 Drawing Sheets

Specification includes a Sequence Listing.

(56) References Cited

U.S. PATENT DOCUMENTS

| | | |
|---|---|---|
| 2014/0037593 A1 | 2/2014 | Alvarez et al. |
| 2019/0322702 A1 | 10/2019 | Alvarez et al. |
| 2020/0031896 A1 | 1/2020 | Cao |
| 2020/0102458 A1 | 4/2020 | Alemseghed et al. |
| 2020/0182872 A1 | 6/2020 | Reinke et al. |
| 2020/0254061 A1 | 8/2020 | Li |
| 2021/0023269 A1 | 1/2021 | Taira et al. |
| 2021/0214408 A1 | 7/2021 | Low et al. |
| 2022/0220154 A1 | 7/2022 | Alvarez |
| 2022/0323641 A1 | 10/2022 | Alvarez et al. |
| 2022/0395610 A1 | 12/2022 | Taira et al. |
| 2023/0203115 A1 | 6/2023 | Alvarez et al. |
| 2023/0233740 A1 | 7/2023 | Alvarez et al. |
| 2024/0018187 A1 | 1/2024 | Alvarez |
| 2024/0131228 A1 | 4/2024 | Alvarez et al. |

FOREIGN PATENT DOCUMENTS

| | | |
|---|---|---|
| JP | 2014508555 A | 4/2014 |
| WO | WO-0202593 A2 | 1/2002 |
| WO | WO-03026590 A2 | 4/2003 |
| WO | WO-2005039616 A1 | 5/2005 |
| WO | WO-2006012414 A2 | 2/2006 |
| WO | WO-2006078464 A2 | 7/2006 |
| WO | WO-2009020550 A2 | 2/2009 |
| WO | WO-2009108934 A2 | 9/2009 |
| WO | WO-2009126648 A1 | 10/2009 |
| WO | WO-2010051032 A1 | 5/2010 |
| WO | WO-2010052715 A2 | 5/2010 |
| WO | WO-2012078671 A2 | 6/2012 |
| WO | WO-2017096328 A1 | 6/2017 |
| WO | WO-2020077265 A1 | 4/2020 |
| WO | WO-2020139901 A1 | 7/2020 |
| WO | WO-2020163766 A1 | 8/2020 |
| WO | WO-2021194604 A2 | 9/2021 |
| WO | WO-2021211683 A2 | 10/2021 |

OTHER PUBLICATIONS

Batt et al.: Characterization of the Polyomavirus Late Polyadenylation Signal. Mol. Cell Biol. 15(9):4783-4790 (1995).
Boris-Lawrie et al.: Recent advances in retrovirus vector technology. Cur. Opin. Genet. Development. 3:102-109 (1993).
Burns et al., "Vesicular Stomatitis Virus G Glycoprotein Pseudotyped Retroviral Vectors: Concentration to Very High Titer and Efficient Gene Transfer into Mammalian and Nonmammalian Cells," Proc. Natl. Acad. Sci. USA 90(17):8033-8037 (1993).
Carlens et al.: Ex vivo T lymphoccyte expansion for retroviral transduction: Influence of serum-free media on variations in cell expansion rates and lymphocyte subset distribution. Exp. Hematol. 28(10):1137-1146 (2000).
Cavalieri, et al., Human T lymphocytes transduced by lentiviral vectors in the absence of TCR activation maintain an intact immune competence. Blood 102(2):497-505 (2003).
Chhabra et al.: BMP-14 Deficiency Inhibits Long Bone Fracture Healing. A Biochemical, Histologic, and Radiographic Assessment. J Orthop Trauma 19(9):629-634 (2005).
Cooper, et al. T-cell clones can be rendered specific for CD19: toward the selective augmentation of the graft-versus-B-lineage leukemia effect. Blood. Feb. 15, 2003;101(4):1637-44. Epub Oct. 10, 2002.
Drosse et al.: Tissue Engineering Part C 14(1):79-88 (2008).
Histing et al.: Small animal bone healing models: standards, tips, and pitfalls results of a consensus meeting. Bone. 49:591-599 (2011).
Kim et al.: In vitro and in vivo osteogenic activity of licochalcone A. Amino Acids. 42:1455-1465 (2012).
Lee et al.: In Vitro and In Vivo Osteogenic Activity of Largazole. ACS Med. Chem. Lett. 2(3):248-251 (2011).
Levitt et al.: Definition of an efficient synthetic poly(A) site. Genes Dev. 3(7):1019-1025 (1989).
Makley et al.: The Effect of Reduced Barometric Pressure on Fracture Healing in Rats. J Bone Joint Surg Am 49(5):903-914 (1967).
Marino et al.: Fracture Healing in Rats Exposed to Extremely Low-Frequency Electric Fields. Clin Orthop Relat Res. (145):239-244 (1979).
Miller, A.D. "Retrovirus packaging cells." Human Gene Therapy 1990; 1(1): 5-14.
Miller et al., "Improved retroviral vectors for gene transfer and expression." Biotechniques Oct. 1989; 7(9):980-982; 984-986; 989-990.
Orkin et al.: Thalassemia due to a mutation in the cleavage-polyadenylation signal of the human beta-globin gene. EMBO J. 4(2):453-456 (1985).
Park et al., "Treating cancer with genetically engineered T cells," Trends Biotechnol., 29(11):550-557, 2011.
PCT/US2021/027230 International Invitation to Pay Additional Fees dated Jul. 20, 2021.
PCT/US2021/027230 International Search Report and Written Opinion dated Oct. 4, 2021.
Poser et al.: A Standardized Critical Size Defect Model in Normal and Osteoporotic Rats to Evaluate Bone Tissue Engineered Constructs. Hindawi Publishing Corporation. BioMed Research International; Article ID 348635 (2014).
Scarpa et al.: Characterization of recombinant helper retroviruses from moloney-based vectors in ecotropic and amphotropic packaging cell lines. Virology. 180(2):849-852 (1991).
Schek et al.: Definition of the Upstream Efficiency Element of the Simian virus 40 Late Polyadenylation Signal by Using In Vitro Analyses. Mol. Cell Biol. 12(12):5386-5393 (1992).
Szymanski et al.: Development and Validation of a Robust and Versatile One-plasmid Regulated Gene Expression System. Mol. Therapy. 15(7):1340-1347 (2007).
Verhoeyen et al., "Lentiviral Vector Gene Transfer into Human T Cells," Methods in Molecular Biology, Methods and Protocols 506:97-114, 2009.
Wang et al.: In vivo osteogenic activity of bone marrow stromal stem cells transfected with Ad-GFP-hBMP-2. Genetics Mol. Res. 13(2):4456-4465 (2014).
Wang et al.: Phenotypic and Functional Attributes of Lentivirus-modified CD19-specific Human CD8+ Central Memory T Cells Manufactured at Clinical Scale. J. Immunother. 35(9):689-701 (2012).
Woychik et al.: Requirement for the 3' flanking region of the bovine growth hormone gene for accurate polyadenylylation. Proc. Natl. Acad. Sci. U.S.A. 81(13):3944-3948 (1984).
Alvarez et al., Tethering of epidermal growth factor (EGF) to beta tricalcium phosphate (βTCP) via fusion to a high affinity, multimeric βTCP-binding peptide: effects on human multipotent stromal cells/connective tissue progenitors. PLoS One. 10(6):e0129600:1-21 (2015).
Bateman et al., Platelet-derived growth factor enhancement of two alloplastic bone matrices. J. Periodontology 76(11):1833-1841 (2005).
Bradshaw et al., SPaRC-null mice exhibit increased adiposity without significant differences in overall body weight. PNaS 100(10):6045-6050 (2003).
Bublil et al., The EGF receptor family: spearheading a merger of signaling and therapeutics. Current Opinion in Cell Biology 19:124-134 (2007).
Cao et al.: Phage display peptide probes for imaging early response to bevacizumab treatment. Amino Acids. 41(5):1103-1112 (2011).
Carrodeguas et al., Alpha-tricalcium phosphate: synthesis, properties and biomedical applications. Acta Biomaterialia 7:3536-3546 (2011).
Chan et al., Expression of epidermal growth factor in transgenic mice causes growth retardation. Journal of Biological Chemistry 275(49):38693-38698 (2000).
Cheng et al., A new protocol for high-yield purification of recombinant human CXCL8(3-72)K11R/G31P expressed in *Escherichia coli*. Protein Expression and Purification 61:65-72 (2008).
Cho et al., The effects of synthetic peptide derived from hBMP-2 on bone formation in rabbit calvarial defect. Tissue Engineering and Regenerative Medicine 5(3):488-497 (2008).

(56) References Cited

OTHER PUBLICATIONS

Citri et al., EGF-ERBB signalling: towards the systems level. Molecular Cell Biology 7:505-516 (2006).
Dickens et al., Crystallographic studies of the role of Mg as a stabilizing impurity in beta-Ca3(PO4)2. I. The crystal structure of pure beta-Ca3(PO4)2. Journal of Solid State Chemistry 10(3):232-248 (1974).
Dickerson et al., Identification and design of peptides for the rapid, high-yield formation of nanoparticulate TiO2 from aqueous solutions at room temperature. Chemistry of Materials 20(4):1578-1584 (2008).
Dudak et al., Enhancing the affinity of SEB-binding peptides by repeating their sequence. Biopolymers 98(2):145-154 (2011).
Erbe et al., Potential of an ultraporous beta-tricalcium phosphate synthetic cancellous bone void filler and bone marrow aspirate composite graft. Eur. Spine J. 10:S141-S146 (2001).
Fan et al., Tethered epidermal growth factor provides a survival advantage to mesenchymal stem cells. Stem Cells 25:1241-1251 (2007).
Fleming Jr. et al.: Intraoperative harvest and concentration of human bone marrow osteoprogenitors for enhancement of spinal fusion. In Orthopedic Tissue Engineering Basic Science and Practice, V.M. Goldberg and A.I. Caplan eds. (NY: Marcel Dekker, Inc.). pp. 51-65 (2004).
Freeman M., Reiterative use of the EGF receptor triggers differentiation of all cell types in the *Drosophila* eye. Cell 87:651-660 (1996).
Friedlaender et al., Osteogenic protein-1 (bone morphogenctic protein-7) in the treatment of tibial nonunions. J. Bone Joint Surg. Am., 83(A Suppl 1, Pt 2):S151-S158 (2001).
Gao et al., Molecular cloning, structure, expression, and chomosomal localization of the human osterix (SP7) gene. Gene 2341:101-110 (2004).
Gibbs et al., Epidermal growth factor and keratinocyte growth factor differentially regulate epidermal migration, growth, and differentiation. Wound Repair and Regeneration 8(3):192-203 (2000).
Glick et al., Ligand recognition by influenza virus. The Journal of Biological Chemistry 266(35):23660-23669 (1991).
Griffith L.G., Emerging design principles in biomaterials and scaffolds for tissue engineering. Ann. N.Y. Acad. Sci. 961:83-95 (2002).
Gronthos et al., The growth factor requirements of STRO-1-positive human bone marrow stromal precursosrs under serum-deprived conditions in vitro. Blood 85(4):929-940 (1995).
Gungormus et al., Regulation of in vitro calcium phosphate mineralization by combinatorially selected hydroxyapatite-binding peptides. Biomacromolecules 9(3):966-973 (2008).
Hamilton et al., Improved bone morphogenetic protein-2 retention in an injectable collagen matrix Using Bifunctional Peptides. PLoS One 8(8):e70715 [1-10] (2013).
Handl et al., Hitting multiple targets with multimeric ligands. Expert Opin. 8(6):565-586 (2004).
Hoang et al., Bone recognition mechanism of porcine osteocalcin from crystal structure. Nature 425:977-980 (2003).
Huang et al., MimoDB 2.0: a mimotope database and beyond. Nucleic Acids Research 40(Database issue):D271-D277 (2012).
Jay et al., Engineered bivalent ligands to bias ErbB receptor-mediated signaling and phenotypes. J. Biol. Chem. 286:27729-27740 (2011).
Kenan et al., Peptide-PEG amphiphiles as brief communication cytophobic coatings for mammalian and bacterial cells. Chemistry & Biology 13:695-700 (2006).
Kim et al., Extracellular calcium-binding peptide-modified ceramics stimulate regeneration of calvarial bone defects. Tissue Engineering and Regenerative Medicine 13:57-65 (2016).
Kimura et al., Effects of platelet derived growth factor, epidermal growth factor and transforming growth factor-beta on the growth of human marrow fibroblasts. British Journal of Haematology 69(1):9-12 (1988).
Kitov et al., Optimization of tether length in nonglycosidically linked bivalent ligands that target sites 2 and 1 of a shiga-like toxin. J. Am. Chem. Soc. 125:3284-3294 (2003).
Kratchmarova et al., Mechanism of divergent growth factor effects in mesenchymal stem cell differentiation. Science 308:1472-1477 (2005).
Krueger et al., Tailoring chimeric ligands for studying and biasing ErbB receptor family interactions. Angew. Chem. Int. Ed. 53:2662-2666 (2014).
Kuhl et al., Tethered epidermal growth factor as a paradigm for growth factor-induced stimulation from the solid phase. Nature Medicine 2(9):1022-1027 (1996).
Kuznetsov et al., Factors required for bone marrow stromal fibroblast colony formation in vitro. British Journal of Haematology 97:561-570 (1997).
Maheshwari et al., Biophysical integration of effects of epidermal growth factor and fibronectin on fibroblast migration. Biophysical Journal 76:2814-2823 (1999).
Marcantonio et al., The influence of tethered epidermal growth factor on connective tissue progenitor colony formation. Biomaterials 30(27):4629-4638 (2009).
Martino et al., Extracellular matrix-inspired growth factor delivery systems for bone regeneration. Advanced Drug Delivery Reviews 94:41-52 (2015).
Martino et al., Growth factors engineered for super-affinity to the extracellular matrix enhance tissue healing. Science 343(6173):885-888 (2014).
Martyre et al., Increased intraplatelet levels of platelet-derived growth factor and transforming growth factor-β in patients with myelofibrosis with myeloid metaplasia. British Journal of Haematology. 77:80-86 (1991).
Matsubara et al., BMP2 regulates osterix through Msx2 and Runx2 during osteoblast differentiation. Journal of Biological Chemistry 283:29119-29125 (2008).
Mehta et al., Synergistic effects of tethered growth factors and adhesion ligands on DNA synthesis and function of primary hepatocytes cultured on soft synthetic hydrogels. Biomaterials 31(17):4657-4671 (2010).
Miettinen et al., Epidermal growth factor receptor function is necessary for normal craniofacial development and palate closure. Nature Genetics 22:69-73 (1999).
Mikami et al., Inductive effects of dexamethasone on the mineralization and the osteoblastic gene expressions in mature osteoblast-like ROS17/2.8 cells. Biochem Biophys Res Comm 362(2):368-372 (2007).
Moll et al., Designed heterodimerizing leucine zippers with a range of pls and stabilities up to 10exp(-15) M. Protein Science 10:649-655 (2001).
Muschler et al.: Engineering principles of clinical cell-based tissue engineering. J Bone Joint Surg Am 86-A:1541-1558 (2004).
Muschler et al., Engineering principles of clinical cell-based tissue engineering. Journal of Bone Joint Surg. 86-A(7):1541-1558 (2004).
NCBI. GenBank Accession No. NP_001191.1: Bone morphogentic protein 2 preproprotein [*Homo sapiens*]. entire document (2018).
Nuschke et al., Epidermal growth factor tethered to beta-tricalcium phosphate bone scaffolds via a high-affinity binding peptide enhances survival of human mesenchymal stem cells/multipotent stromal cells in an immune-competent parafascial implantation assay in mice. Stem Cells Translation Medicine 5:1580-1586 (2016).
Ogose et al., Comparison of hydroxyapatite and beta tricalcium phosphate as bone substitutes after exclusion of bone tumors. Biomedical Materials Research Part B: Applied Biomaterials 72B:94-101 (2005).
Orii et al., Beta-tricalcium phosphate (beta-TCP) graft combined with bone marrow stromal cells (MSCs) for posterolateral spine fusion. J Med Dent Sci 52:51-57 (2005).
Owen et al., Clonal analysis in vitro of osteogenic differentiation of marrow DFU-F. J Cell Science 87:731-738 (1987).
PCT/US2011/063592 international Preliminary Report on Patentability dated Jun. 20, 2013.
PCT/US2011/063592 international Search Report and Written Opinion dated Feb. 14, 2013.

(56) References Cited

OTHER PUBLICATIONS

PCT/US2019/055939 International Preliminary Report on Patentability dated Apr. 22, 2021.
PCT/US2019/055939 International Search Report and Written Opinion dated Feb. 5, 2020.
PCT/US2021/012219 International Invitation to Pay Additional Fees dated Aug. 27, 2021.
PCT/US2021/012219 International Preliminary Report on Patentability dated Sep. 15, 2022.
PCT/US2021/012219 International Search Report and Written Opinion dated Nov. 23, 2021.
PCT/US2021/027230 International Preliminary Report on Patentability dated Oct. 26, 2022.
Pickens et al., Nonspanning bivalent ligands as improved surface receptor binding inhibitors of the cholera toxin B pentamer. Chemistry & Biology 11:1205-1215 (2004).
Pinkas-Kramarski et al., Diversification of neu differentiation factor and epidermal growth factor signaling by combinatorial receptor interactions. The EMBO Journal 15(10):2452-2467 (1996).
Platt et al., Sustained epidermal growth factor receptor levels and activation by tethered ligand binding enhances osteogenic differentiation of multi-potent marrow stromal cells. J. Cell Physiol. 221(2):306-317 (2009).
Qin et al., Amphiregulin is a novel growth factor involved in normal bone development and in the cellular response to parathyroid hormone stimulation. Journal of Biological Chemistry 280:3974-3981 (2005).
Rieker et al., Molecular applications of fusions to leucine zippers. Methods in Enzymology 328:282-296 (2000).
Roy et al.: Identification of a Highly Specific Hydroxyapatite-binding Peptide using Phage Display. Advanced Materials. VCH Publishers. 20(10):1830-1836 (2008).
Sanghvi et al., Biomaterials functionalization using a novel peptide that selectively binds to a conducting polymer. Nature Materials 4:496-502 (2005).
Satomura et al., Receptor tyrosine kinase expression in human bone marrow stromal cells. Journal of Cellular Physiology 177(3):426-438 (1998).
Segvich, S.J. Design of peptides with targeted apatite and human bone marrow stromal cell adhesion for bone tissue engineering. (Doctoral Dissertation), Proquest UMI Publication No. 3343205 (2009).
Seker et al., Quantitative affinity of genetically engineered repeating polypeptides to inorganic surfaces. Biomacromolecules 10:250-257 (2009).
Shen et al., Tuning the erosion rate of artificial protein hydrogels through control of network topology. Nature Materials 5:153-158 (2006).
Sibilia et al., Mice humanized for the EGF receptor display hypomorphic phenotypes in skin, bone and heart. Development 130(19):4515-4525 (2003).
Stemcell Technologies product description for human bone marrow stromal cells, frozen, Cat No. 70022 (2014; made of record).
Su et al., Conformational Selectivity of Peptides for Single-Walled Carbon Nanotubes. J. Phys. Chem. B 110(47):23623-23627 (2006).
Tamama et al., Epidermal growth factor as a candidate for ex vivo expansion of bone marrow-derived mesenchymal stem cells. Stem Cells 24:686-695 (2006).
Termine et al., Osteonetin, a bone-specific protein linking mineral to collagen. Cell 26:99-105 (1981).
Tokumaru et al., Ectodomain shedding of epidermal growth factor receptor ligands is required for keratinocyte migration in cutaneous wound healing. Journal of Cell Biology 151(2):209-219 (2000).
Traverse et al., EGF triggers neuronal differentiation of PC12 cells that overexpress the EGF receptor. Curr Biol., 4(8):694-701 (1994).
Tzahar et al., A hierarchical network of interreceptor interactions determines signal transduction by neu differentiation factor/neuregulin and epidermal growth factor. Molecular and Cellular Biology 16(10):5276-5287 (1996).
U.S. Appl. No. 13/991,842 Office Action dated Jul. 1, 2015.
U.S. Appl. No. 13/991,842 Office Action dated Jul. 13, 2017.
U.S. Appl. No. 13/991,842 Office Action dated Nov. 18, 2016.
U.S. Appl. No. 13/991,842 Office Action dated Nov. 21, 2014.
U.S. Appl. No. 16/892,141 Office Action dated Feb. 5, 2021.
U.S. Appl. No. 16/892,141 Office Action dated Oct. 26, 2020.
U.S. Appl. No. 16/892,141 Restriction Requirement dated Jul. 10, 2020.
Wang et al., Epidermal growth factor receptor-deficient mice have delayed primary encochondral ossification because of defective ostcoclast recruitment. Journal of Biological Chemistry 279(51):53848-53856 (2004).
Whaley et al., Selection of peptides with semiconductor binding specificity for directed nanocrystal assembly. Nature 405:665-668 (2000).
Yashima et al., Crystal structure analysis of beta-tricalcium phosphate Ca3(PO4)2 by neutron powder diffraction. Journal of Solid State Chemistry 175(2):272-277 (2003).
Yazici et al., Bi-functional chimeric peptide coatings for improved osteointegration of titanium implants. Minerals, Metals and Materials Society / AIME 2011 Meeting (2011).
Yuca et al., In vitro labeling of hydroxyapatite minerals by an engineered protein. Biotechnology and Bioengineering 108:1021-1030 (2011).
Zeltinger et al., Effect of pore size and void fraction on cellular adhesion, proliferation, and matrix deposition. Tissue Engineering 7(5):557-572 (2001).
Zhang et al., Artificial polypeptide scaffold for protein immobilization. J Am Chem Soc. 127:10136-10137 (2005).
Zhang et al.: New Ouabain-Conjugated Peptide Found From Phage Displayed Peptide Library. American Journal of Hypertension, Ltd. 17:619-623.
Ziros et al., The bone-specific transcriptional regulator Cbfal is a target of mechanical signals in osteoblastic cells, Journal of Biological Chemistry 277(26):23934-23941 (2002).
Co-pending U.S. Application No. 202318451003, inventor Alvarez; Luis, filed on Aug. 16, 2023.
Co-pending U.S. Application No. 202318547668, inventors Alvarez; Luis et al., filed on Aug. 23, 2023.
U.S. Appl. No. 63/505,026, filed May 30, 2023 entitled Compositions and Methods for Localization of Immunomodulator Activity; Inventors Park et al.
U.S. Appl. No. 63/598,496, filed Nov. 13, 2023 entitled Living Bioreactor Compositions and Methods of Use; Inventors Alvarez et al.

* cited by examiner

Group B rhBMP + ACS

Surgery 1: Defect/Spacer Procedure

↓ 4 weeks

Surgery 2: Graft Treatment Procedure

US 12,264,187 B2

COMPOSITIONS AND METHODS FOR TARGETED THERAPEUTIC DELIVERY TO BONE

PRIORITY CLAIM

This application is a continuation of International Application Serial No. PCT/US2021/027230, filed Apr. 14, 2021, which claims the benefit of U.S. Provisional Patent Application Ser. No. 63/010,639, filed Apr. 15, 2020, both of which are incorporated herein by reference in their entirety.

GOVERNMENT RIGHTS

This invention was made with government support under W81XWH-18-C-0182 and W81XWH-15-C-0028 awarded by the Department of Defense. The government has certain rights in the invention.

SEQUENCE LISTING

The instant application contains a Sequence Listing which has been submitted electronically in XML format and is hereby incorporated by reference in its entirety. Said XML copy, created on Oct. 14, 2022, is named 50222-705.301.xml and is 660,103 bytes in size.

BACKGROUND

In the U.S., an average of six million people break a bone annually. Of these bone defects, the majority heal without problems. However, 5-10% will heal poorly or not at all (American Academy of Orthopaedic Surgeons). Large defects, also known as critical-sized bone defects, may not heal spontaneously and can lead to non-unions. A non-union occurs when there is no indication of healing for at least three months and no expectation of further healing (American Academy of Orthopaedic Surgeons). Currently, bone grafting is regarded as the "gold standard" for treating large or segmental bone defects. However, there are limitations with this treatment such as donor site pain, risk of rejection, limited donor supply and risk of transmission of infectious disease.

The repair of critical and complex bone and cartilage defects is also limited by poor tissue regrowth on implanted orthopedic substrates. Reasons for poor tissue regrowth include the loss of implanted progenitor cells within 48 hours post-implantation and the scarcity of progenitor cells. Another contributing factor is that current orthopedic substrates fail to facilitate sufficient tissue regeneration.

SUMMARY

The present disclosure is based on the discovery that the use of a composition comprising a mammalian growth factor (e.g., bone morphogenetic protein 2 (BMP-2)) or a functional portion thereof, and a targeting polypeptide (e.g., a polypeptide that binds to bone or a carrier material) can vastly improve bone healing and accelerate tissue regrowth. In non-limiting embodiments, the targeting polypeptide binds to a carrier material, such as calcium phosphate (e.g., β-tricalcium phosphate or β-TCP), hydroxyapatite, or other materials suitable for use in an implantable device. Thus, provided herein are chimeric polypeptides comprising one or more targeting polypeptides and a mammalian growth factor, compositions comprising any of these chimeric polypeptides (and optionally, a carrier material), and methods of promoting bone or cartilage formulation, methods of replacing and/or repairing bone or cartilage, and methods of treating a bone fracture or bone loss that include administration of any of these compositions. The compositions and methods provided herein can increase and sustain the number of progenitor cells at sites of bone and/or cartilage injury through stem cell capture. The compositions and methods provided herein can also be applied to soft tissue repair or localized delivery of a therapeutic.

Provided herein is a polypeptide composition comprising: a targeting polypeptide comprising a sequence at least 80% identical to SEQ ID NO: 22 (LLADTTHHRPWT VIGESTHHRPWS IIGESSHHKPFT GLGDTTHHRPWG ILAESTHHKPWT), and a therapeutic polypeptide comprising a sequence at least 80% identical to a sequence selected from SEQ ID NOS: 32, 46-71, 73-77, 79-101, 152, 168, 176, 268. In some embodiments, the therapeutic polypeptide comprises a sequence at least 90% identical to a sequence selected from SEQ ID NOS: 32, 46-71, 73-77, 79-101, 152, 168, 176, 268. In some embodiments, the therapeutic polypeptide comprises a sequence selected from SEQ ID NOS: 32, 46-71, 73-77, 79-101, 152, 168, 176, 268. In some embodiments, the therapeutic polypeptide comprises a sequence at least 80%, 85%, 90%, or 95% identical to SEQ ID NO: 32. In some embodiments, the therapeutic polypeptide comprises SEQ ID NO: 32. In some embodiments, the targeting polypeptide comprises a sequence at least 90% or 95% identical to SEQ ID NO: 22. In some embodiments, the targeting polypeptide comprises SEQ ID NO: 22. In some embodiments, the targeting polypeptide comprises a sequence at least 90% or 95% identical to SEQ ID NO: 22. In some embodiments, the targeting polypeptide comprises SEQ ID NO: 22. In some embodiments, the targeting polypeptide comprises a sequence at least 90% or 95% identical to SEQ ID NO: 22. In some embodiments, the targeting polypeptide comprises SEQ ID NO: 22. In some embodiments, the targeting polypeptide comprises a sequence at least 90% or 95% identical to SEQ ID NO: 22. In some embodiments, the targeting polypeptide comprises SEQ ID NO: 22. In some embodiments, the targeting polypeptide comprises a sequence at least 90% or 95% identical to SEQ ID NO: 22. In some embodiments, the targeting polypeptide comprises SEQ ID NO: 22.

Also provided herein is a polypeptide composition comprising a sequence at least about 80% identical to SEQ ID NO: 551 ((X)QAKHKQRKRLKSSCKRHPLY-VDFSDVGWNDWIVAPPGYHAFYCHGECPFP-LADHLNST NHAIVQTLVNSVNSKIPKACCVPTELSA-ISMLYLDENEKVVLKNYQDMVVEGCGCR), wherein the polypeptide composition comprises X, and X comprises SEQ ID NO: 22 (LLADTTHHRPWTVIGESTHHRPWSII-GESSHHKPFTGLGDTTHHRPWGILAESTHHKPWT). In some embodiments, the composition comprises a sequence at least about 90% or 95% identical to SEQ ID NO: 551.

Also provided herein is a polypeptide composition comprising a sequence at least about 80% identical to SEQ ID NO: 639 ((X)QAKHKQRKRLKSSCKRHPLY-VDFSDVGWNDWIVAPPGYHAFYCHGECPFP-LADHLNST NHAIVQTLVNSVNSKIPKACCVPTELSA-ISMLYLDENEKVVLKNYQDMVVEGCGCR), wherein the polypeptide composition comprises X, and X comprises SEQ ID NO: 2 (VIGESTHHRPWS). In some embodiments, the composition comprises a sequence at least about 90% or 95% identical to SEQ ID NO: 639.

Also provided herein is a polypeptide composition comprising a sequence at least about 80% identical to SEQ ID NO: 519 ((X)QAKHKQRKRLKSSCKRHPLY- VDFSDVGWNDWIVAPPGYHAFYCHGECPFP-LADHLNST NHAIVQTLVNSVNSKIPKACCVPTELSA-ISMLYLDENEKVVLKNYQDMVVEGCGCR), wherein the polypeptide composition comprises X, and X comprises SEQ ID NO: 6 (IIGESSHHKPFT). In some embodiments, the composition comprises a sequence at least about 90% or 95% identical to SEQ ID NO: 519.

Also provided herein is a polypeptide composition comprising a sequence at least about 80% identical to SEQ ID NO: 521 ((X)QAKHKQRKRLKSSCKRHPLY-VDFSDVGWNDWIVAPPGYHAFYCHGECPFP-LADHLNST NHAIVQTLVNSVNSKIPKACCVPTELSA-ISMLYLDENEKVVLKNYQDMVVEGCGCR), wherein the polypeptide composition comprises X, and X comprises SEQ ID NO: 7 (GLGDTTHHRPWG). In some embodiments, the composition comprises a sequence at least about 90% or 95% identical to SEQ ID NO: 521.

Also provided herein is a polypeptide composition comprising a sequence at least about 80% identical to SEQ ID NO: 515 ((X)QAKHKQRKRLKSSCKRHPLY-VDFSDVGWNDWIVAPPGYHAFYCHGECPFP-LADHLNST NHAIVQTLVNSVNSKIPKACCVPTELSA-ISMLYLDENEKVVLKNYQDMVVEGCGCR), wherein the polypeptide composition comprises X, and X comprises SEQ ID NO: 4 (ILAESTHHKPWT). In some embodiments, the composition comprises a sequence at least about 90% or 95% identical to SEQ ID NO: 515.

Also provided herein is a polypeptide composition comprising a sequence at least about 80% identical to SEQ ID NO: 501. In some embodiments, the sequence is at least about 90% or 95% identical to SEQ ID NO: 501. In some embodiments, the sequence comprises SEQ ID NO: 501.

Also provided herein is a polypeptide composition comprising a sequence at least about 80% identical to SEQ ID NO: 507. In some embodiments, the sequence is at least about 90% or 95% identical to SEQ ID NO: 507. In some embodiments, the sequence comprises SEQ ID NO: 507.

Also provided herein is a polypeptide composition comprising a sequence at least about 80% identical to SEQ ID NO: 506. In some embodiments, the sequence is at least about 90% or 95% identical to SEQ ID NO: 506. In some embodiments, the sequence comprises SEQ ID NO: 506.

Also provided herein is a polypeptide composition comprising a sequence at least about 80% identical to SEQ ID NO: 505. In some embodiments, the sequence is at least about 90% or 95% identical to SEQ ID NO: 505. In some embodiments, the sequence comprises SEQ ID NO: 505.

Also provided herein is a polypeptide composition comprising a sequence at least about 80% identical to SEQ ID NO: 504. In some embodiments, the sequence is at least about 90% or 95% identical to SEQ ID NO: 504. In some embodiments, the sequence comprises SEQ ID NO: 504.

Also provided herein is a polypeptide composition comprising a sequence at least about 80% identical to SEQ ID NO: 503. In some embodiments, the sequence is at least about 90% or 95% identical to SEQ ID NO: 503. In some embodiments, the sequence comprises SEQ ID NO: 503.

Also provided herein is a polypeptide composition comprising a sequence at least about 80% identical to SEQ ID NO: 502. In some embodiments, the sequence is at least about 90% or 95% identical to SEQ ID NO: 502. In some embodiments, the sequence comprises SEQ ID NO: 502.

Also provided herein is a polypeptide composition comprising: a targeting polypeptide comprising a sequence at least 80%, identical to SEQ ID NO: 22 (LLADTTHHRPWTVIGESTHHRPWSII-GESSHHKPFTGLGDTTHHRPWGILAESTHHKPWT), and a therapeutic polypeptide comprising a bone morphogenetic protein (BMP). In some embodiments, the BMP is BMP-2.

Also provided herein is a nucleic acid encoding a polypeptide composition described herein. Also provided is a vector comprising the nucleic acid.

Also provided herein is a device comprises a polypeptide composition described herein, and a carrier material. In some embodiments, the polypeptide composition is bound to the carrier material. In some embodiments, the carrier material comprises calcium phosphate. In some embodiments, the carrier material comprises hydroxyapatite. In some embodiments, the carrier material comprises alpha tricalcium phosphate, fluorapatite, bone (e.g., demineralized bone), glasses (bioglasses) such as silicates, vanadates, and related ceramic minerals, or chelated divalent metal ions, or any combination thereof.

Also provided herein is a method of treating a subject in need thereof, the method comprising delivering to the subject a polypeptide composition described herein, or a device described herein. In some embodiments, the polypeptide composition or the device is delivered to treat a bone defect in the subject. In some embodiments, at least about 0.5 mg of polypeptide composition per cc of defect volume is delivered to the subject. In some embodiments, about 0.5 mg to about 10 mg of polypeptide composition per cc of defect volume is delivered to the subject.

Also provided herein is a method of delivering a therapeutic agent to an organ or tissue of a subject, the method comprising delivering to the organ or tissue a carrier material and the therapeutic agent, wherein the therapeutic agent is bound to the carrier material via a targeting polypeptide comprising: (a) a sequence at least 80% identical to SEQ ID NO: 22, (b) a sequence at least 80% identical to SEQ ID NO: 402, (c) a sequence at least 80% identical to SEQ ID NO: 401, (d) a sequence at least 80% identical to SEQ ID NO: 413 ((X1)(X2)), wherein X1 comprises SEQ ID NO: 1, and X2 comprises SEQ ID NO: 2 and SEQ ID NO: 6, (e) a sequence at least 80% identical to SEQ ID NO: 21, (f) a sequence at least 80% identical to SEQ ID NO: 414 ((X1)(X2)), wherein X1 comprises SEQ ID NO: 2, and X2 comprises SEQ ID NO: 6 and SEQ ID NO: 7, (g) a sequence at least 80% identical to SEQ ID NO: 416 ((X1)(X2)), wherein X1 comprises SEQ ID NO: 6, and X2 comprises SEQ ID NO: 7 and SEQ ID NO: 4, (h) a sequence at least 80% identical to SEQ ID NO: 408 ((X1)(X2)), wherein X1 comprises SEQ ID NO: 1, and X2 comprises SEQ ID NO: 2, (i) a sequence at least 80% identical to SEQ ID NO: 20, (j) a sequence at least 80% identical to SEQ ID NO: 409 ((X1)(X2)), wherein X1 comprises SEQ ID NO: 2, and X2 comprises SEQ ID NO: 6, (k) a sequence at least 80% identical to SEQ ID NO: 411 ((X1)(X2)), wherein X1 comprises SEQ ID NO: 6, and X2 comprises SEQ ID NO: 7, (l) a sequence at least 80% identical to SEQ ID NO: 412 ((X1)(X2)), wherein X1 comprises SEQ ID NO: 7, and X2 comprises SEQ ID NO: 4, (m) a sequence at least 80% identical to SEQ ID NO: 2 (VIGESTHHRPWS), (n) a sequence at least 80% identical to SEQ ID NO: 4 (ILAESTHHKPWT), (o) a sequence at least 80% identical to SEQ ID NO: 6 (IIGESSHHKPFT), (p) a sequence at least 80% identical to SEQ ID NO: 7 (GLGDTTHHRPWG), or (q) any combination of two or more of (a) to (p). In some embodiments, the carrier material comprises calcium phosphate. In some embodiments, the targeting polypeptide is connected to the therapeutic agent. In some embodiments, the therapeutic agent comprises a growth factor. In some embodiments, the therapeutic agent comprises BMP. In some embodiments, the BMP comprises BMP-2. In some embodiments, the therapeutic agent comprises a sequence at least about 80% identical to SEQ ID NO: 32. In some embodiments, the therapeutic agent comprises a sequence at least about 80% identical to any one of SEQ ID NOS: 46-71, 73-77, 79-101, 152, 168, 176, 268. In some embodiments, the therapeutic agent is delivered to treat a bone defect in the subject. In some embodiments, at least about 0.5 mg of the therapeutic agent is delivered per cc of defect volume. In some embodiments, about 0.5 mg to about 10 mg of the therapeutic agent is delivered per cc of defect volume.

Also provided herein are chimeric polypeptides comprising: (i) a targeting polypeptide comprising one or more of the following: an amino acid sequence at least about 70%, 75%, 80%, 85%, 90%, 95%, or 100% identical to VIGESTHHRPWS (SEQ ID NO: 2), an amino acid sequence at least about 70%, 75%, 80%, 85%, 90%, 95%, or 100% identical to LIADSTHHSPWT (SEQ ID NO: 3), ILAESTHHKPWT (SEQ ID NO: 4), an amino acid sequence at least about 70%, 75%, 80%, 85%, 90%, 95%, or 100% identical to ILAETTHHRPWS (SEQ ID NO: 5), an amino acid sequence at least about 70%, 75%, 80%, 85%, 90%, 95%, or 100% identical to IIGESSHHKPFT (SEQ ID NO: 6), an amino acid sequence at least about 70%, 75%, 80%, 85%, 90%, 95%, or 100% identical to GLGDTTHHRPWG (SEQ ID NO: 7), an amino acid sequence at least about 70%, 75%, 80%, 85%, 90%, 95%, or 100% identical to VLGDTTHHKPWT (SEQ ID NO: 8), an amino acid sequence at least about 70%, 75%, 80%, 85%, 90%, 95%, or 100% identical to IVADSTHHRPWT (SEQ ID NO: 9), an amino acid sequence at least about 70%, 75%, 80%, 85%, 90%, 95%, or 100% identical to STADTSHHRPS (SEQ ID NO: 10), an amino acid sequence at least about 70%, 75%, 80%, 85%, 90%, 95%, or 100% identical to TSGGESTHHRPS (SEQ ID NO: 11), an amino acid sequence at least about 70%, 75%, 80%, 85%, 90%, 95%, or 100% identical to TSGGESSHHKPS (SEQ ID NO: 12), an amino acid sequence at least about 70%, 75%, 80%, 85%, 90%, 95%, or 100% identical to TGSGDSSHHRPS (SEQ ID NO: 13), an amino acid sequence at least about 70%, 75%, 80%, 85%, 90%, 95%, or 100% identical to GSSGESTHHKPST (SEQ ID NO: 14), an amino acid sequence at least about 70%, 75%, 80%, 85%, 90%, 95%, or 100% identical to VGADSTHHRPVT (SEQ ID NO: 15), an amino acid sequence at least about 70%, 75%, 80%, 85%, 90%, 95%, or 100% identical to GAADTTHHRPVT (SEQ ID NO: 16), an amino acid sequence at least about 70%, 75%, 80%, 85%, 90%, 95%, or 100% identical to AGADTTHHRPVT (SEQ ID NO: 17), an amino acid sequence at least about 70%, 75%, 80%, 85%, 90%, 95%, or 100% identical to GGADTTHHRPAT (SEQ ID NO: 18), and an amino acid sequence at least about 70%, 75%, 80%, 85%, 90%, 95%, or 100% identical to GGADTTHHRPGT (SEQ ID NO: 19); and (ii) a mammalian growth factor.

In some embodiments, the targeting polypeptide comprises the sequence at least about 70%, 75%, 80%, 85%, 90%, 95%, or 100% identical to SEQ ID NO: 2. In some embodiments, the targeting polypeptide comprises the sequence at least about 90% identical to SEQ ID NO: 2. In some embodiments, the targeting polypeptide comprises SEQ ID NO: 2.

In some embodiments, the targeting polypeptide comprises the sequence at least about 70%, 75%, 80%, 85%, 90%, 95%, or 100% identical to SEQ ID NO: 4. In some embodiments, the targeting polypeptide comprises the sequence at least about 90% identical to SEQ ID NO: 4. In some embodiments, the targeting polypeptide comprises SEQ ID NO: 4.

In some embodiments, the targeting polypeptide comprises the sequence at least about 70%, 75%, 80%, 85%, 90%, 95%, or 100% identical to SEQ ID NO: 6. In some embodiments, the targeting polypeptide comprises the sequence at least about 90% identical to SEQ ID NO: 6. In some embodiments, the targeting polypeptide comprises SEQ ID NO: 6.

In some embodiments, the targeting polypeptide comprises the sequence at least about 70%, 75%, 80%, 85%, 90%, 95%, or 100% identical to SEQ ID NO: 7. In some embodiments, the targeting polypeptide comprises the sequence at least about 90% identical to SEQ ID NO: 7. In some embodiments, the targeting polypeptide comprises SEQ ID NO: 7.

In some embodiments, the targeting polypeptide comprises two or more targeting polypeptides. In some embodiments, two or more targeting polypeptides is no more than about 50, 45, 40, 35, 30, 25, 20, 15, or 10 targeting polypeptides. In some embodiments, two or more targeting polypeptides is about 2, 3, 4, 5, 6, 7, 8, 9, 10, 11, 12, 13, 14, 15, 20, 25, or 30 targeting polypeptides. In some embodiments, two or more targeting polypeptides is about 2 to about 10 targeting polypeptides. In some embodiments, two or more targeting polypeptides is about 5 targeting polypeptides.

In some embodiments, each neighboring pair of the two or more targeting polypeptides directly abut each other. In some embodiments, at least two of the two or more targeting polypeptides directly abut each other.

In some embodiments, each neighboring pair of the two or more targeting polypeptides are separated by a linker sequence. In some embodiments, at least two of the two or more targeting polypeptides are separated by a linker sequence.

In some embodiments, the targeting polypeptide comprises at least two different polypeptides.

In some embodiments, the targeting polypeptide includes two or more copies of the same polypeptide.

In some embodiments, the targeting polypeptide further comprises a sequence at least about 70%, 75%, 80%, 85%, 90%, 95%, or 100% identical to SEQ ID NO: 1. In some embodiments, the targeting polypeptide comprises the sequence at least about 90% identical to SEQ ID NO: 1. In some embodiments, the targeting polypeptide comprises SEQ ID NO: 1.

In some embodiments, the targeting polypeptide comprises: (i) a sequence at least about 70%, 75%, 80%, 85%, 90%, 95%, or 100% identical to SEQ ID NO: 1, (ii) a sequence at least about 70%, 75%, 80%, 85%, 90%, 95%, or 100% identical to SEQ ID NO: 2, (iii) a sequence at least about 70%, 75%, 80%, 85%, 90%, 95%, or 100% identical to SEQ ID NO: 4, (iv) a sequence at least about 70%, 75%, 80%, 85%, 90%, 95%, or 100% identical to SEQ ID NO: 6, (v) a sequence at least about 70%, 75%, 80%, 85%, 90%, 95%, or 100% identical to SEQ ID NO: 7, or (vi) any combination of (i) to (v). In some embodiments, the targeting polypeptide comprises (i), (ii), (iii), (iv), and (v). In some embodiments, the targeting polypeptide comprises SEQ ID NO: 2, SEQ ID NO: 4, SEQ ID NO: 6, and SEQ ID NO: 7. In some embodiments, the targeting polypeptide comprises SEQ ID NO: 1, SEQ ID NO: 2, SEQ ID NO: 4, SEQ ID NO: 6, and SEQ ID NO: 7.

In some embodiments, the targeting polypeptide comprises LLADTTHHRPWT (SEQ ID NO: 1) and/or GQVLPTTTPSSP (SEQ ID NO: 44).

In some embodiments, the targeting polypeptide comprises LLADTTHHRPWT (SEQ ID NO: 1) and/or VIGESTHHRPWS (SEQ ID NO: 2).

In some embodiments, the targeting polypeptide comprises a sequence at least about 70%, 75%, 80%, 85%, 90%, 95%, or 100% identical to LLADTTHHRPWTVIGESTHHRPWS (SEQ ID NO: 20). In some embodiments, the targeting polypeptide comprises a sequence at least about 90% identical to SEQ ID NO: 20. In some embodiments, the targeting polypeptide comprises SEQ ID NO: 20.

In some embodiments, the targeting polypeptide comprises a sequence at least about 70%, 75%, 80%, 85%, 90%, 95%, or 100% identical to LLADTTHHRPWT (SEQ ID NO: 1), a sequence at least about 70%, 75%, 80%, 85%, 90%, 95%, or 100% identical to VIGESTHHRPWS (SEQ ID NO: 2), and a sequence at least about 70%, 75%, 80%, 85%, 90%, 95%, or 100% identical to IIGESSHHKPFT (SEQ ID NO: 6). In some embodiments, the targeting polypeptide comprises a sequence at least 90% identical to SEQ ID NO: 1, a sequence at least 90% identical to SEQ ID NO: 2, and a sequence at least 90% identical to SEQ ID NO: 6. In some embodiments, the targeting polypeptide comprises SEQ ID NOS: 1, 2, and 6.

In some embodiments, the targeting polypeptide comprises a sequence at least about 70%, 75%, 80%, 85%, 90%, 95%, or 100% identical to VIGESTHHRPWS (SEQ ID NO: 2), and a sequence at least about 70%, 75%, 80%, 85%, 90%, 95%, or 100% identical to IIGESSHHKPFT (SEQ ID NO: 6). In some embodiments, the targeting polypeptide comprises a sequence at least 90% identical to SEQ ID NO: 2, and a sequence at least 90% identical to SEQ ID NO: 6. In some embodiments, the targeting polypeptide comprises SEQ ID NOS: 2, and 6.

In some embodiments, the targeting polypeptide comprises a sequence at least about 70%, 75%, 80%, 85%, 90%, 95%, or 100% identical to LLADTTHHRPWTVIGESTHHRPWSIIGESSHHKPFT (SEQ ID NO: 21). In some embodiments, the targeting polypeptide comprises a sequence at least about 90% identical to SEQ ID NO: 21. In some embodiments, the targeting polypeptide comprises SEQ ID NO: 21.

In some embodiments, the targeting polypeptide comprises a sequence at least about 70%, 75%, 80%, 85%, 90%, 95%, or 100% identical to

```
                                              (SEQ ID NO: 401)
LLADTTHHRPWTVIGESTHHRPWSIIGESSHHKPFTGLGDTTHHRPWG.
```

In some embodiments, the targeting polypeptide comprises a sequence at least about 90% identical to SEQ ID NO: 401. In some embodiments, the targeting polypeptide comprises SEQ ID NO: 401.

In some embodiments, the targeting polypeptide comprises a sequence at least about 70%, 75%, 80%, 85%, 90%, 95%, or 100% identical to

```
                                              (SEQ ID NO: 402)
VIGESTHHRPWSIIGESSHHKPFTGLGDTTHHRPWGILAESTHHKPWT.
```

In some embodiments, the targeting polypeptide comprises a sequence at least about 90% identical to SEQ ID NO: 402. In some embodiments, the targeting polypeptide comprises SEQ ID NO: 402.

In some embodiments, the targeting polypeptide comprises LLADTTHHRPWT (SEQ ID NO: 1), VIGESTHHRPWS (SEQ ID NO: 2), IIGESSHHKPFT (SEQ ID NO: 6), GLGDTTHHRPWG (SEQ ID NO: 7), and ILAESTHHKPWT (SEQ ID NO: 4).

In some embodiments, the targeting polypeptide comprises a sequence at least about 70%, 75%, 80%, 85%, 90%, 95%, or 100% identical to

```
                                              (SEQ ID NO: 22)
LLADTTHHRPWTVIGESTHHRPWSIIGESSHHKPFTGLGDTTHHRPWGI
LAESTHHKPWT.
```

In some embodiments, the targeting polypeptide comprises a sequence at least about 80% identical to SEQ ID NO: 22. In some embodiments, the targeting polypeptide comprises a sequence at least about 90% identical to SEQ ID NO: 22. In some embodiments, the targeting polypeptide comprises SEQ ID NO: 22.

In some embodiments, the targeting polypeptide comprises a sequence at least about 70%, 75%, 80%, 85%, 90%, 95%, or 100% identical to LLADTTHHRPWT (SEQ ID NO: 1) and a sequence at least about 70%, 75%, 80%, 85%, 90%, 95%, or 100% identical to ILAESTHHKPWT (SEQ ID NO: 4). In some embodiments, the targeting polypeptide comprises a sequence at least 90% identical to SEQ ID NO: 1 and a sequence at least 90% identical to SEQ ID NO: 4. In some embodiments, the targeting polypeptide comprises SEQ ID NO: 1 and SEQ ID NO: 4.

In some embodiments, the targeting polypeptide comprises a sequence at least about 70%, 75%, 80%, 85%, 90%, 95%, or 100% identical to LLADTTHHRPWTILAESTHHKPWT (SEQ ID NO: 23).

In some embodiments, the targeting polypeptide comprises a sequence at least about 70%, 75%, 80%, 85%, 90%, 95%, or 100% identical to

```
                                              (SEQ ID NO: 24)
LLADTTHHRPWTILAESTHHKPWTLLADTTHHRPWTILAESTHHKPWTL
LADTTHHRPWT.
```

In some embodiments, the targeting polypeptide comprises a sequence at least about 70%, 75%, 80%, 85%, 90%, 95%, or 100% identical to LLADTTHHRPWT (SEQ ID NO: 1) and a sequence at least about 70%, 75%, 80%, 85%, 90%, 95%, or 100% identical to GLGDTTHHRPWG (SEQ ID NO: 7). In some embodiments, the targeting polypeptide comprises a sequence at least about 90% identical to SEQ ID NO: 1 and a sequence at least about 70%, 75%, 80%, 85%, 90%, 95%, or 100% identical to SEQ ID NO: 7. In some embodiments, the targeting polypeptide comprises SEQ ID NO: 1 and SEQ ID NO: 7.

In some embodiments, the targeting polypeptide comprises a sequence at least about 70%, 75%, 80%, 85%, 90%, 95%, or 100% identical to LLADTTHHRPWTGLGDTTHHRPWG (SEQ ID NO: 25).

In some embodiments, the targeting polypeptide comprises a sequence at least about 70%, 75%, 80%, 85%, 90%, 95%, or 100% identical to

```
                                              (SEQ ID NO: 26)
               LLADTTHHRPWTGLGDTTHHRPWGLLADTTHHRPWT.
```

In some embodiments, the targeting polypeptide comprises a sequence at least about 70%, 75%, 80%, 85%, 90%, 95%, or 100% identical to (SEQ ID NO: 27)
LLADTTHHRPWTGLGDTTHHRPWGLLADTTHHRPWTGLGDTTHHRPWGL
LADTTHHRPWT.

In some embodiments, the targeting polypeptide comprises a sequence at least about 70%, 75%, 80%, 85%, 90%, 95%, or 100% identical to (SEQ ID NO: 28)
LLADTTHHRPWTGLGDTTHHRPWGLLADTTHHRPWTGLGDTTHHRPWGL
LADTTHHRPWTGLGDTTHHRPWGLLADTTHHRPWT.

In some embodiments, the targeting polypeptide comprises a sequence at least about 70%, 75%, 80%, 85%, 90%, 95%, or 100% identical to STADTSHHRPS (SEQ ID NO: 10), a sequence at least about 70%, 75%, 80%, 85%, 90%, 95%, or 100% identical to TSGGESTHHRPS (SEQ ID NO: 11), a sequence at least about 70%, 75%, 80%, 85%, 90%, 95%, or 100% identical to TSGGESSHHKPS (SEQ ID NO: 12), a sequence at least about 70%, 75%, 80%, 85%, 90%, 95%, or 100% identical to TGSGDSSHHRPS (SEQ ID NO: 13), and a sequence at least about 70%, 75%, 80%, 85%, 90%, 95%, or 100% identical to GSSGESTHHKPST (SEQ ID NO: 14).

In some embodiments, the targeting polypeptide comprises a sequence at least about 70%, 75%, 80%, 85%, 90%, 95%, or 100% identical to (SEQ ID NO: 29)
STADTSHHRPSTSGGESTHHRPSTSGGESSHHKPSTGSGDSSHHRPSGS
SGESTHHKPST.

In some embodiments, the targeting polypeptide comprises a sequence at least about 70%, 75%, 80%, 85%, 90%, 95%, or 100% identical to VGADSTHHRPVT (SEQ ID NO: 15), a sequence at least about 70%, 75%, 80%, 85%, 90%, 95%, or 100% identical to GAADTTHHRPVT (SEQ ID NO: 16), a sequence at least about 70%, 75%, 80%, 85%, 90%, 95%, or 100% identical to AGADTTHHRPVT (SEQ ID NO: 17), a sequence at least about 70%, 75%, 80%, 85%, 90%, 95%, or 100% identical to GGADTTHHRPAT (SEQ ID NO: 18) and a sequence at least about 70%, 75%, 80%, 85%, 90%, 95%, or 100% identical to GGADTTHHRPGT (SEQ ID NO: 19).

In some embodiments, the targeting polypeptide comprises a sequence at least about 70%, 75%, 80%, 85%, 90%, 95%, or 100% identical to (SEQ ID NO: 30)
VGADSTHHRPVTGAADTTHHRPVTAGADTTHHRPVTGGADTTHHRPATG
GADTTHHRPGT.

In some embodiments, the targeting polypeptide comprises a sequence at least about 70%, 75%, 80%, 85%, 90%, 95%, or 100% identical to STADTSHHRPS (SEQ ID NO: 10), a sequence at least about 70%, 75%, 80%, 85%, 90%, 95%, or 100% identical to LLADTTHHRPWT (SEQ ID NO: 1), a sequence at least about 70%, 75%, 80%, 85%, 90%, 95%, or 100% identical to TSGGESTHHRPS (SEQ ID NO: 11), a sequence at least about 70%, 75%, 80%, 85%, 90%, 95%, or 100% identical to VGADSTHHRPVT (SEQ ID NO: 15), a sequence at least about 70%, 75%, 80%, 85%, 90%, 95%, or 100% identical to TSGGESSHHKPS (SEQ ID NO: 12), a sequence at least about 70%, 75%, 80%, 85%, 90%, 95%, or 100% identical to GAADTTHHRPVT (SEQ ID NO: 16), a sequence at least about 70%, 75%, 80%, 85%, 90%, 95%, or 100% identical to TGSGDSSHHRPS (SEQ ID NO: 13), a sequence at least about 70%, 75%, 80%, 85%, 90%, 95%, or 100% identical to GSSGESTHHKPST (SEQ ID NO: 14), and a sequence at least about 70%, 75%, 80%, 85%, 90%, 95%, or 100% identical to GGADTTHHRPAT (SEQ ID NO: 18).

In some embodiments, the targeting polypeptide comprises a sequence at least about 70%, 75%, 80%, 85%, 90%, 95%, or 100% identical to (SEQ ID NO: 31)
STADTSHHRPSLLADTTHHRPWTTSGGESTHHRPSVGADSTHHRPVTTS
GGESSHHKPSGAADTTHHRPVTTGSGDSSHHRPSGSSGESTHHKPSTGG
ADTTHHRPAT.

In some embodiments, the targeting polypeptide comprises an amino acid sequence of Formula I: $A_0B_0C_0D_0E_0F_0G_0H_0I_0J_0K_0L_0$ (Formula I) (SEQ ID NO: 35), wherein: $A_0$ is V, L, I, G, S, T or A; $B_0$ is I, L, V, Q, T, S, G or A; $C_0$ is G, A, V or S; $D_0$ is E, D, L or G; $E_0$ is S, T, P T, E or D; $F_0$ is T or S; $G_0$ is H, T or S; $H_0$ is H or T; $I_0$ is R, S, K, P or H; $J_0$ is P, S, R or K; $K_0$ is W, F, S, P, V, A or G; and $L_0$ is absent or is S, T G, (or A). In some embodiments, Formula I does not comprise LLADTTHHRPWT (SEQ ID NO: 1).

In some embodiments, the targeting polypeptide comprises two or more amino acid sequences having Formula I. In some embodiments, at least two of the two or more amino acid sequences are different. In some embodiments, at least two or the two or more amino acid sequences are the same. In some embodiments, two or more is about 2, 3, 4, 5, 6, 7, 8, 9, or 10.

In some embodiments, at least two of the two or more amino acid sequences having Formula I directly abut each other. In some embodiments, each of the two or more amino acid sequences having Formula I directly abut each other.

In some embodiments, at least two of the two or more amino acid sequences of Formula I are separated by a linker sequence. In some embodiments, each of the two or more amino acid sequences having Formula I are separated by a linker sequence.

In some embodiments of any of the chimeric polypeptides described herein, the mammalian growth factor comprises one or more of the following: epidermal growth factor (EGF), platelet derived growth factor (PDGF), insulin like growth factor (IGF-1), fibroblast growth factor (FGF), fibroblast growth factor 2 (FGF2), fibroblast growth factor 18 (FGF18), transforming growth factor alpha (TGF-α), transforming growth factor beta (TGF-β), transforming growth factor beta 1 (TGF-β1), transforming growth factor beta 3 (TGF-β3), osteogenic protein 1 (OP-1), osteogenic protein 2 (OP-2), osteogenic protein 3 (OP-3), bone morphogenetic protein 2 (BMP-2), bone morphogenetic protein 3 (BMP-3), bone morphogenetic protein 4 (BMP-4), bone morphogenetic protein 5 (BMP-5), bone morphogenetic protein 6 (BMP-6), bone morphogenetic protein 7 (BMP-7), bone morphogenetic protein (BMP-9), bone morphogenetic protein 10 (BMP-10), bone morphogenetic protein 11 (BMP-11), bone morphogenetic protein 12 (BMP-12) bone morphogenetic protein 13 (BMP-13), bone morphogenetic protein 15 (BMP-15), dentin phosphoprotein (DPP), vegetal related growth factor (Vgr), growth differentiation factor 1 (GDF-1), growth differentiation factor 3 (GDF-3), growth differentiation factor 5 (GDF-5), growth differentiation factor 6 (GDF-6), growth differentiation factor 7 (GDF-7), growth differentiation factor 8 (GDF8), growth differentiation factor 11 (GDF11), growth differentiation factor 15

(GDF15), vascular endothelial growth factor (VEGF), hyaluronic acid binding protein (HABP), collagen binding protein (CBP), fibroblast growth factor 18 (FGF-18), keratinocyte growth factor (KGF), tumor necrosis factor alpha (TNFα), tumor necrosis factor (TNF)-related apoptosis inducing ligand (TRAIL), wnt family member 1 (WNT1), wnt family member 2 (WNT2), wnt family member 2B (WNT2B), wnt family member 3 (WNT3), wnt family member 3A (WNT3A), wnt family member 4 (WNT4), wnt family member 5A (WNT5A), wnt family member 5B (WNT5B), wnt family member 6 (WNT6), wnt family member 7A (WNT7A), wnt family member 7B (WNT7B), wnt family member 8A (WNT8A), wnt family member 8B (WNT8B), wnt family member 9A (WNT9A), wnt family member 9B (WNT9B), wnt family member 10A (WNT10A), wnt family member 10B (WNT10B), wnt family member 11 (WNT11), neuregulin 1 (NRG1), or wnt family member 16 (WNT16).

In some embodiments of any of the chimeric polypeptides described herein, the mammalian growth factor comprises a functional portion of one or more of the following: epidermal growth factor (EGF), platelet derived growth factor (PDGF), insulin like growth factor (IGF-1), fibroblast growth factor (FGF), fibroblast growth factor 2 (FGF2), fibroblast growth factor 18 (FGF18), transforming growth factor alpha (TGF-α), transforming growth factor beta (TGF-β), transforming growth factor beta 1 (TGF-β1), transforming growth factor beta 3 (TGF-β3), osteogenic protein 1 (OP-1), osteogenic protein 2 (OP-2), osteogenic protein 3 (OP-3), bone morphogenetic protein 2 (BMP-2), bone morphogenetic protein 3 (BMP-3), bone morphogenetic protein 4 (BMP-4), bone morphogenetic protein 5 (BMP-5), bone morphogenetic protein 6 (BMP-6), bone morphogenetic protein 7 (BMP-7), bone morphogenetic protein (BMP-9), bone morphogenetic protein 10 (BMP-10), bone morphogenetic protein 11 (BMP-11), bone morphogenetic protein 12 (BMP-12) bone morphogenetic protein 13 (BMP-13), bone morphogenetic protein 15 (BMP-15), dentin phosphoprotein (DPP), vegetal related growth factor (Vgr), growth differentiation factor 1 (GDF-1), growth differentiation factor 3 (GDF-3), growth differentiation factor 5 (GDF-5), growth differentiation factor 6 (GDF-6), growth differentiation factor 7 (GDF-7), growth differentiation factor 8 (GDF8), growth differentiation factor 11 (GDF11), growth differentiation factor 15 (GDF15), vascular endothelial growth factor (VEGF), hyaluronic acid binding protein (HABP), collagen binding protein (CBP), fibroblast growth factor 18 (FGF-18), keratinocyte growth factor (KGF), tumor necrosis factor alpha (TNFα), tumor necrosis factor (TNF)-related apoptosis inducing ligand (TRAIL), wnt family member 1 (WNT1), wnt family member 2 (WNT2), wnt family member 2B (WNT2B), wnt family member 3 (WNT3), wnt family member 3A (WNT3A), wnt family member 4 (WNT4), wnt family member 5A (WNT5A), wnt family member 5B (WNT5B), wnt family member 6 (WNT6), wnt family member 7A (WNT7A), wnt family member 7B (WNT7B), wnt family member 8A (WNT8A), wnt family member 8B (WNT8B), wnt family member 9A (WNT9A), wnt family member 9B (WNT9B), wnt family member 10A (WNT10A), wnt family member 10B (WNT10B), wnt family member 11 (WNT11), neuregulin 1 (NRG1), or wnt family member 16 (WNT16).

In some embodiments, the mammalian growth factor comprises BMP-2. In some embodiments, the mammalian growth factor comprises a functional portion of BMP-2. In some embodiments, the mammalian growth factor comprises the mature BMP-2 peptide without signal sequence.

In some embodiments, the functional portion of BMP-2 comprises a sequence at least about 70%, 75%, 80%, 85%, 90%, 95%, or 100% identical to

```
                                            (SEQ ID NO: 32)
QAKHKQRKRLKSSCKRHPLYVDFSDVGWNDWIVAPPGYHAFYCHGECPF
PLADHLNSTNHAIVQTLVNSVNSKIPKACCVPTELSAISMLYLDENEKV
VLKNYQDMVVEGCGCR.
```

In some embodiments, the mammalian growth factor comprises a sequence at least about 70%, 75%, 80%, 85%, 90%, 95%, or 100% identical to a sequence of Table B. In some embodiments, the mammalian growth factor comprises a sequence at least about 90% identical to SEQ ID NO: 32. In some embodiments, the mammalian growth factor comprises SEQ ID NO: 32.

In some embodiments, the chimeric polypeptide comprises (a) the targeting polypeptide comprising: (i) a sequence at least about 70%, 75%, 80%, 85%, 90%, 95%, or 100% identical to SEQ ID NO: 1, (ii) a sequence at least about 70%, 75%, 80%, 85%, 90%, 95%, or 100% identical to SEQ ID NO: 2, (iii) a sequence at least about 70%, 75%, 80%, 85%, 90%, 95%, or 100% identical to SEQ ID NO: 4, (iv) a sequence at least about 70%, 75%, 80%, 85%, 90%, 95%, or 100% identical to SEQ ID NO: 6, (v) a sequence at least about 70%, 75%, 80%, 85%, 90%, 95%, or 100% identical to SEQ ID NO: 7, or (vi) any combination of (i) to (v); and (b) the mammalian growth factor comprising a functional portion of BMP-2. In some embodiments, the functional portion of BMP-2 comprises SEQ ID NO: 32. In some embodiments, the chimeric polypeptide comprises the targeting polypeptide comprising SEQ ID NO: 2, SEQ ID NO: 4, SEQ ID NO: 6, and SEQ ID NO: 7; and the mammalian growth factor comprising SEQ ID NO: 32. In some embodiments, the targeting polypeptide and mammalian growth factor are connected via a linker polypeptide.

In some embodiments, the chimeric polypeptide comprises the targeting polypeptide comprising a sequence at least about 70%, 75%, 80%, 85%, 90%, 95%, or 100% identical to SEQ ID NO: 402; and the mammalian growth factor comprising a sequence at least about 70%, 75%, 80%, 85%, 90%, 95%, or 100% identical to SEQ ID NO: 32. In some embodiments, the chimeric polypeptide comprises the targeting polypeptide comprising a sequence at least about 90% identical to SEQ ID NO: 402, and the mammalian growth factor comprising a sequence at least about 90% identical to SEQ ID NO: 32. In some embodiments, the targeting polypeptide and mammalian growth factor are connected via a linker polypeptide.

In some embodiments, the chimeric polypeptide comprises the targeting polypeptide comprising a sequence at least about 70%, 75%, 80%, 85%, 90%, 95%, or 100% identical to SEQ ID NO: 22; and the mammalian growth factor comprising a sequence at least about 70%, 75%, 80%, 85%, 90%, 95%, or 100% identical to SEQ ID NO: 32. In some embodiments, the chimeric polypeptide comprises the targeting polypeptide comprising a sequence at least about 90% identical to SEQ ID NO: 22, and the mammalian growth factor comprising a sequence at least about 90% identical to SEQ ID NO: 32. In some embodiments, the targeting polypeptide and mammalian growth factor are connected via a linker polypeptide.

In some embodiments of any of the chimeric polypeptides described herein, the chimeric polypeptide further comprises a linker sequence. In some embodiments, the linker sequence connects the targeting polypeptide and the mammalian growth factor.

In some embodiments, the linker sequence comprises a sequence at least about 70%, 75%, 80%, 85%, 90%, 95%, or 100% identical to

TGGSGEGGTGASTGGSAGTGGSGGTTSGEAGGSSGAG. (SEQ ID NO: 33)

In some embodiments, the linker sequence comprises at least about 70%, 75%, 80%, 85%, 90%, 95%, or 100% identical to GAGTG (SEQ ID NO: 34).

In some embodiments, the chimeric polypeptide comprises a flexible linker comprising a sequence of about 5 to about 50 amino acids, where at least about five of the amino acids have no regular secondary structure. In some embodiments, regular secondary structure comprises any helical structure like an alpha helix or $3_{10}$ helix or 7t helix, a beta turn, omega loop, and/or a beta sheet. In some embodiments, the flexible linker comprises at least about 50%, 55%, 60%, 65%, 70%, 75%, 80%, 85% or 90% glycine, alanine, serine, glycine and alanine, glycine and serine, alanine and serine, or glycine, alanine, and serine. In some embodiments, the linker comprises 1, 2, 3, 4, or 5 GSEG (SEQ ID NO: 702). In some embodiments, the linker comprises 1, 2, 3, 4, or 5 SEGG (SEQ ID NO: 703).

In some embodiments, the chimeric polypeptide comprises a linker sequence at least about 70%, 75%, 80%, 85%, 90%, 95%, or 100% identical to

ASGAGGSEGGGSEGGTSGATGAGTSTSGGGASTGGGTG. (SEQ ID NO: 701)

In some embodiments, the linker comprises a sequence at least about 90% identical to SEQ ID NO: 701. In some embodiments, the linker comprises SEQ ID NO: 701.

In some embodiments, the chimeric polypeptide comprises a sequence at least about 70%, 75%, 80%, 85%, 90%, 95%, or 100% identical to (SEQ ID NO: 502)
MPIGSLLADTTHHRPWTVIGESTHHRPWSIIGESSHHKPFTGLGDTTHH

RPWGILAESTHHKPWTASGAGGSEGGGSEGGTSGATGAGTSTSGGGAST

GGGTGQAKHKQRKRLKSSCKRHPLYVDFSDVGWNDWIVAPPGYHAFYCH

GECPFPLADHLNSTNHAIVQTLVNSVNSKIPKACCVPTELSAISMLYLD

ENEKVVLKNYQDMVVEGCGCR.

In some embodiments, the chimeric polypeptide comprises a sequence at least about 90% identical to SEQ ID NO: 502. In some embodiments, the chimeric polypeptide comprises a sequence at least about 91% identical to SEQ ID NO: 502. In some embodiments, the chimeric polypeptide comprises a sequence at least about 92% identical to SEQ ID NO: 502. In some embodiments, the chimeric polypeptide comprises a sequence at least about 93% identical to SEQ ID NO: 502. In some embodiments, the chimeric polypeptide comprises a sequence at least about 94% identical to SEQ ID NO: 502. In some embodiments, the chimeric polypeptide comprises a sequence at least about 95% identical to SEQ ID NO: 502. In some embodiments, the chimeric polypeptide comprises a sequence at least about 96% identical to SEQ ID NO: 502. In some embodiments, the chimeric polypeptide comprises a sequence at least about 97% identical to SEQ ID NO: 502. In some embodiments, the chimeric polypeptide comprises a sequence at least about 98% identical to SEQ ID NO: 502. In some embodiments, the chimeric polypeptide comprises a sequence at least about 99% identical to SEQ ID NO: 502. In some embodiments, the chimeric polypeptide comprises SEQ ID NO: 502.

In some embodiments of any of the chimeric polypeptides described herein, the chimeric polypeptide binds to a carrier material. In some embodiments, the targeting polypeptide binds to the carrier material. In some embodiments, the carrier material comprises calcium phosphate. In some embodiments, the carrier material comprises β-TCP. In some embodiments, the carrier material comprises hydroxyapatite. In some embodiments, the targeting polypeptide binds to the carrier material with a $K_D$ of about 1 picomolar to about 100 micromolar. In some embodiments, the targeting polypeptide binds to β-TCP with a $K_D$ of about 1 picomolar to about 100 micromolar. In some embodiments, the $K_D$ is measured using any method known in the art and/or described herein.

Also provided herein are compositions comprising any of one of the chimeric polypeptides described herein.

In some embodiments, the composition comprises a carrier material. In some embodiments, the carrier material comprises calcium phosphate. In some embodiments, the carrier material comprises β-TCP. In some embodiments, the carrier material comprises hydroxyapatite. In some embodiments, the carrier material is formulated as a powder, a putty, or a paste. In some embodiments, the carrier material comprises a scaffold, a fiber, a mesh, or a sponge.

In some embodiments of any of the compositions described herein, the composition is a pharmaceutical composition.

Also provided herein are kits comprising any of the polypeptides, carrier materials and/or compositions described herein.

Also provided herein are targeting polypeptides of any of the chimeric polypeptides described herein.

Also provided herein are methods of promoting bone or cartilage formation in a subject in need thereof that include: administering to the subject a therapeutically effective amount of any of the polypeptides and/or compositions described herein.

Also provided herein are methods of replacing and/or repairing bone or cartilage in a subject in need thereof that include: administering to the subject a therapeutically effective amount of any of the polypeptides and/or compositions described herein.

Also provided herein are methods of treating a bone fracture or bone loss in a subject in need thereof, that include: administering to the subject a therapeutically effective amount of any of the polypeptides and/or compositions described herein.

In some embodiments of any of the methods described herein, the subject has a bone fracture. In some embodiments of any of the methods described herein, the subject has a bone defect. In some embodiments of any of the methods described herein, the subject has a cartilage tear or cartilage defect. In some embodiments of any of the methods described herein, the subject has cartilage loss.

The term "subject" as used herein refers to any mammal. A subject therefore refers to, for example, mice, rats, dogs, cats, horses, cows, pigs, guinea pigs, rats, humans, monkeys, and the like. When the subject is a human, the subject may be referred to herein as a patient. In some embodiments, the subject or "subject in need of treatment" may be a canine (e.g., a dog), feline (e.g., a cat), equine (e.g., a horse), ovine, bovine, porcine, caprine, primate, e.g., a simian (e.g., a monkey (e.g., marmoset, baboon), or an ape (e.g., a gorilla, chimpanzee, orangutan, or gibbon), a human, or a rodent (e.g., a mouse, a guinea pig, a hamster, or a rat). In some embodiments, the subject or "subject in need of treatment" may be a non-human mammal, especially mammals that are conventionally used as models for demonstrating therapeutic efficacy in humans (e.g., murine, lapine, porcine, canine, or primate animals) may be employed.

In some embodiments, the term "therapeutically effective amount" refers to an amount of a polypeptide or composition effective to "treat" a disease, condition or disorder in a subject. In some cases, therapeutically effective amount of the polypeptide or composition reduces the severity of symptoms of the disease, condition or disorder. In some instances, the disease, condition or disorder comprises a defect in an organ or tissue.

"Affinity" refers to the strength of the sum total of non-covalent interactions between a (3-TCP binding sequence (or a chimeric polypeptide or polypeptide comprising a β-TCP binding sequence) and its binding partner (e.g., β-TCP). Affinity can be measured by common methods known in the art, including those described herein. Affinity can be determined, for example, using surface plasmon resonance (SPR) technology (e.g., BIACORE®) or biolayer interferometry (e.g., FORTEBIO®). Additional methods for determining affinity are known in the art.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known for instance, using publicly available computer software such as BLAST, BLAST-2, ALIGN or Megalign (DNASTAR) software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 14C is a Dose-Response model fit curve using non-linear least squares regression built based on bone volume data in 2.5 cm central region (red dots). The solid blue central line is the fit of the dose-response model. The three orange points from bottom to top identify the model-estimated doses at which 50%, 75%, and 90% of maximum effect is achieved on the log scale. The orange lines are 75% confidence intervals for such doses. The dose-response analysis showed that there is a statistically significant effect of the dose of tBMP-2 on the total bone volume generated in the central 2.5 cm region (p=0.0003). The modeling curve illustrates that the initial response increases rapidly with dose across the range from "No dose" to "low dose" (=2.14 mg/cc dose), and then more slowly as the plateau is attained. Above 2.14 mg/cc dose, there appears to be little additional benefit of increased tBMP-2 dose to get higher bone volume (dose-response curve becomes plateau line). A dose of 2 mg/cc of defect volume is sufficient to achieve complete response.

FIG. 14D is a ranking of postmortem radiographs (AP and ML views) of the 22 tibia defects. Higher rank number indicates greater bone formation in the tibial defect (1=complete bone healing to 22=no healing). Control and Low dose groups resulted in almost no new bone growth in defect site. Robust bone formation with some bone bridging was seen in the high and medium doses of tBMP-2 groups (9 of 15 goats). High and Medium groups led to a significant large new bone formation in the defect site compared to the other groups ("A" and "B").

DETAILED DESCRIPTION

Figure 1A:
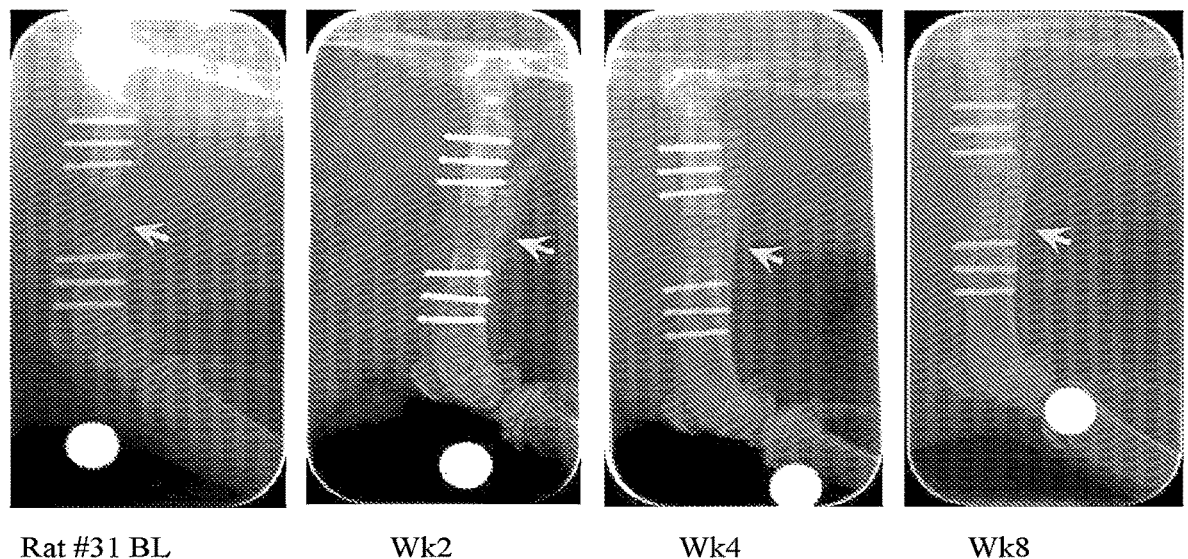
FIG. 1A are representative in vivo radiographs (latero-medial orientation) of animals from experimental Group A.

Provided herein are polypeptides for targeted delivery of a therapeutic agent to a region of a subject comprising a defect. In some embodiments, the region comprises bone and the therapeutic agent is delivered to treat a bone defect. In some embodiments, the polypeptide is a targeting polypeptide comprising one or more of the polypeptides of Table A.

In some embodiments, the targeting polypeptide comprises Formula I: $A_0B_0C_0D_0E_0F_0G_0H_0I_0J_0K_0L_0$ (Formula I) (SEQ ID NO: 35), where: $A_0$ is V, L, I, G, S, T or A; $B_0$ is I, L, V, Q, T, S, G or A; $C_0$ is G, A, V or S; $D_0$ is E, D, L or G; $E_0$ is S, T, P T, E or D; $F_0$ is T or S; $G_0$ is H, T or S; $H_0$ is H or T; $I_0$ is R, S, K, P or H; $J_0$ is P, S, R or K; $K_0$ is W, F, S, P, V, A or G; and $L_0$ is absent or is S, T G, (or A). In some embodiments, Formula I does not include LLADTTHHRPWT (SEQ ID NO: 1).

Also provided herein are chimeric polypeptides comprising the targeting polypeptide and a therapeutic agent. In some embodiments, the therapeutic agent comprises one or more of the polypeptides of Table B. In some embodiments, any of the targeting and/or chimeric polypeptides described herein can bind to one or more substrates comprising β TCP (e.g., a Mastergraft strip, Vitoss Foam Pack, chronOS Strip, Vitoss Micromorsels, LifeInk500, Hyperelastic Bone, bioactive glass, β TCP powder, β TCP spray dried powder, hydroxyapatite powder, hydroxyapatite-coated bone screw, β TCP granules, hydroxyapatite granules, and ReBOSSIS). In some embodiments, any of the targeting and/or chimeric polypeptides described herein can bind to silicon nitride or a substrate comprising silicon nitride.

Also provided herein are compositions that comprise any of the targeting and/or chimeric polypeptides described herein. In some embodiments, the compositions further comprise a substrate including β TCP (e.g., a Mastergraft strip, Vitoss Foam Pack, chronOS Strip, Vitoss Micromorsels, LifeInk500, Hyperelastic Bone, bioactive glass, β TCP powder, β TCP spray dried powder, hydroxyapatite powder, hydroxyapatite-coated bone screw, β TCP granules, hydroxyapatite granules, and ReBOSSIS). In some embodiments, the compositions further comprise a substrate comprising silicon nitride.

Also provided herein are kits that include any of these compositions. Also provided are methods of promoting bone or cartilage formation in a subject in need thereof, methods of replacing and/or repairing bone or cartilage in a subject in need thereof, and methods of treating a bone fraction or bone loss in a subject in need thereof that include administering to the subject any of the compositions described herein.

Non-limiting aspects of these polypeptides, compositions, kits, and methods are described below, and can be used in any combination without limitation. Additional aspects of these polypeptides, compositions, kits, and methods are known in the art.

Chimeric Polypeptides

In one aspect, provided herein are chimeric polypeptides comprising a targeting polypeptide (e.g., a polypeptide capable of binding to a carrier material) and a therapeutic agent. As used herein, the term "chimeric polypeptide" is interchangeable with a "fusion protein", "polypeptide composition" and the like. In some examples, the therapeutic agent comprises one or more of the peptides of Table B, or a functional portion thereof. In some examples, the chimeric polypeptide comprises a targeting polypeptide comprising a sequence at least about 70%, 75%, 80%, 85%, 90%, 95%, or 100% identical to one or more of SEQ ID NOS: 1-43 or 401-422. In some embodiments, the targeting polypeptide comprises Formula I. In some embodiments, the targeting polypeptide comprises two or more targeting polypeptides. In some embodiments, two or more targeting polypeptides is no more than about 50, 45, 40, 35, 30, 25, 20, 15, or 10 targeting polypeptides. In some embodiments, two or more targeting polypeptides is about 2, 3, 4, 5, 6, 7, 8, 9, 10, 11, 12, 13, 14, 15, 20, 25, or 30 targeting polypeptides. In some embodiments, two or more targeting polypeptides is about 2 to about 10 targeting polypeptides. In some embodiments, two or more targeting polypeptides is about 5 targeting polypeptides.

In some examples, the targeting polypeptide of the chimeric polypeptide comprise Formula I: $A_0B_0C_0D_0E_0F_0G_0H_0I_0J_0K_0L_0$ (Formula I) (SEQ ID NO: 35), wherein: $A_0$ is V, L, I, G, S, T, or A; $B_0$ is I, L, V, Q, T, S, G, or A; $C_0$ is G, A, V, or S; $D_0$ is E, D, L, or G; $E_0$ is S, T, P T, E, or D; $F_0$ is T or S; $G_0$ is H, T, or S; $H_0$ is H or T; $I_0$ is R, S, K, P, or H; $J_0$ is P, S, R, or K; $K_0$ is W, F, S, P, V, A, or G; and $L_0$ is absent or is S, T, G, or A.

Non-limiting examples of targeting polypeptides that may be present in any of the chimeric polypeptides described herein are listed in Table A below.

TABLE A

Exemplary targeting polypeptide sequences

| Sequence | SEQ ID NO: |
|---|---|
| LLADTTHHRPWT | 1 |
| VIGESTHHRPWS | 2 |
| LIADSTHHSPWT | 3 |
| ILAESTHHKPWT | 4 |
| ILAETTHHRPWS | 5 |
| IIGESSHHKPFT | 6 |
| GLGDTTHHRPWG | 7 |
| VLGDTTHHKPWT | 8 |
| IVADSTHHRPWT | 9 |
| STADTSHHRPS | 10 |
| TSGGESTHHRPS | 11 |
| TSGGESSHHKPS | 12 |
| TGSGDSSHHRPS | 13 |
| GSSGESTHHKPST | 14 |
| VGADSTHHRPVT | 15 |
| GAADTTHHRPVT | 16 |

TABLE A-continued

Exemplary targeting polypeptide sequences

| Sequence | SEQ ID NO: |
|---|---|
| AGADTTHHRPVT | 17 |
| GGADTTHHRPAT | 18 |
| GGADTTHHRPGT | 19 |
| LLADTTHHRPWTVIGESTHHRPWS | 20 |
| LLADTTHHRPWTVIGESTHHRPWSIIGESSHHKPFT | 21 |
| LLADTTHHRPWTVIGESTHHRPWSIIGESSHHKPFTGLGDTTHHRPWGILAESTHHKPWT | 22 |
| LLADTTHHRPWTILAESTHHKPWT | 23 |
| LLADTTHHRPWTILAESTHHKPWTLLADTTHHRPWTILAESTHHKPWTLLADTTHHRPWT | 24 |
| LLADTTHHRPWTGLGDTTHHRPWG | 25 |
| LLADTTHHRPWTGLGDTTHHRPWGLLADTTHHRPWT | 26 |
| LLADTTHHRPWTGLGDTTHHRPWGLLADTTHHRPWTGLGDTTHHRPWGLLADTTHHRPWT | 27 |
| LLADTTHHRPWTGLGDTTHHRPWGLLADTTHHRPWTGLGDTTHHRPWGLLADTTHHRPWTGLGDTTHHRPWGLLADTTHHRPWT | 28 |
| STADTSHHRPSTSGGESTHHRPSTSGGESSHHKPSTGSGDSSHHRPSGSSGESTHHKPST | 29 |
| VGADSTHHRPVTGAADTTHHRPVTAGADTTHHRPVTGGADTTHHRPATGGADTTHHRPGT | 30 |
| STADTSHHRPSLLADTTHHRPWTTSGGESTHHRPSVGADSTHHRPVTTSGGESSHHKPSGAADTTHHRPVTTGSGDSSHHRPSGSSGESTHHKPSTGGADTTHHRPAT | 31 |
| AAADTTHHRPWT | 36 |
| AAADTTHHRPWTAAADTTHHRPWTAAADTTHHRPWTAAADTTHHRPWTAAADTTHHRPWT | 37 |
| LLADAAHHRPWTLLADAAHHRPWTLLADAAHHRPWTLLADAAHHRPWTLLADAAHHRPWT | 38 |
| LLADTTAARPWTLLADTTAARPWTLLADTTAARPWTLLADTTAARPWTLLADTTAARPWT | 39 |
| LLADTTHHRPWTLLADTTHHRPWT | 40 |
| LLADTTHHRPWTLLADTTHHRPWTLLADTTHHRPWT | 41 |
| LLADTTHHRPWTLLADTTHHRPWTLLADTTHHRPWTLLADTTHHRPWTLLADTTHHRPWT | 42 |
| STSGSTVIGESTHHRPWSLIADSTHHSPWTILAESTHHKPWTILAETTHHRPWSIIGESSHHKPFTGLGDTTHHRPWGVLGDTTHHKPWTIVADSTHHRPWTGQVLPTTTPSSPSTTSGS | 43 |
| LLADTTHHRPWTVIGESTHHRPWSIIGESSHHKPFTGLGDTTHHRPWG | 401 |
| VIGESTHHRPWSIIGESSHHKPFTGLGDTTHHRPWGILAESTHHKPWT | 402 |
| (X1)(X2), wherein X1 comprises SEQ ID NO: 1 and X2 comprises one or more of SEQ ID NOS: 1-31,35-43, or 401-402. | 403 |
| (X1)(X2), wherein X1 comprises SEQ ID NO: 2 and X2 comprises one or more of SEQ ID NOS: 1-31,35-43, or 401-402. | 404 |
| (X1)(X2), wherein X1 comprises SEQ ID NO: 4 and X2 comprises one or more of SEQ ID NOS: 1-31,35-43, or 401-402. | 405 |
| (X1)(X2), wherein X1 comprises SEQ ID NO: 6 and X2 comprises one or more of SEQ ID NOS: 1-31,35-43, or 401-402. | 406 |

TABLE A-continued

Exemplary targeting polypeptide sequences

| Sequence | SEQ ID NO: |
|---|---|
| (X1)(X2), wherein X1 comprises SEQ ID NO: 7 and X2 comprises one or more of SEQ ID NOS: 1-31, 35-43, or 401-402. | 407 |
| (X1)(X2), wherein X1 comprises SEQ ID NO: 1 and X2 comprises one or more of SEQ ID NOS: 2, 4, 6, or 7. | 408 |
| (X1)(X2), wherein X1 comprises SEQ ID NO: 2 and X2 comprises one or more of SEQ ID NOS: 1, 4, 6, or 7. | 409 |
| (X1)(X2), wherein X1 comprises SEQ ID NO: 4 and X2 comprises one or more of SEQ ID NOS: 1, 2, 6, or 7. | 410 |
| (X1)(X2), wherein X1 comprises SEQ ID NO: 6 and X2 comprises one or more of SEQ ID NOS: 1, 4, 2, or 7. | 411 |
| (X1)(X2), wherein X1 comprises SEQ ID NO: 7 and X2 comprises one or more of SEQ ID NOS: 1, 4, 6, or 2. | 412 |
| (X1)(X2), wherein X1 comprises SEQ ID NO: 1 and X2 comprises two or more of SEQ ID NOS: 2, 4, 6, or 7. | 413 |
| (X1)(X2), wherein X1 comprises SEQ ID NO: 2 and X2 comprises two or more of SEQ ID NOS: 1, 4, 6, or 7. | 414 |
| (X1)(X2), wherein X1 comprises SEQ ID NO: 4 and X2 comprises two or more of SEQ ID NOS: 1, 2, 6, or 7. | 415 |
| (X1)(X2), wherein X1 comprises SEQ ID NO: 6 and X2 comprises two or more of SEQ ID NOS: 1, 4, 2, or 7. | 416 |
| (X1)(X2), wherein X1 comprises SEQ ID NO: 7 and X2 comprises two or more of SEQ ID NOS: 1, 4, 6, or 2. | 417 |
| (X1)(X2), wherein X1 comprises SEQ ID NO: 1 and X2 comprises three or more of SEQ ID NOS: 2, 4, 6, or 7. | 418 |
| (X1)(X2), wherein X1 comprises SEQ ID NO: 2 and X2 comprises three or more of SEQ ID NOS: 1, 4, 6, or 7. | 419 |
| (X1)(X2), wherein X1 comprises SEQ ID NO: 4 and X2 comprises three or more of SEQ ID NOS: 1, 2, 6, or 7. | 420 |
| (X1)(X2), wherein X1 comprises SEQ ID NO: 6 and X2 comprises three or more of SEQ ID NOS: 1, 4, 2, or 7. | 421 |
| (X1)(X2), wherein X1 comprises SEQ ID NO: 7 and X2 comprises three or more of SEQ ID NOS: 1, 4, 6, or 2. | 422 |

TABLE C

Exemplary Chimeric Polypeptides

| Sequence | SEQ ID NO |
|---|---|
| ASGAGGSEGGGSEGGTSGATGAGTSTSGGGASTGGGTGQAKHKQRKRLKSSCKRHPL YVDFSDVGWNDWIVAPPGYHAFYCHGECPFPLADHLNSTNHAIVQTLVNSVNSKIPK ACCVPTELSAISMLYLDENEKVVLKNYQDMVVEGCGCR | 501 |
| MPIGSLLADTTHHRPWTVIGESTHHRPWSIIGESSHHKPFTGLGDTTHHRPWGILAEST HHKPWTASGAGGSEGGGSEGGTSGATGAGTSTSGGGASTGGGTGQAKHKQRKRLKS SCKRHPLYVDFSDVGWNDWIVAPPGYHAFYCHGECPFPLADHLNSTNHAIVQTLVNS VNSKIPKACCVPTELSAISMLYLDENEKVVLKNYQDMVVEGCGCR | 502 |
| LLADTTHHRPWTVIGESTHHRPWSIIGESSHHKPFTGLGDTTHHRPWGILAESTHHKP WTASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR | 503 |

TABLE C-continued

Exemplary Chimeric Polypeptides

| Sequence | SEQ ID NO |
|---|---|
| VIGESTHHRPWSIIGESSHHKPFTGLGDTTHHRPWGILAESTHHKPWTASGAGGSEGG GSEGGTSGATGAGTSTSGGGASTGGGTGQAKHKQRKRLKSSCKRHPLYVDFSDVGW NDWIVAPPGYHAFYCHGECPFPLADHLNSTNHAIVQTLVNSVNSKIPKACCVPTELSAI SMLYLDENEKVVLKNYQDMVVEGCGCR | 504 |
| IIGESSHHKPFTGLGDTTHHRPWGILAESTHHKPWTASGAGGSEGGGSEGGTSGATGA GTSTSGGGASTGGGTGQAKHKQRKRLKSSCKRHPLYVDFSDVGWNDWIVAPPGYHA FYCHGECPFPLADHLNSTNHAIVQTLVNSVNSKIPKACCVPTELSAISMLYLDENEKVV LKNYQDMVVEGCGCR | 505 |
| GLGDTTHHRPWGILAESTHHKPWTASGAGGSEGGGSEGGTSGATGAGTSTSGGGAST GGGTGQAKHKQRKRLKSSCKRHPLYVDFSDVGWNDWIVAPPGYHAFYCHGECPFPL ADHLNSTNHAIVQTLVNSVNSKIPKACCVPTELSAISMLYLDENEKVVLKNYQDMVV EGCGCR | 506 |
| ILAESTHHKPWTASGAGGSEGGGSEGGTSGATGAGTSTSGGGASTGGGTGQAKHKQR KRLKSSCKRHPLYVDFSDVGWNDWIVAPPGYHAFYCHGECPFPLADHLNSTNHAIVQ TLVNSVNSKIPKACCVPTELSAISMLYLDENEKVVLKNYQDMVVEGCGCR | 507 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises Formula 1 and optionally a linker (e.g., X may comprise Formula I + linker) | 508 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises Formula I | 509 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 1, and optionally a linker | 510 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 1 | 511 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 2, and optionally a linker | 639 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 2 | 512 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 3, and optionally a linker | 513 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 3 | 514 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 4, and optionally a linker | 515 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 4 | 516 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 5, and optionally a linker | 517 |

TABLE C-continued

Exemplary Chimeric Polypeptides

| Sequence | SEQ ID NO |
|---|---|
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 5 | 518 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 6, and optionally a linker | 519 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 6 | 520 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 7, and optionally a linker | 521 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 7 | 522 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 8, and optionally a linker | 523 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 8 | 524 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 9, and optionally a linker | 525 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 9 | 526 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 10, and optionally a linker | 527 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 10 | 528 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 11, and optionally a linker | 529 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 11 | 530 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 12, and optionally a linker | 531 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 12 | 532 |

TABLE C-continued

Exemplary Chimeric Polypeptides

| Sequence | SEQ ID NO |
|---|---|
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 13, and optionally a linker | 533 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 13 | 534 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 14, and optionally a linker | 535 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 14 | 536 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 15, and optionally a linker | 537 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 15 | 538 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 16, and optionally a linker | 539 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 16 | 540 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 17, and optionally a linker | 541 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 17 | 542 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 18, and optionally a linker | 543 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 18 | 544 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 19, and optionally a linker | 545 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 19 | 546 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 20, and optionally a linker | 547 |

TABLE C-continued

Exemplary Chimeric Polypeptides

| Sequence | SEQ ID NO |
|---|---|
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 20 | 548 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 21, and optionally a linker | 549 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 21 | 550 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 22, and optionally a linker | 551 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 22 | 552 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 23, and optionally a linker | 553 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 23 | 554 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 24, and optionally a linker | 555 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 24 | 556 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 25, and optionally a linker | 557 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 25 | 558 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 26, and optionally a linker | 559 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 26 | 560 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 27, and optionally a linker | 561 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 27 | 562 |

TABLE C-continued

Exemplary Chimeric Polypeptides

| Sequence | SEQ ID NO |
|---|---|
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 28, and optionally a linker | 563 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 28 | 564 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 29, and optionally a linker | 565 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 29 | 566 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 30, and optionally a linker | 567 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 30 | 568 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 31, and optionally a linker | 569 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 31 | 570 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 32, and optionally a linker | 571 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 32 | 572 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 33, and optionally a linker | 573 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 33 | 574 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 34, and optionally a linker | 575 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 34 | 576 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 35, and optionally a linker | 577 |

TABLE C-continued

Exemplary Chimeric Polypeptides

| Sequence | SEQ ID NO |
|---|---|
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 35 | 578 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 36, and optionally a linker | 579 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 36 | 580 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 37, and optionally a linker | 581 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 37 | 582 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 38, and optionally a linker | 583 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 38 | 584 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 39, and optionally a linker | 585 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 39 | 586 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 40, and optionally a linker | 587 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 40 | 588 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 41, and optionally a linker | 589 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 41 | 590 |
| (X)QAKHKQRKRLKSSCKRHPLYVDFSDVGWNDWIVAPPGYHAFYCHGECPFPLADH LNSTNHAIVQTLVNSVNSKIPKACCVPTELSAISMLYLDENEKVVLKNYQDMVVEGC GCR<br>Wherein X comprises SEQ ID NO: 42, and optionally a linker | 591 |
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR<br>Wherein X comprises SEQ ID NO: 42 | 592 |

TABLE C-continued

Exemplary Chimeric Polypeptides

| Sequence | SEQ ID NO |
|---|---|
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 43, and optionally a linker | 593 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 43 | 594 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 401, and optionally a linker | 595 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 401 | 596 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 402, and optionally a linker | 597 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 402 | 598 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 403, and optionally a linker | 599 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 403 | 600 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 404, and optionally a linker | 601 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 404 | 602 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 405, and optionally a linker | 603 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 405 | 604 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 406, and optionally a linker | 605 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 406 | 606 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 407, and optionally a linker | 607 |

TABLE C-continued

Exemplary Chimeric Polypeptides

| Sequence | SEQ ID NO |
|---|---|
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 407 | 608 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 408, and optionally a linker | 609 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 408 | 610 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 409, and optionally a linker | 611 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 409 | 612 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 410, and optionally a linker | 613 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 410 | 614 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 411, and optionally a linker | 615 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 411 | 616 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 412, and optionally a linker | 617 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 412 | 618 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 413, and optionally a linker | 619 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 413 | 620 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 414, and optionally a linker | 621 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 414 | 622 |

TABLE C-continued

Exemplary Chimeric Polypeptides

| Sequence | SEQ ID NO |
|---|---|
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 415, and optionally a linker | 623 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 415 | 624 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 416, and optionally a linker | 625 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 416 | 626 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 417, and optionally a linker | 627 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 417 | 628 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 418, and optionally a linker | 629 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 418 | 630 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 419, and optionally a linker | 631 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 419 | 632 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 420, and optionally a linker | 633 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 420 | 634 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 421, and optionally a linker | 635 |
| (X)ASGAGGSEGGGSEGGTSGATGAGTSTSGGGASTGGGTGQAKHKQRKRLKSSCKR<br>HPLYVDFSDVGWNDWIVAPPGYHAFYCHGECPFPLADHLNSTNHAIVQTLVNSVNSK<br>IPKACCVPTELSAISMLYLDENEKVVLKNYQDMVVEGCGCR<br>Wherein X comprises SEQ ID NO: 421 | 636 |
| (X)QAKHKQRKRLKSSCKRHPLYVDFSDVGWNDWIVAPPGYHAFYCHGECPFPLADH<br>LNSTNHAIVQTLVNSVNSKIPKACCVPTELSAISMLYLDENEKVVLKNYQDMVVEGC<br>GCR<br>Wherein X comprises SEQ ID NO: 422, and optionally a linker | 637 |

TABLE C-continued

Exemplary Chimeric Polypeptides

| Sequence | SEQ ID NO |
|---|---|
| (X)ASGAGGSEGGGSEGGTSGATGAGTSTSGGGASTGGGTGQAKHKQRKRLKSSCKR HPLYVDFSDVGWNDWIVAPPGYHAFYCHGECPFPLADHLNSTNHAIVQTLVNSVNSK IPKACCVPTELSAISMLYLDENEKVVLKNYQDMVVEGCGCR Wherein X comprises SEQ ID NO: 422 | 638 |

In some embodiments, any of the chimeric polypeptides described herein comprise one or more targeting polypeptides. In some embodiments, the chimeric polypeptide comprises one to about ten targeting polypeptides. For instance, the chimeric polypeptide comprises about 1, 2, 3, 4, 5, 6, 7, 8, 9, or 10 targeting polypeptides. In some embodiments, the targeting polypeptide comprises one or more polypeptides that bind to a carrier material. In some embodiments, the one or more polypeptides is about 1, 2, 3, 4, 5, 6, 7, 8, 9, or 10 polypeptides. In some embodiments, the targeting polypeptide comprises from about 10 to about 100, from about 10 to about 90, from about 10 to about 80, from about 10 to about 70, from about 10 to about 60, from about 10 to about 50, from about 10 to about 40, from about 10 to about 30, from about 20 to about 100, from about 20 to about 90, from about 20 to about 80, from about 20 to about 70, from about 20 to about 60, from about 20 to about 50, from about 20 to about 40, or from about 30 to about 80 amino acids.

In some embodiments, the chimeric polypeptide comprises an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 1. In some embodiments, the chimeric polypeptide comprises one or more therapeutic agents of Table B, or a sequence at least about 70%, 75%, 80%, 85%, 90%, 95%, or 100% identical to a therapeutic agent of Table B. As a non-limiting example, the therapeutic agent comprises a sequence at least about 70%, 75%, 80%, 85%, 90%, 95%, or 100% identical to SEQ ID NO: 32. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 2. In some embodiments, the chimeric polypeptide comprises one or more therapeutic agents of Table B, or a sequence at least about 70%, 75%, 80%, 85%, 90%, 95%, or 100% identical to a therapeutic agent of Table B. As a non-limiting example, the therapeutic agent comprises a sequence at least about 70%, 75%, 80%, 85%, 90%, 95%, or 100% identical to SEQ ID NO: 32. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 3. In some embodiments, the chimeric polypeptide comprises one or more therapeutic agents of Table B, or a sequence at least about 70%, 75%, 80%, 85%, 90%, 95%, or 100% identical to a therapeutic agent of Table B. As a non-limiting example, the therapeutic agent comprises a sequence at least about 70%, 75%, 80%, 85%, 90%, 95%, or 100% identical to SEQ ID NO: 32. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 4. In some embodiments, the chimeric polypeptide comprises one or more therapeutic agents of Table B, or a sequence at least about 70%, 75%, 80%, 85%, 90%, 95%, or 100% identical to a therapeutic agent of Table B. As a non-limiting example, the therapeutic agent comprises a sequence at least about 70%, 75%, 80%, 85%, 90%, 95%, or 100% identical to SEQ ID NO: 32. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 5. In some embodiments, the chimeric polypeptide comprises one or more therapeutic agents of Table B, or a sequence at least about 70%, 75%, 80%, 85%, 90%, 95%, or 100% identical to a therapeutic agent of Table B. As a non-limiting example, the therapeutic agent comprises a sequence at least about 70%, 75%, 80%, 85%, 90%, 95%, or 100% identical to SEQ ID NO: 32. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 6. In some embodiments, the chimeric polypeptide comprises one or more therapeutic agents of Table B, or a sequence at least about 70%, 75%, 80%, 85%, 90%, 95%, or 100% identical to a therapeutic agent of Table B. As a non-limiting example, the therapeutic agent comprises a sequence at least about 70%, 75%, 80%, 85%, 90%, 95%, or 100% identical to SEQ ID NO: 32. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 7. In some embodiments, the chimeric polypeptide comprises one or more therapeutic agents of Table B, or a sequence at least about 70%, 75%, 80%, 85%, 90%, 95%, or 100% identical to a therapeutic agent of Table B. As a non-limiting example, the therapeutic agent comprises a sequence at least about 70%, 75%, 80%, 85%, 90%, 95%, or 100% identical to SEQ ID NO: 32. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 8. In some embodiments, the chimeric polypeptide comprises one or more therapeutic agents of Table B, or a sequence at least about 70%, 75%, 80%, 85%, 90%, 95%, or 100% identical to a therapeutic agent of Table B. As a non-limiting example, the therapeutic agent comprises a sequence at least about 70%, 75%, 80%, 85%, 90%, 95%, or 100% identical to SEQ ID NO: 32. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 9. In some embodiments, the chimeric polypeptide comprises one or more therapeutic agents of Table B, or a sequence at least about 70%, 75%, 80%, 85%, 90%, 95%, or 100% identical to a therapeutic agent of Table B. As a non-limiting example, the therapeutic agent comprises a sequence at least about 70%, 75%, 80%, 85%, 90%, 95%, or 100% identical to SEQ ID NO: 32. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 10. In some embodiments, the chimeric polypeptide comprises one or more therapeutic agents of Table B, or a sequence at least about 70%, 75%, 80%, 85%, 90%, 95%, or 100% identical to a therapeutic agent of Table B. As a non-limiting example, the therapeutic agent comprises a sequence at least about 70%, 75%, 80%, 85%, 90%, 95%, or 100% identical to SEQ ID NO: 32. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 11. In some embodiments, the chimeric polypeptide comprises one or more therapeutic agents of Table B, or a sequence at least about 70%, 75%, 80%, 85%, 90%, 95%, or 100% identical to a therapeutic agent of Table B. As a non-limiting example, the therapeutic agent comprises a sequence at least about 70%, 75%, 80%, 85%, 90%, 95%, or 100% identical to SEQ ID NO: 32. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 12. In some embodiments, the chimeric polypeptide comprises one or more therapeutic agents of Table B, or a sequence at least about 70%, 75%, 80%, 85%, 90%, 95%, or 100% identical to a therapeutic agent of Table B. As a non-limiting example, the therapeutic agent comprises a sequence at least about 70%, 75%, 80%, 85%, 90%, 95%, or 100% identical to SEQ ID NO: 32. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 13. In some embodiments, the chimeric polypeptide comprises one or more therapeutic agents of Table B, or a sequence at least about 70%, 75%, 80%, 85%, 90%, 95%, or 100% identical to a therapeutic agent of Table B. As a non-limiting example, the therapeutic agent comprises a sequence at least about 70%, 75%, 80%, 85%, 90%, 95%, or 100% identical to SEQ ID NO: 32. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 14. In some embodiments, the chimeric polypeptide comprises one or more therapeutic agents of Table B, or a sequence at least about 70%, 75%, 80%, 85%, 90%, 95%, or 100% identical to a therapeutic agent of Table B. As a non-limiting example, the therapeutic agent comprises a sequence at least about 70%, 75%, 80%, 85%, 90%, 95%, or 100% identical to SEQ ID NO: 32. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 15. In some embodiments, the chimeric polypeptide comprises one or more therapeutic agents of Table B, or a sequence at least about 70%, 75%, 80%, 85%, 90%, 95%, or 100% identical to a therapeutic agent of Table B. As a non-limiting example, the therapeutic agent comprises a sequence at least about 70%, 75%, 80%, 85%, 90%, 95%, or 100% identical to SEQ ID NO: 32. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 16. In some embodiments, the chimeric polypeptide comprises one or more therapeutic agents of Table B, or a sequence at least about 70%, 75%, 80%, 85%, 90%, 95%, or 100% identical to a therapeutic agent of Table B. As a non-limiting example, the therapeutic agent comprises a sequence at least about 70%, 75%, 80%, 85%, 90%, 95%, or 100% identical to SEQ ID NO: 32. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 17. In some embodiments, the chimeric polypeptide comprises one or more therapeutic agents of Table B, or a sequence at least about 70%, 75%, 80%, 85%, 90%, 95%, or 100% identical to a therapeutic agent of Table B. As a non-limiting example, the therapeutic agent comprises a sequence at least about 70%, 75%, 80%, 85%, 90%, 95%, or 100% identical to SEQ ID NO: 32. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 18. In some embodiments, the chimeric polypeptide comprises one or more therapeutic agents of Table B, or a sequence at least about 70%, 75%, 80%, 85%, 90%, 95%, or 100% identical to a therapeutic agent of Table B. As a non-limiting example, the therapeutic agent comprises a sequence at least about 70%, 75%, 80%, 85%, 90%, 95%, or 100% identical to SEQ ID NO: 32. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises an amino acid sequence that has at least 70% (e.g., at least 75%, at least 80%, at least 85%, at least 90%, at least 95%, at least 96%, at least 97%, at least 98%, at least 99%, or 100%) sequence identity to SEQ ID NO: 19. In some embodiments, the chimeric polypeptide comprises one or more therapeutic agents of Table B, or a sequence at least about 70%, 75%, 80%, 85%, 90%, 95%, or 100% identical to a therapeutic agent of Table B. As a non-limiting example, the therapeutic agent comprises a sequence at least about 70%, 75%, 80%, 85%, 90%, 95%, or 100% identical to SEQ ID NO: 32. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 501. In some embodiments, the chimeric polypeptide comprises SEQ ID NO: 501. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 502. In some embodiments, the chimeric polypeptide comprises SEQ ID NO: 502. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, NO: 503. In some embodiments, the chimeric polypeptide comprises SEQ ID NO: 503. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 504. In some embodiments, the chimeric polypeptide comprises SEQ ID NO: 504. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 505. In some embodiments, the chimeric polypeptide comprises SEQ ID NO: 505. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 506. In some embodiments, the chimeric polypeptide comprises SEQ ID NO: 506. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 507. In some embodiments, the chimeric polypeptide comprises SEQ ID NO: 507. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 508, wherein the chimeric polypeptide comprises X. In some embodiments, the chimeric polypeptide comprises SEQ ID NO: 508. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 509, wherein the chimeric polypeptide comprises X. In some embodiments, the chimeric polypeptide comprises SEQ ID NO: 509. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 510, wherein the chimeric polypeptide comprises X. In some embodiments, the chimeric polypeptide comprises SEQ ID NO: 510. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 511, wherein the chimeric polypeptide comprises X. In some embodiments, the chimeric polypeptide comprises SEQ ID NO: 511. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 512, wherein the chimeric polypeptide comprises X. In some embodiments, the chimeric polypeptide comprises SEQ ID NO: 512. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 513, wherein the chimeric polypeptide comprises X. In some embodiments, the chimeric polypeptide comprises SEQ ID NO: 513. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 514, wherein the chimeric polypeptide comprises X. In some embodiments, the chimeric polypeptide comprises SEQ ID NO: 514. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 515, wherein the chimeric polypeptide comprises X. In some embodiments, the chimeric polypeptide comprises SEQ ID NO: 515. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 516, wherein the chimeric polypeptide comprises X. In some embodiments, the chimeric polypeptide comprises SEQ ID NO: 516. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99%, or 100% identical to SEQ ID NO: 517, wherein the chimeric polypeptide comprises X. In some embodiments, the chimeric polypeptide comprises SEQ ID NO: 517. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 518, wherein the chimeric polypeptide comprises X. In some embodiments, the chimeric polypeptide comprises SEQ ID NO: 518. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 519, wherein the chimeric polypeptide comprises X. In some embodiments, the chimeric polypeptide comprises SEQ ID NO: 519. In some aspects, further provided are compositions comprising the chimeric polypeptide and a carrier material, e.g., a carrier material provided herein. Non-limiting exemplary carrier materials may comprise one or more of the following: tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 520, wherein the chimeric polypeptide comprises X. In some embodiments, the chimeric polypeptide comprises SEQ ID NO: 520. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 521, wherein the chimeric polypeptide comprises X. In some embodiments, the chimeric polypeptide comprises SEQ ID NO: 521. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 522, wherein the chimeric polypeptide comprises X. In some embodiments, the chimeric polypeptide comprises SEQ ID NO: 522. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 523, wherein the chimeric polypeptide comprises X. In some embodiments, the chimeric polypeptide comprises SEQ ID NO: 523. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 524, wherein the chimeric polypeptide comprises X. In some embodiments, the chimeric polypeptide comprises SEQ ID NO: 524. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 525, wherein the chimeric polypeptide comprises X. In some embodiments, the chimeric polypeptide comprises SEQ ID NO: 525. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 526, wherein the chimeric polypeptide comprises X. In some embodiments, the chimeric polypeptide comprises SEQ ID NO: 526. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 527, wherein the chimeric polypeptide comprises X. In some embodiments, the chimeric polypeptide comprises SEQ ID NO: 527. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 528, wherein the chimeric polypeptide comprises X. In some embodiments, the chimeric polypeptide comprises SEQ ID NO: 528. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 529, wherein the chimeric polypeptide comprises X. In some embodiments, the chimeric polypeptide comprises SEQ ID NO: 529. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 530, wherein the chimeric polypeptide comprises X. In some embodiments, the chimeric polypeptide comprises SEQ ID NO: 530. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 531, wherein the chimeric polypeptide comprises X. In some embodiments, the chimeric polypeptide comprises SEQ ID NO: 531. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 532, wherein the chimeric polypeptide comprises X. In some embodiments, the chimeric polypeptide comprises SEQ ID NO: 532. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 533, wherein the chimeric polypeptide comprises X. In some embodiments, the chimeric polypeptide comprises SEQ ID NO: 533. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 534, wherein the chimeric polypeptide comprises X. In some embodiments, the chimeric polypeptide comprises SEQ ID NO: 534. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 535, wherein the chimeric polypeptide comprises X. In some embodiments, the chimeric polypeptide comprises SEQ ID NO: 535. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 536, wherein the chimeric polypeptide comprises X. In some embodiments, the chimeric polypeptide comprises SEQ ID NO: 536. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 537, wherein the chimeric polypeptide comprises X. In some embodiments, the chimeric polypeptide comprises SEQ ID NO: 537. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 538, wherein the chimeric polypeptide comprises X. In some embodiments, the chimeric polypeptide comprises SEQ ID NO: 538. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 539, wherein the chimeric polypeptide comprises X. In some embodiments, the chimeric polypeptide comprises SEQ ID NO: 539. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 540, wherein the chimeric polypeptide comprises X. In some embodiments, the chimeric polypeptide comprises SEQ ID NO: 540. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 541, wherein the chimeric polypeptide comprises X. In some embodiments, the chimeric polypeptide comprises SEQ ID NO: 541. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 542, wherein the chimeric polypeptide comprises X. In some embodiments, the chimeric polypeptide comprises SEQ ID NO: 542. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 543, wherein the chimeric polypeptide comprises X. In some embodiments, the chimeric polypeptide comprises SEQ ID NO: 543. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 544, wherein the chimeric polypeptide comprises X. In some embodiments, the chimeric polypeptide comprises SEQ ID NO: 544. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 545, wherein the chimeric polypeptide comprises X. In some embodiments, the chimeric polypeptide comprises SEQ ID NO: 545. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 546, wherein the chimeric polypeptide comprises X. In some embodiments, the chimeric polypeptide comprises SEQ ID NO: 546. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 547, wherein the chimeric polypeptide comprises X. In some embodiments, the chimeric polypeptide comprises SEQ ID NO: 547. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 548, wherein the chimeric polypeptide comprises X. In some embodiments, the chimeric polypeptide comprises SEQ ID NO: 548. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 549, wherein the chimeric polypeptide comprises X. In some embodiments, the chimeric polypeptide comprises SEQ ID NO: 549. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 550, wherein the chimeric polypeptide comprises X. In some embodiments, the chimeric polypeptide comprises SEQ ID NO: 550. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 551, wherein the chimeric polypeptide comprises X. In some embodiments, the chimeric polypeptide comprises SEQ ID NO: 551. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 552, wherein the chimeric polypeptide comprises X. In some embodiments, the chimeric polypeptide comprises SEQ ID NO: 552. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 553, wherein the chimeric polypeptide comprises X. In some embodiments, the chimeric polypeptide comprises SEQ ID NO: 553. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 554, wherein the chimeric polypeptide comprises X. In some embodiments, the chimeric polypeptide comprises SEQ ID NO: 554. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 555, wherein the chimeric polypeptide comprises X. In some embodiments, the chimeric polypeptide comprises SEQ ID NO: 555. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 556, wherein the chimeric polypeptide comprises X. In some embodiments, the chimeric polypeptide comprises SEQ ID NO: 556. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 557, wherein the chimeric polypeptide comprises X. In some embodiments, the chimeric polypeptide comprises SEQ ID NO: 557. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 558, wherein the chimeric polypeptide comprises X. In some embodiments, the chimeric polypeptide comprises SEQ ID NO: 558. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 559, wherein the chimeric polypeptide comprises X. In some embodiments, the chimeric polypeptide comprises SEQ ID NO: 559. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 560, wherein the chimeric polypeptide comprises X. In some embodiments, the chimeric polypeptide comprises SEQ ID NO: 560. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 561, wherein the chimeric polypeptide comprises X. In some embodiments, the chimeric polypeptide comprises SEQ ID NO: 561. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 562, wherein the chimeric polypeptide comprises X. In some embodiments, the chimeric polypeptide comprises SEQ ID NO: 562. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 563, wherein the chimeric polypeptide comprises X. In some embodiments, the chimeric polypeptide comprises SEQ ID NO: 563. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 564, wherein the chimeric polypeptide comprises X. In some embodiments, the chimeric polypeptide comprises SEQ ID NO: 564. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 565, wherein the chimeric polypeptide comprises X. In some embodiments, the chimeric polypeptide comprises SEQ ID NO: 565. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 566, wherein the chimeric polypeptide comprises X. In some embodiments, the chimeric polypeptide comprises SEQ ID NO: 566. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 567, wherein the chimeric polypeptide comprises X. In some embodiments, the chimeric polypeptide comprises SEQ ID NO: 567. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 568, wherein the chimeric polypeptide comprises X. In some embodiments, the chimeric polypeptide comprises SEQ ID NO: 568. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 569, wherein the chimeric polypeptide comprises X. In some embodiments, the chimeric polypeptide comprises SEQ ID NO: 569. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 570, wherein the chimeric polypeptide comprises X. In some embodiments, the chimeric polypeptide comprises SEQ ID NO: 570. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 571, wherein the chimeric polypeptide comprises X. In some embodiments, the chimeric polypeptide comprises SEQ ID NO: 571. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 572, wherein the chimeric polypeptide comprises X. In some embodiments, the chimeric polypeptide comprises SEQ ID NO: 572. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 573, wherein the chimeric polypeptide comprises X. In some embodiments, the chimeric polypeptide comprises SEQ ID NO: 573. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 574, wherein the chimeric polypeptide comprises X. In some embodiments, the chimeric polypeptide comprises SEQ ID NO: 574. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 575, wherein the chimeric polypeptide comprises X. In some embodiments, the chimeric polypeptide comprises SEQ ID NO: 575. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 576, wherein the chimeric polypeptide comprises X. In some embodiments, the chimeric polypeptide comprises SEQ ID NO: 576. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 577, wherein the chimeric polypeptide comprises X. In some embodiments, the chimeric polypeptide comprises SEQ ID NO: 577. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 578, wherein the chimeric polypeptide comprises X. In some embodiments, the chimeric polypeptide comprises SEQ ID NO: 578. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 579, wherein the chimeric polypeptide comprises X. In some embodiments, the chimeric polypeptide comprises SEQ ID NO: 579. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 580, wherein the chimeric polypeptide comprises X. In some embodiments, the chimeric polypeptide comprises SEQ ID NO: 580. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 581, wherein the chimeric polypeptide comprises X. In some embodiments, the chimeric polypeptide comprises SEQ ID NO: 581. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 582, wherein the chimeric polypeptide comprises X. In some embodiments, the chimeric polypeptide comprises SEQ ID NO: 582. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 583, wherein the chimeric polypeptide comprises X. In some embodiments, the chimeric polypeptide comprises SEQ ID NO: 583. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 584, wherein the chimeric polypeptide comprises X. In some embodiments, the chimeric polypeptide comprises SEQ ID NO: 584. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 585, wherein the chimeric polypeptide comprises X. In some embodiments, the chimeric polypeptide comprises SEQ ID NO: 585. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 586, wherein the chimeric polypeptide comprises X. In some embodiments, the chimeric polypeptide comprises SEQ ID NO: 586. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 587, wherein the chimeric polypeptide comprises X. In some embodiments, the chimeric polypeptide comprises SEQ ID NO: 587. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 588, wherein the chimeric polypeptide comprises X. In some embodiments, the chimeric polypeptide comprises SEQ ID NO: 588. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 589, wherein the chimeric polypeptide comprises X. In some embodiments, the chimeric polypeptide comprises SEQ ID NO: 589. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 590, wherein the chimeric polypeptide comprises X. In some embodiments, the chimeric polypeptide comprises SEQ ID NO: 590. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 591, wherein the chimeric polypeptide comprises X. In some embodiments, the chimeric polypeptide comprises SEQ ID NO: 591. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 592, wherein the chimeric polypeptide comprises X. In some embodiments, the chimeric polypeptide comprises SEQ ID NO: 592. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 593, wherein the chimeric polypeptide comprises X. In some embodiments, the chimeric polypeptide comprises SEQ ID NO: 593. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 594, wherein the chimeric polypeptide comprises X. In some embodiments, the chimeric polypeptide comprises SEQ ID NO: 594. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 595, wherein the chimeric polypeptide comprises X. In some embodiments, the chimeric polypeptide comprises SEQ ID NO: 595. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 596, wherein the chimeric polypeptide comprises X. In some embodiments, the chimeric polypeptide comprises SEQ ID NO: 596. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 597, wherein the chimeric polypeptide comprises X. In some embodiments, the chimeric polypeptide comprises SEQ ID NO: 597. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 598, wherein the chimeric polypeptide comprises X. In some embodiments, the chimeric polypeptide comprises SEQ ID NO: 598. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 599, wherein the chimeric polypeptide comprises X. In some embodiments, the chimeric polypeptide comprises SEQ ID NO: 599. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 600, wherein the chimeric polypeptide comprises X. In some embodiments, the chimeric polypeptide comprises SEQ ID NO: 600. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 601, wherein the chimeric polypeptide comprises X. In some embodiments, the chimeric polypeptide comprises SEQ ID NO: 601. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 602, wherein the chimeric polypeptide comprises X. In some embodiments, the chimeric polypeptide comprises SEQ ID NO: 602. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 603, wherein the chimeric polypeptide comprises X. In some embodiments, the chimeric polypeptide comprises SEQ ID NO: 603. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 604, wherein the chimeric polypeptide comprises X. In some embodiments, the chimeric polypeptide comprises SEQ ID NO: 604. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 605, wherein the chimeric polypeptide comprises X. In some embodiments, the chimeric polypeptide comprises SEQ ID NO: 605. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 606, wherein the chimeric polypeptide comprises X. In some embodiments, the chimeric polypeptide comprises SEQ ID NO: 606. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 607, wherein the chimeric polypeptide comprises X. In some embodiments, the chimeric polypeptide comprises SEQ ID NO: 607. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 608, wherein the chimeric polypeptide comprises X. In some embodiments, the chimeric polypeptide comprises SEQ ID NO: 608. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 609, wherein the chimeric polypeptide comprises X. In some embodiments, the chimeric polypeptide comprises SEQ ID NO: 609. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 610, wherein the chimeric polypeptide comprises X. In some embodiments, the chimeric polypeptide comprises SEQ ID NO: 610. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 611, wherein the chimeric polypeptide comprises X. In some embodiments, the chimeric polypeptide comprises SEQ ID NO: 611. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 612, wherein the chimeric polypeptide comprises X. In some embodiments, the chimeric polypeptide comprises SEQ ID NO: 612. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 613, wherein the chimeric polypeptide comprises X. In some embodiments, the chimeric polypeptide comprises SEQ ID NO: 613. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 614, wherein the chimeric polypeptide comprises X. In some embodiments, the chimeric polypeptide comprises SEQ ID NO: 614. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 615, wherein the chimeric polypeptide comprises X. In some embodiments, the chimeric polypeptide comprises SEQ ID NO: 615. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 616, wherein the chimeric polypeptide comprises X. In some embodiments, the chimeric polypeptide comprises SEQ ID NO: 616. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 617, wherein the chimeric polypeptide comprises X. In some embodiments, the chimeric polypeptide comprises SEQ ID NO: 617. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 618, wherein the chimeric polypeptide comprises X. In some embodiments, the chimeric polypeptide comprises SEQ ID NO: 618. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 619, wherein the chimeric polypeptide comprises X. In some embodiments, the chimeric polypeptide comprises SEQ ID NO: 619. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 620, wherein the chimeric polypeptide comprises X. In some embodiments, the chimeric polypeptide comprises SEQ ID NO: 620. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 621, wherein the chimeric polypeptide comprises X. In some embodiments, the chimeric polypeptide comprises SEQ ID NO: 621. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 622, wherein the chimeric polypeptide comprises X. In some embodiments, the chimeric polypeptide comprises SEQ ID NO: 622. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 623, wherein the chimeric polypeptide comprises X. In some embodiments, the chimeric polypeptide comprises SEQ ID NO: 623. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 624, wherein the chimeric polypeptide comprises X. In some embodiments, the chimeric polypeptide comprises SEQ ID NO: 624. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 625, wherein the chimeric polypeptide comprises X. In some embodiments, the chimeric polypeptide comprises SEQ ID NO: 625. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 626, wherein the chimeric polypeptide comprises X. In some embodiments, the chimeric polypeptide comprises SEQ ID NO: 626. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 627, wherein the chimeric polypeptide comprises X. In some embodiments, the chimeric polypeptide comprises SEQ ID NO: 627. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 628, wherein the chimeric polypeptide comprises X. In some embodiments, the chimeric polypeptide comprises SEQ ID NO: 628. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 629, wherein the chimeric polypeptide comprises X. In some embodiments, the chimeric polypeptide comprises SEQ ID NO: 629. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 630, wherein the chimeric polypeptide comprises X. In some embodiments, the chimeric polypeptide comprises SEQ ID NO: 630. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 631, wherein the chimeric polypeptide comprises X. In some embodiments, the chimeric polypeptide comprises SEQ ID NO: 631. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 632, wherein the chimeric polypeptide comprises X. In some embodiments, the chimeric polypeptide comprises SEQ ID NO: 632. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 633, wherein the chimeric polypeptide comprises X. In some embodiments, the chimeric polypeptide comprises SEQ ID NO: 633. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 634, wherein the chimeric polypeptide comprises X. In some embodiments, the chimeric polypeptide comprises SEQ ID NO: 634. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 635, wherein the chimeric polypeptide comprises X. In some embodiments, the chimeric polypeptide comprises SEQ ID NO: 635. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 636, wherein the chimeric polypeptide comprises X. In some embodiments, the chimeric polypeptide comprises SEQ ID NO: 636. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 637, wherein the chimeric polypeptide comprises X. In some embodiments, the chimeric polypeptide comprises SEQ ID NO: 637. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 638, wherein the chimeric polypeptide comprises X. In some embodiments, the chimeric polypeptide comprises SEQ ID NO: 638. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide comprises a sequence at least about 75%, 80%, 85%, 90%, 91%, 92%, 93%, 94%, 95%, 96%, 97%, 98%, 99% or 100% identical to SEQ ID NO: 639, wherein the chimeric polypeptide comprises X. In some embodiments, the chimeric polypeptide comprises SEQ ID NO: 639. In some aspects, further provided are compositions comprising the chimeric polypeptide and a carrier material, e.g., a carrier material provided herein. Non-limiting exemplary carrier materials may comprise one or more of the following: tricalcium phosphate, beta tricalcium phosphate, alpha tricalcium phosphate, fluorapatite, bone (e.g., demineralized bone), glasses (bioglasses) such as silicates, vanadates, and related ceramic minerals, and chelated divalent metal ions. In some aspects, further provided are methods of treating a defect in an organ and/or tissue comprising administering to a subject in need thereof the chimeric polypeptide and/or composition.

In some embodiments, the chimeric polypeptide further comprises a linker sequence between two targeting polypeptides. In some embodiments, the chimeric polypeptide further comprises a linker sequence between the targeting polypeptide and therapeutic agent.

In some embodiments, the chimeric polypeptide comprises a signal sequence at its N-terminus. In some embodiments, the chimeric polypeptide comprises a tag sequence (e.g., a poly-His tag, chitin-binding protein (CBP), maltose-binding protein (MBP), strep-tag, glutathione-S-transferase (GST), thioredoxin, or Fc region). Additional examples of tags are known in the art.

In some embodiments, the chimeric polypeptide comprises a lead sequence at its N-terminus that may assist with expression of the polypeptide. As a non-limiting example, the lead sequence comprises MPIGS (SEQ ID NO: 704).

Non-limiting exemplary embodiments of a chimeric polypeptide are provided herein: (1) In a first embodiment, the chimeric polypeptide comprises a targeting polypeptide. (2) The chimeric polypeptide of embodiment 1, wherein the targeting polypeptide comprises a sequence at least about 70%, 75%, 80%, 85%, 90%, 95%, or 100% identical to SEQ ID NO: 1. (3) The chimeric polypeptide of embodiment 1, wherein the targeting polypeptide comprises SEQ ID NO: 1. (4) The chimeric polypeptide of any previous embodiment, wherein the targeting polypeptide comprises a sequence at least about 70%, 75%, 80%, 85%, 90%, 95%, or 100% identical to SEQ ID NO: 2. (5) The chimeric polypeptide of any previous embodiment, wherein the targeting polypeptide comprises SEQ ID NO: 2. (6) The chimeric polypeptide of any previous embodiment, wherein the targeting polypeptide comprises a sequence at least about 70%, 75%, 80%, 85%, 90%, 95%, or 100% identical to SEQ ID NO: 3. (7) The chimeric polypeptide of any previous embodiment, wherein the targeting polypeptide comprises SEQ ID NO: 3. (8) The chimeric polypeptide of any previous embodiment, wherein the targeting polypeptide comprises a sequence at least about 70%, 75%, 80%, 85%, 90%, 95%, or 100% identical to SEQ ID NO: 4. (9) The chimeric polypeptide of any previous embodiment, wherein the targeting polypeptide comprises SEQ ID NO: 4. (10) The chimeric polypeptide of any previous embodiment, wherein the targeting polypeptide comprises a sequence at least about 70%, 75%, 80%, 85%, 90%, 95%, or 100% identical to SEQ ID NO: 5. (11) The chimeric polypeptide of any previous embodiment, wherein the targeting polypeptide comprises SEQ ID NO: 5. (12) The chimeric polypeptide of any previous embodiment, wherein the targeting polypeptide comprises a sequence at least about 70%, 75%, 80%, 85%, 90%, 95%, or 100% identical to SEQ ID NO: 6. (13) The chimeric polypeptide of any previous embodiment, wherein the targeting polypeptide comprises SEQ ID NO: 6. (14) The chimeric polypeptide of any previous embodiment, wherein the targeting polypeptide comprises a sequence at least about 70%, 75%, 80%, 85%, 90%, 95%, or 100% identical to SEQ ID NO: 7. (15) The chimeric polypeptide of any previous embodiment, wherein the targeting polypeptide comprises SEQ ID NO: 7. (16) The chimeric polypeptide of any previous embodiment, wherein the targeting polypeptide comprises a sequence at least about 70%, 75%, 80%, 85%, 90%, 95%, or 100% identical to SEQ ID NO: 8. (17) The chimeric polypeptide of any previous embodiment, wherein the targeting polypeptide comprises SEQ ID NO: 8. (18) The chimeric polypeptide of any previous embodiment, wherein the targeting polypeptide comprises a sequence at least about 70%, 75%, 80%, 85%, 90%, 95%, or 100% identical to SEQ ID NO: 9. (19) The chimeric polypeptide of any previous embodiment, wherein the targeting polypeptide comprises SEQ ID NO: 9. (20) The chimeric polypeptide of any previous embodiment, wherein the targeting polypeptide comprises a sequence at least about 70%, 75%, 80%, 85%, 90%, 95%, or 100% identical to SEQ ID NO: 10. (21) The chimeric polypeptide of any previous embodiment, wherein the targeting polypeptide comprises SEQ ID NO: 10. (22) The chimeric polypeptide of any previous embodiment, wherein the targeting polypeptide comprises a sequence at least about 70%, 75%, 80%, 85%, 90%, 95%, or 100% identical to SEQ ID NO: 11. (23) The chimeric polypeptide of any previous embodiment, wherein the targeting polypeptide comprises SEQ ID NO: 11. (24) The chimeric polypeptide of any previous embodiment, wherein the targeting polypeptide comprises a sequence at least about 70%, 75%, 80%, 85%, 90%, 95%, or 100% identical to SEQ ID NO: 12. (25) The chimeric polypeptide of any previous embodiment, wherein the targeting polypeptide comprises SEQ ID NO: 12. (26) The chimeric polypeptide of any previous embodiment, wherein the targeting polypeptide comprises a sequence at least about 70%, 75%, 80%, 85%, 90%, 95%, or 100% identical to SEQ ID NO: 13. (27) The chimeric polypeptide of any previous embodiment, wherein the targeting polypeptide comprises SEQ ID NO: 13. (28) The chimeric polypeptide of any previous embodiment, wherein the targeting polypeptide comprises a sequence at least about 70%, 75%, 80%, 85%, 90%, 95%, or 100% identical to SEQ ID NO: 14. (29) The chimeric polypeptide of any previous embodiment, wherein the targeting polypeptide comprises SEQ ID NO: 14. (30) The chimeric polypeptide of any previous embodiment, wherein the targeting polypeptide comprises a sequence at least about 70%, 75%, 80%, 85%, 90%, 95%, or 100% identical to SEQ ID NO: 15. (31) The chimeric polypeptide of any previous embodiment, wherein the targeting polypeptide comprises SEQ ID NO: 15. (32)

The chimeric polypeptide of any previous embodiment, wherein the targeting polypeptide comprises a sequence at least about 70%, 75%, 80%, 85%, 90%, 95%, or 100% identical to SEQ ID NO: 16. (33) The chimeric polypeptide of any previous embodiment, wherein the targeting polypeptide comprises SEQ ID NO: 16. (34) The chimeric polypeptide of any previous embodiment, wherein the targeting polypeptide comprises a sequence at least about 70%, 75%, 80%, 85%, 90%, 95%, or 100% identical to SEQ ID NO: 17. (35) The chimeric polypeptide of any previous embodiment, wherein the targeting polypeptide comprises SEQ ID NO: 17. (36) The chimeric polypeptide of any previous embodiment, wherein the targeting polypeptide comprises a sequence at least about 70%, 75%, 80%, 85%, 90%, 95%, or 100% identical to SEQ ID NO: 18. (37) The chimeric polypeptide of any previous embodiment, wherein the targeting polypeptide comprises SEQ ID NO: 18. (38) The chimeric polypeptide of any previous embodiment, wherein the targeting polypeptide comprises a sequence at least about 70%, 75%, 80%, 85%, 90%, 95%, or 100% identical to SEQ ID NO: 19. (39) The chimeric polypeptide of any previous embodiment, wherein the targeting polypeptide comprises SEQ ID NO: 19. (40) The chimeric polypeptide of any previous embodiment, wherein the targeting polypeptide comprises a sequence at least about 70%, 75%, 80%, 85%, 90%, 95%, or 100% identical to SEQ ID NO: 20. (41) The chimeric polypeptide of any previous embodiment, wherein the targeting polypeptide comprises SEQ ID NO: 20. (42) The chimeric polypeptide of any previous embodiment, wherein the targeting polypeptide comprises a sequence at least about 70%, 75%, 80%, 85%, 90%, 95%, or 100% identical to SEQ ID NO: 21. (43) The chimeric polypeptide of any previous embodiment, wherein the targeting polypeptide comprises SEQ ID NO: 21. (44) The chimeric polypeptide of any previous embodiment, wherein the targeting polypeptide comprises a sequence at least about 70%, 75%, 80%, 85%, 90%, 95%, or 100% identical to SEQ ID NO: 22. (45) The chimeric polypeptide of any previous embodiment, wherein the targeting polypeptide comprises SEQ ID NO: 22. (46) The chimeric polypeptide of any previous embodiment, wherein the targeting polypeptide comprises a sequence at least about 70%, 75%, 80%, 85%, 90%, 95%, or 100% identical to SEQ ID NO: 23. (47) The chimeric polypeptide of any previous embodiment, wherein the targeting polypeptide comprises SEQ ID NO: 23. (48) The chimeric polypeptide of any previous embodiment, wherein the targeting polypeptide comprises a sequence at least about 70%, 75%, 80%, 85%, 90%, 95%, or 100% identical to SEQ ID NO: 24. (49) The chimeric polypeptide of any previous embodiment, wherein the targeting polypeptide comprises SEQ ID NO: 24. (50) The chimeric polypeptide of any previous embodiment, wherein the targeting polypeptide comprises a sequence at least about 70%, 75%, 80%, 85%, 90%, 95%, or 100% identical to SEQ ID NO: 25. (51) The chimeric polypeptide of any previous embodiment, wherein the targeting polypeptide comprises SEQ ID NO: 25. (52) The chimeric polypeptide of any previous embodiment, wherein the targeting polypeptide comprises a sequence at least about 70%, 75%, 80%, 85%, 90%, 95%, or 100% identical to SEQ ID NO: 26. (53) The chimeric polypeptide of any previous embodiment, wherein the targeting polypeptide comprises SEQ ID NO: 26. (54) The chimeric polypeptide of any previous embodiment, wherein the targeting polypeptide comprises a sequence at least about 70%, 75%, 80%, 85%, 90%, 95%, or 100% identical to SEQ ID NO: 27. (55) The chimeric polypeptide of any previous embodiment, wherein the targeting polypeptide comprises SEQ ID NO: 27. (56) The chimeric polypeptide of any previous embodiment, wherein the targeting polypeptide comprises a sequence at least about 70%, 75%, 80%, 85%, 90%, 95%, or 100% identical to SEQ ID NO: 28. (57) The chimeric polypeptide of any previous embodiment, wherein the targeting polypeptide comprises SEQ ID NO: 28. (58) The chimeric polypeptide of any previous embodiment, wherein the targeting polypeptide comprises a sequence at least about 70%, 75%, 80%, 85%, 90%, 95%, or 100% identical to SEQ ID NO: 29. (59) The chimeric polypeptide of any previous embodiment, wherein the targeting polypeptide comprises SEQ ID NO: 29. (60) The chimeric polypeptide of any previous embodiment, wherein the targeting polypeptide comprises a sequence at least about 70%, 75%, 80%, 85%, 90%, 95%, or 100% identical to SEQ ID NO: 30. (61) The chimeric polypeptide of any previous embodiment, wherein the targeting polypeptide comprises SEQ ID NO: 30. (62) The chimeric polypeptide of any previous embodiment, wherein the targeting polypeptide comprises a sequence at least about 70%, 75%, 80%, 85%, 90%, 95%, or 100% identical to SEQ ID NO: 31. (63) The chimeric polypeptide of any previous embodiment, wherein the targeting polypeptide comprises SEQ ID NO: 31. (64) The chimeric polypeptide of any previous embodiment, wherein the targeting polypeptide comprises a sequence at least about 70%, 75%, 80%, 85%, 90%, 95%, or 100% identical to SEQ ID NO: 32. (65) The chimeric polypeptide of any previous embodiment, wherein the targeting polypeptide comprises SEQ ID NO: 32. (66) The chimeric polypeptide of any previous embodiment, wherein the targeting polypeptide comprises a sequence at least about 70%, 75%, 80%, 85%, 90%, 95%, or 100% identical to SEQ ID NO: 33. (67) The chimeric polypeptide of any previous embodiment, wherein the targeting polypeptide comprises SEQ ID NO: 33. (68) The chimeric polypeptide of any previous embodiment, wherein the targeting polypeptide comprises a sequence at least about 70%, 75%, 80%, 85%, 90%, 95%, or 100% identical to SEQ ID NO: 34. (69) The chimeric polypeptide of any previous embodiment, wherein the targeting polypeptide comprises SEQ ID NO: 34. (70) The chimeric polypeptide of any previous embodiment, wherein the targeting polypeptide comprises a sequence at least about 70%, 75%, 80%, 85%, 90%, 95%, or 100% identical to SEQ ID NO: 35. (71) The chimeric polypeptide of any previous embodiment, wherein the targeting polypeptide comprises SEQ ID NO: 35. (72) The chimeric polypeptide of any previous embodiment, wherein the targeting polypeptide comprises a sequence at least about 70%, 75%, 80%, 85%, 90%, 95%, or 100% identical to SEQ ID NO: 36. (73) The chimeric polypeptide of any previous embodiment, wherein the targeting polypeptide comprises SEQ ID NO: 36. (74) The chimeric polypeptide of any previous embodiment, wherein the targeting polypeptide comprises a sequence at least about 70%, 75%, 80%, 85%, 90%, 95%, or 100% identical to SEQ ID NO: 37. (75) The chimeric polypeptide of any previous embodiment, wherein the targeting polypeptide comprises SEQ ID NO: 37. (76) The chimeric polypeptide of any previous embodiment, wherein the targeting polypeptide comprises a sequence at least about 70%, 75%, 80%, 85%, 90%, 95%, or 100% identical to SEQ ID NO: 38. (77) The chimeric polypeptide of any previous embodiment, wherein the targeting polypeptide comprises SEQ ID NO: 38. (78) The chimeric polypeptide of any previous embodiment, wherein the targeting polypeptide comprises a sequence at least about 70%, 75%, 80%, 85%, 90%, 95%, or 100% identical to SEQ ID NO: 39. (79) The chimeric polypeptide of any previous embodiment, wherein the targeting polypeptide comprises SEQ ID NO: 39. (80) The chimeric polypeptide of any previous embodiment, wherein the targeting polypeptide comprises a sequence at least about 70%, 75%, 80%, 85%, 90%, 95%, or 100% identical to SEQ ID NO: 40. (81) The chimeric polypeptide of any previous embodiment, wherein the targeting polypeptide comprises SEQ ID NO: 40. (82) The chimeric polypeptide of any previous embodiment, wherein the targeting polypeptide comprises a sequence at least about 70%, 75%, 80%, 85%, 90%, 95%, or 100% identical to SEQ ID NO: 41. (83) The chimeric polypeptide of any previous embodiment, wherein the targeting polypeptide comprises SEQ ID NO: 41. (84) The chimeric polypeptide of any previous embodiment, wherein the targeting polypeptide comprises a sequence at least about 70%, 75%, 80%, 85%, 90%, 95%, or 100% identical to SEQ ID NO: 42. (85) The chimeric polypeptide of any previous embodiment, wherein the targeting polypeptide comprises SEQ ID NO: 42. (86) The chimeric polypeptide of any previous embodiment, wherein the targeting polypeptide comprises a sequence at least about 70%, 75%, 80%, 85%, 90%, 95%, or 100% identical to SEQ ID NO: 43. (87) The chimeric polypeptide of any previous embodiment, wherein the targeting polypeptide comprises SEQ ID NO: 43. (88) The chimeric polypeptide of any previous embodiment, wherein the targeting polypeptide comprises a sequence at least about 70%, 75%, 80%, 85%, 90%, 95%, or 100% identical to SEQ ID NO: 401. (89) The chimeric polypeptide of any previous embodiment, wherein the targeting polypeptide comprises SEQ ID NO: 401. (90) The chimeric polypeptide of any previous embodiment, wherein the targeting polypeptide comprises a sequence at least about 70%, 75%, 80%, 85%, 90%, 95%, or 100% identical to SEQ ID NO: 402. (91) The chimeric polypeptide of any previous embodiment, wherein the targeting polypeptide comprises SEQ ID NO: 402. (92) The chimeric polypeptide of any previous embodiment, wherein the targeting polypeptide comprises a sequence at least about 70%, 75%, 80%, 85%, 90%, 95%, or 100% identical to SEQ ID NO: 403. (93) The chimeric polypeptide of any previous embodiment, wherein the targeting polypeptide comprises SEQ ID NO: 403. (94) The chimeric polypeptide of any previous embodiment, wherein the targeting polypeptide comprises a sequence at least about 70%, 75%, 80%, 85%, 90%, 95%, or 100% identical to SEQ ID NO: 404. (95) The chimeric polypeptide of any previous embodiment, wherein the targeting polypeptide comprises SEQ ID NO: 404. (96) The chimeric polypeptide of any previous embodiment, wherein the targeting polypeptide comprises a sequence at least about 70%, 75%, 80%, 85%, 90%, 95%, or 100% identical to SEQ ID NO: 405. (97) The chimeric polypeptide of any previous embodiment, wherein the targeting polypeptide comprises SEQ ID NO: 405. (98) The chimeric polypeptide of any previous embodiment, wherein the targeting polypeptide comprises a sequence at least about 70%, 75%, 80%, 85%, 90%, 95%, or 100% identical to SEQ ID NO: 406. (99) The chimeric polypeptide of any previous embodiment, wherein the targeting polypeptide comprises SEQ ID NO: 406. (100) The chimeric polypeptide of any previous embodiment, wherein the targeting polypeptide comprises a sequence at least about 70%, 75%, 80%, 85%, 90%, 95%, or 100% identical to SEQ ID NO: 407. (101) The chimeric polypeptide of any previous embodiment, wherein the targeting polypeptide comprises SEQ ID NO: 407. (102) The chimeric polypeptide of any previous embodiment, wherein the targeting polypeptide comprises a sequence at least about 70%, 75%, 80%, 85%, 90%, 95%, or 100% identical to SEQ ID NO: 408. (103) The chimeric polypeptide of any previous embodiment, wherein the targeting polypeptide comprises SEQ ID NO: 408. (104) The chimeric polypeptide of any previous embodiment, wherein the targeting polypeptide comprises a sequence at least about 70%, 75%, 80%, 85%, 90%, 95%, or 100% identical to SEQ ID NO: 409. (105) The chimeric polypeptide of any previous embodiment, wherein the targeting polypeptide comprises SEQ ID NO: 409. (106) The chimeric polypeptide of any previous embodiment, wherein the targeting polypeptide comprises a sequence at least about 70%, 75%, 80%, 85%, 90%, 95%, or 100% identical to SEQ ID NO: 410. (107) The chimeric polypeptide of any previous embodiment, wherein the targeting polypeptide comprises SEQ ID NO: 410. (108) The chimeric polypeptide of any previous embodiment, wherein the targeting polypeptide comprises a sequence at least about 70%, 75%, 80%, 85%, 90%, 95%, or 100% identical to SEQ ID NO: 411. (109) The chimeric polypeptide of any previous embodiment, wherein the targeting polypeptide comprises SEQ ID NO: 411. (110) The chimeric polypeptide of any previous embodiment, wherein the targeting polypeptide comprises a sequence at least about 70%, 75%, 80%, 85%, 90%, 95%, or 100% identical to SEQ ID NO: 412. (111) The chimeric polypeptide of any previous embodiment, wherein the targeting polypeptide comprises SEQ ID NO: 412. (112) The chimeric polypeptide of any previous embodiment, wherein the targeting polypeptide comprises a sequence at least about 70%, 75%, 80%, 85%, 90%, 95%, or 100% identical to SEQ ID NO: 413. (113) The chimeric polypeptide of any previous embodiment, wherein the targeting polypeptide comprises SEQ ID NO: 413. (114) The chimeric polypeptide of any previous embodiment, wherein the targeting polypeptide comprises a sequence at least about 70%, 75%, 80%, 85%, 90%, 95%, or 100% identical to SEQ ID NO: 414. (115) The chimeric polypeptide of any previous embodiment, wherein the targeting polypeptide comprises SEQ ID NO: 414. (116) The chimeric polypeptide of any previous embodiment, wherein the targeting polypeptide comprises a sequence at least about 70%, 75%, 80%, 85%, 90%, 95%, or 100% identical to SEQ ID NO: 415. (117) The chimeric polypeptide of any previous embodiment, wherein the targeting polypeptide comprises SEQ ID NO: 415. (118) The chimeric polypeptide of any previous embodiment, wherein the targeting polypeptide comprises a sequence at least about 70%, 75%, 80%, 85%, 90%, 95%, or 100% identical to SEQ ID NO: 416. (119) The chimeric polypeptide of any previous embodiment, wherein the targeting polypeptide comprises SEQ ID NO: 416. (120) The chimeric polypeptide of any previous embodiment, wherein the targeting polypeptide comprises a sequence at least about 70%, 75%, 80%, 85%, 90%, 95%, or 100% identical to SEQ ID NO: 417. (121) The chimeric polypeptide of any previous embodiment, wherein the targeting polypeptide comprises SEQ ID NO: 417. (122) The chimeric polypeptide of any previous embodiment, wherein the targeting polypeptide comprises a sequence at least about 70%, 75%, 80%, 85%, 90%, 95%, or 100% identical to SEQ ID NO: 418. (123) The chimeric polypeptide of any previous embodiment, wherein the targeting polypeptide comprises SEQ ID NO: 418. (124) The chimeric polypeptide of any previous embodiment, wherein the targeting polypeptide comprises a sequence at least about 70%, 75%, 80%, 85%, 90%, 95%, or 100% identical to SEQ ID NO: 419. (125) The chimeric polypeptide of any previous embodiment, wherein the targeting polypeptide comprises SEQ ID NO: 419. (126) The chimeric polypeptide of any previous embodiment, wherein the targeting polypeptide comprises a sequence at least about 70%, 75%, 80%, 85%, 90%, 95%, or 100% identical to SEQ ID NO: 420. (127) The chimeric polypeptide of any previous embodiment, wherein the targeting polypeptide comprises SEQ ID NO: 420. (128) The chimeric polypeptide of any previous embodiment, wherein the targeting polypeptide comprises a sequence at least about 70%, 75%, 80%, 85%, 90%, 95%, or 100% identical to SEQ ID NO: 421. (129) The chimeric polypeptide of any previous embodiment, wherein the targeting polypeptide comprises SEQ ID NO: 421. (130) The chimeric polypeptide of any previous embodiment, wherein the targeting polypeptide comprises a sequence at least about 70%, 75%, 80%, 85%, 90%, 95%, or 100% identical to SEQ ID NO: 422. (131) The chimeric polypeptide of any previous embodiment, wherein the targeting polypeptide comprises SEQ ID NO: 422. (132) The chimeric polypeptide of any previous embodiments, wherein the targeting polypeptide comprises Formula I. (133) The chimeric polypeptide of any previous embodiment, comprising a therapeutic agent. (134) The chimeric polypeptide of embodiment 133, wherein the therapeutic agent comprises a mammalian growth factor. (135) The chimeric polypeptide of embodiment 133 or embodiment 134, wherein the therapeutic agent comprises a bone morphogenetic protein (BMP). (136) The chimeric polypeptide of embodiment 135, wherein the BMP comprises BMP-2. (137) The chimeric polypeptide of embodiment 135, wherein the BMP comprises a sequence at least about 70%, 75%, 80%, 85%, 90%, 95%, or 100% identical to SEQ ID NO: 32. (138) The chimeric polypeptide of embodiment 135, wherein the BMP comprises SEQ ID NO: 32. (139) The chimeric polypeptide of embodiment 133 or embodiment 134, wherein the therapeutic agent comprises a sequence at least about 70%, 75%, 80%, 85%, 90%, 95%, or 100% identical to a sequence set forth in Table B. (140) The chimeric polypeptide of embodiment 133 or embodiment 134, wherein the therapeutic agent comprises two or more therapeutic sequences, each therapeutic sequence at least about 70%, 75%, 80%, 85%, 90%, 95%, or 100% identical to a sequence set forth in Table B. (141) The chimeric polypeptide of embodiment 140, wherein the two or more is 2, 3, 4, or 5 therapeutic sequences. (142) The chimeric polypeptide of embodiment 140, wherein the two or more is from two to about ten. (143) The chimeric polypeptide of any previous embodiment, comprising a linker. (144) The chimeric polypeptide of embodiment 143, wherein the linker comprises GSEG (SEQ ID NO: 702). (145) The chimeric polypeptide of embodiment 143 or embodiment 144, wherein the linker comprises SEGG (SEQ ID NO: 703). (146) The chimeric polypeptide of any one of embodiments 143-145, wherein the linker comprises a sequence at least about 70%, 75%, 80%, 85%, 90%, 95%, 96%, 97%, 98%, or 99% identical to SEQ ID NO: 701, or wherein the linker comprises SEQ ID NO: 701. (147) The chimeric polypeptide of any previous embodiment, comprising a sequence at least about 70%, 75%, 80%, 85%, 90%, 95%, 96%, 97%, 98%, or 99% identical to SEQ ID NO: 501, or wherein the chimeric polypeptide comprises SEQ ID NO: 501. (148) The chimeric polypeptide of any previous embodiment, comprising a sequence at least about 70%, 75%, 80%, 85%, 90%, 95%, 96%, 97%, 98%, or 99% identical to SEQ ID NO: 502, or wherein the chimeric polypeptide comprises SEQ ID NO: 502. (149) The chimeric polypeptide of any previous embodiment, comprising a sequence at least about 70%, 75%, 80%, 85%, 90%, 95%, 96%, 97%, 98%, or 99% identical to SEQ ID NO: 503, or wherein the chimeric polypeptide comprises SEQ ID NO: 503. (150) The chimeric polypeptide of any previous embodiment, comprising a sequence at least about 70%, 75%, 80%, 85%, 90%, 95%, 96%, 97%, 98%, or 99% identical to SEQ ID NO: 504, or wherein the chimeric polypeptide comprises SEQ ID NO: 504. (151) The chimeric polypeptide of any previous embodiment, comprising a sequence at least about 70%, 75%, 80%, 85%, 90%, 95%, 96%, 97%, 98%, or 99% identical to SEQ ID NO: 505, or wherein the chimeric polypeptide comprises SEQ ID NO: 505. (152) The chimeric polypeptide of any previous embodiment, comprising a sequence at least about 70%, 75%, 80%, 85%, 90%, 95%, 96%, 97%, 98%, or 99% identical to SEQ ID NO: 506, or wherein the chimeric polypeptide comprises SEQ ID NO: 506. (153) The chimeric polypeptide of any previous embodiment, comprising a sequence at least about 70%, 75%, 80%, 85%, 90%, 95%, 96%, 97%, 98%, or 99% identical to SEQ ID NO: 507, or wherein the chimeric polypeptide comprises SEQ ID NO: 507. (154) The chimeric polypeptide of any previous embodiment, comprising a sequence at least about 70%, 75%, 80%, 85%, 90%, 95%, 96%, 97%, 98%, or 99% identical to SEQ ID NO: 508 and the sequence comprises X; or wherein the chimeric polypeptide comprises SEQ ID NO: 508. (155) The chimeric polypeptide of any previous embodiment, comprising a sequence at least about 70%, 75%, 80%, 85%, 90%, 95%, 96%, 97%, 98%, or 99% identical to SEQ ID NO: 509 and the sequence comprises X; or wherein the chimeric polypeptide comprises SEQ ID NO: 509. (156) The chimeric polypeptide of any previous embodiment, comprising a sequence at least about 70%, 75%, 80%, 85%, 90%, 95%, 96%, 97%, 98%, or 99% identical to SEQ ID NO: 510 and the sequence comprises X; or wherein the chimeric polypeptide comprises SEQ ID NO: 510. (157) The chimeric polypeptide of any previous embodiment, comprising a sequence at least about 70%, 75%, 80%, 85%, 90%, 95%, 96%, 97%, 98%, or 99% identical to SEQ ID NO: 511 and the sequence comprises X; or wherein the chimeric polypeptide comprises SEQ ID NO: 511. (158) The chimeric polypeptide of any previous embodiment, comprising a sequence at least about 70%, 75%, 80%, 85%, 90%, 95%, 96%, 97%, 98%, or 99% identical to SEQ ID NO: 512 and the sequence comprises X; or wherein the chimeric polypeptide comprises SEQ ID NO: 512. (159) The chimeric polypeptide of any previous embodiment, comprising a sequence at least about 70%, 75%, 80%, 85%, 90%, 95%, 96%, 97%, 98%, or 99% identical to SEQ ID NO: 513 and the sequence comprises X; or wherein the chimeric polypeptide comprises SEQ ID NO: 513. (160) The chimeric polypeptide of any previous embodiment, comprising a sequence at least about 70%, 75%, 80%, 85%, 90%, 95%, 96%, 97%, 98%, or 99% identical to SEQ ID NO: 514 and the sequence comprises X; or wherein the chimeric polypeptide comprises SEQ ID NO: 514. (161) The chimeric polypeptide of any previous embodiment, comprising a sequence at least about 70%, 75%, 80%, 85%, 90%, 95%, 96%, 97%, 98%, or 99% identical to SEQ ID NO: 515 and the sequence comprises X; or wherein the chimeric polypeptide comprises SEQ ID NO: 515. (162) The chimeric polypeptide of any previous embodiment, comprising a sequence at least about 70%, 75%, 80%, 85%, 90%, 95%, 96%, 97%, 98%, or 99% identical to SEQ ID NO: 516 and the sequence comprises X; or wherein the chimeric polypeptide comprises SEQ ID NO: 516. (163) The chimeric polypeptide of any previous embodiment, comprising a sequence at least about 70%, 75%, 80%, 85%, 90%, 95%, 96%, 97%, 98%, or 99% identical to SEQ ID NO: 517 and the sequence comprises X; or wherein the chimeric polypeptide comprises SEQ ID NO: 517. (164) The chimeric polypeptide of any previous embodiment, comprising a sequence at least about 70%, 75%, 80%, 85%, 90%, 95%, 96%, 97%, 98%, or 99% identical to SEQ ID NO: 518 and the sequence comprises X; or wherein the chimeric polypeptide comprises SEQ ID NO: 518. (165) The chimeric polypeptide of any previous embodiment, comprising a sequence at least about 70%, 75%, 80%, 85%, 90%, 95%, 96%, 97%, 98%, or 99% identical to SEQ ID NO: 519 and the sequence comprises X; or wherein the chimeric polypeptide comprises SEQ ID NO: 519. (166) The chimeric polypeptide of any previous embodiment, comprising a sequence at least about 70%, 75%, 80%, 85%, 90%, 95%, 96%, 97%, 98%, or 99% identical to SEQ ID NO: 520 and the sequence comprises X; or wherein the chimeric polypeptide comprises SEQ ID NO: 520. (167) The chimeric polypeptide of any previous embodiment, comprising a sequence at least about 70%, 75%, 80%, 85%, 90%, 95%, 96%, 97%, 98%, or 99% identical to SEQ ID NO: 521 and the sequence comprises X; or wherein the chimeric polypeptide comprises SEQ ID NO: 521. (168) The chimeric polypeptide of any previous embodiment, comprising a sequence at least about 70%, 75%, 80%, 85%, 90%, 95%, 96%, 97%, 98%, or 99% identical to SEQ ID NO: 522 and the sequence comprises X; or wherein the chimeric polypeptide comprises SEQ ID NO: 522. (169) The chimeric polypeptide of any previous embodiment, comprising a sequence at least about 70%, 75%, 80%, 85%, 90%, 95%, 96%, 97%, 98%, or 99% identical to SEQ ID NO: 523 and the sequence comprises X; or wherein the chimeric polypeptide comprises SEQ ID NO: 523. (170) The chimeric polypeptide of any previous embodiment, comprising a sequence at least about 70%, 75%, 80%, 85%, 90%, 95%, 96%, 97%, 98%, or 99% identical to SEQ ID NO: 524 and the sequence comprises X; or wherein the chimeric polypeptide comprises SEQ ID NO: 524. (171) The chimeric polypeptide of any previous embodiment, comprising a sequence at least about 70%, 75%, 80%, 85%, 90%, 95%, 96%, 97%, 98%, or 99% identical to SEQ ID NO: 525 and the sequence comprises X; or wherein the chimeric polypeptide comprises SEQ ID NO: 525. (172) The chimeric polypeptide of any previous embodiment, comprising a sequence at least about 70%, 75%, 80%, 85%, 90%, 95%, 96%, 97%, 98%, or 99% identical to SEQ ID NO: 526 and the sequence comprises X; or wherein the chimeric polypeptide comprises SEQ ID NO: 526. (173) The chimeric polypeptide of any previous embodiment, comprising a sequence at least about 70%, 75%, 80%, 85%, 90%, 95%, 96%, 97%, 98%, or 99% identical to SEQ ID NO: 527 and the sequence comprises X; or wherein the chimeric polypeptide comprises SEQ ID NO: 527. (174) The chimeric polypeptide of any previous embodiment, comprising a sequence at least about 70%, 75%, 80%, 85%, 90%, 95%, 96%, 97%, 98%, or 99% identical to SEQ ID NO: 528 and the sequence comprises X; or wherein the chimeric polypeptide comprises SEQ ID NO: 528. (175) The chimeric polypeptide of any previous embodiment, comprising a sequence at least about 70%, 75%, 80%, 85%, 90%, 95%, 96%, 97%, 98%, or 99% identical to SEQ ID NO: 529 and the sequence comprises X; or wherein the chimeric polypeptide comprises SEQ ID NO: 529. (176) The chimeric polypeptide of any previous embodiment, comprising a sequence at least about 70%, 75%, 80%, 85%, 90%, 95%, 96%, 97%, 98%, or 99% identical to SEQ ID NO: 530 and the sequence comprises X; or wherein the chimeric polypeptide comprises SEQ ID NO: 530. (177) The chimeric polypeptide of any previous embodiment, comprising a sequence at least about 70%, 75%, 80%, 85%, 90%, 95%, 96%, 97%, 98%, or 99% identical to SEQ ID NO: 531 and the sequence comprises X; or wherein the chimeric polypeptide comprises SEQ ID NO: 531. (178) The chimeric polypeptide of any previous embodiment, comprising a sequence at least about 70%, 75%, 80%, 85%, 90%, 95%, 96%, 97%, 98%, or 99% identical to SEQ ID NO: 532 and the sequence comprises X; or wherein the chimeric polypeptide comprises SEQ ID NO: 532. (179) The chimeric polypeptide of any previous embodiment, comprising a sequence at least about 70%, 75%, 80%, 85%, 90%, 95%, 96%, 97%, 98%, or 99% identical to SEQ ID NO: 533 and the sequence comprises X; or wherein the chimeric polypeptide comprises SEQ ID NO: 533. (180) The chimeric polypeptide of any previous embodiment, comprising a sequence at least about 70%, 75%, 80%, 85%, 90%, 95%, 96%, 97%, 98%, or 99% identical to SEQ ID NO: 534 and the sequence comprises X; or wherein the chimeric polypeptide comprises SEQ ID NO: 534. (181) The chimeric polypeptide of any previous embodiment, comprising a sequence at least about 70%, 75%, 80%, 85%, 90%, 95%, 96%, 97%, 98%, or 99% identical to SEQ ID NO: 535 and the sequence comprises X; or wherein the chimeric polypeptide comprises SEQ ID NO: 535. (182) The chimeric polypeptide of any previous embodiment, comprising a sequence at least about 70%, 75%, 80%, 85%, 90%, 95%, 96%, 97%, 98%, or 99% identical to SEQ ID NO: 536 and the sequence comprises X; or wherein the chimeric polypeptide comprises SEQ ID NO: 536. (183) The chimeric polypeptide of any previous embodiment, comprising a sequence at least about 70%, 75%, 80%, 85%, 90%, 95%, 96%, 97%, 98%, or 99% identical to SEQ ID NO: 537 and the sequence comprises X; or wherein the chimeric polypeptide comprises SEQ ID NO: 537. (184) The chimeric polypeptide of any previous embodiment, comprising a sequence at least about 70%, 75%, 80%, 85%, 90%, 95%, 96%, 97%, 98%, or 99% identical to SEQ ID NO: 538 and the sequence comprises X; or wherein the chimeric polypeptide comprises SEQ ID NO: 538. (185) The chimeric polypeptide of any previous embodiment, comprising a sequence at least about 70%, 75%, 80%, 85%, 90%, 95%, 96%, 97%, 98%, or 99% identical to SEQ ID NO: 539 and the sequence comprises X; or wherein the chimeric polypeptide comprises SEQ ID NO: 539. (186) The chimeric polypeptide of any previous embodiment, comprising a sequence at least about 70%, 75%, 80%, 85%, 90%, 95%, 96%, 97%, 98%, or 99% identical to SEQ ID NO: 540 and the sequence comprises X; or wherein the chimeric polypeptide comprises SEQ ID NO: 540. (187) The chimeric polypeptide of any previous embodiment, comprising a sequence at least about 70%, 75%, 80%, 85%, 90%, 95%, 96%, 97%, 98%, or 99% identical to SEQ ID NO: 541 and the sequence comprises X; or wherein the chimeric polypeptide comprises SEQ ID NO: 541. (188) The chimeric polypeptide of any previous embodiment, comprising a sequence at least about 70%, 75%, 80%, 85%, 90%, 95%, 96%, 97%, 98%, or 99% identical to SEQ ID NO: 542 and the sequence comprises X; or wherein the chimeric polypeptide comprises SEQ ID NO: 542. (189) The chimeric polypeptide of any previous embodiment, comprising a sequence at least about 70%, 75%, 80%, 85%, 90%, 95%, 96%, 97%, 98%, or 99% identical to SEQ ID NO: 543 and the sequence comprises X; or wherein the chimeric polypeptide comprises SEQ ID NO: 543. (190) The chimeric polypeptide of any previous embodiment, comprising a sequence at least about 70%, 75%, 80%, 85%, 90%, 95%, 96%, 97%, 98%, or 99% identical to SEQ ID NO: 544 and the sequence comprises X; or wherein the chimeric polypeptide comprises SEQ ID NO: 544. (191) The chimeric polypeptide of any previous embodiment, comprising a sequence at least about 70%, 75%, 80%, 85%, 90%, 95%, 96%, 97%, 98%, or 99% identical to SEQ ID NO: 545 and the sequence comprises X; or wherein the chimeric polypeptide comprises SEQ ID NO: 545. (192) The chimeric polypeptide of any previous embodiment, comprising a sequence at least about 70%, 75%, 80%, 85%, 90%, 95%, 96%, 97%, 98%, or 99% identical to SEQ ID NO: 546 and the sequence comprises X; or wherein the chimeric polypeptide comprises SEQ ID NO: 546. (193) The chimeric polypeptide of any previous embodiment, comprising a sequence at least about 70%, 75%, 80%, 85%, 90%, 95%, 96%, 97%, 98%, or 99% identical to SEQ ID NO: 547 and the sequence comprises X; or wherein the chimeric polypeptide comprises SEQ ID NO: 547. (194) The chimeric polypeptide of any previous embodiment, comprising a sequence at least about 70%, 75%, 80%, 85%, 90%, 95%, 96%, 97%, 98%, or 99% identical to SEQ ID NO: 548 and the sequence comprises X; or wherein the chimeric polypeptide comprises SEQ ID NO: 548. (195) The chimeric polypeptide of any previous embodiment, comprising a sequence at least about 70%, 75%, 80%, 85%, 90%, 95%, 96%, 97%, 98%, or 99% identical to SEQ ID NO: 549 and the sequence comprises X; or wherein the chimeric polypeptide comprises SEQ ID NO: 549. (196) The chimeric polypeptide of any previous embodiment, comprising a sequence at least about 70%, 75%, 80%, 85%, 90%, 95%, 96%, 97%, 98%, or 99% identical to SEQ ID NO: 550 and the sequence comprises X; or wherein the chimeric polypeptide comprises SEQ ID NO: 550. (197) The chimeric polypeptide of any previous embodiment, comprising a sequence at least about 70%, 75%, 80%, 85%, 90%, 95%, 96%, 97%, 98%, or 99% identical to SEQ ID NO: 551 and the sequence comprises X; or wherein the chimeric polypeptide comprises SEQ ID NO: 551. (198) The chimeric polypeptide of any previous embodiment, comprising a sequence at least about 70%, 75%, 80%, 85%, 90%, 95%, 96%, 97%, 98%, or 99% identical to SEQ ID NO: 552 and the sequence comprises X; or wherein the chimeric polypeptide comprises SEQ ID NO: 552. (199) The chimeric polypeptide of any previous embodiment, comprising a sequence at least about 70%, 75%, 80%, 85%, 90%, 95%, 96%, 97%, 98%, or 99% identical to SEQ ID NO: 553 and the sequence comprises X; or wherein the chimeric polypeptide comprises SEQ ID NO: 553. (200) The chimeric polypeptide of any previous embodiment, comprising a sequence at least about 70%, 75%, 80%, 85%, 90%, 95%, 96%, 97%, 98%, or 99% identical to SEQ ID NO: 554 and the sequence comprises X; or wherein the chimeric polypeptide comprises SEQ ID NO: 554. (201) The chimeric polypeptide of any previous embodiment, comprising a sequence at least about 70%, 75%, 80%, 85%, 90%, 95%, 96%, 97%, 98%, or 99% identical to SEQ ID NO: 555 and the sequence comprises X; or wherein the chimeric polypeptide comprises SEQ ID NO: 555. (202) The chimeric polypeptide of any previous embodiment, comprising a sequence at least about 70%, 75%, 80%, 85%, 90%, 95%, 96%, 97%, 98%, or 99% identical to SEQ ID NO: 556 and the sequence comprises X; or wherein the chimeric polypeptide comprises SEQ ID NO: 556. (203) The chimeric polypeptide of any previous embodiment, comprising a sequence at least about 70%, 75%, 80%, 85%, 90%, 95%, 96%, 97%, 98%, or 99% identical to SEQ ID NO: 557 and the sequence comprises X; or wherein the chimeric polypeptide comprises SEQ ID NO: 557. (204) The chimeric polypeptide of any previous embodiment, comprising a sequence at least about 70%, 75%, 80%, 85%, 90%, 95%, 96%, 97%, 98%, or 99% identical to SEQ ID NO: 558 and the sequence comprises X; or wherein the chimeric polypeptide comprises SEQ ID NO: 558. (205) The chimeric polypeptide of any previous embodiment, comprising a sequence at least about 70%, 75%, 80%, 85%, 90%, 95%, 96%, 97%, 98%, or 99% identical to SEQ ID NO: 559 and the sequence comprises X; or wherein the chimeric polypeptide comprises SEQ ID NO: 559. (206) The chimeric polypeptide of any previous embodiment, comprising a sequence at least about 70%, 75%, 80%, 85%, 90%, 95%, 96%, 97%, 98%, or 99% identical to SEQ ID NO: 560 and the sequence comprises X; or wherein the chimeric polypeptide comprises SEQ ID NO: 560. (207) The chimeric polypeptide of any previous embodiment, comprising a sequence at least about 70%, 75%, 80%, 85%, 90%, 95%, 96%, 97%, 98%, or 99% identical to SEQ ID NO: 561 and the sequence comprises X; or wherein the chimeric polypeptide comprises SEQ ID NO: 561. (208) The chimeric polypeptide of any previous embodiment, comprising a sequence at least about 70%, 75%, 80%, 85%, 90%, 95%, 96%, 97%, 98%, or 99% identical to SEQ ID NO: 562 and the sequence comprises X; or wherein the chimeric polypeptide comprises SEQ ID NO: 562. (209) The chimeric polypeptide of any previous embodiment, comprising a sequence at least about 70%, 75%, 80%, 85%, 90%, 95%, 96%, 97%, 98%, or 99% identical to SEQ ID NO: 563 and the sequence comprises X; or wherein the chimeric polypeptide comprises SEQ ID NO: 563. (210) The chimeric polypeptide of any previous embodiment, comprising a sequence at least about 70%, 75%, 80%, 85%, 90%, 95%, 96%, 97%, 98%, or 99% identical to SEQ ID NO: 564 and the sequence comprises X; or wherein the chimeric polypeptide comprises SEQ ID NO: 564. (211) The chimeric polypeptide of any previous embodiment, comprising a sequence at least about 70%, 75%, 80%, 85%, 90%, 95%, 96%, 97%, 98%, or 99% identical to SEQ ID NO: 565 and the sequence comprises X; or wherein the chimeric polypeptide comprises SEQ ID NO: 565. (212) The chimeric polypeptide of any previous embodiment, comprising a sequence at least about 70%, 75%, 80%, 85%, 90%, 95%, 96%, 97%, 98%, or 99% identical to SEQ ID NO: 566 and the sequence comprises X; or wherein the chimeric polypeptide comprises SEQ ID NO: 566. (213) The chimeric polypeptide of any previous embodiment, comprising a sequence at least about 70%, 75%, 80%, 85%, 90%, 95%, 96%, 97%, 98%, or 99% identical to SEQ ID NO: 567 and the sequence comprises X; or wherein the chimeric polypeptide comprises SEQ ID NO: 567. (214) The chimeric polypeptide of any previous embodiment, comprising a sequence at least about 70%, 75%, 80%, 85%, 90%, 95%, 96%, 97%, 98%, or 99% identical to SEQ ID NO: 568 and the sequence comprises X; or wherein the chimeric polypeptide comprises SEQ ID NO: 568. (215) The chimeric polypeptide of any previous embodiment, comprising a sequence at least about 70%, 75%, 80%, 85%, 90%, 95%, 96%, 97%, 98%, or 99% identical to SEQ ID NO: 569 and the sequence comprises X; or wherein the chimeric polypeptide comprises SEQ ID NO: 569. (216) The chimeric polypeptide of any previous embodiment, comprising a sequence at least about 70%, 75%, 80%, 85%, 90%, 95%, 96%, 97%, 98%, or 99% identical to SEQ ID NO: 570 and the sequence comprises X; or wherein the chimeric polypeptide comprises SEQ ID NO: 570. (217) The chimeric polypeptide of any previous embodiment, comprising a sequence at least about 70%, 75%, 80%, 85%, 90%, 95%, 96%, 97%, 98%, or 99% identical to SEQ ID NO: 571 and the sequence comprises X; or wherein the chimeric polypeptide comprises SEQ ID NO: 571. (218) The chimeric polypeptide of any previous embodiment, comprising a sequence at least about 70%, 75%, 80%, 85%, 90%, 95%, 96%, 97%, 98%, or 99% identical to SEQ ID NO: 572 and the sequence comprises X; or wherein the chimeric polypeptide comprises SEQ ID NO: 572. (219) The chimeric polypeptide of any previous embodiment, comprising a sequence at least about 70%, 75%, 80%, 85%, 90%, 95%, 96%, 97%, 98%, or 99% identical to SEQ ID NO: 573 and the sequence comprises X; or wherein the chimeric polypeptide comprises SEQ ID NO: 573. (220) The chimeric polypeptide of any previous embodiment, comprising a sequence at least about 70%, 75%, 80%, 85%, 90%, 95%, 96%, 97%, 98%, or 99% identical to SEQ ID NO: 574 and the sequence comprises X; or wherein the chimeric polypeptide comprises SEQ ID NO: 574. (221) The chimeric polypeptide of any previous embodiment, comprising a sequence at least about 70%, 75%, 80%, 85%, 90%, 95%, 96%, 97%, 98%, or 99% identical to SEQ ID NO: 575 and the sequence comprises X; or wherein the chimeric polypeptide comprises SEQ ID NO: 575. (222) The chimeric polypeptide of any previous embodiment, comprising a sequence at least about 70%, 75%, 80%, 85%, 90%, 95%, 96%, 97%, 98%, or 99% identical to SEQ ID NO: 576 and the sequence comprises X; or wherein the chimeric polypeptide comprises SEQ ID NO: 577. (223) The chimeric polypeptide of any previous embodiment, comprising a sequence at least about 70%, 75%, 80%, 85%, 90%, 95%, 96%, 97%, 98%, or 99% identical to SEQ ID NO: 578 and the sequence comprises X; or wherein the chimeric polypeptide comprises SEQ ID NO: 579. (224) The chimeric polypeptide of any previous embodiment, comprising a sequence at least about 70%, 75%, 80%, 85%, 90%, 95%, 96%, 97%, 98%, or 99% identical to SEQ ID NO: 580 and the sequence comprises X; or wherein the chimeric polypeptide comprises SEQ ID NO: 580. (225) The chimeric polypeptide of any previous embodiment, comprising a sequence at least about 70%, 75%, 80%, 85%, 90%, 95%, 96%, 97%, 98%, or 99% identical to SEQ ID NO: 581 and the sequence comprises X; or wherein the chimeric polypeptide comprises SEQ ID NO: 581. (226) The chimeric polypeptide of any previous embodiment, comprising a sequence at least about 70%, 75%, 80%, 85%, 90%, 95%, 96%, 97%, 98%, or 99% identical to SEQ ID NO: 582 and the sequence comprises X; or wherein the chimeric polypeptide comprises SEQ ID NO: 582. (227) The chimeric polypeptide of any previous embodiment, comprising a sequence at least about 70%, 75%, 80%, 85%, 90%, 95%, 96%, 97%, 98%, or 99% identical to SEQ ID NO: 583 and the sequence comprises X; or wherein the chimeric polypeptide comprises SEQ ID NO: 583. (228) The chimeric polypeptide of any previous embodiment, comprising a sequence at least about 70%, 75%, 80%, 85%, 90%, 95%, 96%, 97%, 98%, or 99% identical to SEQ ID NO: 584 and the sequence comprises X; or wherein the chimeric polypeptide comprises SEQ ID NO: 584. (229) The chimeric polypeptide of any previous embodiment, comprising a sequence at least about 70%, 75%, 80%, 85%, 90%, 95%, 96%, 97%, 98%, or 99% identical to SEQ ID NO: 585 and the sequence comprises X; or wherein the chimeric polypeptide comprises SEQ ID NO: 585. (230) The chimeric polypeptide of any previous embodiment, comprising a sequence at least about 70%, 75%, 80%, 85%, 90%, 95%, 96%, 97%, 98%, or 99% identical to SEQ ID NO: 586 and the sequence comprises X; or wherein the chimeric polypeptide comprises SEQ ID NO: 586. (231) The chimeric polypeptide of any previous embodiment, comprising a sequence at least about 70%, 75%, 80%, 85%, 90%, 95%, 96%, 97%, 98%, or 99% identical to SEQ ID NO: 587 and the sequence comprises X; or wherein the chimeric polypeptide comprises SEQ ID NO: 587. (232) The chimeric polypeptide of any previous embodiment, comprising a sequence at least about 70%, 75%, 80%, 85%, 90%, 95%, 96%, 97%, 98%, or 99% identical to SEQ ID NO: 588 and the sequence comprises X; or wherein the chimeric polypeptide comprises SEQ ID NO: 588. (233) The chimeric polypeptide of any previous embodiment, comprising a sequence at least about 70%, 75%, 80%, 85%, 90%, 95%, 96%, 97%, 98%, or 99% identical to SEQ ID NO: 589 and the sequence comprises X; or wherein the chimeric polypeptide comprises SEQ ID NO: 589. (234) The chimeric polypeptide of any previous embodiment, comprising a sequence at least about 70%, 75%, 80%, 85%, 90%, 95%, 96%, 97%, 98%, or 99% identical to SEQ ID NO: 590 and the sequence comprises X; or wherein the chimeric polypeptide comprises SEQ ID NO: 590. (235) The chimeric polypeptide of any previous embodiment, comprising a sequence at least about 70%, 75%, 80%, 85%, 90%, 95%, 96%, 97%, 98%, or 99% identical to SEQ ID NO: 591 and the sequence comprises X; or wherein the chimeric polypeptide comprises SEQ ID NO: 591. (236) The chimeric polypeptide of any previous embodiment, comprising a sequence at least about 70%, 75%, 80%, 85%, 90%, 95%, 96%, 97%, 98%, or 99% identical to SEQ ID NO: 592 and the sequence comprises X; or wherein the chimeric polypeptide comprises SEQ ID NO: 592. (237) The chimeric polypeptide of any previous embodiment, comprising a sequence at least about 70%, 75%, 80%, 85%, 90%, 95%, 96%, 97%, 98%, or 99% identical to SEQ ID NO: 593 and the sequence comprises X; or wherein the chimeric polypeptide comprises SEQ ID NO: 593. (238) The chimeric polypeptide of any previous embodiment, comprising a sequence at least about 70%, 75%, 80%, 85%, 90%, 95%, 96%, 97%, 98%, or 99% identical to SEQ ID NO: 594 and the sequence comprises X; or wherein the chimeric polypeptide comprises SEQ ID NO: 594. (239) The chimeric polypeptide of any previous embodiment, comprising a sequence at least about 70%, 75%, 80%, 85%, 90%, 95%, 96%, 97%, 98%, or 99% identical to SEQ ID NO: 595 and the sequence comprises X; or wherein the chimeric polypeptide comprises SEQ ID NO: 595. (240) The chimeric polypeptide of any previous embodiment, comprising a sequence at least about 70%, 75%, 80%, 85%, 90%, 95%, 96%, 97%, 98%, or 99% identical to SEQ ID NO: 596 and the sequence comprises X; or wherein the chimeric polypeptide comprises SEQ ID NO: 596. (241) The chimeric polypeptide of any previous embodiment, comprising a sequence at least about 70%, 75%, 80%, 85%, 90%, 95%, 96%, 97%, 98%, or 99% identical to SEQ ID NO: 597 and the sequence comprises X; or wherein the chimeric polypeptide comprises SEQ ID NO: 597. (242) The chimeric polypeptide of any previous embodiment, comprising a sequence at least about 70%, 75%, 80%, 85%, 90%, 95%, 96%, 97%, 98%, or 99% identical to SEQ ID NO: 598 and the sequence comprises X; or wherein the chimeric polypeptide comprises SEQ ID NO: 598. (243) The chimeric polypeptide of any previous embodiment, comprising a sequence at least about 70%, 75%, 80%, 85%, 90%, 95%, 96%, 97%, 98%, or 99% identical to SEQ ID NO: 599 and the sequence comprises X; or wherein the chimeric polypeptide comprises SEQ ID NO: 599. (244) The chimeric polypeptide of any previous embodiment, comprising a sequence at least about 70%, 75%, 80%, 85%, 90%, 95%, 96%, 97%, 98%, or 99% identical to SEQ ID NO: 600 and the sequence comprises X; or wherein the chimeric polypeptide comprises SEQ ID NO: 600. (245) The chimeric polypeptide of any previous embodiment, comprising a sequence at least about 70%, 75%, 80%, 85%, 90%, 95%, 96%, 97%, 98%, or 99% identical to SEQ ID NO: 601 and the sequence comprises X; or wherein the chimeric polypeptide comprises SEQ ID NO: 601. (246) The chimeric polypeptide of any previous embodiment, comprising a sequence at least about 70%, 75%, 80%, 85%, 90%, 95%, 96%, 97%, 98%, or 99% identical to SEQ ID NO: 602 and the sequence comprises X; or wherein the chimeric polypeptide comprises SEQ ID NO: 602. (247) The chimeric polypeptide of any previous embodiment, comprising a sequence at least about 70%, 75%, 80%, 85%, 90%, 95%, 96%, 97%, 98%, or 99% identical to SEQ ID NO: 603 and the sequence comprises X; or wherein the chimeric polypeptide comprises SEQ ID NO: 603. (248) The chimeric polypeptide of any previous embodiment, comprising a sequence at least about 70%, 75%, 80%, 85%, 90%, 95%, 96%, 97%, 98%, or 99% identical to SEQ ID NO: 604 and the sequence comprises X; or wherein the chimeric polypeptide comprises SEQ ID NO: 604. (249) The chimeric polypeptide of any previous embodiment, comprising a sequence at least about 70%, 75%, 80%, 85%, 90%, 95%, 96%, 97%, 98%, or 99% identical to SEQ ID NO: 605 and the sequence comprises X; or wherein the chimeric polypeptide comprises SEQ ID NO: 605. (250) The chimeric polypeptide of any previous embodiment, comprising a sequence at least about 70%, 75%, 80%, 85%, 90%, 95%, 96%, 97%, 98%, or 99% identical to SEQ ID NO: 606 and the sequence comprises X; or wherein the chimeric polypeptide comprises SEQ ID NO: 606. (251) The chimeric polypeptide of any previous embodiment, comprising a sequence at least about 70%, 75%, 80%, 85%, 90%, 95%, 96%, 97%, 98%, or 99% identical to SEQ ID NO: 607 and the sequence comprises X; or wherein the chimeric polypeptide comprises SEQ ID NO: 607. (252) The chimeric polypeptide of any previous embodiment, comprising a sequence at least about 70%, 75%, 80%, 85%, 90%, 95%, 96%, 97%, 98%, or 99% identical to SEQ ID NO: 608 and the sequence comprises X; or wherein the chimeric polypeptide comprises SEQ ID NO: 608. (253) The chimeric polypeptide of any previous embodiment, comprising a sequence at least about 70%, 75%, 80%, 85%, 90%, 95%, 96%, 97%, 98%, or 99% identical to SEQ ID NO: 609 and the sequence comprises X; or wherein the chimeric polypeptide comprises SEQ ID NO: 609. (254) The chimeric polypeptide of any previous embodiment, comprising a sequence at least about 70%, 75%, 80%, 85%, 90%, 95%, 96%, 97%, 98%, or 99% identical to SEQ ID NO: 610 and the sequence comprises X; or wherein the chimeric polypeptide comprises SEQ ID NO: 610. (255) The chimeric polypeptide of any previous embodiment, comprising a sequence at least about 70%, 75%, 80%, 85%, 90%, 95%, 96%, 97%, 98%, or 99% identical to SEQ ID NO: 611 and the sequence comprises X; or wherein the chimeric polypeptide comprises SEQ ID NO: 611. (256) The chimeric polypeptide of any previous embodiment, comprising a sequence at least about 70%, 75%, 80%, 85%, 90%, 95%, 96%, 97%, 98%, or 99% identical to SEQ ID NO: 612 and the sequence comprises X; or wherein the chimeric polypeptide comprises SEQ ID NO: 612. (257) The chimeric polypeptide of any previous embodiment, comprising a sequence at least about 70%, 75%, 80%, 85%, 90%, 95%, 96%, 97%, 98%, or 99% identical to SEQ ID NO: 613 and the sequence comprises X; or wherein the chimeric polypeptide comprises SEQ ID NO: 613. (258) The chimeric polypeptide of any previous embodiment, comprising a sequence at least about 70%, 75%, 80%, 85%, 90%, 95%, 96%, 97%, 98%, or 99% identical to SEQ ID NO: 614 and the sequence comprises X; or wherein the chimeric polypeptide comprises SEQ ID NO: 614. (259) The chimeric polypeptide of any previous embodiment, comprising a sequence at least about 70%, 75%, 80%, 85%, 90%, 95%, 96%, 97%, 98%, or 99% identical to SEQ ID NO: 615 and the sequence comprises X; or wherein the chimeric polypeptide comprises SEQ ID NO: 615. (260) The chimeric polypeptide of any previous embodiment, comprising a sequence at least about 70%, 75%, 80%, 85%, 90%, 95%, 96%, 97%, 98%, or 99% identical to SEQ ID NO: 616 and the sequence comprises X; or wherein the chimeric polypeptide comprises SEQ ID NO: 616. (261) The chimeric polypeptide of any previous embodiment, comprising a sequence at least about 70%, 75%, 80%, 85%, 90%, 95%, 96%, 97%, 98%, or 99% identical to SEQ ID NO: 617 and the sequence comprises X; or wherein the chimeric polypeptide comprises SEQ ID NO: 617. (262) The chimeric polypeptide of any previous embodiment, comprising a sequence at least about 70%, 75%, 80%, 85%, 90%, 95%, 96%, 97%, 98%, or 99% identical to SEQ ID NO: 618 and the sequence comprises X; or wherein the chimeric polypeptide comprises SEQ ID NO: 618. (263) The chimeric polypeptide of any previous embodiment, comprising a sequence at least about 70%, 75%, 80%, 85%, 90%, 95%, 96%, 97%, 98%, or 99% identical to SEQ ID NO: 619 and the sequence comprises X; or wherein the chimeric polypeptide comprises SEQ ID NO: 619. (264) The chimeric polypeptide of any previous embodiment, comprising a sequence at least about 70%, 75%, 80%, 85%, 90%, 95%, 96%, 97%, 98%, or 99% identical to SEQ ID NO: 620 and the sequence comprises X; or wherein the chimeric polypeptide comprises SEQ ID NO: 620. (265) The chimeric polypeptide of any previous embodiment, comprising a sequence at least about 70%, 75%, 80%, 85%, 90%, 95%, 96%, 97%, 98%, or 99% identical to SEQ ID NO: 621 and the sequence comprises X; or wherein the chimeric polypeptide comprises SEQ ID NO: 621. (266) The chimeric polypeptide of any previous embodiment, comprising a sequence at least about 70%, 75%, 80%, 85%, 90%, 95%, 96%, 97%, 98%, or 99% identical to SEQ ID NO: 622 and the sequence comprises X; or wherein the chimeric polypeptide comprises SEQ ID NO: 622. (267) The chimeric polypeptide of any previous embodiment, comprising a sequence at least about 70%, 75%, 80%, 85%, 90%, 95%, 96%, 97%, 98%, or 99% identical to SEQ ID NO: 623 and the sequence comprises X; or wherein the chimeric polypeptide comprises SEQ ID NO: 623. (268) The chimeric polypeptide of any previous embodiment, comprising a sequence at least about 70%, 75%, 80%, 85%, 90%, 95%, 96%, 97%, 98%, or 99% identical to SEQ ID NO: 624 and the sequence comprises X; or wherein the chimeric polypeptide comprises SEQ ID NO: 624. (269) The chimeric polypeptide of any previous embodiment, comprising a sequence at least about 70%, 75%, 80%, 85%, 90%, 95%, 96%, 97%, 98%, or 99% identical to SEQ ID NO: 625 and the sequence comprises X; or wherein the chimeric polypeptide comprises SEQ ID NO: 625. (270) The chimeric polypeptide of any previous embodiment, comprising a sequence at least about 70%, 75%, 80%, 85%, 90%, 95%, 96%, 97%, 98%, or 99% identical to SEQ ID NO: 626 and the sequence comprises X; or wherein the chimeric polypeptide comprises SEQ ID NO: 626. (271) The chimeric polypeptide of any previous embodiment, comprising a sequence at least about 70%, 75%, 80%, 85%, 90%, 95%, 96%, 97%, 98%, or 99% identical to SEQ ID NO: 627 and the sequence comprises X; or wherein the chimeric polypeptide comprises SEQ ID NO: 627. (272) The chimeric polypeptide of any previous embodiment, comprising a sequence at least about 70%, 75%, 80%, 85%, 90%, 95%, 96%, 97%, 98%, or 99% identical to SEQ ID NO: 628 and the sequence comprises X; or wherein the chimeric polypeptide comprises SEQ ID NO: 628. (273) The chimeric polypeptide of any previous embodiment, comprising a sequence at least about 70%, 75%, 80%, 85%, 90%, 95%, 96%, 97%, 98%, or 99% identical to SEQ ID NO: 629 and the sequence comprises X; or wherein the chimeric polypeptide comprises SEQ ID NO: 629. (274) The chimeric polypeptide of any previous embodiment, comprising a sequence at least about 70%, 75%, 80%, 85%, 90%, 95%, 96%, 97%, 98%, or 99% identical to SEQ ID NO: 630 and the sequence comprises X; or wherein the chimeric polypeptide comprises SEQ ID NO: 630. (275) The chimeric polypeptide of any previous embodiment, comprising a sequence at least about 70%, 75%, 80%, 85%, 90%, 95%, 96%, 97%, 98%, or 99% identical to SEQ ID NO: 631 and the sequence comprises X; or wherein the chimeric polypeptide comprises SEQ ID NO: 631. (276) The chimeric polypeptide of any previous embodiment, comprising a sequence at least about 70%, 75%, 80%, 85%, 90%, 95%, 96%, 97%, 98%, or 99% identical to SEQ ID NO: 632 and the sequence comprises X; or wherein the chimeric polypeptide comprises SEQ ID NO: 632. (277) The chimeric polypeptide of any previous embodiment, comprising a sequence at least about 70%, 75%, 80%, 85%, 90%, 95%, 96%, 97%, 98%, or 99% identical to SEQ ID NO: 633 and the sequence comprises X; or wherein the chimeric polypeptide comprises SEQ ID NO: 633. (278) The chimeric polypeptide of any previous embodiment, comprising a sequence at least about 70%, 75%, 80%, 85%, 90%, 95%, 96%, 97%, 98%, or 99% identical to SEQ ID NO: 634 and the sequence comprises X; or wherein the chimeric polypeptide comprises SEQ ID NO: 634. (279) The chimeric polypeptide of any previous embodiment, comprising a sequence at least about 70%, 75%, 80%, 85%, 90%, 95%, 96%, 97%, 98%, or 99% identical to SEQ ID NO: 635 and the sequence comprises X; or wherein the chimeric polypeptide comprises SEQ ID NO: 635. (280) The chimeric polypeptide of any previous embodiment, comprising a sequence at least about 70%, 75%, 80%, 85%, 90%, 95%, 96%, 97%, 98%, or 99% identical to SEQ ID NO: 636 and the sequence comprises X; or wherein the chimeric polypeptide comprises SEQ ID NO: 636. (281) The chimeric polypeptide of any previous embodiment, comprising a sequence at least about 70%, 75%, 80%, 85%, 90%, 95%, 96%, 97%, 98%, or 99% identical to SEQ ID NO: 637 and the sequence comprises X; or wherein the chimeric polypeptide comprises SEQ ID NO: 637. (282) The chimeric polypeptide of any previous embodiment, comprising a sequence at least about 70%, 75%, 80%, 85%, 90%, 95%, 96%, 97%, 98%, or 99% identical to SEQ ID NO: 638 and the sequence comprises X; or wherein the chimeric polypeptide comprises SEQ ID NO: 638. (283) A composition comprising the chimeric polypeptide of any previous embodiment. (284) The composition of embodiment 283, further comprising a carrier material. (285) The composition of embodiment 284, wherein the targeting polypeptide binds to the carrier material. (286) The composition of embodiment 284 or embodiment 285, wherein the carrier material comprises calcium phosphate. (287) The composition of embodiment 286, wherein the calcium phosphate comprises tri-calcium phosphate. (288) The composition of embodiment 287, wherein the tri-calcium phosphate comprises β-tricalcium phosphate. (289) The composition of any one of embodiments 284-288, wherein the carrier material comprises hydroxyapatite. (290) The composition of any one of embodiments 284-289, wherein the carrier material comprises alpha tricalcium phosphate, fluorapatite, bone (e.g., demineralized bone), glasses (bioglasses) such as silicates, vanadates, and related ceramic minerals, or chelated divalent metal ions, or any combination thereof (291) The composition of any one of embodiments 284-290, wherein the carrier material comprises a fiber, powder, putty, paste, mesh, sponge, or scaffold, or a combination thereof. (292) A method of treating a subject in need thereof, the method comprising delivering to the subject the chimeric polypeptide of any one of embodiments 1-282. (293) A method of treating a subject in need thereof, the method comprising delivering to the subject the composition of any one of embodiments 283-291. (294) The method of embodiment 292 or embodiment 293, wherein the chimeric polypeptide is used to treat a bone defect in the subject. (295) The method of embodiment 292 or embodiment 293, wherein the chimeric polypeptide is used to treat a cartilage defect in the subject. (296) The method of embodiment 292 or embodiment 293, wherein the chimeric polypeptide is used to treat a soft tissue defect in the subject. (297) The method of embodiment 292 or embodiment 293, wherein the chimeric polypeptide is used to treat a tendon defect in the subject. (298) The method of embodiment 292 or embodiment 293, wherein the chimeric polypeptide is used to treat a fascia defect in the subject. (299) The method of embodiment 292 or embodiment 293, wherein the chimeric polypeptide is used to treat a ligament defect in the subject. (300) The method of embodiment 292 or embodiment 293, wherein the chimeric polypeptide is used to treat an organ defect in the subject. (301) The method of embodiment 292 or embodiment 293, wherein the chimeric polypeptide is used to treat a osteotendinous tissue defect in the subject. (302) The method of embodiment 292 or embodiment 293, wherein the chimeric polypeptide is used to treat a dermal defect in the subject. (303) The method of embodiment 292 or embodiment 293, wherein the chimeric polypeptide is used to treat a osteochondral defect in the subject. (304) The method of embodiment 292 or embodiment 293, wherein the method is performed for spinal fusion in the subject. (305) The method of embodiment 304, wherein the spinal fusion comprises posterior lumbar fusion (PLF). (306) The method of embodiment 304, wherein the spinal fusion comprises interbody fusion. (307) The method of embodiment 292 or embodiment 293, wherein the method is performed for trauma repair of bone. (308) The method of embodiment 292 or embodiment 293, wherein the method is performed for dental repair. (309) The method of embodiment 292 or embodiment 293, wherein the method is performed for craniomaxillofacial repair. (310) The method of embodiment 292 or embodiment 293, wherein the method is performed for ankle fusion. (311) The method of embodiment 292 or embodiment 293, wherein the method is performed for kyphoplasty. (312) The method of embodiment 292 or embodiment 293, wherein the method is performed for balloon osteoplasty. (313) The method of embodiment 292 or embodiment 293, wherein the method is performed for scaphoid facture repair. (314) The method of embodiment 292 or embodiment 293, wherein the method is performed for tendeno-osseous repair. (315) The method of embodiment 292 or embodiment 293, wherein the method is performed to treat osteoporosis. (316) The method of embodiment 292 or embodiment 293, wherein the method is performed to treat avascular necrosis. (317) The method of embodiment 292 or embodiment 293, wherein the method is performed to treat congenital skeletal malformations. (318) The method of embodiment 292 or embodiment 293, wherein the method is performed for costal reconstruction. (319) The method of embodiment 292 or embodiment 293, wherein the method is performed for subchondral bone repair. (320) The method of embodiment 292 or embodiment 293, wherein the method is performed for cartilage repair. (321) The method of embodiment 292 or embodiment 293, wherein the method is performed on a hair follicle (BMP-2 is involved in hair follicle development). (322) The method of any one of embodiments 292-321, wherein the subject is a mammal. (323) The method of any one of embodiments 292-321, wherein the subject is a human. (324) The method of any one of embodiments 292-321, wherein the subject is a non-human mammal. (325) The method of embodiment 324, wherein the method is used in veterinary applications. (326) The method of any one of embodiments 292-325, wherein the delivery comprises surgical implantation into the subject.

A variety of different methods known in the art can be used to determine the $K_D$ values of any of the chimeric polypeptides described herein for binding of a target polypeptide to a carrier material, e.g., β-TCP. As non-limiting examples, an electrophoretic mobility shift assay, a filter binding assay, surface plasmon resonance, and a biomolecular binding kinetics assay, etc.

In some embodiments, the chimeric polypeptides provided herein are useful orthopedic materials, and can be used as bone void fillers and for bone reconstructions. In some embodiments, the chimeric polypeptides described herein are osteo-conductive and easily resorbed.

Linkers

In some instances, a neighboring pair of two targeting polypeptides directly abut each other. In some instances, a neighboring pair of two targeting polypeptides are separated by a linker sequence.

In some embodiments of a chimeric polypeptide provided herein comprising a targeting polypeptide and a therapeutic agent, the targeting polypeptide and therapeutic agent are separated by a linker sequence. In some embodiments, a linker sequence is present between two targeting polypeptides and/or between a targeting polypeptide and a therapeutic agent. In some instances, the therapeutic agent comprises a mammalian growth factor. For instance, BMP-2 comprising SEQ ID NO: 32. In some instances, the targeting polypeptide comprises one or more sequences of Table B. In some embodiments of a chimeric polypeptide comprising a linker positioned between the targeting polypeptide and a therapeutic agent, the presence of the linker increases solubility of the chimeric polypeptide as compared to a chimeric polypeptide without the linker. In some embodiments, the linker is optimized in sequence and/or length. In some embodiments, a chimeric polypeptide comprising the linker is more soluble than the chimeric polypeptide without the linker. In some embodiments, a therapeutic agent in a chimeric polypeptide comprising the linker is more bioavailable than without the linker.

In some embodiments, the linker comprises a sequence of about 5 to about 50 amino acids. In some embodiments, the linker is a flexible linker, where at least about five of the amino acids have no regular secondary structure. In some embodiments, regular secondary structure comprises any helical structure like an alpha helix or $3_{10}$ helix or 7 helix, a beta turn, omega loop, and/or a beta sheet. In some embodiments, the linker comprises at least about 50%, 55%, 60%, 65%, 70%, 75%, 80%, 85% or 90% glycine, alanine, serine, glycine and alanine, glycine and serine, alanine and serine, or glycine, alanine, and serine. In some embodiments, the linker comprises at least about 50%, 55%, 60%, 65%, 70%, 75%, 80%, 85% or 90% a combination of alanine, serine, glycine, and threonine. In some embodiments, the linker comprises 1, 2, 3, 4, or 5 sequences having GSEG (SEQ ID NO: 702). In some embodiments, the linker comprises 1, 2, 3, 4, or 5 sequences having SEGG (SEQ ID NO: 703). In some embodiments, a linker comprising a majority of A, S, G, and T provide improved solubility of the chimeric polypeptide. In some embodiments, a linker comprising a length of about 30 to about 45 amino acids provides improved solubility of the chimeric polypeptide.

In some embodiments, the linker comprises a sequence at least about 70%, 75%, 80%, 85%, 90%, 95%, or 100% identical to ASGAGGSEGGGSEGGTSGATGAGTST-SGGGASTGGGTG (SEQ ID NO: 701). In some embodiments, the linker comprises at least about 10, 15, 20, 25, or 30 contiguous amino acids of SEQ ID NO: 701. In some embodiments, the linker comprises a sequence at least about 90% identical to SEQ ID NO: 701. In some embodiments, the linker comprises SEQ ID NO: 701. In some embodiments, the linker sequence is positioned between a targeting polypeptide and a therapeutic agent. In some instances, the therapeutic agent comprises a mammalian growth factor. For instance, BMP-2 comprising SEQ ID NO: 32. In some instances, the targeting polypeptide comprises one or more sequences of Table A.

In some embodiments, a linker sequence comprises or consists of TGGSGEGGTGASTGGSAGTGGS-GGTTSGEAGGSSGAG (SEQ ID NO: 33) or GSGATG (SEQ ID NO: 45). In some instances the chimeric polypeptide comprises a linker that has an amino acid sequence that has at least 70% (e.g., at least 75%, at least 80%, at least 85%, at least 90%, at least 95%, at least 96%, at least 97%, at least 98%, at least 99%) sequence identity to SEQ ID NO: 33.

In some embodiments, a linker sequence comprises GSGS (SEQ ID NO: 705), GSGSGS (SEQ ID NO: 706), SGSG (SEQ ID NO: 707), SGSGSG (SEQ ID NO: 708), GSSG (SEQ ID NO: 709), SS, or GGGGS (SEQ ID NO: 710), or a combination thereof.

In some embodiments, a linker sequence can be 1 amino acid to about 100 amino acids, 1 amino acid to about 95 amino acids, 1 amino acid to about 90 amino acids, 1 amino acid to about 85 amino acids, 1 amino acid to about 80 amino acids, 1 amino acid to about 75 amino acids, 1 amino acid to about 70 amino acids, 1 amino acid to about 65 amino acids, 1 amino acid to about 60 amino acids, 1 amino acid to about 55 amino acids, 1 amino acid to about 50 amino acids, 1 amino acid to about 45 amino acids, 1 amino acid to about 40 amino acids, 1 amino acid to about 35 amino acids, 1 amino acid to about 30 amino acids, 1 amino acid to about 25 amino acids, 1 amino acid to about 20 amino acids, 1 amino acid to about 15 amino acids, 1 amino acid to about 10 amino acids, 1 amino acid to about 5 amino acids, about 5 amino acids to about 100 amino acids, about 5 amino acids to about 95 amino acids, about 5 amino acids to about 90 amino acids, about 5 amino acids to about 85 amino acids, about 5 amino acids to about 80 amino acids, about 5 amino acids to about 75 amino acids, about 5 amino acids to about 70 amino acids, about 5 amino acids to about 65 amino acids, about 5 amino acids to about 60 amino acids, about 5 amino acids to about 55 amino acids, about 5 amino acids to about 50 amino acids, about 5 amino acids to about 45 amino acids, about 5 amino acids to about 40 amino acids, about 5 amino acids to about 35 amino acids, about 5 amino acids to about 30 amino acids, about 5 amino acids to about 25 amino acids, about 5 amino acids to about 20 amino acids, about 5 amino acids to about 15 amino acids, about 5 amino acids to about 10 amino acids, about 10 amino acids to about 100 amino acids, about 10 amino acids to about 95 amino acids, about 10 amino acids to about 90 amino acids, about 10 amino acids to about 85 amino acids, about 10 amino acids to about 80 amino acids, about 10 amino acids to about 75 amino acids, about 10 amino acids to about 70 amino acids, about 10 amino acids to about 65 amino acids, about 10 amino acids to about 60 amino acids, about 10 amino acids to about 55 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 20 amino acids, about 10 amino acids to about 15 amino acids about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 65 amino acids, about 20 amino acids to about 60 amino acids, about 20 amino acids to about 55 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 65 amino acids, about 30 amino acids to about 60 amino acids, about 30 amino acids to about 55 amino acids, about 30 amino acids to about 50 amino acids, about 30 amino acids to about 45 amino acids, about 30 amino acids to about 40 amino acids, about 30 amino acids to about 35 amino acids.

Growth Factors

A targeting polypeptide as described herein can be tethered to a mammalian growth factor. In some instances, a linker sequence (e.g., any of the linker sequences described herein or known in the art) is disposed between the targeting polypeptide and the mammalian growth factor.

Mammalian growth factors can be osteoinductive molecules that are capable of initiating and enhancing the bone repair process. Bone morphogenetic proteins (BMP) represent a distinct subset of the transforming growth factor-β (TGFbeta) family. A number of these BMP (BMP-2, BMP-7, and BMP-14) enhance the speed of bone healing in defects and non-unions.

Non-limiting examples of mammalian growth factors are described herein. In some instances, the mammalian growth factor comprises: epidermal growth factor (EGF), platelet derived growth factor (PDGF), insulin like growth factor (IGF-1), fibroblast growth factor (FGF), fibroblast growth factor 2 (FGF2), fibroblast growth factor 18 (FGF18), transforming growth factor alpha (TGF-α), transforming growth factor beta (TGF-β), transforming growth factor beta 1 (TGF-β1), transforming growth factor beta 3 (TGF-β3), osteogenic protein 1 (OP-1), osteogenic protein 2 (OP-2), osteogenic protein 3 (OP-3), bone morphogenetic protein 2 (BMP-2), bone morphogenetic protein 3 (BMP-3), bone morphogenetic protein 4 (BMP-4), bone morphogenetic protein 5 (BMP-5), bone morphogenetic protein 6 (BMP-6), bone morphogenetic protein 7 (BMP-7), bone morphogenetic protein (BMP-9), bone morphogenetic protein 10 (BMP-10), bone morphogenetic protein 11 (BMP-11), bone morphogenetic protein 12 (BMP-12), bone morphogenetic protein 13 (BMP-13), bone morphogenetic protein 15 (BMP-15), dentin phosphoprotein (DPP), vegetal related growth factor (Vgr), growth differentiation factor 1 (GDF-1), growth differentiation factor 3 (GDF-3), growth differentiation factor 5 (GDF-5), growth differentiation factor 6 (GDF-6), growth differentiation factor 7 (GDF-7), growth differentiation factor 8 (GDF8), growth differentiation factor 11 (GDF11), growth differentiation factor 15 (GDF15), vascular endothelial growth factor (VEGF), hyaluronic acid binding protein (HABP), and collagen binding protein (CBP), fibroblast growth factor 18 (FGF-18), keratinocyte growth factor (KGF), tumor necrosis factor alpha (TNFα), tumor necrosis factor (TNF)-related apoptosis inducing ligand (TRAIL), wnt family member 1 (WNT1), wnt family member 2 (WNT2), wnt family member 2B (WNT2B), wnt family member 3 (WNT3), wnt family member 3A (WNT3A), wnt family member 4 (WNT4), wnt family member 5A (WNT5A), wnt family member 5B (WNT5B), wnt family member 6 (WNT6), wnt family member 7A (WNT7A), wnt family member 7B (WNT7B), wnt family member 8A (WNT8A), wnt family member 8B (WNT8B), wnt family member 9A (WNT9A), wnt family member 9B (WNT9B), wnt family member 10A (WNT10A), wnt family member 10B (WNT10B), wnt family member 11 (WNT11), neuregulin 1 (NRG1), or wnt family member 16 (WNT16), or a mature peptide or functional portion thereof. In some embodiments, a chimeric polypeptide provided herein comprises one or more mammalian growth factors.

For example, the mammalian growth factor can be a human growth factor. Non-limiting examples of mammalian growth factors and mature peptides and/or functional portions thereof are provided in Table B. As used herein, reference to a mammalian growth factor includes a non-human mammalian growth factor. For instance, a mammalian growth factor includes a non-human mammalian growth factor homologous to a human growth factor, such as one or more of the human growth factors of Table B.

In some embodiments, a non-human mammalian growth factor is homologous to a human growth factor if the non-human mammalian growth factor is at least about 80% identical to the human growth factor as determined using the NCBI Blast alignment algorithm as of the date of this filing. In some cases, the coverage is at least about 90%.

In some embodiments, a non-human mammalian growth factor is homologous to a human growth factor if the non-human mammalian growth factor has at least about 80% positives as compared to the human mammalian growth factor as determined using the NCBI Blast alignment algorithm as of the date of this filing. In some cases, the coverage is at least about 90%.

In some embodiments, a non-human mammalian growth factor is homologous to a human growth factor if the non-human mammalian growth factor aligned with the human growth factor using the NCBI Blast as of the date of this filing has an E value of less than about 1E-40, at least about 1E-50, 1E-60, 1E-70, or 1E-10, with a query cover of at least about 90%.

TABLE B

Exemplary human growth factors

| Name | Exemplary Human Protein Sequence | SEQ ID NO: |
|---|---|---|
| EGF | NSDSECPLSHDGYCLHDGVCMYIEALDKYACNCVVGYIGERCQY RDLKWWELR | 46 |
| PDGF | EEAEIPREVIERLARSQIHSIRDLQRLLEIDSVGSEDSLDTSLRAHGV HATKHVPEKRPLPIRRKR | 47 |
| IGF-1 | GPETLCGAELVDALQFVCGDRGFYFNKPTGYGSSSRRAPQTGIVDE CCFRSCDLRRLEMYCAPLKPAKSA | 48 |
| FGF | FNLPPGNYKKPKLLYCSNGGHFLRILPDGTVDGTRDRSDQHIQLQL SAESVGEVYIKSTETGQYLAMDTDGLLYGSQTPNEECLFLERLEEN HYNTYISKKHAEKNWFVGLKKNGSCKRGPRTHYGQKAILFLPLPV SSD | 49 |
| FGF2 | PALPEDGGSGAFPPGHFKDPKRLYCKNGGFFLRIHPDGRVDGVRE KSDPHIKLQLQAEERGVVSIKGVCANRYLAMKEDGRLLASKCVTD ECFFFERLESNNYNTYRSRKYTSWYVALKRTGQYKLGSKTGPGQK AILFLPMSAKS | 50 |
| FGF18 | EENVDFRIHVENQTRARDDVSRKQLRLYQLYSRTSGKHIQVLGRRI SARGEDGDKYAQLLVETDTFGSQVRIKGKETEFYLCMNRKGKLV GKPDGTSKECVFIEKVLENNYTALMSAKYSGWYVGFTKKGRPRK GPKTRENQQDVHFMKRYPKGQPELQKPFKYTTVTKRSRRIRPTHP A | 51 |
| TGF-α | ENSTSPLSADPPVAAAVVSHFNDCPDSHTQFCFHGTCRFLVQEDKP ACVCHSGYVGARCEHADLLAVVAASQKKQAITALVVVSIVALAV LIITCVLIHCCQVRKHCEWCRALICRHEKPSALLKGRTACCHSETV V | 52 |
| TGF-α | VVSHFNDCPDSHTQFCFHGTCRFLVQEDKPACVCHSGYVGARCEH ADLLA | 152 |
| TGF-β1 | ALDTNYCFSSTEKNCCVRQLYIDFRKDLGWKWIHEPKGYHANFCL GPCPYIWSLDTQYSKVLALYNQHNPGASAAPCCVPQALEPLPIVYY VGRKPKVEQLSNMIVRSCKCS | 53 |
| TGF-β3 | ALDTNYCFRNLEENCCVRPLYIDFRQDLGWKWVHEPKGYYANFC SGPCPYLRSADTTHSTVLGLYNTLNPEASASPCCVPQDLEPLTILYY VGRTPKVEQLSNMVVKSCKCS | 54 |
| OP-2 (BMP-8) | AVRPLRRRQPKKSNELPQANRLPGIFDDVHGSHGRQVCRRHELYV SFQDLGWLDWVIAPQGYSAYYCEGECSFPLDSCMNATNHAILQSL VHLMMPDAVPKACCAPTKLSATSVLYYDSSNNVILRKHRNMVVK ACGCH | 55 |
| BMP8A | AVRPLRRRQPKKSNELPQANRLPGIFDDVRGSHGRQVCRRHELYV SFQDLGWLDWVIAPQGYSAYYCEGECSFPLDSCMNATNHAILQSL VHLMKPNAVPKACCAPTKLSATSVLYYDSSNNVILRKHRNMVVK ACGCH | 56 |
| BMP-2 | QAKHKQRKRLKSSCKRHPLYVDFSDVGWNDWIVAPPGYHAFYCH GECPFPLADHLNSTNHAIVQTLVNSVNSKIPKACCVPTELSAISMLY LDENEKVVLKNYQDMVVEGCGCR | 32 |
| BMP-3 | QWIEPRNCARRYLKVDFADIGWSEWIISPKSFDAYYCSGACQFPMP KSLKPSNHATIQSIVRAVGVVPGIPEPCCVPEKMSSLSILFFDENKN VVLKVYPNMTVESCACR | 57 |
| BMP-4 | SPKHHSQRARKKNKNCRRHSLYVDFSDVGWNDWIVAPPGYQAFY CHGDCPFPLADHLNSTNHAIVQTLVNSVNSSIPKACCVPTELSAISM LYLDEYDKVVLKNYQEMVVEGCGCR | 58 |
| BMP-5 | AANKRKNQNRNKSSSHQDSSRMSSVGDYNTSEQKQACKKHELYV SFRDLGWQDWIIAPEGYAAFYCDGECSFPLNAHMNATNHAIVQTL VHLMFPDHVPKPCCAPTKLNAISVLYFDDSSNVILKKYRNMVVRS CGCH | 59 |
| BMP-6/VGR | SASSRRRQQSRNRSTQSQDVARVSSASDYNSSELKTACRKHELYV SFQDLGWQDWIIAPKGYAANYCDGECSFPLNAHMNATNHAIVQT LVHLMNPEYVPKPCCAPTKLNAISVLYFDDNSNVILKKYRNMVVR ACGCH | 60 |

TABLE B-continued

Exemplary human growth factors

| Name | Exemplary Human Protein Sequence | SEQ ID NO: |
|---|---|---|
| BMP-7/OP-1 | STGSKQRSQNRSKTPKNQEALRMANVAENSSSDQRQACKKHELY VSFRDLGWQDWIIAPEGYAAYYCEGECAFPLNSYMNATNHAIVQT LVHFINPETVPKPCCAPTQLNAISVLYFDDSSNVILKKYRNMVVRA CGCH | 61 |
| BMP-9 | SAGAGSHCQKTSLRVNFEDIGWDSWIIAPKEYEAYECKGGCFFPLA DDVTPTKHAIVQTLVHLKFPTKVGKACCVPTKLSPISVLYKDDMG VPTLKYHYEGMSVAECGCR | 62 |
| BMP-10 | NAKGNYCKRTPLYIDFKEIGWDSWIIAPPGYEAYECRGVCNYPLAE HLTPTKHAIIQALVHLKNSQKASKACCVPTKLEPISILYLDKGVVTY KFKYEGMAVSECGCR | 63 |
| BMP-11/GDF-11 | NLGLDCDEHSSESRCCRYPLTVDFEAFGWDWIIAPKRYKANYCSG QCEYMFMQKYPHTHLVQQANPRGSAGPCCTPTKMSPINMLYFND KQQIIYGKIPGMVVDRCGCS | 64 |
| BMP-12 | TALAGTRTAQGSGGGAGRGHGRRGRSRCSRKPLHVDFKELGWDD WIIAPLDYEAYHCEGLCDFPLRSHLEPTNHAIIQTLLNSMAPDAAPA SCCVPARLSPISILYIDAANNVVYKQYEDMVVEACGCR | 65 |
| BMP-13/GDF-6 | TAFASRHGKRHGKKSRLRCSKKPLHVNFKELGWDDWIIAPLEYEA YHCEGVCDFPLRSHLEPTNHAIIQTLMNSMDPGSTPPSCCVPTKLTP ISILYIDAGNNVVYKQYEDMVVESCGCR | 66 |
| BMP-15 | QADGISAEVTASSSKHSGPENNQCSLHPFQISFRQLGWDHWIIAPPF YTPNYCKGTCLRVLRDGLNSPNHAIIQNLINQLVDQSVPRPSCVPY KYVPISVLMIEANGSILYKEYEGMIAESCTCR | 67 |
| DPP isoform 1 | IPVPQSKPLERHVEKSMNLHLLARSNVSVQDELNASGTIKESGVLV HEGDRGRQENTQDGHKGEGNGSKWAEVGGKSFSTYSTLANEEGN IEGWNGDTGKAETYGHDGIHGKEENITANGIQGQVSIIDNAGATNR SNTNGNTDKNTQNGDVGDAGHNEDVAVVQEDGPQVAGSNNSTD NEDEIIENSCRNEGNTSEITPQINSKRNGTKEAEVTPGTGEDAGLDN SDGSPSGNGADEDEDEGSGDDEDEEAGNGKDSSNNSKGQEGQDH GKEDDHDSSIGQNSDSKEYYDPEGKEDPHNEVDGDKTSKSEENSA GIPEDNGSQRIEDTQKLNHRESKRVENRITKESETHAVGKSQDKGI EIKGPSSGNRNITKEVGKGNEGKEDKGQHGMILGKGNVKTQGEVV NIEGPGQKSEPGNKVGHSNTGSDSNSDGYDSYDFDDKSMQG | 68 |
| DPP isoform 2 | IPVPQSKPLERHVEKSMNLHLLARSNVSVQDELNASGTIKESGVLV HEGDRGRQENTQDGHKGEGNGSKWAEVGGKSFSTYSTLANEEGN IEGWNGDTGKAETYGHDGIHGKEENITANGIQGQVSIIDNAGATNR SNTNGNTDKNTQNGDVGDAGHNEDVAVVQEDGPQVAGSNNSTD NEDEIIENSCRNEGNTSEITPQINSKRNGTKEAEVTPGTGEDAGLDN SDGSPSGNGADEDEDEGSGDDEDEEAGNGKDSSNNSKGQEGQDH GKEDDHDSSIGQNSDSKEYYDPEGKEDPHNEVDGDKTSKSEENSA GIPEDNGSQRIEDTQKLNHRESKRVENRITKESETHAVGKSQDKGI EIKGPSSGNRNITKEVGKGNEGKEDKGQHGMILGKGNVKTQGEVV NIEGPGQKSEPGNKVGHSNTGSDSNSDGYDSYDFDDKSMQGDDP NSSDESNGNDDANSESDNNSSSRGDASYNSDESKDNGNGSDSKGA EDDDSDSTSDTNNSDSNGNGNNGNDDNDKSDSGKGKSDSSDSDSS DSSNSSDSSDSSDSDSSDSNSSSDSDSSDSDSSDSSDSSDSSNSSD SSDSSDSSDSSDSSDSKSDSSKSESDSSDSDSKSDSSDSNSSDSS DNSDSSDSSNSSNSSDSSDSSDSSDSSSSSDSSNSSDSSDSSDSSNSSE SSDSSDSSDSDSSDSSDSSNSNSSDSDSSNSSDSSDSSNSSDSSDSS DS SNSSDSSDSSDSSNSSDSSDSSDSSDSSNSSDSNDSSNSSDSSDSS NSSDSSNSSDSSDSDSSDSSNSSDSSNSSDSSDSSNSSDSSDSSDSSDS SDGSDSDSSNRDSSNSDSSDSSDSSNSSDSDSSDSNESSNSSDSS DSSNSSDSDSSDSSNSSDSSDSSNSSDSSESSNSSDNSNSSDSSNSSD SSDSSDSSNSSDSSNSSDSSNSSDSSNSSDSDSSNSSDSSDSSDSS DSSDSSDSSNSSDSSDSSSDSSNSSDSSNSSDSSNSSDSSDSSDSSD SSDSSDSSDSSNSSDSSDSSDSSDSSDSSDSSDSSSESSDSSDS SNSSDSSDSSDSDSSDSSDSSDSSNSSDSSDSSDSSDSSDSS NSSDSSDSSESSDSSDSSDSSDSSDSSDSSDSSNSSDSSDSSD SSDSSDSSDSSDSSDSSDSSDSSNSSDSSDSSDSSDSSDSNESSDS SDSSDSSNSSDSSDSSDSSDSTSDSNDESDSQSKSGNGNNNGSD SDSDSEGSDSNHSTSDD | 168 |
| DPP isoform 3 | DDPNSSDESNGNDDANSESDNNSSSRGDASYNSDESKDNGNGSDS KGAEDDDSDSTSDTNNSDSNGNGNNGNDDNDKSDSGKGKSDSSD SDSSDSSNSSDSSDSSDSSDSNSSSDSDSSDSDSSDSSDSSDSSDSS NSSDSSDSSDSSDSSDSSDSKSDSSKSESDSSDSDSKSDSSDSNS SDSSDNSDSSDSSNSSNSSDSSDSSDSSDSSDSSSSSSDSSNSSDSSDSSDSS NSSESSDSSDSSDSSDSSDSSDSSDSSDSSDSSNSNSSDSDSSNSSDSSDSS | 268 |

TABLE B-continued

Exemplary human growth factors

| Name | Exemplary Human Protein Sequence | SEQ ID NO: |
|---|---|---|
| | DSSDDSSNSSDSSDSSDSSNSSDSSDSSDSSDSSDSSNSSDSNDSSNSS DSSDSSNSSDSSNSSDSSDSSDSSDSDSSNSSDSSNSSDSSDSSNSSDS SDSSDSSDGSDSDSSNRSDSSNSSDSSDSSDSSNSSDSSDSSDSNESS NSSDSSDSSNSDSSDSSNSSDSSDSSNSSDSSESSNSSDNSNSSD SSNSSDSSDSSNSSDSSNSSDSSNSSDSSDSNSSDSSDSSNSSDSS DSSDSSDSSDSSNSSDSSDSSDSSNSSDSSNSSDSSNSSDSSD SSDSSDSSDSSDSSDSSNSSDSSDSSDSSDSSDSSDSSDSSES SDSSDSSNSSDSSDSSDSSDSSDSSDSSDSSDSSNSSDSSDSSDSS DSSDSSNSSDSSESSDSSDSSDSSDSSDSSDSSDSSDSSNSSD SSDSSDSSDSSDSSDSSDSSDSSDSSDSSDSSDSSDSSDSSDS NESSDSSDSSDSSDSSNSSDSSDSSDSSDSTSDSNDESDSQSKSGNG NNNGSDSDSDSEGSDSNHSTSDD | |
| GDF-1 | DAEPVLGGGPGGACRARRLYVSFREVGWHRWVIAPRGFLANYCQ GQCALPVALSGSGGPPALNHAVLRALMHAAAPGAADLPCCVPAR LSPISVLFFDNSDNVVLRQYEDMVVDECGCR | 69 |
| GDF-3 | AAIPVPKLSCKNLCHRHQLFINFRDLGWHKWIIAPKGFMANYCHG ECPFSLTISLNSSNYAFMQALMHAVDPEIPQAVCIPTKLSPISMLYQ DNNDNVILRHYEDMVVDECGCG | 70 |
| GDF-5 | APLATRQGKRPSKNLKARCSRKALHVNFKDMGWDDWIIAPLEYE AFHCEGLCEFPLRSHLEPTNHAVIQTLMNSMDPESTPPTCCVPTRLS PISILFIDSANNVVYKQYEDMVVESCGCR | 71 |
| GDF8 | DFGLDCDEHSTESRCCRYPLTVDFEAFGWDWIIAPKRYKANYCSG ECEFVFLQKYPHTHLVHQANPRGSAGPCCTPTKMSPINMLYFNGK EQIIYGKIPAMVVDRCGCS | 73 |
| GDF15 | ARARNGDHCPLGPGRCCRLHTVRASLEDLGWADWVLSPREVQVT MCIGACPSQFRAANMHAQIKTSLHRLKPDTVPAPCCVPASYNPMV LIQKTDTGVSLQTYDDLLAKDCHCI | 74 |
| VEGF | APMAEGGGQNHHEVVKFMDVYQRSYCHPIETLVDIFQEYPDEIEYI FKPSCVPLMRCGGCCNDEGLECVPTEESNITMQIMRIKPHQGQHIG EMSFLQHNKCECRPKKDRARQEKKSVRGKGKGQKRKRKKSRYKS WSVYVGARCCLMPWSLPGPHPCGPCSERRKHLFVQDPQTCKCSC KNTDSRCKARQLELNERTCRCDKPRR | 75 |
| HABP Isoform 1 | FSLMSLLESLDPDWTPDQYDYSYEDYNQEENTSSTLTHAENPDWY YTEDQADPCQPNPCEHGGDCLVHGSTFTCSCLAPFSGNKCQKVQN TCKDNPCGRGQCLITQSPPYYRCVCKHPYTGPSCSQVVPVCRPNPC QNGATCSRHKRRSKFTCACPDQFKGKFCEIGSDDCYVGDGYSYRG KMNRTVNQHACLYWNSHLLLQENYNMFMEDAETHGIGEHNFCR NPDADEKPWCFIKVTNDKVKWEYCDVSACSAQDVAYPEESPTEPS TKLPGFDSCGKTEIAERKIKR | 76 |
| HABP Isoform 2 | IYGGFKSTAGKHPWQASLQSSLPLTISMPQGHFCGGALIHPCWVLT AAHCTDIKTRHLKVVLGDQDLKKEEFHEQSFRVEKIFKYSHYNER DEIPHNDIALLKLKPVDGHCALESKYVKTVCLPDGSFPSGSECHISG WGVTETGKGSRQLLDAKVKLIANTLCNSRQLYDHMIDDSMICAG NLQKPGQDTCQGDSGGPLTCEKDGTYYVYGIVSWGLECGKRPGV YTQVTKFLNWIKATIKSESGF | 176 |
| CBP | AEVKKPAAAAAPGTAEKLSPKAATLAERSAGLAFSLYQAMAKDQ AVENILVSPVVVASSLGLVSLGGKATTASQAKAVLSAEQLRDEEV HAGLGELLRSLSNSTARNVTWKLGSRLYGPSSVSFADDFVRSSKQ HYNCEHSKINFRDKRSALQSINEWAAQTTDGKLPEVTKDVERTDG ALLVNAMFFKPHWDEKFHHKMVDNRGFMVTRSYTVGVMMMHR TGLYNYYDDEKEKLQIVEMPLAHKLSSLIILMPHHVEPLERLEKLL TKEQLKIWMGKMQKKAVAISLPKGVVEVTHDLQKHLAGLGLTEA IDKNKADLSRMSGKKDLYLASVFHATAFELDTDGNPFDQDIYGRE ELRSPKLFYADHPFIFLVRDTQSGSLLFIGRLVRPKGDKMRDEL | 77 |
| KGF | CNDMTPEQMATNVNCSSPERHTRSYDYMEGGDIRVRRLFCRTQW YLRIDKRGKVKGTQEMKNNYNIMEIRTVAVGIVAIKGVESEFYLA MNKEGKLYAKKECNEDCNFKELILENHYNTYASAKWTHNGGEMF VALNQKGIPVRGKKTKKEQKTAHFLPMAIT | 79 |
| TNFα | GPQREEFPRDLSLISPLAQAVRSSSRTPSDKPVAHVVANPQAEGQL QWLNRRANALLANGVELRDNQLVVPSEGLYLIYSQVLFKGQGCPS THVLLTHTISRIAVSYQTKVNLLSAIKSPCQRETPEGAEAKPWYEPI YLGGVFQLEKGDRLSAEINRPDYLDFAESGQVYFGIIAL | 80 |

TABLE B-continued

Exemplary human growth factors

| Name | Exemplary Human Protein Sequence | SEQ ID NO: |
|---|---|---|
| TRAIL | TNELKQMQDKYSKSGIACFLKEDDSYWDPNDEESMNSPCWQVK<br>WQLRQLVRKMILRTSEETISTVQEKQQNISPLVRERGPQRVAAHIT<br>GTRGRSNTLSSPNSKNEKALGRKINSWESSRSGHSFLSNLHLRNGE<br>LVIHEKGFYYIYSQTYFRFQEEIKENTKNDKQMVQYIYKYTSYPDPI<br>LLMKSARNSCWSKDAEYGLYSIYQGGIFELKENDRIFVSVTNEHLI<br>DMDHEASFFGAFLVG | 81 |
| WNT1 | ANSSGRWWGIVNVASSTNLLTDSKSLQLVLEPSLQLLSRKQRRLIR<br>QNPGILHSVSGGLQSAVRECKWQFRNRRWNCPTAPGPHLFGKIVN<br>RGCRETAFIFAITSAGVTHSVARSCSEGSIESCTCDYRRGPGGPDW<br>HWGGCSDNIDFGRLFGREFVDSGEKGRDLRFLMNLHNNEAGRTT<br>VFSEMRQECKCHGMSGSCTVRTCWMRLPTLRAVGDVLRDRFGA<br>SRVLYGNRGSNRASRAELLRLEPEDPAHKPPSPHDLVYFEKSPNFC<br>TYSGRLGTAGTAGRACNSSPALDGCELLCCGRGHRTRTQRVTER<br>CNCTFHWCCHVSCRNCTHTRVLHECL | 82 |
| WNT2 | SWWYMRATGGSSRVMCDNVPGLVSSQRQLCHRHPDVMRAISQG<br>VAEWTAECQHQFRQHRWNCNTLDRDHSLFGRVLLRSSRESAFVY<br>AISSAGVVFAITRACSQGEVKSCSCDPKKMGSAKDSKGIFDWGGC<br>SDNIDYGIKFARAFVDAKERKGKDARALMNLHNNRAGRKAVKRF<br>LKQECKCHGVSGSCTLRTCWLAMADFRKTGDYLWRKYNGAIQV<br>VMNQDGTGFTVANERFKKPTKNDLVYFENSPDYCIRDREAGSLGT<br>AGRVCNLTSRGMDSCEVMCCGRGYDTSHVTRMTKCGCKFHWCC<br>AVRCQDCLEALDVHTCKAPKNADWTTAT | 83 |
| WNT2B | SWWYIGALGARVICDNIPGLVSRQRQLCQRYPDIMRSVGEGAREW<br>IRECQHQFRHHRWNCTTLDRDHTVFGRVMLRSSREAAFVYAISSA<br>GVVHAITRACSQGELSVCSCDPYTRGRHHDQRGDFDWGGCSDNIH<br>YGVRFAKAFVDAKEKRLKDARALMNLHNNRCGRTAVRRFLKLEC<br>KCHGVSGSCTLRTCWRALSDFRRTGDYLRRRYDGAVQVMATQD<br>GANFTAARQGYRRATRTDLVYFDNSPDYCVLDKAAGSLGTAGRV<br>CSKTSKGTDGCEIMCCGRGYDTTRVTRVTQCECKFHWCCAVRCK<br>ECRNTVDVHTCKAPKKAEWLDQT | 84 |
| WNT3 | GYPIWWSLALGQQYTSLGSQPLLCGSIPGLVPKQLRFCRNYIEIMPS<br>VAEGVKLGIQECQHQFRGRRWNCTTIDDSLAIFGPVLDKATRESAF<br>VHAIASAGVAFAVTRSCAEGTSTICGCDSHHKGPPGEGWKWGGCS<br>EDADFGVLVSREFADARENRPDARSAMNKHNNEAGRTTILDHMH<br>LKCKCHGLSGSCEVKTCWWAQPDFRAIGDFLKDKYDSASEMVVE<br>KHRESRGWVETLRAKYSLFKPPTERDLVYYENSPNFCEPNPETGSF<br>GTRDRTCNVTSHGIDGCDLLCCGRGHNTRTEKRKEKCHCIFHWCC<br>YVSCQECIRIYDVHTCK | 85 |
| WNT3A | SYPIWWSLAVGPQYSSLGSQPILCASIPGLVPKQLRFCRNYVEIMPS<br>VAEGIKIGIQECQHQFRGRRWNCTTVHDSLAIFGPVLDKATRESAF<br>VHAIASAGVAFAVTRSCAEGTAAICGCSSRHQGSPGKGWKWGGC<br>SEDIEFGGMVSREFADARENRPDARSAMNRHNNEAGRQAIASHM<br>HLKCKCHGLSGSCEVKTCWWSQPDFRAIGDFLKDKYDSASEMVV<br>EKHRESRGWVETLRPRYTYFKVPTERDLVYYEASPNFCEPNPETGS<br>FGTRDRTCNVSSHGIDGCDLLCCGRGHNARAERRREKCRCVFHW<br>CCYVSCQECTRVYDVHTCK | 86 |
| WNT4 | SNWLYLAKLSSVGSISEEETCEKLKGLIQRQVQMCKRNLEVMDSV<br>RRGAQLAIEECQYQFRNRRWNCSTLDSLPVFGKVVTQGTREAAFV<br>YAISSAGVAFAVTRACSSGELEKCGCDRTVHGVSPQGFQWSGCSD<br>NIAYGVAFSQSFVDVRERSKGASSSRALMNLHNNEAGRKAILTHM<br>RVECKCHGVSGSCEVKTCWRAVPPFRQVGHALKEKFDGATEVEP<br>RRVGSSRALVPRNAQFKPHTDEDLVYLEPSPDFCEQDMRSGVLGT<br>RGRTCNKTSKAIDGCELLCCGRGHTAQVELAERCSCKFHWCCFV<br>KCRQCQRLVELHTCR | 87 |
| WNT5A | IIGAQPLCSQLAGLSQGQKKLCHLYQDHMQYIGEGAKTGIKECQY<br>QFRHRRWNCSTVDNTSVFGRVMQIGSRETAFTYAVSAAGVVNAM<br>SRACREGELSTCGCSRAARPKDLPRDWLWGGCGDNIDYGYRFAK<br>EFVDARERERIHAKGSYESARILMNLHNNEAGRRTVYNLADVACK<br>CHGVSGSCSLKTCWLQLADFRKVGDALKEKYDSAAAMRLNSRGK<br>LVQVNSRFNSPTTQDLVYIDPSPDYCVRNESTGSLGTQGRLCNKTS<br>EGMDGCELMCCGRGYDQFKTVQTERCHCKFHWCCYVKCKKCTE<br>IVDQFVCK | 88 |
| WNT5B | QLLTDANSWWSLALNPVQRPEMFIIGAQPVCSQLPGLSPGQRKLC<br>QLYQEHMAYIGEGAKTGIKECQHQFRQRRWNCSTADNASVFGRV<br>MQIGSRETAFTHAVSAAGVVNAISRACREGELSTCGCSRTARPKDL<br>PRDWLWGGCGDNVEYGYRFAKEFVDAREREKNFAKGSEEQGRV<br>LMNLQNNEAGRRAVYKMADVACKCHGVSGSCSLKTCWLQLAEF | 89 |

TABLE B-continued

Exemplary human growth factors

| Name | Exemplary Human Protein Sequence | SEQ ID NO: |
|---|---|---|
| | RKVGDRLKEKYDSAAAMRVTRKGRLELVNSRFTQPTPEDLVYVD<br>PSPDYCLRNESTSGLGTQGRLCNKTSEGMDGCELMCCGRGYNQF<br>KSVQVERCHCKFHWCCFVRCKKCTEIVDQYICK | |
| WNT6 | LWWAVGSPLVMDPTSICRKARRLAGRQAELCQAEPEVVAELARG<br>ARLGVRECQFQFRFRRWNCSSHSKAFGRILQQDIRETAFVFAITAA<br>GASHAVTQACSMGELLQCGCQAPRGRAPPRPSGLPGTPGPPGPAG<br>SPEGSAAWEWGGCGDDVDFGDEKSRLFMDARHKRGRGDIRALV<br>QLHNNEAGRLAVRSHTRTECKCHGLSGSCALRTCWQKLPPFREVG<br>ARLLERFHGASRVMGTNDGKALLPAVRTLKPPGRADLLYAADSP<br>DFCAPNRRTGSPGTRGRACNSSAPDLSGCDLLCCGRGHRQESVQL<br>EENCLCRFHWCCVVQCHRCRVRKELSLCL | 90 |
| WNT7A | LGASIICNKIPGLAPRQRAICQSRPDAIIVIGEGSQMGLDECQFQFRN<br>GRWNCSALGERTVFGKELKVGSREAAFTYAIIAAGVAHAITAACT<br>QGNLSDCGCDKEKQGQYHRDEGWKWGGCSADIRYGIGFAKVFV<br>DAREIKQNARTLMNLHNNEAGRKILEENMKLECKCHGVSGSCTTK<br>TCWTTLPQFRELGYVLKDKYNEAVHVEPVRASRNKRPTFLKIKKP<br>LSYRKPMDTDLVYIEKSPNYCEEDPVTGSVGTQGRACNKTAPQAS<br>GCDLMCCGRGYNTHQYARVWQCNCKFHWCCYVKCNTCSERTE<br>MYTCK | 91 |
| WNT7B | ALSSVVALGANIICNKIPGLAPRQRAICQSRPDAIIVIGEGAQMGINE<br>CQYQFRFGRWNCSALGEKTVFGQELRVGSREAAFTYAITAAGVA<br>HAVTAACSQGNLSNCGCDREKQGYYNQAEGWKWGGCSADVRY<br>GIDFSRRFVDAREIKKNARRLMNLHNNEAGRKVLEDRMQLECKC<br>HGVSGSCTTKTCWTTLPKFREVGHLLKEKYNAAVQVEVVRASRL<br>RQPTFLRIKQLRSYQKPMETDLVYIEKSPNYCEEDAATGSVGTQGR<br>LCNRTSPGADGCDTMCCGRGYNTHQYTKVWQCNCKFHWCCFVK<br>CNTCSERTEVFTCK | 92 |
| WNT8A | VNNFLITGPKAYLTYTTSVALGAQSGIEECKFQFAWERWNCPENA<br>LQLSTHNRLRSATRETSFIHAISSAGVMYIITKNCSMGDFENCGCDG<br>SNNGKTGGHGWIWGGCSDNVEFGERISKLFVDSLEKGKDARALM<br>NLHNNRAGRLAVRATMKRTCKCHGISGSCSIQTCWLQLAEFREM<br>GDYLKAKYDQALKIEMDKRQLRAGNSAEGHWVPAEAFLPSAEAE<br>LIFLEESPDYCTCNSSLGIYGTEGRECLQNSHNTSRWERRSCGRLCT<br>ECGLQVEERKTEVISSCNCKFQWCCTVKCDQCRHVVSKYYCARSP<br>GSAQSLGKGSA | 93 |
| WNT8B | WSVNNFLMTGPKAYLIYSSSVAAGAQSGIEECKYQFAWDRWNCP<br>ERALQLSSHGGLRSANRETAFVHAISSAGVMYTLTRNCSLGDFDN<br>CGCDDSRNGQLGGQGWLWGGCSDNVGFGEAISKQFVDALETGQ<br>DARAAMNLHNNEAGRKAVKGTMKRTCKCHGVSGSCTTQTCWLQ<br>LPEFREVGAHLKEKYHAALKVDLLQGAGNSAAGRGAIADTFRSIS<br>TRELVHLEDSPDYCLENKTLGLLGTEGRECLRRGRALGRWERRSC<br>RRLCGDCGLAVEERRAETVSSCNCKFHWCCAVRCEQCRRRVTKY<br>FCSRAERPRGGAAHKPGRKP | 94 |
| WNT9A | YFGLTGSEPLTILPLTLEPEAAAQAHYKACDRLKLERKQRRMCRR<br>DPGVAETLVEAVSMSALECQFQFRFERWNCTLEGRYRASLLKRGF<br>KETAFLYAISSAGLTHALAKACSAGRMERCTCDEAPDLENREAWQ<br>WGGCGDNLKYSSKFVKEFLGRRSSKDLRARVDFHNNLVGVKVIK<br>AGVETTCKCHGVSGSCTVRTCWRQLAPPHEVGKHLKHKYETALK<br>VGSTTNEAAGEAGAISPPRGRASGAGGSDPLPRTPELVHLDDSPSF<br>CLAGRFSPGTAGRRCHREKNCESICCGRGHNTQSRVVTRPCQCQV<br>RWCCYVECRQCTQREEVYTCKG | 95 |
| WNT9B | SYFGLTGREVLTPFPGLGTAAAPAQGGAHLKQCDLLKLSRRQKQL<br>CRREPGLAETLRDAAHLGLLECQFQFRHERWNCSLEGRMGLLKR<br>GFKETAFLYAVSSAALTHTLARACSAGRMERCTCDDSPGLESRQA<br>WQWGVCGDNLKYSTKFLSNFLGSKRGNKDLRARADAHNTHVGI<br>KAVKSGLRTTCKCHGVSGSCAVRTCWKQLSPFRETGQVLKLRYD<br>SAVKVSSATNEALGRLELWAPARQGSLTKGLAPRSGDLVYMEDSP<br>SFCRPSKYSPGTAGRVCSREASCSSLCCGRGYDTQSRLVAFSCHCQ<br>VQWCCYVECQQCVQEELVYTCKH | 96 |
| WNT10A | MPRSAPNDILDLRLPPEPVLNANTVCLTLPGLSRRQMEVCVRHPDV<br>AASAIQGIQIAIHECQHQFRDQRWNCSSLETRNKIPYESPIFSRGFRE<br>SAFAYAIAAAGVVHAVSNACALGKLKACGCDASRRGDEEAFRRK<br>LHRLQLDALQRGKGLSHGVPEHPALPTASPGLQDSWEWGGCSPD<br>MGFGERFSKDFLDSREPHRDIHARMRLHNNRVGRQAVMENMRRK<br>CKCHGTSGSCQLKTCWQVTPEFRTVGALLRSRFHRATLIRPHNRN | 97 |

TABLE B-continued

Exemplary human growth factors

| Name | Exemplary Human Protein Sequence | SEQ ID NO: |
|---|---|---|
| | GGQLEPGPAGAPSPAPGAPGPRRRASPADLVYFEKSPDFCEREPRL<br>DSAGTVGRLCNKSSAGSDGCGSMCCGRGHNILRQTRSERCHCRFH<br>WCCFVVCEECRITEWVSVCK | |
| WNT10B | NEILGLKLPGEPPLTANTVCLTLSGLSKRQLGLCLRNPDVTASALQ<br>GLHIAVHECQHQLRDQRWNCSALEGGGRLPHHSAILKRGFRESAF<br>SFSMLAAGVMHAVATACSLGKLVSCGCGWKGSGEQDRLRAKLL<br>QLQALSRGKSFPHSLPSPGPGSSPSPGPQDTWEWGGCNHDMDFGE<br>KFSRDFLDSREAPRDIQARMRIHNNRVGRQVVTENLKRKCKCHGT<br>SGSCQFKTCWRAAPEFRAVGAALRERLGRAIFIDTHNRNSGAFQPR<br>LRPRRLSGELVYFEKSPDFCERDPTMGSPGTRGRACNKTSRLLDGC<br>GSLCCGRGHNVLRQTRVERCHCRFHWCCYVLCDECKVTEWVNV<br>CK | 98 |
| WNT11 | IKWLALSKTPSALALNQTQHCKQLEGLVSAQVQLCRSNLELMHTV<br>VHAAREVMKACRRAFADMRWNCSSIELAPNYLLDLERGTRESAF<br>VYALSAAAISHAIARACTSGDLPGCSCGPVPGEPPGPGNRWGGCA<br>DNLSYGLLMGAKFSDAPMKVKKTGSQANKLMRLHNSEVGRQAL<br>RASLEMKCKCHGVSGSCSIRTCWKGLQELQDVAADLKTRYLSAT<br>KVVHRPMGTRKHLVPKDLDIRPVKDSELVYLQSSPDFCMKNEKV<br>GSHGTQDRQCNKTSNGSDSCDLMCCGRGYNPYTDRVVERCHCKY<br>HWCCYVTCRRCERTVERYVCK | 99 |
| WNT16 | NWMWLGIASFGVPEKLGCANLPLNSRQKELCKRKPYLLPSIREGA<br>RLGIQECGSQFRHERWNCMITAAATTAPMGASPLFGYELSSGTKET<br>AFIYAVMAAGLVHSVTRSCSAGNMTECSCDTTLQNGGSASEGWH<br>WGGCSDDVQYGMWFSRKFLDFPIGNTTGKENKVLLAMNLHNNE<br>AGRQAVAKLMSVDCRCHGVSGSCAVKTCWKTMSSFEKIGHLLKD<br>KYENSIQISDKTKRKMRRREKDQRKIPIHKDDLLYVNKSPNYCVED<br>KKLGIPGTQGRECNRTSEGADGCNLLCCGRGYNTHVVRHVERCEC<br>KFIWCCYVRCRRCESMTDVHTCK | 100 |
| NRG1 | SHLVKCAEKEKTFCVNGGECFMVKDLSNPSRYLCKCPNEFTGDRC<br>QNYVMASFYKHLGIEFMEAE | 101 |

As used herein, reference to a mammalian growth factor includes the mature peptide of any mammalian growth factor herein. In some embodiments, the mature peptide is a canonically accepted mature peptide. For instance, in some embodiments the mammalian growth factor does not comprise a signal sequence. In some embodiments, the mammalian growth factor does not comprise the full-length pro-protein. In some embodiments, the mammalian growth factor has the amino acid sequence of the secreted growth factor in vivo. Furthermore, as used herein, reference to a mammalian growth factor includes a functional portion of the mammalian growth factor. A function portion of the mammalian growth factor is a region that has a therapeutic effect. For instance, a functional portion of a mammalian growth factor is osteoinductive. As another example, a functional portion of a mammalian growth factor is capable of initiating and/or enhancing bone repair. A functional portion of a mammalian growth factor may have osteogenic activity.

Non-limiting in vitro assays to determine whether a growth factor or portion thereof, such as those described herein, has osteogenic activity are described in Kim et al., Amino Acids 42:1455-1465, 2012; Lee et al., ACS Med. Chem. Lett. 2(3):248-251, 2011; and Wang et al., Genetics Mol. Res. 13(2):4456-4465, 2014.

In some embodiments, the mammalian growth factor comprises a sequence that is at least 70% identical (e.g., at least 75% identical, at least 80% identical, at least 85% identical, at least 90% identical, at least 95% identical, or at least 99% identical) to any of the sequences in Table B or any secreted human growth factor, and has osteogenic activity. In some embodiments, the amino acids in a mammalian growth factor that are conserved between different species are likely important for osteogenic activity and may not be mutated, while amino acids in a mammalian growth factor that are not conserved between different species are not likely important for osteogenic activity and may be mutated.

In some embodiments, the mammalian growth factor comprises BMP-2. In some embodiments, the mammalian growth factor is a mature peptide of BMP-2 (e.g., does not comprise a signal sequence). In some embodiments, the mammalian growth factor comprises a functional portion of BMP-2. In some embodiments, the functional portion of BMP-2 comprises a sequence at least about 70%, 75%, 80%, 85%, 90%, 95%, or 100% identical to QAKHKQRKRLKSSCKRHPLYVDFSDVGWND-WIVAPPGYHAFYCHGECPFPLADHLNSTNH AIVQTLVNSVNSKIPKACCVPTELSAISM-LYLDENEKVVLKNYQDMVVEGCGCR (SEQ ID NO: 32). In some embodiments, the mammalian growth factor comprises a sequence at least about 70%, 75%, 80%, 85%, 90%, 95%, or 100% identical to SEQ ID NO: 32. In some embodiments, the mammalian growth factor comprises a sequence at least about 90% identical to SEQ ID NO: 32. In some embodiments, the mammalian growth factor comprises SEQ ID NO: 32.

Targeting Polypeptides

Also provided herein are targeting polypeptides. In some embodiments, the targeting polypeptide comprises two or more targeting polypeptides. In some embodiments, two or more targeting polypeptides is no more than about 50, 45, 40, 35, 30, 25, 20, 15, or 10 targeting polypeptides. In some embodiments, two or more targeting polypeptides is about 2, 3, 4, 5, 6, 7, 8, 9, 10, 11, 12, 13, 14, 15, 20, 25, or 30 targeting polypeptides. In some embodiments, two or more targeting polypeptides is about 2 to about 10 targeting polypeptides. In some embodiments, two or more targeting polypeptides is about 5 targeting polypeptides. In some embodiments, the targeting polypeptide binds to a carrier material, as noted elsewhere herein. As a non-limiting example, the targeting polypeptide binds to a calcium phosphate.

In some embodiments, the targeting polypeptide comprises a sequence at least about 70%, 75%, 80%, 85%, 90%, 95%, or 100% identical to SEQ ID NO: 1. In some embodiments, the targeting polypeptide comprises a sequence at least about 70%, 75%, 80%, 85%, 90%, 95%, or 100% identical to SEQ ID NO: 2. In some embodiments, the targeting polypeptide comprises a sequence at least about 70%, 75%, 80%, 85%, 90%, 95%, or 100% identical to SEQ ID NO: 3. In some embodiments, the targeting polypeptide comprises a sequence at least about 70%, 75%, 80%, 85%, 90%, 95%, or 100% identical to SEQ ID NO: 4. In some embodiments, the targeting polypeptide comprises a sequence at least about 70%, 75%, 80%, 85%, 90%, 95%, or 100% identical to SEQ ID NO: 5. In some embodiments, the targeting polypeptide comprises a sequence at least about 70%, 75%, 80%, 85%, 90%, 95%, or 100% identical to SEQ ID NO: 6. In some embodiments, the targeting polypeptide comprises a sequence at least about 70%, 75%, 80%, 85%, 90%, 95%, or 100% identical to SEQ ID NO: 7. In some embodiments, the targeting polypeptide comprises a sequence at least about 70%, 75%, 80%, 85%, 90%, 95%, or 100% identical to SEQ ID NO: 8. In some embodiments, the targeting polypeptide comprises a sequence at least about 70%, 75%, 80%, 85%, 90%, 95%, or 100% identical to SEQ ID NO: 9. In some embodiments, the targeting polypeptide comprises a sequence at least about 70%, 75%, 80%, 85%, 90%, 95%, or 100% identical to SEQ ID NO: 10. In some embodiments, the targeting polypeptide comprises a sequence at least about 70%, 75%, 80%, 85%, 90%, 95%, or 100% identical to SEQ ID NO: 11. In some embodiments, the targeting polypeptide comprises a sequence at least about 70%, 75%, 80%, 85%, 90%, 95%, or 100% identical to SEQ ID NO: 12. In some embodiments, the targeting polypeptide comprises a sequence at least about 70%, 75%, 80%, 85%, 90%, 95%, or 100% identical to SEQ ID NO: 13. In some embodiments, the targeting polypeptide comprises a sequence at least about 70%, 75%, 80%, 85%, 90%, 95%, or 100% identical to SEQ ID NO: 14. In some embodiments, the targeting polypeptide comprises a sequence at least about 70%, 75%, 80%, 85%, 90%, 95%, or 100% identical to SEQ ID NO: 15. In some embodiments, the targeting polypeptide comprises a sequence at least about 70%, 75%, 80%, 85%, 90%, 95%, or 100% identical to SEQ ID NO: 16. In some embodiments, the targeting polypeptide comprises a sequence at least about 70%, 75%, 80%, 85%, 90%, 95%, or 100% identical to SEQ ID NO: 17. In some embodiments, the targeting polypeptide comprises a sequence at least about 70%, 75%, 80%, 85%, 90%, 95%, or 100% identical to SEQ ID NO: 18. In some embodiments, the targeting polypeptide comprises a sequence at least about 70%, 75%, 80%, 85%, 90%, 95%, or 100% identical to SEQ ID NO: 19. In some embodiments, the targeting polypeptide comprises a sequence at least about 70%, 75%, 80%, 85%, 90%, 95%, or 100% identical to SEQ ID NO: 20. In some embodiments, the targeting polypeptide comprises a sequence at least about 70%, 75%, 80%, 85%, 90%, 95%, or 100% identical to SEQ ID NO: 21. In some embodiments, the targeting polypeptide comprises a sequence at least about 70%, 75%, 80%, 85%, 90%, 95%, or 100% identical to SEQ ID NO: 22. In some embodiments, the targeting polypeptide comprises a sequence at least about 70%, 75%, 80%, 85%, 90%, 95%, or 100% identical to SEQ ID NO: 23. In some embodiments, the targeting polypeptide comprises a sequence at least about 70%, 75%, 80%, 85%, 90%, 95%, or 100% identical to SEQ ID NO: 24. In some embodiments, the targeting polypeptide comprises a sequence at least about 70%, 75%, 80%, 85%, 90%, 95%, or 100% identical to SEQ ID NO: 25. In some embodiments, the targeting polypeptide comprises a sequence at least about 70%, 75%, 80%, 85%, 90%, 95%, or 100% identical to SEQ ID NO: 26. In some embodiments, the targeting polypeptide comprises a sequence at least about 70%, 75%, 80%, 85%, 90%, 95%, or 100% identical to SEQ ID NO: 27. In some embodiments, the targeting polypeptide comprises a sequence at least about 70%, 75%, 80%, 85%, 90%, 95%, or 100% identical to SEQ ID NO: 28. In some embodiments, the targeting polypeptide comprises a sequence at least about 70%, 75%, 80%, 85%, 90%, 95%, or 100% identical to SEQ ID NO: 29. In some embodiments, the targeting polypeptide comprises a sequence at least about 70%, 75%, 80%, 85%, 90%, 95%, or 100% identical to SEQ ID NO: 30. In some embodiments, the targeting polypeptide comprises a sequence at least about 70%, 75%, 80%, 85%, 90%, 95%, or 100% identical to SEQ ID NO: 31. In some embodiments, the targeting polypeptide comprises a sequence at least about 70%, 75%, 80%, 85%, 90%, 95%, or 100% identical to SEQ ID NO: 36. In some embodiments, the targeting polypeptide comprises a sequence at least about 70%, 75%, 80%, 85%, 90%, 95%, or 100% identical to SEQ ID NO: 37. In some embodiments, the targeting polypeptide comprises a sequence at least about 70%, 75%, 80%, 85%, 90%, 95%, or 100% identical to SEQ ID NO: 38. In some embodiments, the targeting polypeptide comprises a sequence at least about 70%, 75%, 80%, 85%, 90%, 95%, or 100% identical to SEQ ID NO: 39. In some embodiments, the targeting polypeptide comprises a sequence at least about 70%, 75%, 80%, 85%, 90%, 95%, or 100% identical to SEQ ID NO: 40. In some embodiments, the targeting polypeptide comprises a sequence at least about 70%, 75%, 80%, 85%, 90%, 95%, or 100% identical to SEQ ID NO: 41. In some embodiments, the targeting polypeptide comprises a sequence at least about 70%, 75%, 80%, 85%, 90%, 95%, or 100% identical to SEQ ID NO: 42. In some embodiments, the targeting polypeptide comprises a sequence at least about 70%, 75%, 80%, 85%, 90%, 95%, or 100% identical to SEQ ID NO: 43. In some embodiments, the targeting polypeptide comprises a sequence at least about 70%, 75%, 80%, 85%, 90%, 95%, or 100% identical to SEQ ID NO: 401. In some embodiments, the targeting polypeptide comprises a sequence at least about 70%, 75%, 80%, 85%, 90%, 95%, or 100% identical to SEQ ID NO: 402. In some embodiments, the targeting polypeptide comprises a sequence at least about 70%, 75%, 80%, 85%, 90%, 95%, or 100% identical to SEQ ID NO: 403. In some embodiments, the targeting polypeptide comprises a sequence at least about 70%, 75%, 80%, 85%, 90%, 95%, or 100% identical to SEQ ID NO: 404. In some embodiments, the targeting polypeptide comprises a sequence at least about 70%, 75%, 80%, 85%, 90%, 95%, or 100% identical to SEQ ID NO: 405. In some embodiments, the targeting polypeptide comprises a sequence at least about 70%, 75%, 80%, 85%, 90%, 95%, or 100% identical to SEQ ID NO: 406. In some embodiments, the targeting polypeptide comprises a sequence at least about 70%, 75%, 80%, 85%, 90%, 95%, or 100% identical to SEQ ID NO: 407. In some embodiments, the targeting polypeptide comprises a sequence at least about 70%, 75%, 80%, 85%, 90%, 95%, or 100% identical to SEQ ID NO: 408. In some embodiments, the targeting polypeptide comprises a sequence at least about 70%, 75%, 80%, 85%, 90%, 95%, or 100% identical to SEQ ID NO: 409. In some embodiments, the targeting polypeptide comprises a sequence at least about 70%, 75%, 80%, 85%, 90%, 95%, or 100% identical to SEQ ID NO: 410. In some embodiments, the targeting polypeptide comprises a sequence at least about 70%, 75%, 80%, 85%, 90%, 95%, or 100% identical to SEQ ID NO: 411. In some embodiments, the targeting polypeptide comprises a sequence at least about 70%, 75%, 80%, 85%, 90%, 95%, or 100% identical to SEQ ID NO: 412. In some embodiments, the targeting polypeptide comprises a sequence at least about 70%, 75%, 80%, 85%, 90%, 95%, or 100% identical to SEQ ID NO: 413. In some embodiments, the targeting polypeptide comprises a sequence at least about 70%, 75%, 80%, 85%, 90%, 95%, or 100% identical to SEQ ID NO: 414. In some embodiments, the targeting polypeptide comprises a sequence at least about 70%, 75%, 80%, 85%, 90%, 95%, or 100% identical to SEQ ID NO: 415. In some embodiments, the targeting polypeptide comprises a sequence at least about 70%, 75%, 80%, 85%, 90%, 95%, or 100% identical to SEQ ID NO: 416. In some embodiments, the targeting polypeptide comprises a sequence at least about 70%, 75%, 80%, 85%, 90%, 95%, or 100% identical to SEQ ID NO: 417. In some embodiments, the targeting polypeptide comprises a sequence at least about 70%, 75%, 80%, 85%, 90%, 95%, or 100% identical to SEQ ID NO: 418. In some embodiments, the targeting polypeptide comprises a sequence at least about 70%, 75%, 80%, 85%, 90%, 95%, or 100% identical to SEQ ID NO: 419. In some embodiments, the targeting polypeptide comprises a sequence at least about 70%, 75%, 80%, 85%, 90%, 95%, or 100% identical to SEQ ID NO: 420. In some embodiments, the targeting polypeptide comprises a sequence at least about 70%, 75%, 80%, 85%, 90%, 95%, or 100% identical to SEQ ID NO: 421. In some embodiments, the targeting polypeptide comprises a sequence at least about 70%, 75%, 80%, 85%, 90%, 95%, or 100% identical to SEQ ID NO: 422.

In some embodiments, the targeting polypeptide comprises Formula I:

$A_0B_0C_0D_0E_0F_0G_0H_0I_0J_0K_0L_0$ (Formula I) (SEQ ID NO: 35), where: $A_0$ is V, L, I, G, S, T, or A; $B_0$ is I, L, V, Q, T, S, G, or A; $C_0$ is G, A, V, or S; $D_0$ is E, D, L, or G; $E_0$ is S, T, P T, E, or D; $F_0$ is T or S; $G_0$ is H, T, or S; $H_0$ is H or T; $I_0$ is R, S, K, P, or H; $J_0$ is P, S, R, or K; $K_0$ is W, F, S, P, V, A, or G; and $L_0$ is absent or is S, T, G, (or A). In some embodiments, Formula I does not include LLADTTHHRPWT (SEQ ID NO: 1).

(1) Provided herein is a first embodiment of a targeting polypeptide comprising Formula I. (2) The targeting polypeptide of embodiment 1, wherein A0 is V. (3) The targeting polypeptide of embodiment 1, wherein A0 is L. (4) The targeting polypeptide of embodiment 1, wherein A0 is I. (5) The targeting polypeptide of embodiment 1, wherein A0 is G. (6) The targeting polypeptide of embodiment 1, wherein A0 is S. (7) The targeting polypeptide of embodiment 1, wherein A0 is T. (8) The targeting polypeptide of embodiment 1, wherein A0 is A. (9) The targeting polypeptide of any one of embodiments 1-8, wherein B0 is I. (10) The targeting polypeptide of any one of embodiments 1-8, wherein B0 is L. (11) The targeting polypeptide of any one of embodiments 1-8, wherein B0 is V. (12) The targeting polypeptide of any one of embodiments 1-8, wherein B0 is Q. (13) The targeting polypeptide of any one of embodiments 1-8, wherein B0 is T. (14) The targeting polypeptide of any one of embodiments 1-8, wherein B0 is S. (15) The targeting polypeptide of any one of embodiments 1-8, wherein B0 is G. (16) The targeting polypeptide of any one of embodiments 1-8, wherein B0 is A. (17) The targeting polypeptide of any one of embodiments 1-16, wherein C0 is G. (18) The targeting polypeptide of any one of embodiments 1-16, wherein C0 is A. (19) The targeting polypeptide of any one of embodiments 1-16, wherein C0 is V. (20) The targeting polypeptide of any one of embodiments 1-16, wherein C0 is S. (21) The targeting polypeptide of any one of embodiments 1-20, wherein D0 is E. (22) The targeting polypeptide of any one of embodiments 1-20, wherein D0 is D. (23) The targeting polypeptide of any one of embodiments 1-20, wherein D0 is L. (24) The targeting polypeptide of any one of embodiments 1-20, wherein D0 is G. (25) The targeting polypeptide of any one of embodiments 1-24, wherein E0 is S. (26) The targeting polypeptide of any one of embodiments 1-24, wherein E0 is T. (27) The targeting polypeptide of any one of embodiments 1-24, wherein E0 is P. (28) The targeting polypeptide of any one of embodiments 1-24, wherein E0 is E. (29) The targeting polypeptide of any one of embodiments 1-24, wherein E0 is D. (30) The targeting polypeptide of any one of embodiments 1-29, wherein F0 is T. (31) The targeting polypeptide of any one of embodiments 1-29, wherein F0 is S. (32) The targeting polypeptide of any one of embodiments 1-31, wherein G0 is H. (33) The targeting polypeptide of any one of embodiments 1-31, wherein G0 is T. (34) The targeting polypeptide of any one of embodiments 1-31, wherein G0 is S. (35) The targeting polypeptide of any one of embodiments 1-34, wherein H0 is H. (36) The targeting polypeptide of any one of embodiments 1-34, wherein H0 is T. (37) The targeting polypeptide of any one of embodiments 1-36, wherein I0 is R. (38) The targeting polypeptide of any one of embodiments 1-36, wherein I0 is S. (39) The targeting polypeptide of any one of embodiments 1-36, wherein I0 is K. (40) The targeting polypeptide of any one of embodiments 1-36, wherein I0 is P. (41) The targeting polypeptide of any one of embodiments 1-36, wherein I0 is H. (42) The targeting polypeptide of any one of embodiments 1-41, wherein J0 is P. (43) The targeting polypeptide of any one of embodiments 1-41, wherein J0 is S. (44) The targeting polypeptide of any one of embodiments 1-41, wherein J0 is R. (45) The targeting polypeptide of any one of embodiments 1-41, wherein J0 is K. (46) The targeting polypeptide of any one of embodiments 1-45, wherein K0 is W. (47) The targeting polypeptide of any one of embodiments 1-45, wherein K0 is F. (48) The targeting polypeptide of any one of embodiments 1-45, wherein K0 is S. (49) The targeting polypeptide of any one of embodiments 1-45, wherein K0 is P. (50) The targeting polypeptide of any one of embodiments 1-45, wherein K0 is V. (51) The targeting polypeptide of any one of embodiments 1-45, wherein K0 is A. (52) The targeting polypeptide of any one of embodiments 1-45, wherein K0 is G. (53) The targeting polypeptide of any one of embodiments 1-52, wherein L0 is absent. (54) The targeting polypeptide of any one of embodiments 1-52, wherein L0 is S. (55) The targeting polypeptide of any one of embodiments 1-52, wherein L0 is T. (56) The targeting polypeptide of any one of embodiments 1-52, wherein L0 is G. (57) The targeting polypeptide of any one of embodiments 1-52, wherein L0 is A. (58) A chimeric polypeptide comprising the targeting polypeptide of any one of embodiments 1-57. (59) The chimeric polypeptide of embodiment 58, comprising a therapeutic agent. (60) The chimeric polypeptide of embodiment 59, wherein the therapeutic agent comprises a sequence at least about 70%, 75%, 80%, 85%, 90%, 91%, 92%, 93%, 94%, 95%, 96%, 97%, 98%, 99%, or 100% identical one or more sequences of Table B.

In some embodiments, the targeting polypeptides described herein can have a total length of about 5 amino acids to about 200 amino acids, about 5 amino acids to about 100 amino acids, about 5 amino acids to about 80 amino acids, about 5 amino acids to about 60 amino acids, about 10 amino acids to about 100 amino acids, about 10 amino acids to about 80 amino acids, about 10 amino acids to about 80 amino acids, about 20 amino acids to about 100 amino acids, about 20 amino acids to about 80 amino acids, about 20 amino acids to about 60 amino acids, about 30 amino acids to about 100 amino acids, about 30 amino acids to about 80 amino acids, about 30 amino acids to about 60 amino acids, about 40 amino acids to about 100 amino acids, about 40 amino acids to about 80 amino acids, about 40 amino acids to about 60 amino acids, or about 60 amino acids.

Nucleic Acids/Vectors

Also provided herein are nucleic acids that encode any of the chimeric polypeptides or targeting polypeptides described herein.

Also provided herein are vectors that include any of the nucleic acids provided herein. A "vector" according to the present disclosure is a polynucleotide capable of inducing the expression of a recombinant protein (e.g., any of the chimeric polypeptides or targeting polypeptides described) in a host cell. A vector provided herein can be, e.g., in circular or linearized form. Non-limiting examples of vectors include plasmids, SV40 vectors, adenoviral viral vectors, and adeno-associated virus (AAV) vectors. Non-limiting examples of vectors include lentiviral vectors or retroviral vectors, e.g., gamma-retroviral vectors. See, e.g., Carlens et al., *Exp. Hematol.* 28(10:1137-1146, 2000; Park et al., *Trends Biotechnol.* 29(11):550-557, 2011; and Alonso-Camino et al., *Mol. Ther. Nucleic Acids* 2:e93, 2013. Non-limiting examples of retroviral vectors include those derived from Moloney murine leukemia virus, myeloproliferative sarcoma virus, murine embryonic stem cell virus, murine stem cell virus, spleen focus forming virus, or adeno-associated virus. Non-limiting examples of retroviral vectors are described in, e.g., U.S. Pat. Nos. 5,219,740 and 6,207,453; Miller et al., *BioTechniques* 7:980-990, 1989; Miller, *Human Gene Therapy* 1:5-14, 1990; Scarpa et al., *Virology* 180:849-852, 1991; Burns et al., *Proc. Natl. Acad. Sci. U.S.A.* 90:8033-8037, 1993; and Boris-Lawrie et al., *Cur. Opin. Genet. Develop.* 3:102-109, 1993. Exemplary lentiviral vectors are described in, e.g., Wang et al., *J Immunother.* 35(9):689-701, 2003; Cooper et al., *Blood* 101:1637-1644, 2003; Verhoeyen et al., *Methods Mol. Biol.* 506:97-114, 2009; and Cavalieri et al., *Blood* 102(2):497-505, 2003.

Exemplary vectors, in which any of the nucleic acids provided herein can be inserted, are described in, e.g., Ausubel et al., Eds. "Current Protocols in Molecular Biology" Current Protocols, 1993; and Sambrook et al., Eds. "Molecular Cloning: A Laboratory Manual," 2nd ed., Cold Spring Harbor Press, 1989.

In some embodiments, the vectors further include a promoter and/or enhancer operably linked to any of the nucleic acids described herein. Non-limiting examples of promoters include promoters from human cytomegalovirus (CMV), mouse phosphoglycerate kinase 1, polyoma adenovirus, thyroid stimulating hormone α, vimentin, simian virus 40 (SV40), tumor necrosis factor, β-globin, α-fetoprotein, γ-globin, β-interferon, γ-glutamyl transferase, human ubiquitin C (UBC), mouse mammary tumor virus (MMTV), Rous sarcoma virus, glyceraldehyde-3-phosphate dehydrogenase, β-actin, metallothionein II (MT II), amylase, human EF1α, cathepsin, MI muscarinic receptor, retroviral LTR (e.g. human T-cell leukemia virus HTLV), AAV ITR, interleukin-2, collagenase, platelet-derived growth factor, adenovirus E2, stromelysin, murine MX, rat insulin, glucose regulated protein 78, human immunodeficiency virus, glucose regulated protein 94, α-2-macroglobulin, MHC class I, HSP70, proliferin, immunoglobulin light chain, T-cell receptor, HLA DQα, HLA DQβ, interleukin-2 receptor, MHC class II, prealbumin (transthyretin), elastase I, albumin, c-fos, neural cell adhesion molecule (NCAM), H2B histone, rat growth hormone, human serum amyloid (SAA), muscle creatinine kinase, troponin I (TN I), and Gibbon Ape Leukemia Virus (GALV). In some embodiments, the promoter may be an inducible promoter or a constitutive promoter. Additional examples of promoters are known in the art.

In some examples, the vectors provided herein further include a poly(A) sequence, which is operably linked and positioned 3' to the sequence encoding the chimeric polypeptide or targeting polypeptide. Non-limiting examples of a poly(A) sequence include those derived from bovine growth hormone (Woychik et al., *Proc. Natl. Acad. Sci. U.S.A.* 81(13): 3944-3948, 1984, and U.S. Pat. No. 5,122,458), mouse-β-globin, mouse-α-globin (Orkin et al., *EMBO J.* 4(2): 453-456, 1985), human collagen, polyoma virus (Batt et al., *Mol. Cell Biol.* 15(9):4783-4790, 1995), the Herpes simplex virus thymidine kinase gene (HSV TK), IgG heavy chain gene polyadenylation signal (U.S. Patent Application Publication No. 2006/0040354), human growth hormone (hGH) (Szymanski et al., *Mol. Therapy* 15(7):1340-1347, 2007), SV40 poly(A) site, e.g., SV40 late and early poly(A) site (Schek et al., *Mol. Cell Biol.* 12(12):5386-5393, 1992). In some embodiments, the poly(A) sequence includes a highly conserved upstream element (AATAAA). The this AATAAA sequence can, e.g., be substituted with other hexanucleotide sequences with homology to AATAAA which are capable of signaling polyadenylation, including, e.g., ATTAAA, AGTAAA, CATAAA, TATAAA, GATAAA, ACTAAA, AATATA, AAGAAA, AATAAT, AAAAAA, AATGAA, AATCAA, AACAAA, AATCAA, AATAAC, AATAGA, AATTAA, and AATAAG. See, e.g., WO 06012414 A2).

A poly(A) sequence can, e.g., be a synthetic polyadenylation site. See, e.g., Levitt el al, *Genes Dev.* 3(7): 1019-1025, 1989). In some examples, a poly(A) sequence can be the polyadenylation signal of soluble neuropilin-1: AAATAAAATACGAAATG (SEQ ID NO: 711). Additional examples of poly(A) sequences are known in the art. Additional examples and aspects of vectors are also known in the art.

Methods of Making A Chimeric Polypeptide

Also provided herein are methods of making a chimeric polypeptide (e.g., any of the chimeric polypeptides described herein) or a targeting polypeptide (e.g., any of the targeting polypeptides described herein) that include: introducing into a cell a nucleic acid sequence encoding the chimeric polypeptide or the targeting polypeptide to produce a recombinant cell; and culturing the recombinant cell under conditions sufficient for the expression of the chimeric polypeptide or targeting polypeptide. In some embodiments, the introducing step includes introducing into a cell an expression vector including a nucleic acid sequence encoding the chimeric polypeptide or the targeting polypeptide to produce a recombinant cell. In some embodiments, the expression vector includes chaperones (e.g., GroES, GroEL) and glutathione to aid with in vitro folding.

A chimeric polypeptide or targeting polypeptide described herein can be produced by any cell, e.g., a eukaryotic cell or a prokaryotic cell. As used herein, the term "eukaryotic cell" refers to a cell having a distinct, membrane-bound nucleus. Such cells may include, for example, mammalian (e.g., rodent, non-human primate, or human), insect, fungal, or plant cells. In some embodiments, the eukaryotic cell is a yeast cell, such as *Saccharomyces cerevisiae*. In some embodiments, the eukaryotic cell is a higher eukaryote, such as mammalian, avian, plant, or insect cells. In some embodiments, the eukaryotic cell is a mammalian cell (e.g., a Chinese Hamster Ovary (CHO) cell). As used herein, the term "prokaryotic cell" refers to a cell that does not have a distinct, membrane-bound nucleus. In some embodiments, the prokaryotic cell is a bacterial cell. In some embodiments, the bacterial cell is a chemically competent *E. coli* K12 cell (e.g., Shuffle® T7; New England BioLabs) or a BL21(DE3) pLysS chemically competent *E. coli* cell.

Methods of culturing cells are well known in the art. Cells can be maintained in vitro under conditions that favor proliferation, differentiation, and growth. Briefly, cells can be cultured by contacting a cell (e.g., any cell) with a cell culture medium that includes the necessary growth factors and supplements to support cell viability and growth.

Methods of introducing nucleic acids and expression vectors into a cell (e.g., a eukaryotic cell) are known in the art. Non-limiting examples of methods that can be used to introduce a nucleic acid into a cell include lipofection, transfection, electroporation, microinjection, calcium phosphate transfection, dendrimer-based transfection, cationic polymer transfection, cell squeezing, sonoporation, optical transfection, impalection, hydrodynamic delivery, magnetofection, viral transduction (e.g., adenoviral and lentiviral transduction), and nanoparticle transfection.

Provided herein are methods that further include isolation of the chimeric polypeptide or the targeting polypeptide from a cell (e.g., a eukaryotic cell) using techniques well-known in the art (e.g., ammonium sulfate precipitation, polyethylene glycol precipitation, cobalt column, heparin column, ion-exchange chromatography (anion or cation), chromatography based on hydrophobic interaction, metal-affinity chromatography, ligand-affinity chromatography, and size exclusion chromatography).

Carrier Materials

In one aspect, provided herein are carrier materials that may be combined with a targeting polypeptide, therapeutic agent, and/or chimeric polypeptide herein. In some embodiments, the targeting polypeptide binds to the carrier material. In some embodiments, a carrier material is a material for which a targeting polypeptide herein is capable of binding. In some embodiments, the targeting polypeptide is coated on the surface of the carrier material. Non-limiting examples of carrier materials include calcium phosphate (e.g., tricalcium phosphate), hydroxyapatite, fluorapatite, bone (e.g., demineralized bone), glasses (bioglasses) such as silicates, and vanadates. In an example embodiment, the carrier material comprises a ceramic material.

In some embodiments, provided are devices comprising a carrier material and an agent. In some cases, the agent comprises a therapeutic agent. In some cases, the agent comprises a targeting polypeptide. In some cases, the agent comprises a chimeric polypeptide comprising a targeting polypeptide and a therapeutic agent.

In some embodiments, the targeting polypeptide has an affinity for the carrier material, or a component of the carrier material. In some embodiments, the dissociation constant (KD) for binding between the targeting polypeptide and the carrier material or component thereof is: (i) at least about 1 fM, at least about 10 fM, at least about 100 fM, or at least about 1 pM; and (ii) less than about 100 μM, less than about 90 μM less than about 80 μM, less than about 70 μM, less than about 60 μM, less than about 50 μM, less than about 40 μM, less than about 30 μM, less than about 20 μM, less than about 10 μM, less than about 5 μM, less than about 1 μM, or less than about 100 pM.

In some embodiments, the carrier material is a material in a subject, e.g., a mammalian subject. In some embodiments, the carrier material comprises bone. In some embodiments, the targeting polypeptide binds to bone with a KD of: (i) at least about 1 fM, at least about 10 fM, at least about 100 fM, or at least about 1 pM; and (ii) less than about 100 μM, less than about 90 μM, less than about 80 μM, less than about 70 μM, less than about 60 μM, less than about 50 μM, less than about 40 μM, less than about 30 μM, less than about 20 μM, less than about 10 μM, less than about 5 μM, less than about 1 μM, or less than about 100 pM.

In some embodiments, the carrier material comprises demineralized bone. In some embodiments, the targeting polypeptide binds to bone with a KD of: (i) at least about 1 fM, at least about 10 fM, at least about 100 fM, or at least about 1 pM; and (ii) less than about 100 μM, less than about 90 μM, less than about 80 μM, less than about 70 μM, less than about 60 μM, less than about 50 μM, less than about 40 μM, less than about 30 μM, less than about 20 μM, less than about 10 μM, less than about 5 μM, less than about 1 μM, or less than about 100 pM.

In some embodiments, the carrier material comprises cartilage. In some embodiments, the targeting polypeptide binds to cartilage with a KD of: (i) at least about 1 fM, at least about 10 fM, at least about 100 fM, or at least about 1 pM; and (ii) less than about 100 μM, less than about 90 μM, less than about 80 μM, less than about 70 μM, less than about 60 μM, less than about 50 μM, less than about 40 μM, less than about 30 μM, less than about 20 μM, less than about 10 μM, less than about 5 μM, less than about 1 μM, or less than about 100 pM.

In some embodiments, the carrier material comprises calcium phosphate. In some embodiments, the carrier material comprises tricalcium phosphate. In some embodiments, the targeting polypeptide binds to tricalcium phosphate with a KD of: (i) at least about 1 fM, at least about 10 fM, at least about 100 fM, or at least about 1 pM; and (ii) less than about 100 μM, less than about 90 μM, less than about 80 μM, less than about 70 μM, less than about 60 μM, less than about 50 μM, less than about 40 μM, less than about 30 μM, less than about 20 μM, less than about 10 μM, less than about 5 μM, less than about 1 μM, or less than about 100 pM.

In some embodiments, the carrier material comprises β-TCP. In some embodiments, the targeting polypeptide binds to β-TCP with a KD of: (i) at least about 1 fM, at least about 10 fM, at least about 100 fM, or at least about 1 pM; and (ii) less than about 100 μM, less than about 90 μM, less than about 80 μM, less than about 70 μM, less than about 60 μM, less than about 50 μM, less than about 40 μM, less than about 30 μM, less than about 20 μM, less than about 10 μM, less than about 5 μM, less than about 1 μM, or less than about 100 pM.

In some embodiments, the carrier material comprises alpha tricalcium phosphate. In some embodiments, the targeting polypeptide binds to alpha tricalcium phosphate with a KD of: (i) at least about 1 fM, at least about 10 fM, at least about 100 fM, or at least about 1 pM; and (ii) less than about 100 μM, less than about 90 μM, less than about 80 μM, less than about 70 μM, less than about 60 μM, less than about 50

μM, less than about 40 μM, less than about 30 μM, less than about 20 μM, less than about 10 μM, less than about 5 μM, less than about 1 μM, or less than about 100 pM.

In some embodiments, the carrier material comprises hydroxyapatite. In some embodiments, the targeting polypeptide binds to hydroxyapatite with a KD of: (i) at least about 1 fM, at least about 10 fM, at least about 100 fM, or at least about 1 pM; and (ii) less than about 100 μM, less than about 90 μM, less than about 80 μM, less than about 70 μM, less than about 60 μM, less than about 50 μM, less than about 40 μM, less than about 30 μM, less than about 20 μM, less than about 10 μM, less than about 5 μM, less than about 1 μM, or less than about 100 pM.

In some embodiments, the carrier material comprises fluorapatite. In some embodiments, the targeting polypeptide binds to β-TCP with a KD of: (i) at least about 1 fM, at least about 10 fM, at least about 100 fM, or at least about 1 pM; and (ii) less than about 100 μM, less than about 90 μM, less than about 80 μM, less than about 70 μM, less than about 60 μM, less than about 50 μM, less than about 40 μM, less than about 30 μM, less than about 20 μM, less than about 10 μM, less than about 5 μM, less than about 1 μM, or less than about 100 pM.

In some embodiments, the carrier material comprises glass. In some embodiments, the glass comprises a bioglass. In some embodiments, the glass comprises a silicate. In some embodiments, the targeting polypeptide binds to a glass with a KD of: (i) at least about 1 fM, at least about 10 fM, at least about 100 fM, or at least about 1 pM; and (ii) less than about 100 μM, less than about 90 μM, less than about 80 μM, less than about 70 μM, less than about 60 μM, less than about 50 μM, less than about 40 μM, less than about 30 μM, less than about 20 μM, less than about 10 μM, less than about 5 μM, less than about 1 μM, or less than about 100 pM.

In some embodiments, the carrier material comprises a ceramic mineral. In some embodiments, the targeting polypeptide binds to the ceramic mineral with a KD of: (i) at least about 1 fM, at least about 10 fM, at least about 100 fM, or at least about 1 pM; and (ii) less than about 100 μM, less than about 90 μM, less than about 80 μM, less than about 70 μM, less than about 60 μM, less than about 50 μM, less than about 40 μM, less than about 30 μM, less than about 20 μM, less than about 10 μM, less than about 5 μM, less than about 1 μM, or less than about 100 pM.

In some embodiments, the carrier material comprises a vanadate.

In some embodiments, the carrier material comprises a chelated divalent metal ion.

In some embodiments, a dissociation constant is measured using any method known in the art and/or mentioned herein. In some embodiments, the dissociation constant is measured using a release assay, wherein sample protein released into solution is quantified using ELISA. In some embodiments, the dissociation constant is measured using released fluorescence, e.g., using a carrier material bound to green fluorescent protein (GFP). In some embodiments, the dissociation constant is measured using the targeting polypeptide. In some embodiments, the dissociation constant is measured using a chimeric polypeptide comprising the targeting polypeptide. In some embodiments, the dissociation constant is measured using the carrier material. In some embodiments, the dissociation constant is measured using the component of the carrier material (e.g., a tricalcium phosphate or a hydroxyapatite).

In some embodiments, the targeting polypeptide is capable of remaining bound to the carrier polypeptide in a physiological buffer (e.g., phosphate buffered saline) at 37° C. for at least about 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. In some embodiments, the binding is measured using the targeting polypeptide. In some embodiments, the binding is measured using a chimeric polypeptide comprising the targeting polypeptide. In some embodiments, the binding is measured using the carrier material. In some embodiments, the binding is measured using the component of the carrier material (e.g., a tricalcium phosphate or a hydroxyapatite).

β-TCP

Sintering of tricalcium phosphate, $Ca_3(PO_4)_2$, causes its structure to convert to β-TCP (CAS No. 7758-87-4). β-TCP is an osteoconductive material that supports bone mineralization by easily dissolving at low pH and serves as a rigid substrate for cell attachment.

In some embodiments, reference to β-TCP includes reference to a carrier material comprising β-TCP. For instance, compositions described herein comprising a chimeric polypeptide and β-TCP include compositions comprising the chimeric polypeptide and a carrier material comprising β-TCP. In some embodiments, the β-TCP carrier material comprises at least about 10%, 15%, 20%, 25%, 30%, 35%, 40%, 45%, 50%, 55%, 60%, 65%, 70%, 75%, 80%, 85%, 90%, or 95% by weight β-TCP. In a non-limiting example, the β-TCP carrier material comprises about 30% to about 50%, or about 40%, β-TCP. β-TCP as described herein can be in a variety of different forms. Examples of such forms include a granular form, a porous form, a powder, a putty (e.g., a moldable putty), a paste, a scaffold, fiber form, a coating on a solid surface (e.g., a coating on a medical device), or any combination thereof. In addition, the β-TCP can be used in a variety of different shapes (e.g., a cross, a ladder, a sphere, an ellipsoid, a square, a triangular pyramid, a rod, a cone, a torus, or a wedge, or any combination thereof) and sizes (e.g., largest average diameter of about 1 mm, about 2 mm, about 3 mm, about 4 mm, about 5 mm, about 6 mm, about 7 mm, about 8 mm, about 9 mm, about 1 cm, about 2 cm, about 3 cm, about 4 cm, about 5 cm, about 6 cm, about 7 cm, about 8 cm, about 9 cm, or about 10 cm). In some embodiments, a β-TCP carrier material is porous (e.g., about 90%, about 91%, about 92%, about 93%, about 94%, about 95%, about 96%, about 97%, about 98%, or about 99% porous when dry (no hydration)). In some embodiments, a β-TCP carrier material is about 90% to about 99%, or about 95% to about 99% porous when dry. In some embodiments, a β-TCP carrier material is about 98% porous when dry.

In some embodiments, a β-TCP carrier material comprises one or more additional materials. In some embodiments, the one or more additional materials comprises siloxane-containing vaterite (SiV). In some embodiments, the one or more additional materials comprises poly(L-lactide-co-glycolide) (PLGa, CAS No. 30846-39-0). In some embodiments, the carrier material comprises about 40% by weight β-TCP, about 30% by weight SiV, and about 30% by weight PLGa.

In some embodiments, the β-TCP is in the form of fibers. In some embodiments, the fiber is formed by electrospinning. In some embodiments, the fiber is resorbable. In some embodiments, the fiber diameter is from about 1 μM to about 500 μM, or from about 1 μM to about 300 μM, from about 3 μM to about 250 μM, or from about 3 μM to about 150 μM. In some embodiments, the maximum fiber diameter is about 500 μM, about 400 μM, about 300 μM, or about 250 μM. In some embodiments, the true density (pycnometry) is from about 1 g/cm3 to about 10 g/cm3, from about 1 g/cm3 to about 5 g/cm3, or about 1, 2, 3, 4, or 5 g/cm3. For example, the true density is about 2.5 g/cm3.

In some embodiments, the β-TCP fiber comprises β-TCP and a bioabsorbable polymer. In some embodiments, the β-TCP fiber comprises β-TCP and calcium carbonate. In some cases, the calcium carbonate comprises silicone. In some embodiments, the β-TCP fiber comprises β-TCP, a bioabsorbable polymer or resin, and calcium carbonate. In some embodiments, the β-TCP fiber is biodegradable. In some embodiments, the bioabsorbable polymer comprises polylactic acid (PLA) and/or polylactic acid-glycolic acid copolymer (PLGA). A non-limiting example for preparing a β-TCP fiber herein comprises electrospinning. In some embodiments, the β-TCP fiber comprises a PLGA resin comprising calcium phosphate particles, where the fiber is produced using electrospinning. In some embodiments, the calcium phosphate particles comprise silicon.

In some embodiments, the β-TCP fiber comprises PLA and β-TCP silicon-comprising vaterite. In some embodiments, the β-TCP fiber comprises a biodegradable fiber produced by electrospinning, wherein the biodegradable fiber comprises calcium phosphate particles in an amount of 40% to 60% by weight, silicon-releasing calcium carbonate particles in an amount of 10% by weight or more, and a poly-L-lactic acid polymer in an amount of 30% by weight or more as the remainder, and wherein an amount of amorphous phase of the poly-L-lactic acid polymer is from 75% to 98% by weight.

As a non-limiting example, the β-TCP fiber comprises ReBOSSIS® (ORTHOReBIRTH). As another non-limiting example, the β-TCP fiber comprises ReBOSSIS85 Bone Void Filler (ORTHOReBIRTH).

In some embodiments, a targeting polypeptide herein is combined with a β-TCP fiber. In some embodiments, the targeting polypeptide comprises a sequence at least about 70%, 75%, 80%, 85%, 90%, 95%, or 100% identical to one or more of SEQ ID NO: 1-31, 36-43, or 401-422. In some embodiments, the targeting polypeptide is part of a chimeric polypeptide further comprising a therapeutic agent. In some embodiments, the therapeutic agent comprises a mammalian growth factor. In some embodiments, the mammalian growth factor comprises the mature peptide of the mammalian growth factor. As a non-limiting example, the mammalian growth factor comprises the mature peptide of BMP-2, comprising a sequence at least about 70%, 75%, 80%, 85%, 90%, 95%, or 100% identical to SEQ ID NO: 32. In some embodiments, the β-TCP fiber is ReBOSSIS85 Bone Void Filler.

In an exemplary embodiment, a chimeric polypeptide comprises a sequence at least about 70%, 75%, 80%, 85%, 90%, 95%, or 100% identical to SEQ ID NO: 502.

Compositions and Kits

Also provided herein are compositions (e.g., pharmaceutical compositions) that include any of the chimeric polypeptides or targeting polypeptides described herein. In some examples, the compositions can further include β-TCP (e.g., any of the types of β-TCP described herein). In some examples, the β-TCP is formulated as a powder, a putty (e.g., a moldable putty), a paste, a scaffold (e.g., a porous scaffold), a sponge, and/or a coating on a solid surface (e.g., a coating on a medical device). In some examples, the β-TCP can be disposed on or in a scaffold, a mesh, or a sponge (e.g., a resorbable sponge).

In some instances, the compositions (e.g., pharmaceutical compositions) are disposed in a sterile vial or a pre-loaded syringe.

In some instances, the compositions (e.g., pharmaceutical compositions) are formulated for different routes of administration (e.g., intraarticular, injection into a joint, or injection proximal to a bone fissure or fracture). Single or multiple administrations of any of the pharmaceutical compositions described herein can be given to a subject depend on, for example: the dosage and frequency as required and tolerated by the subject. A dosage of the pharmaceutical composition should provide a sufficient quantity of the chimeric polypeptide to effective treat or ameliorate conditions (e.g., bone defects, bone fractures, cartilage defects, or cartilage loss), or symptoms.

Also provided herein are kits that include any of the chimeric polypeptides or any of the targeting polypeptides described herein, or any of the compositions (e.g., pharmaceutical compositions) described herein. In some embodiments, the kits can include instructions for performing any of the methods described herein. In some instances, the kits can include at least one dose of any of the compositions (e.g., pharmaceutical compositions) described herein. In some embodiments, the kits can include a syringe for administering any of the pharmaceutical compositions described herein. The kits described herein are not so limited; other variations will be apparent to one of ordinary skill in the art.

Methods of Making a Composition

Also provided herein are methods of producing any of the compositions described herein. Any of the compositions provided herein can be produced using the methods described herein or methods known in the art. For example, to create a β-TCP scaffold, granulated β-TCP powder can be sintered, sieved, and fabricated into a desired shape (e.g., any of the shapes described herein). In some examples, the purity of the β-TCP present in any of the compositions described herein can be greater than about 75%, greater than 80%, greater than 85%, greater than 90%, greater than 95%, or greater than 99% pure. In some examples, the purity of β-TCP present in any of the compositions described herein can be greater than 1%, greater than 2%, greater than 3%, greater than 4%, greater than 5%, greater than 6%, greater than 7%, greater than 8%, greater than 9%, greater than 10%, greater than 12%, greater than 14%, greater than 15%, greater than 16%, greater than 18%, greater than 20%, greater than 22%, greater than 24%, greater than 25%, greater than 26%, greater than 28%, greater than 30%, greater than 32%, greater than 34%, greater than 35%, greater than 36%, greater 38%, greater 40%, greater than 42%, greater than 44%, greater than 45%, greater than 46%, greater than 48%, greater than 50%, greater than 52%, greater than 54%, greater than 55%, greater than 56%, greater than 58%, greater than 60%, greater than 62%, greater than 64%, greater than 65%, greater than 66%, greater than 68%, greater than 70%, greater than 72%, greater than 74%. In some examples, the β-TCP is made using a similar method but as a composite with other agents, such as a biocompatible polymer, e.g., polylactide-co-glycolide.

As will be apparent to those of skill in the art, the composition can further include one or more pore forming agents. Examples of pore forming agents include, e.g., inorganic salts, such as sodium chloride, saccharides (e.g., sucrose or glucose), gelatin (e.g., gelatin spheres), or paraffin (e.g., paraffin spheres).

The compositions described herein can be generated by contacting any of the chimeric polypeptides or any of the targeting polypeptides to any of the types of β-TCP described herein. In some embodiments, the β-TCP can be in the form of a granular/powder form, a porous form, a putty (e.g., a moldable putty), a paste, a scaffold, and/or a coating on a solid surface (e.g., a coating on a medical device).

Methods of Treatment

In one aspect, provided herein are methods of treating a subject with a polypeptide or composition described herein. For example, the subject is treated with a chimeric polypeptide described herein. As another example, the subject is treated with a composition described herein. For instance, a chimeric polypeptide comprising BMP-2 and a carrier comprising calcium phosphate. In some embodiments, the subject is suffering from a defect in bone, cartilage, soft tissue, tendon, fascia, ligament, organ, osteotendinous tissue, dermal, or osteochondral, or a combination of one or more of the aforementioned defects. In some embodiments, a defect is a lack of bone, cartilage, soft tissue, tendon, fascia, ligament, organ, osteotendinous tissue, dermal, or osteochondral, or a combination of one or more of the aforementioned defects. In some embodiments, a defect in the subject arises from trauma. In some embodiments, a defect in the subject arises due to a congenital condition. In some embodiments, a defect in the subject arises due to an acquired condition. Non-limiting examples of conditions suitable for treatment with a polypeptide or composition described herein include osteoarthritis, disc degeneration, congenital defect, spinal stenosis, spondylolisthesis, spondylosis, bone fracture, scoliosis, kyphosis, spinal fusion (PLF, and interbody fusions), trauma repair of bone, dental repair, craniomaxillofacial repair, ankle fusion, kyphoplasty, balloon osteoplasty, scaphoid facture repair, tendeno-osseous repair, osteoporosis, avascular necrosis, congenital skeletal malformations, costal reconstruction, subchondral bone repair, cartilage repair (e.g., at low doses), or trauma, or a combination thereof. BMP-2 is also involved in hair follicle development, therefore the methods may comprise treatment to hair follicles. The trauma may be to the bone, cartilage, soft tissue, tendon, fascia, ligament, organ, osteotendinous tissue, or dermal tissue, or osteochondral tissue. In some embodiments, the method is to treat an osteochondral injury.

In some embodiments, a defect refers to the absence, loss, and/or break in a tissue and/or organ of the body.

In some embodiments, a "bone defect" refers to the absence or loss (e.g., partial loss) of bone at an anatomical location in a subject where it would otherwise be present in a control healthy subject. A bone defect may be the result of, e.g., an infection (e.g., osteomyelitis), a tumor, a trauma, or an adverse event of a treatment. A bone defect may also affect the muscles, soft tissue, tendons, or joints surrounding the bone defect and cause injury. In some embodiments, a bone defect includes damage to a soft tissue.

In some embodiments, a "cartilage defect" refers to the absence or loss (e.g., partial loss) of cartilage at an anatomical location in a subject where it would otherwise be present in a control healthy subject. A cartilage defect may be the result of, e.g., disease, osteochondritis, osteonecrosis, or trauma. For example, a cartilage defect may affect the knee joint.

The method may comprise spinal fusion. In some embodiments, spinal fusion is a surgical technique to join two or more vertebrae. In some embodiments, the spinal fusion comprises PLF. In some embodiments, the spinal fusion comprises interbody fusions Provided herein are methods of promoting bone or cartilage formation in a subject in need thereof that include: administering to the subject a therapeutically effective amount of any of the compositions described herein. Some embodiments of these methods can further include first selecting a subject in need of bone or cartilage formation. In some embodiments, the composition is administered to the subject proximal to the desired site of bone or cartilage formation in the subject.

Also provided herein are methods of replacing and/or repairing bone or cartilage in a subject in need thereof that include: administering to the subject a therapeutically effective amount of any of the compositions described herein. Some embodiments of these methods can further include first selecting a subject in need of bone replacement, bone repair, cartilage replacement, or cartilage repair. In some embodiments, the composition is administered to the subject proximal to the desired site of bone or cartilage replacement or repair in the subject.

Also provided herein are methods of treating a bone fracture or bone loss in a subject in need thereof, the method comprising administering to the subject a therapeutically effective amount of any of the compositions described herein. Some embodiments of these methods can further include first selecting a subject having a bone fracture or bone loss. In some embodiments, the composition is administered to the subject proximal to the bone fracture or the site of bone loss in the subject.

Also provided herein are methods of repairing soft tissue in a subject in need thereof that include: administering to the subject a therapeutically effective amount of any of the compositions described herein. Some embodiments of these methods can further include first selecting a subject having a bone fracture or bone loss. In some embodiments, the composition is administered to the subject proximal to the bone fracture or the site of bone loss in the subject.

Also provided herein are methods of localized delivery of a therapeutic to a subject in need thereof that include: administering to the subject a therapeutically effective amount of any of the compositions described herein. Some embodiments of these methods can further include first selecting a subject having a bone fracture or bone loss. In some embodiments, the composition is administered to the subject proximal to the bone fracture or the site of bone loss in the subject.

In some instances, the subject has a bone fracture or a bone defect.

In some instances, the subject requires a vertebral fusion of the spine.

In some instances, the subject has a cartilage tear or cartilage defect.

In other instances, the subject has cartilage loss.

Methods of determining the efficacy of treatment of a bone fracture or bone loss in a subject are known in the art and include, e.g., imaging techniques (e.g., magnetic resonance imaging, X-ray, or computed tomography).

Methods of detecting bone or cartilage formation, or replacement or repair of bone or cartilage in a subject are also known in the art and include, e.g., imaging techniques (e.g., magnetic resonance imaging, X-ray, or computed tomography).

Suitable animal models for treatment of a bone fraction or bone loss, bone or cartilage formation, or bone or cartilage replacement or repair are known in the art. Non-limiting examples of such animal models are described in the Examples and in, e.g., Drosse et al., *Tissue Engineering Part C* 14(1):79-88, 2008; Histing et al., *Bone* 49:591-599, 2011; and Poser et al., Hindawi Publishing Corporation, BioMed Research International; Article ID 348635, 2014.

As used herein, a method of treatment comprises administering to the subject a polypeptide or composition herein.

In some embodiments, the subject is administered a chimeric peptide described herein, (e.g., comprising a targeting polypeptide and optionally a growth factor). In some embodiments, the subject is administered a composition comprising a chimeric peptide described herein and a carrier material. As a non-limiting example, the carrier material is a ceramic material. For instance, the ceramic material comprises calcium phosphate and/or hydroxyapatite.

In some embodiments, administration comprises implanting a polypeptide or composition herein.

In some embodiments, a polypeptide and/or composition herein comprising BMP-2 is administered to the subject. In some embodiments, the BMP-2 comprises a sequence at least about 70%, 75%, 80%, 85%, 90%, 95%, or 100% identical to SEQ ID NO: 32. In some embodiments, the BMP-2 is administered to induce formation of bone in the subject. In some embodiments, the BMP-2 is administered to induce formation of cartilage. In some embodiments, the BMP-2 is administered in a spinal fusion.

In some embodiments, about 0.5 mg to about 10 mg of a polypeptide is administered for every cubic centimeter (cc) of defect volume. For instance, about 0.5-10 mg, about 0.5-9 mg, about 0.5-8 mg, about 0.5-7 mg, about 0.5-6 mg, about 0.5-5 mg, about 0.5-4 mg, about 0.5-3 mg, about 0.5-2 mg, about 1-10 mg, about 1-9 mg, about 1-8 mg, about 1-7 mg, about 1-6 mg, about 1-5 mg, about 1-4 mg, about 1-3 mg, about 1-2 mg, about 2-10 mg, about 2-9 mg, about 2-8 mg, about 2-7 mg, about 2-6 mg, about 2-5 mg, about 2-4 mg, about 2-3 mg, about 3-10 mg, about 3-9 mg, about 3-8 mg, about 3-7 mg, about 3-6 mg, about 3-5 mg, about 3-4 mg, about 4-10 mg, about 4-9 mg, about 4-8 mg, about 4-7 mg, about 4-6 mg, or about 4-5 mg polypeptide is administered for every cc of the defect volume. In some embodiments, at least about 0.5, 1, 1.5, 2, 2.5 or 3 mg of the polypeptide is administered for every cc of the defect volume. In some cases, the polypeptide comprises a chimeric peptide described herein. In some cases, the polypeptide comprises one or more targeting polypeptide, e.g., as described herein. In some cases, the polypeptide comprises a growth factor, e.g., as described herein. In some cases, the defect volume is calculated or estimated by multiplying the length of the defect by the area of the defect (pi multiplied by defect radius squared).

Additional non-limiting embodiments of methods provided herein:

(1) In a first embodiment, provided is a method of delivering a therapeutic agent to an organ or tissue of a subject, the method comprising delivering to the organ or tissue a carrier material comprising the therapeutic agent. (2) The method of embodiment 1, wherein delivery comprises surgically introducing the carrier material to the organ or tissue. (3) The method of embodiment 1 or embodiment 2, wherein the tissue comprises cartilage. (4) The method of anyone of embodiments 1-3, wherein the organ comprises bone. (5) The method of any one of embodiments 1-4, wherein the therapeutic agent is bound to the carrier material. (6) The method of any one of embodiments 1-5, wherein the therapeutic agent is non-covalently bound to the carrier material. (7) The method of any one of embodiments 1-6, wherein the therapeutic agent binds to the carrier material or component thereof with a dissociation constant from about 1 fM to about 100 µM. (8) The method of embodiment 7, wherein the dissociation constant is from about 1 pM to about 100 µM. (9) The method of embodiment 7, wherein the dissociation constant is from about 1 nM to about 100 µM. (10) The method of embodiment 7, wherein the dissociation constant is from about 10 nM to about 100 µM. (11) The method of embodiment 7, wherein the dissociation constant is from about 10 nM to about 10 µM. (12) The method of any one of embodiments 1-11, wherein the carrier material comprises calcium phosphate. (13) The method of any one of embodiments 1-12, wherein the carrier material comprises tricalcium phosphate. (14) The method of any one of embodiments 1-13, wherein the carrier material comprises beta tricalcium phosphate. (15) The method of any one of embodiments 1-14, wherein the carrier material comprises about 20% to about 60% beta tricalcium phosphate by weight. (16) The method of any one of embodiments 1-15, wherein the carrier material comprises about 30% to about 50% beta tricalcium phosphate by weight. (17) The method of any one of embodiments 1-16, wherein the carrier material comprises about 35% to about 45% beta tricalcium phosphate by weight. (18) The method of any one of embodiments 1-17, wherein the carrier material comprises about 35%, 36%, 37%, 38%, 39%, 40%, 41%, 42%, 43%, 44%, or 45% beta tricalcium phosphate by weight. (19) The method of any one of embodiments 1-18, wherein the carrier material comprises about 40% beta tricalcium phosphate by weight. (20) The method of any one of embodiments 1-19, wherein the carrier material comprises alpha tricalcium phosphate. (21) The method of any one of embodiments 1-20, wherein the carrier material comprises hydroxyapatite. (22) The method of any one of embodiments 1-21, wherein the carrier material comprises fluorapatite. (23) The method of any one of embodiments 1-22, wherein the carrier material comprises bone. (24) The method of any one of embodiments 1-23, wherein the carrier material comprises demineralized bone. (25) The method of any one of embodiments 1-24, wherein the carrier material comprises a glass. (26) The method of embodiment 25, wherein the glass comprises a silicate. (27) The method of any one of embodiments 1-26, wherein the carrier material comprises a vanadate. (28) The method of any one of embodiments 1-27, wherein the carrier material comprises a ceramic mineral. (29) The method of any one of embodiments 1-28, wherein the carrier material comprises a chelated divalent metal ion. (30) The method of any one of embodiments 1-28, wherein the carrier material or a component thereof is in the form of fibers. (31) The method of any one of embodiments 1-28, wherein the carrier material or a component thereof is in a granular form. (32) The method of any one of embodiments 1-28, wherein the carrier material or a component thereof is in a porous form. (33) The method of any one of embodiments 1-28, wherein the carrier material or a component thereof is a powder. (34) The method of any one of embodiments 1-28, wherein the carrier material or a component thereof is a putty. (35) The method of any one of embodiments 1-28, wherein the carrier material or a component thereof is a paste. (36) The method of any one of embodiments 30-35, wherein the component thereof comprises calcium phosphate (e.g., tricalcium phosphate such as beta-TCP or alpha-TCP). (37) The method of any one of embodiments 30-35, wherein the component thereof comprises hydroxyapatite, demineralized bone, fluorapatite, a glass, vanadate, ceramic material, or chelated divalent metal ion, or any combination thereof. (38) The method of any one of embodiments 1-37, wherein the subject comprises a defect in organ or tissue, and the therapeutic agent is delivered to reduce or eliminate the defect in the organ or tissue. (39) The method of embodiment 38, wherein the defect in the organ or tissue comprises a bone defect. (40) The method of embodiment 38 or embodiment 39, wherein the defect in the organ or tissue comprises a cartilage defect. (41) The method of any one of embodiments 38-40, wherein the defect in the organ or tissue comprises a soft tissue defect. (42) The method of any one of embodiments 38-41, wherein the defect in the organ or tissue comprises a tendon defect. (43) The method of any one of embodiments 38-42, wherein the defect in the organ or tissue comprises a fascia defect. (44) The method of any one of embodiments 38-43, wherein the defect in the organ or tissue comprises a ligament defect. (45) The method of any one of embodiments 38-44, wherein the defect in the organ or tissue comprises an osteotendinous tissue defect. (46) The method of any one of embodiments 38-45, wherein the defect in the organ or tissue comprises a dermal defect. (47) The method of any one of embodiments 38-46, wherein the defect in the organ or tissue comprises an osteochondral defect. (48) The method of any one of embodiments 1-47, wherein the method is performed for spinal fusion in the subject. (49) The method of embodiment 48, wherein the spinal fusion comprises posterior lumbar fusion (PLF). (50) The method of embodiment 48, wherein the spinal fusion comprises interbody fusion. (51) The method of any one of embodiments 1-47, wherein the method is performed for trauma repair of bone. (52) The method of any one of embodiments 1-47, wherein the method is performed for dental repair. (53) The method of any one of embodiments 1-47, wherein the method is performed for craniomaxillofacial repair. (54) The method of any one of embodiments 1-47, wherein the method is performed for ankle fusion. (55) The method of any one of embodiments 1-47, wherein the method is performed for kyphoplasty. (56) The method of any one of embodiments 1-47, wherein the method is performed for balloon osteoplasty. (57) The method of any one of embodiments 1-47, wherein the method is performed for scaphoid facture repair. (58) The method of any one of embodiments 1-47, wherein the method is performed for tendeno-osseous repair. (59) The method of any one of embodiments 1-47, wherein the method is performed to treat osteoporosis. (60) The method of any one of embodiments 1-47, wherein the method is performed to treat avascular necrosis. (61) The method of any one of embodiments 1-47, wherein the method is performed to treat congenital skeletal malformations. (62) The method of any one of embodiments 1-47, wherein the method is performed for costal reconstruction. (63) The method of any one of embodiments 1-47, wherein the method is performed for subchondral bone repair. (64) The method of any one of embodiments 1-47, wherein the method is performed for cartilage repair. (65) The method of any one of embodiments 1-47, wherein the method is performed on a hair follicle (BMP-2 is involved in hair follicle development). (66) The method of any one of embodiments 1-65, wherein the subject is a mammal. (67) The method of any one of embodiments 1-66, wherein the subject is a human. (68) The method of any one of embodiments 1-67, wherein the subject is a non-human mammal. (69) The method of embodiment 68, wherein the method is used in veterinary applications. (70) The method of any one of embodiments 1-69, wherein the therapeutic agent is bound to the carrier material via a targeting polypeptide. (71) The method of embodiment 70, wherein the targeting polypeptide is connected to the therapeutic agent. (72) The method of embodiment 71, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 1. (73) The method of embodiment 71 or embodiment 72, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 2. (74) The method of any one of embodiments 71-73, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 3. (75) The method of any one of embodiments 71-74, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 4. (76) The method of any one of embodiments 71-75, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 5. (77) The method of any one of embodiments 71-76, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 6. (78) The method of any one of embodiments 71-77, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 7. (79) The method of any one of embodiments 71-78, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 8. (80) The method of any one of embodiments 71-79, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 9. (81) The method of any one of embodiments 71-80, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 10. (82) The method of any one of embodiments 71-81, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 11. (83) The method of any one of embodiments 71-82, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 12. (84) The method of any one of embodiments 71-83, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 13. (85) The method of any one of embodiments 71-84, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 14. (86) The method of any one of embodiments 71-85, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 15. (87) The method of any one of embodiments 71-86, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 16. (88) The method of any one of embodiments 71-87, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 17. (89) The method of any one of embodiments 71-88, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 18. (90) The method of any one of embodiments 71-89, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 19. (91) The method of any one of embodiments 71-90, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 20. (92) The method of any one of embodiments 71-91, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 21. (93) The method of any one of embodiments 71-92, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 22. (94) The method of any one of embodiments 71-93, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 23. (95) The method of any one of embodiments 71-94, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 24. (96) The method of any one of embodiments 71-95, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 25. (97) The method of any one of embodiments 71-96, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 26. (98) The method of any one of embodiments 71-97, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 27. (99) The method of any one of embodiments 71-98, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 28. (100) The method of any one of embodiments 71-99, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 29. (101) The method of any one of embodiments 71-100, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 30. (102) The method of any one of embodiments 71-101, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 31. (103) The method of any one of embodiments 71-102, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 35. (104) The method of any one of embodiments 71-103, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 36. (105) The method of any one of embodiments 71-104, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 37. (106) The method of any one of embodiments 71-105, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 38. (107) The method of any one of embodiments 71-106, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 39. (108) The method of any one of embodiments 71-107, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 40. (109) The method of any one of embodiments 71-108, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 41. (110) The method of any one of embodiments 71-109, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 42. (111) The method of any one of embodiments 71-110, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 43. (112) The method of any one of embodiments 71-111, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 401. (113) The method of any one of embodiments 71-112, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 402. (114) The method of any one of embodiments 71-113, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 403. (115) The method of any one of embodiments 71-114, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 404. (116) The method of any one of embodiments 71-115, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 405. (117) The method of any one of embodiments 71-116, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 406. (118) The method of any one of embodiments 71-117, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 407. (119) The method of any one of embodiments 71-118, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 408. (120) The method of any one of embodiments 71-119, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 409. (121) The method of any one of embodiments 71-120, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 410. (122) The method of any one of embodiments 71-121, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO:

411. (123) The method of any one of embodiments 71-122, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 412. (124) The method of any one of embodiments 71-123, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 413. (125) The method of any one of embodiments 71-124, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 414. (126) The method of any one of embodiments 71-125, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 415. (127) The method of any one of embodiments 71-126, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 416. (128) The method of any one of embodiments 71-127, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 417. (129) The method of any one of embodiments 71-128, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 418. (130) The method of any one of embodiments 71-129, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 419. (131) The method of any one of embodiments 71-130, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 420. (132) The method of any one of embodiments 71-131, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 421. (133) The method of any one of embodiments 71-132, wherein the targeting polypeptide comprises a sequence at least about 70%, 75%, 80%, 85%, 90%, 91%, 92%, 93%, 94%, 95%, 96%, 97%, 98%, 99%, or 100% identical to SEQ ID NO: 422. (134) The method of any one of embodiments 70-133, wherein the therapeutic agent and targeting polypeptide are connected via a linker. (135) The method of embodiment 134, wherein the linker comprises a peptide. (136) The method of embodiment 135, wherein the linker comprises a sequence at least about 70%, 75%, 80%, 85%, 90%, 91%, 92%, 93%, 94%, 95%, 96%, 97%, 98%, 99%, or 100% identical to SEQ ID NO: 701. (137) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 32. (138) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 46. (139) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 47. (140) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 152. (141) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 168. (142) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 268. (143) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 176. (144) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 48. (145) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 49. (146) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 50. (147) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 51. (148) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 52. (149) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 53. (150) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 54. (151) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 55. (152) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 56. (153) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 57. (154) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 58. (155) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 59. (156) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 60. (157) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 61. (158) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 62. (159) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 63. (160) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 64. (161) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 65. (162) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 66. (163) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 67. (164) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 68. (165) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 69. (166) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 70. (167) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 71. (168) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 72. (169) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 73. (170) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 74. (171) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 75. (172) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 76. (173) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 77. (174) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 78. (175) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 79. (176) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 80. (177) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 81. (178) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 82. (179) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 83. (180) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 84. (181) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 85. (182) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 86. (183) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 87. (184) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 88. (185) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 89. (186) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 90. (187) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 91. (188) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 92. (189) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 93. (190) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 94. (191) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 95. (192) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 96. (193) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 97. (194) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 98. (195) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 99. (196) The method of any previous embodiment, wherein the therapeutic agent comprises a sequence at least about 70%, 75%, 80%, 85%, 90%, 91%, 92%, 93%, 94%, 95%, 96%, 97%, 98%, 99%, or 100% identical to SEQ ID NO: 100. (197) The method of any previous embodiment, wherein the therapeutic agent is part of a composition comprising any one of SEQ ID NOS: 501-648.

Also provided herein are devices comprising a biological material. In some cases, the biological material comprises a growth factor as listed in Table B, or a polypeptide comprising a sequence at least about 80%, 81%, 82%, 83%, 84%, 85%, 86%, 87%, 88%, 89%, 90%, 91%, 92%, 93%, 94%, 95%, 96%, 97%, 98%, 99%, or 100% identical to a sequence of Table B.

In some embodiments, provided is a method of coating a device with a biologic material, the method comprising coating the device with any targeting polypeptide herein. In some embodiments, provided is a method of coating a device with a biologic material, the method comprising coating the device with any chimeric polypeptide herein. In some embodiments, provided is a method of coating a device with a biologic material, the method comprising coating the device with any polypeptide comprising a polypeptide of Table A. In some embodiments, provided is a method of coating a device with a biologic material, the method comprising coating the device with any polypeptide comprising a polypeptide of Table B. In some embodiments, provided is a method of coating a device with a biologic material, the method comprising coating the device with any polypeptide comprising a polypeptide of Table C. In any of the previous embodiments, the composition and/or biologic material is non-covalently bound to the device. In any of the previous embodiments, the device comprises one or more carrier materials described herein.

The following examples do not limit the scope of the claims.

EXAMPLES

Example 1. A Preclinical Study of tBMP-2 in a β-TCP Carrier in a Rat Critical Size Femoral Defect Model The aim of this study was to examine the safety and effect of modified recombinant human bone morphogenetic protein (rhBMP) known as tBMP-2 in a beta-tricalcium phosphate (β-TCP) putty matrix in the replacement and repair of bone in a rat critical size defect model. The tBMP-2 used in this study comprises MPIGSLLADTTHHRPWTVI-GESTHHRPWSIIGESSFIHKPFTGLGDTTHHRPWGI-LAESTHHKP WTASGAGGSEGGGSEGGTSGAT-GAGTSTSGGGASTGGGTGQAKHKQRKRLKSSCKR-HPLY VDFSDVGWNDWIVAPPGYHAFYCHGECPFP-LADHLNSTNHAIVQTLVNSVNSKIPKACCVPT ELSA-ISMLYLDENEKVVLKNYQDMVVEGCGCR (SEQ ID NO: 502). The tBMP-2 variant exhibits very tight binding to calcium phosphate ceramics and thus allows for targeted delivery of tBMP-2 to implant sites. This was achieved by surgically creating the defect using the RatFix internal fixator system, then filling that defect with tBMP-2+β-TCP putty, or β-TCP putty alone as a control. The positive control was a dose-adjusted commercially available (Medtronic) preparation for human use of rhBMP with an absorbable collagen sponge (ACS). The animals were monitored clinically and had bi-weekly radiographs until their scheduled end-points at four or eight weeks post-administration of treatment. Ex vivo histology was conducted on organs and tissues, and the treated leg was subjected to µCT, histomorphometry, and/or mechanical strength testing.

This report covers animal arrival, assignment to groups, surgical creation of defect and administration of test, reference or control item. In addition, this report covers the post-operative period up to and including Week 8, and end-point in vivo and ex vivo measurements. Included are the clinical summaries, radiographs, end-point clinical pathology and organ histopathology, histomorphometry of treated legs (odd-numbered animals), and mechanical strength testing of treated legs (even-numbered animals).

On arrival at the Test Facility, all animals underwent a Veterinary health check and were weighed. Based on the weights, the animals were assigned to groups A) tBMP-2+β-TCP putty; B) rhBMP+ACS; or C) β-TCP putty alone. The animals then had at least five days to acclimatize to their new surroundings and diet.

On the day of surgery, the animals were anaesthetized, the defect was created and the bone supported with the internal fixator following the method supplied by the manufacturer with some refinements to the surgical procedure. The pre-prepared test, reference or control item was then inserted into the defect. The surgical site was closed and the animal went immediately for X-ray. Following completion of the baseline radiograph, post-operative pain relief was administered and the animal was returned to its cage for recovery. Post-operative analgesia and antibiotic therapy were continued for at least two days, and longer when required.

A number of the original animals were removed from the study and replaced prior to surgery as they were getting too large for the fixator system specifications. The second, replacement group also had a thorough Veterinary health check and were weighed prior to being assigned to groups. The allocation of animals to either four or eight-week end-point groups was adjusted to include animals from both weight ranges at both end-points.

A total of 61 animals were successfully administered assigned treatment and recovered from surgery. Of these, one animal was euthanized five days post-operatively due to poor recovery and inappetence. The animal was replaced. Two animals which were found to have dislodged bone plates during their 2-week post-operative radiographs were humanely killed and not replaced. Two animals did not successfully recover from surgery, one died immediately post-surgery, and the other had an unstable bone plate which could not be fixed, and so was humanely killed. Both of these animals were replaced immediately.

The animals were monitored at least once daily, and their clinical signs scored. Any animal with unusual findings or considered to be not eating and gaining weight normally was monitored more frequently, and veterinary advice was sought. When unusual findings were noted, this resulted in possible treatment with additional antibiotic or analgesic therapy, fluid supplementation), and in four cases euthanasia (three broken bones and one with continued weight loss).

All relevant animals received bone-labelling dyes at 10 days (calcein green) and 3 days (xylenol orange) prior to their scheduled end-point date. All animals had end-point blood samples collected. There were no clinically significant differences found between any of the groups for any biochemical or haematological parameter at either end-point time. Three haematology samples were clotted and could not be analyzed.

In all specimens examined, there was evidence of extensive mineralization akin to mature trabecular bone in samples from animals in the tBMP-2+β-TCP putty group (Group A). This mineralization appears to be lamella (mature) bone rather than the woven bone that occurs in early callus formation (presence of osteocytes). Group A animals also had osteoclasts present (suggesting active remodeling), and red blood cells and adipocytes, indicating angiogenesis and infiltration of cells to most regions of the callus. Whilst there is mineralized bone in the specimens from the rhBMP+ACS group animals, there are extensive regions of unmineralized fibrous and cartilaginous tissue within the callus region. The callus development in these samples appears to be at an earlier stage than that observed in the Group A animals. The Group C (β-TCP putty) samples show no evidence of mineralization, bone formation or bone remodeling even at eight weeks post-application of treatment.

The mechanical testing analyses showed the tBMP-2+β-TCP group animals (Group A) had significantly stronger bones at the four and eight week end-point times than either of the other treatment groups.

In conclusion, the bone specimens form the tBMP-2+β-TCP putty group clearly demonstrated vastly improved bone healing at 4 and 8 weeks post-surgery when compared to samples from animals in the rhBMP+ACS or the β-TCP putty alone treatment groups.

The aim of this study was to evaluate the performance of a modified variant of recombinant human BMP-2 (rhBMP-2) called tBMP-2. The tBMP-2 variant exhibits very tight binding to calcium phosphate ceramics and thus allows for targeted delivery of tBMP-2 to implant sites. The ability to tether BMP-2 in this manner can allow for longer persistence times, lower doses, and, it is expected, superior outcomes as compared to the treatment controls studied herein.

Animals

The rat is a validated animal model for assessing the effect of treatments on critical-sized defects in the femur (4-6). Sixty male rats (plus spares) were required: ten animals in each group per time point. One animal was replaced after successful administration of the test item at day 5 post-surgery as he was losing weight and not eating. Animals that were euthanized or humanely killed after successful administration of the test item were necropsied and had tissue collected for histopathology. The number of animals used in this study was considered sufficient for evaluation of results.

The animals were housed in conventional conditions (targeted temperature 22±3° C., 12/12-hour light/dark cycle) in standard open top cages that satisfy the size requirements specified in the Animal Welfare Regulations (Animal Welfare Act 1985, v 15.10.2015. Attorney General's Department, Government of South Australia). Animals were housed individually for the entirety of the experiment. The animals had access to standard laboratory rat chow (Specialty Feeds, Glen Forest, Australia) 25-30 g/day. Immediately post-operatively, and when rats were not thriving, the food was soaked in water for easier palatability. Chlorinated tap water was provided to the animals ad libitum. Food and water were not withheld at any time.

Each animal was uniquely identified by a subcutaneously implanted microchip which was scanned using a barcode reader. For the purpose of the study, each animal was also given a number from 1-70 (to include replacement and spared required). As the initial batch of animals gained weight too quickly, some animals were replaced prior to surgery. The replacement animals were given the number of the animal they replaced and the suffix (a) was added. Numbers went up to 68a with a couple of gaps.

Animals were assigned to groups by a weight-ordered distribution. The heavier animals were used first. The animals gained weight rapidly, even on the restricted food allowance. Two weeks into the surgeries, it was deemed necessary to remove some animals from the study (n=16) as these animals were already too heavy (>425 g). These animals were replaced with animals in the 250-300 g range. The replacement animals were also assigned to treatment groups on a weight-ordered distribution. As the first surgical group had originally been assigned to the 8-week end-point group, animals were reassigned to either 4- or 8-week end-points to ensure the lighter animals were evenly distributed amongst the treatment and end-point times.

Analgesia/Antibiotic Therapy

All interventional procedures were performed under isoflurane in $O_2$ anaesthesia. Induction and maintenance of surgical depth anesthesia was at 2-4% isoflurane (Baxter International, Sydney, Australia) in a flow of 1-2 L/minute $O_2$. Post-operatively, after closure of the wound, a topical application of local anesthetic in the form of Marcaine (Bupivacaine, 0.5%, AstraZeneca, Frewville, SA, Australia) up to 2.5 mg/Kg was applied to the area around the wound. The animals received 0.1 mg/kg buprenorphine (Temgesic, Reckitt-Benckiser, Melrose Park, Australia) subcutaneously post-operatively after X-ray. They also received 0.1 mg/kg subcutaneously twice daily for two days post-operatively. Additionally, they were given a non-steroidal anti-inflammatory treatment in the form of Carprieve (Carprofen, 50 mg/mL, Norbrook Laboratories, Tullamarine, Australia) at a dose of 5 mg/kg subcutaneously post-operatively and once daily for at least two days post-surgery.

All animals received cephalosporin (Cefazolin, Hospira Inc, Lake Forest IL, USA) 20 mg/kg subcutaneously intra-operatively and twice daily for two days post-operatively. Any animals that needed re-suturing of their wounds received antibiotic treatment for up to fourteen days post-repair. Antibiotic therapy was ceased if suspected to be causing diarrhea and/or weight loss.

Microchip Implantation

The microchip was inserted into the scruff of the neck (after clipping hair) using a microchip implanter. The microchip was inserted until completely covered by skin. The wounds were closed with one or two wound clips if required. The area was swabbed with betadine. This was performed under isoflurane in $O_2$ anaesthesia at the same time as the defect surgery and test- or reference-item placement.

Critical-Size Defect Creation

The defects were created in the right femur of all rats as described for the RatFix RISystem. Briefly, all anaesthetized rats were placed on a warming pad in lateral recumbency with the right leg facing upwards. The surgical site was shaved and aseptically prepared with iodine or chlorhexidine scrub and solution. A skin incision between the greater trochanter and the knee joint was made and the superficial fascia incised. The intermuscular plane between the vastus lateralis and the biceps femoris was separated and the periosteum of the femur incised. The PEEK plate was fitter into the jug and secured with suture material. The jig-plate assembly was fixed to the craniolateral surface of the femur by pulling the sutures through under the femur, allowing the assembly to be tightened to the femur.

After predrilling the holes in the PEEL plate using the supplied drill bit, the plate was attached to the femur by six bicortical titanium screws. Standardised 6-mm defects were created (marked on the plate) using the Gigli wire saw guided by the sawing device of the jig. After defect sawing, the jig and bone piece were removed. The fresh defect was flushed with sterile saline and dried with gauze in preparation of test item or reference item, or vehicle administration into the defect size. In the event that the plate itself was damaged with the cutting wire, reducing stability, that animal would be replaced. No replacements due to plate damage were required.

Baseline Radiographs

Baseline radiographs were taken immediately after creation of the defect and administration of the test or reference item to show position of treatment articles (where visible), and placement of the plate, whilst the animal was still under anaesthesia.

Radiographic Assessments

X-rays were taken on the anaesthetized animals (isoflurane) immediately after surgery, and at 2, 4 (end-point for half of the animals), 6 and 8 weeks (end-point for the remaining animals) post-operatively. The radiographs were taken in lateromedial and craniocaudal projections for assessment of bone healing and to exclude implant loosening or failure. All in-life radiographs were taken using a Villa Visitor Mobile X-ray Unit (Villa Sistemi Medicali, Buccinasco, Italy), using a dental image capture device (Soredex, Digora Optime, Tuusula, Finland). The images were transferred to the PIRL picture archiving and communication system (PACS, Carestream Vue Motion, Rochester, USA) by the radiographer for storage and access.

Bone Labelling

At 10 days prior to their prescribed end-point, all animals received an intraperitoneal injection of calcein green (25 mg/kg in saline). At 3 days prior to their prescribed end-point all animals received an injection of xylenol orange (10 mg/mL, 25 mg/kg, intraperitoneal) to double-label the bone for histomorphometric analyses.

Blood Collection/Haematology

All blood collections were performed on anaesthetized animals at their end-point radiograph. Blood was collected via cardiac puncture.

Blood samples were evaluated for the parameters specified in Tables 1 and 2. For Table 1, samples of approximately 2 mL were collected into tubes containing $K_2$EDTA anticoagulant for haematological analyses. Analyses were performed on an Abbott Cell Dyn. 3700 (Abbott Laboratories, North Ryde, Australia). For Table 2, samples of approximately 5 mL were collected into tubes containing a clot activator for biochemical analysis. Analyses were performed on a Siemens Advia 1800 (Siemens Healthcare Diagnostics Inc., Flanders, NJ, USA).

TABLE 1

Haematology Parameters to be reported

| | |
|---|---|
| Haemoglobin (Hb) | White Cell Count (WCC) |
| Erythrocyte count (RBC) | Mean Corpuscular Volume (MCV) |
| Packed Cell Volume (PCV)/Haematocrit (HCT) | Mean Corpuscular Haemoglobin (MCH)* |
| Mean Corpuscular Haemoglobin Concentration (MCHC)* | Red Cell Distribution Width (RDW) |
| Platelets (Pit) | |
| White Blood Cell Differential: Neutrophils, Lymphocytes, Monocytes, Eosinophils, Basophils | |

*Calculated values

TABLE 2

Serum Chemistry Parameters to be reported

| | | |
|---|---|---|
| Electrolytes: | Anion Gap* (AG) | Albumin (Alb) |
| Sodium (Sod) | Glucose (Glue) | Globulin* (Glob) |
| Potassium (Pot) | Urea | Protein (Tot Prot) |
| Chloride (Chi) | Creatinine (Creat) | Total bilirubin (Tot Bili) |
| Bicarbonate (Bicarb) | Cholesterol (Chol) | Lactate Dehydrogenase (LD) |
| Lipid Studies: | Urate (Uric Acid, UA) | Alkaline phosphatase (ALP) |
| Triglycerides (Trig) | Phosphate (Phos) | Total Calcium (Tot. Ca) |
| High Density Lipoproteins (HDL) | Gamma glutamyltransferase (GGT) | Alanine aminotransferase (ALT) |
| Low Density Lipoproteins (LDL) | Asparatate aminotransferase (AST) | |
| Chol/HDL* | | |

*Calculated values

Mechanical Strength Testing

This was performed on half of the animals at each time point. All tissue was placed in 0.9% NaCl-soaked gauzed in 50-mL sterile urine pots to avoid freezer burn and stored frozen at −20° C. until testing. Tissue was prepared immediately and frozen within one hour of collection to avoid autolysis. Immediately before testing, tissues were thawed, and the internal fixator device carefully cut in the middle section. Tissue was test at room temperature (approximately 23° C.). The ultimate breaking strength was measured by using a load frame (model 5542, Instron, Canton, MA) and a 3-point bend fixture (model 2810-400, Instron) at a crosshead speed of 10 mm/min. The load cell for this testing (Instron 2530-416) had a maximum capacity of 500 N. The data (force in kg and extension in mm) was collected and analyzed with a vendor-provided commercial mathematical software package (Bluehill2, Instron).

Histological Analyses

Specimen were fixed in 10% formalin for 7 days prior to processing. Formalin-fixed bones were cut using a slow-speed saw (Buehler Ltd, IL, USA) along the sagittal plane using a diamond-tipped cutting blade before being submerged in 70% ethanol. Subsequently, bones were processed for resin embedding via several dehydration steps. Briefly, bones were submerged in 2×90% ethanol and 1×100% ethanol steps over 48 hours. Bones were then transferred into a solution containing methylmethacrylate (MMA) and 10% v/v polyethylene glycol (PEG) and stored at room temperature for 10-14 days. Resin embedding then occurs by preparing a solution of MMA, 10% PEG, and 0.4% peroxydicarbonate (Perkadox) and incubation at 37° C. for 24 hours to allow the resin to harden. The exposed cut surface was placed facing down in the tube. The resin-set bones were then removed from their tubes and fixed to stubs for sectioning. For each bone, 5-µm thick sections were cut using a tungsten-carbide blade (Leica RM2255, Wetzlar, GER). Sections were placed on to gel-coated slides and dipped 2 times in a spreading solution (70% ethanol/30% 2-ethoxyethanol) heated to 70° C. To ensure adherence to the slide, sections were flattened, covered by strips of polyethylene and clamped together separated by blotting paper, before being placed into a 37° C. oven. Prior to commencing staining procedures, sections were placed in acetone for 15 minutes, unless otherwise stated. All sections were digitally scanned at 100× magnification (3D Histech scanner, TMA-MASTER01).

Von Koss+Haemaotoxylin and Eosin (H&E) Staining

Acetone treated sections were rinsed in demineralised water for 2 minutes. Sections were then placed in a 1% silver nitrate solution and placed in front of a UV lamp for 60 minutes. Washed slides were then treated with 2.5% sodium thiosulphate solution for 5 minutes. Washed slides were then counterstained with H&E. To stain for H&E, sections were placed in haematoxylin for 8 minutes to stain cell nuclei before being rinsed in demineralised water for 2 minutes and dipped in acid alcohol (%), typically, 4-5 minutes. After rinsing in demineralised water, sections were dipped in lithium carbonate 4-5 times and placed in eosin for 4 minutes. Once removed, excess eosin was removed with a squeeze bottle of absolute alcohol, sections were hydrated, placed in xylene and mounted in xylene-based mounting medium.

Tartrate-Resistant Acid Phosphatase (TRAP) Stain for Analysis of Osteoclasts

Acetone treated sections underwent a 60-minute incubation in Tris-HCL buffer (pH 9.4) at 37° C. for 60 minutes in an acid phosphatase (AcP) stain prepared by adding 0.0355 g of tartaric acid dissolved in 35 mL of sodium acetate (pH 5.2) to 100 µL basic fucshin in a 100 µL solution containing 0.4 mg of sodium nitrite. This solution was then added to a solution containing 0.04 g Napthol ASBI phosphate (Sigma-Aldrich, Missouri, USA) in 2 mL dimethylformamide. Subsequently, two washed were performed before the sections were counterstained in haematoxylin for 8 minutes, then rinsed in demineralised water, then dipped in acid alcohol 4 times, rinsed again, dipped in lithium carbonate 4 times and then dehydrated, placed in xylene and mounted in DPX. Quantification of osteoclast number per bone perimeter mm was performed by identifying cells (stained pink-red) on the surface of bone (stained blue-purple) and calculated by the OsteoMeasure histomorphometry system.

Double Fluorochrome Labelling of Bone Sections for Measures of Bone Formation

Acetone sections were immediately placed in xylene and mounted in DPX. Slides were viewed under a fluorescent microscope (Olympus BX53; Olympus, Tokyo, JP).

Histomorphometry

Those animals which did not have mechanical testing of femurs will undergo histological analysis of the defect and treatments. Following µCT of the femurs, they were opened at the wound site, and the internal fixator device carefully removed. They were placed in 70% ethanol. Femurs were placed in PMMA, polymethyl methacrylate (10% polyethylene glycol [PEG] in methylmethacrylate) for 10-14 days, then polymerized in PMMA containing 10% Perkadox 16 (di[4-tert-butylcyclohexyl] peroxydicarbonate) at 37° C. for 24 hours. Sections were stained with H&E, and tartrate resistant acid phosphatase (TRAP) for analysis.

Humane Killing

Animals were humanely killed on day 28±2 days (n=30) or day 56±3 (n=30) immediately following their end-point radiograph and blood collection, and whilst still under anaesthesia, with an intracardiac injection of a lethal dose of sodium pentobarbitone of 60 mg/mL formulation (Lethabarb®) at 200 mg/kg. Death was confirmed by lack of respiration and palpable heartbeat, loss of corneal reflex and loss of colour of mucous membranes.

Necropsy

All animals were subjected to a comprehensive necropsy. A comprehensive necropsy is defined as examination of the external surface of the body, all orifices, and the cranial, thoracic, and abdominal cavities, and their contents. If abnormalities were found in tissues or organs other than those listed below, they were also collected for histology.

Organ and Tissue Collection

Whole organs, sections of the issues listed in Table 3 below were dissected free and fixed in 10% neutral buffered formalin. This was done for twelve animals from each groups (six animals from each group at each time-point). The animals were selected such that at least one from each group was selected at each end-point (staggered as surgeries were staggered).

TABLE 3

Organ and Tissue Samples Collected From Each Animal

| | | |
|---|---|---|
| Adrenal gland | Lesions | Skin (containing implant[s]) |
| Brain | Liver | Spinal cord (cervical, thoracic, and lumbar) |
| Cecum | Lymph node (mesenteric) | Spleen |
| Duodenum | Pancreas | Sternum (+ bone marrow) |
| Eye | Pituitary Gland | Stomach |
| Heart | Rectum | Thymus |

TABLE 3-continued

Organ and Tissue Samples Collected From Each Animal

| Ileum | Salivary gland (mandibular) | Tongue |
|---|---|---|
| Jejunum | Sciatic nerve | Epididymis |
| Kidney | Skeletal muscle (thigh) | |
| Femur with bone marrow (articular surface of the distal end) | Lung (with mainstem bronchi) | Prostate/seminal vesicles, bladder, testes |

Treated Limb Collection and Storage

Immediately following confirmation of death, the treated leg was removed and placed in either 10% neutral buffered formalin (n=5 animals/group/time point), or wrapped in saline-soaked gauze and placed at −20° C. for at least 48 hours (n=10 animals/group/time point).

μCT

All legs had μCT measurements (Bruker Skyscan 1076, Brussels, Belgium) of the defect performed to quantify newly mineralized bone volume. This was done on all animals at each end-point time. The bones were either formalin-fixed (105 neutral buffered formalin) or frozen at −20° C. for 3-5 days prior to testing. The plate was adjusted to the longitudinal axis of the device. Scanning parameters and intensity were recorded and were in the vicinity of a source voltage of 70 kV with an intensity of 114 μA. The end-point μCT was manually and subjectively scored as described by Chhabra et al. (2005) using the grading system described in Table 4.

TABLE 4

Radiographic Grading Scale of Fracture Callus Formation

| Grade | Amount of Callus Formation |
|---|---|
| 0 | No callus |
| 1 | Little-to-moderate callus |
| 2 | Profuse callus tissue |
| 3 | Bridging periosteal callus |
| 4 | Mature callus with interfragmentary bridging |
| 5 | Callus resorption after solid union |

Study Design

The study was performed as outlined in Table 5. There were three groups with 20 animals/group. All animals underwent surgery to create a critical-size defect (6-mm) in the mid diaphysis of the right femur (RatFix RISystem), and had inserted into the defect test item, reference item or vehicle. The animals were monitored at least once daily and were weighed at least twice weekly. They underwent radiographic evaluation immediately post-operatively, and at 2, 4, 6, and 8 weeks post-surgery. Ten animals from each group (n=30 animals) were scheduled to have end-point data (μCT, mechanical testing, histomorphometry, clinical pathology) collected 4 weeks post-operatively and the remaining animals (n=30 animals) were scheduled for end-point data collection 8-weeks post operatively. Of these, six from each group (chosen such that there was a representative from each group from the majority of surgical days) at each end-point had tissues and organs collected for histology.

TABLE 5

Study design

| Group | Treatment | Nomenclature | End-Point (n) Week 4 | End-Point (n) Week 8 |
|---|---|---|---|---|
| A | tBMP-2 + β-TCP putty | tBMP-2 + β-TCP putty | 10 | 10 |
| B | rhBMP-2 + absorbable collagen sponge (ACS) | rhBMP2 + ACS | 10 | 10 |
| C | β-TCP putty | β-TCP putty | 10 | 10 |

Group A animals received tBMP-2+β-TCP (0.615-0.620 mg tBMP-2 in β-TCP putty to fill defect); Group B animals received InFUSE™ Bone Graft of rhBMP-2+ACS (2 μg rhBMP-2 on ACS to fill defect); Group C animals received β-TCP to fill the defect. All test and control items were mixed on the day of surgery (tBMP-coated β-TCP to putty or rhBMP to ACS). Following administration of the treatment article, the wounds were closed in two muscle layers with subcutis and intracutaneous vicryl sutures. The wounds were closed exteriorly with intradermal sutures to prevent chewing by the rats. The wounds were washed with liberal amounts chlorhexidine solution. A small amount of tea tree oil was applied to the area surrounding the actual wound to prevent the animals from worrying the suture side.

Route of Administration

The anticipated route of human administration is by surgical implantation into a bone defect. Therefore, that route was used in this study. The bone defects were surgically created, the area flushed with saline, then the test or control items were placed in the defect immediately.

Preparation of Test Item (tBMP-2+β-TCP Putty)

For each rat, 195 μL of tBMP-2 (stock 3.53 mg/mL) were added to a pre-weighed aliquot of 47 mg β-TCP granules and mixed gently for 2-3 hours. All liquid was removed, and retained for analysis. The pellet was washed with 1 mL of sterile phosphate-buffered saline (PBS pH 7.4) and mixed gently to wash away any excess unbound protein. As much as possible of the liquid was removed with a pipette, and sterile pre-weighed putty was added to the protein-coated β-TCP. β-TCP and putty were mixed 1:1. The entire tBMP-2+β-TCP putty formulation was placed in the surgically-created defect. Assuming approximately 90% binding, the final dose of tBMP which was administered to the rat in the defect was 615-620 μg. Sterility was maintained at all steps. β-TCP binding to tBMP-2 was done no more than 48 hours prior to surgery. If β-TCP was bound/washed the day before surgery, it was stored at 4° C. β-TCP and putty were not mixed more than one hour prior to implantation, as it will dehydrate with time and become less malleable.

Reference Item

Recombinant human bone morphogenetic protein+absorbable collagen sponge (InFUSE™ Bone Graft; size XX small; Medtronic Sofamor Danek, Inc) was used as per packet insert with modifications as described below. BMP-2 vial contents were reconstituted with the provided sterile water to give 1.5 mg/mL rhBMP-2. This concentration is intended for human use. To bring this concentration to the range typically used in rats, it was diluted 1 in 60 with PBS (25 μg/mL). A defect volume of approximately 75.5 mm$^3$ was assumed, therefore the ACS was trimmed to form a 6-mm×4-mm block for insertion into the defect. Diluted rhBMP solution (80 μL) were added to the ACS in a dropwise fashion at least 15 minutes prior to insertion into the defect. This resulted in 2 μg tBMP-2 in the defect. Sterility was maintained.

β-TCP Putty

β-TCP granules (46-48 mg aliquots), carboxymethyl cellulose putty (48-50 mg aliquots). Under sterile conditions, the β-TCP granules were washed with 1 mL of sterile PBS and mixed gently. As much as possible of the liquid was removed using a pipette. Pre-weighed sterile carboxymethyl cellulose (approximately 2 mg more than the β-TCP putty formulation was inserted into the defect.

Dose Formulation

The rhBMP-2+absorbable collagen sponge and the tBMP-2+β-TCP putty were prepared as described above. The final dose each rat received of the BMP-2 formulations was 2 μg rhBMP-2 for the reference item and approximately 615-620 μg tBMP of the test item.

Animal Assignments and Body Weights

On arrival, the initial animals were numbered 1-63, of which 60 were assigned to the study. The animals were fed ad lib on arrival, but this was reduced to 35-30 g when it was found at their third weighing that they were gaining weight too quickly. The initial surgeries were delayed by one week, and as the animal's weights continued to increase, the decision was made to remove the heaviest sixteen animals from the study and get replacement animals. The replacement animals were assigned numbers.

Figure 1B:
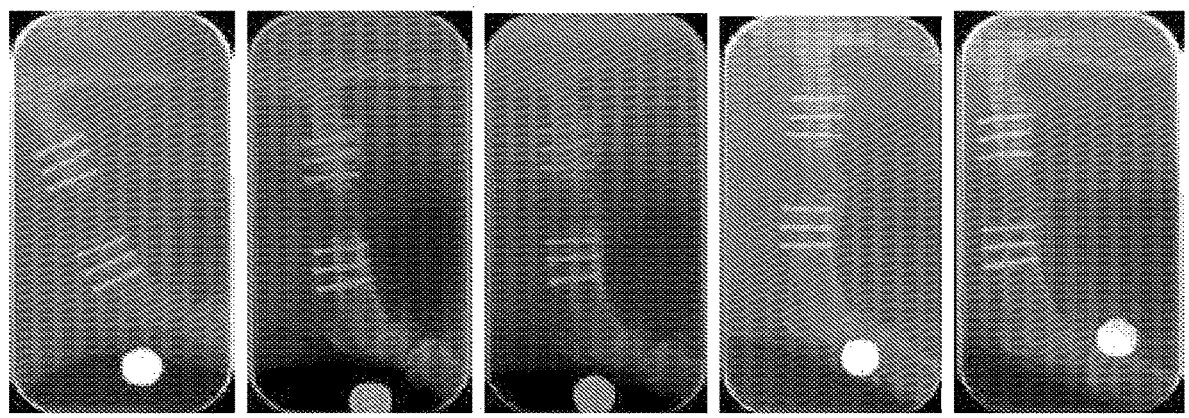
FIG. 1B are representative in vivo radiographs (latero-medial orientation) of animals from experimental Group B.
Figure 1B:
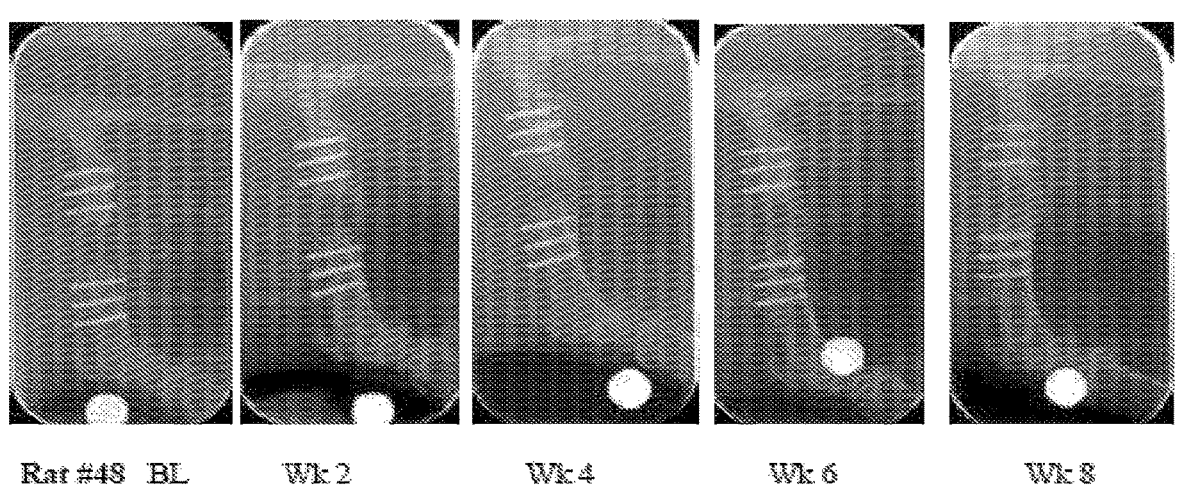
Figure 1C:
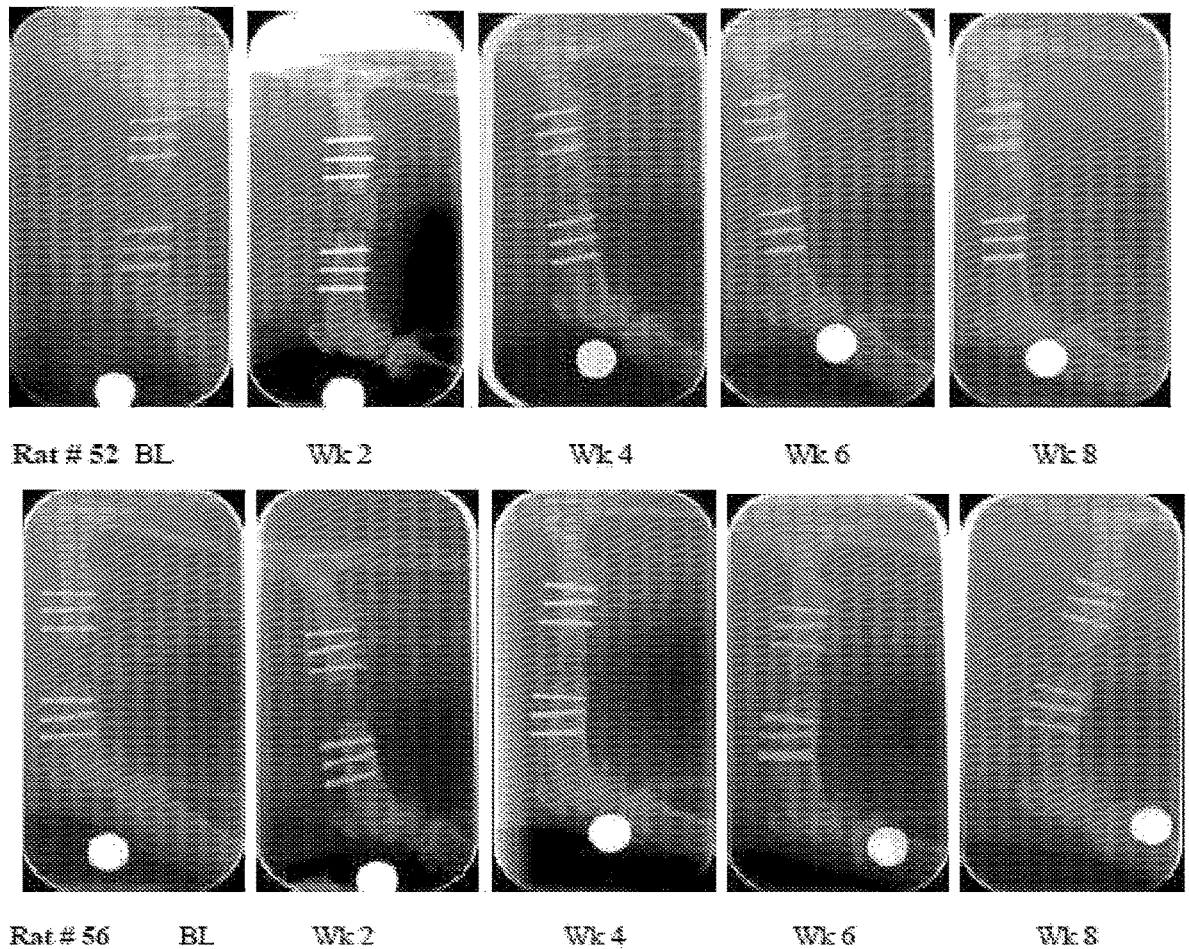
FIG. 1C are representative in vivo radiographs (latero-medial orientation) of animals from experimental Group C.

All animals were weighed on arrival and assigned to one of three groups on a weight-ordered distribution. All allocations to group and end-point times were done to ensure there were no significant differences in weight prior to the surgical intervention between any of the groups in terms of treatment to be administered, or time to end-point (either 4- or 8-weeks post-surgery). There were no significant differences in weights at assignment to study between any of the groups for either the initial group of animals or the replacement group, or at any time for the duration of the study (FIG. 1A, FIG. 1B and FIG. 1C).

Example 2. Radiographic, Mechanical, Histomorphometric and Histological Analyses of 4 and 8 Week Post-Fracture Healing in Three Experimental Rat Fracture Groups (A, B and C)

To assess the extent of mineralized bone material within the callus region of fractures in three experimental rat groups (A, B and C), radiographic scoring of callus formation, mechanical testing of the callus strength, high resolution micro computed tomography (μCT), and quantitative histological analyses of bone formation and resorption were conducted.

Radiographic Assessment

Sagittal radiographic images were generated using a Faxitron X-ray with fixed exposure settings. Radiographic scoring specifically on callus formation healing was based on Chhabra et al. (2005) *J Orthop Trauma* 19(9): 629-634, and modified from Marino et al. (1979) *Clin Orthop Relat Res* (145): 239-244 and Makley et al. (1967) *J Bone Joint Surg Am* 49(5): 903-914 (Table 4). Scoring was performed in one session on de-identified, randomised radiographs. Both the posterior and anterior aspect of the cortex at the site of fracture was scored. The average score for each specimen was recorded.

Figure 2:
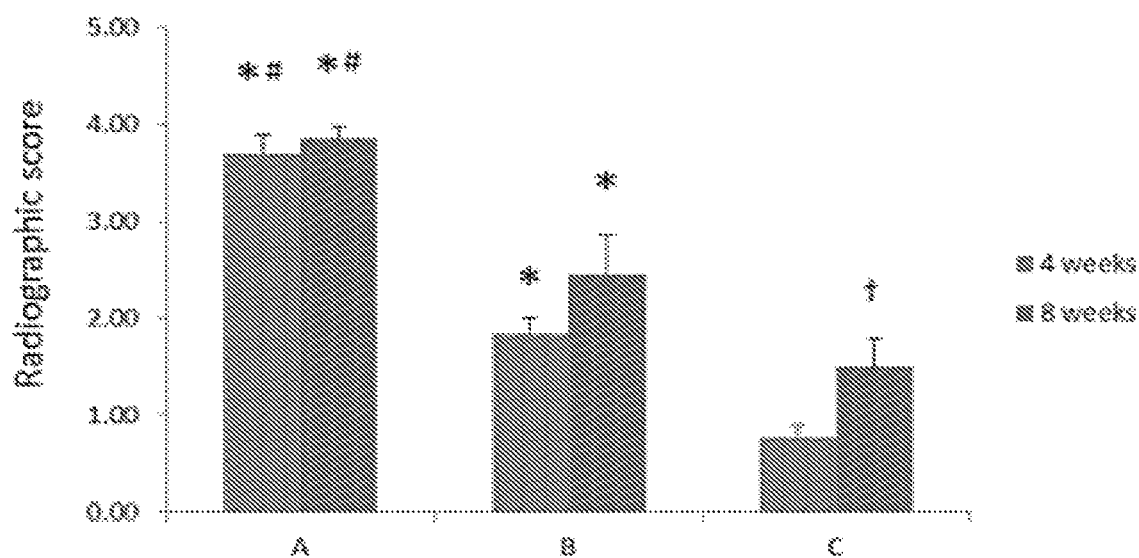
FIG. 2 is a representative graph of the mean radiographic score (+SEM, n=9-10) of animals from each Group at four weeks- and eight weeks-post-surgery (for each Group A-C, the bar on the left is 4 weeks and the bar on the right is 8 weeks). *$P<0.01$ vs Group C1 #$P<0.01$ vs Group V; +$P<0.01$ vs Group C at 4 weeks.

Baseline radiographs were taken on all animals as soon as possible after surgery whilst still under anaesthetic, at two weeks, four weeks (end-point for half of the animals), six weeks and eight weeks (end-point for remaining animals) post-surgery. They were taken in lateromedial and craniocaudal views. FIG. 2 shows representative radiographs of animals from all groups at 0, 2, 4, 6, and 8 weeks post-surgery. The defect was only visible in Group B animals that received the rhBMP+ACS. The putty (with or without protein) in animals from Groups A and C appear to be outside the confines of the defect (more obvious in mediolateral view). This was the case in all animals, even when the surgeon reported that the putty appeared to be completely contained within the defect, and touching the muscle tissue had been completely avoided on insertion of the test or control items.

Ex vivo radiographs, as with the in vivo radiographs showed that the putty and/or bone growth was not confined to the defect area in Groups A and C, as it was in Group B images (FIG. 2).

Figure 3A:
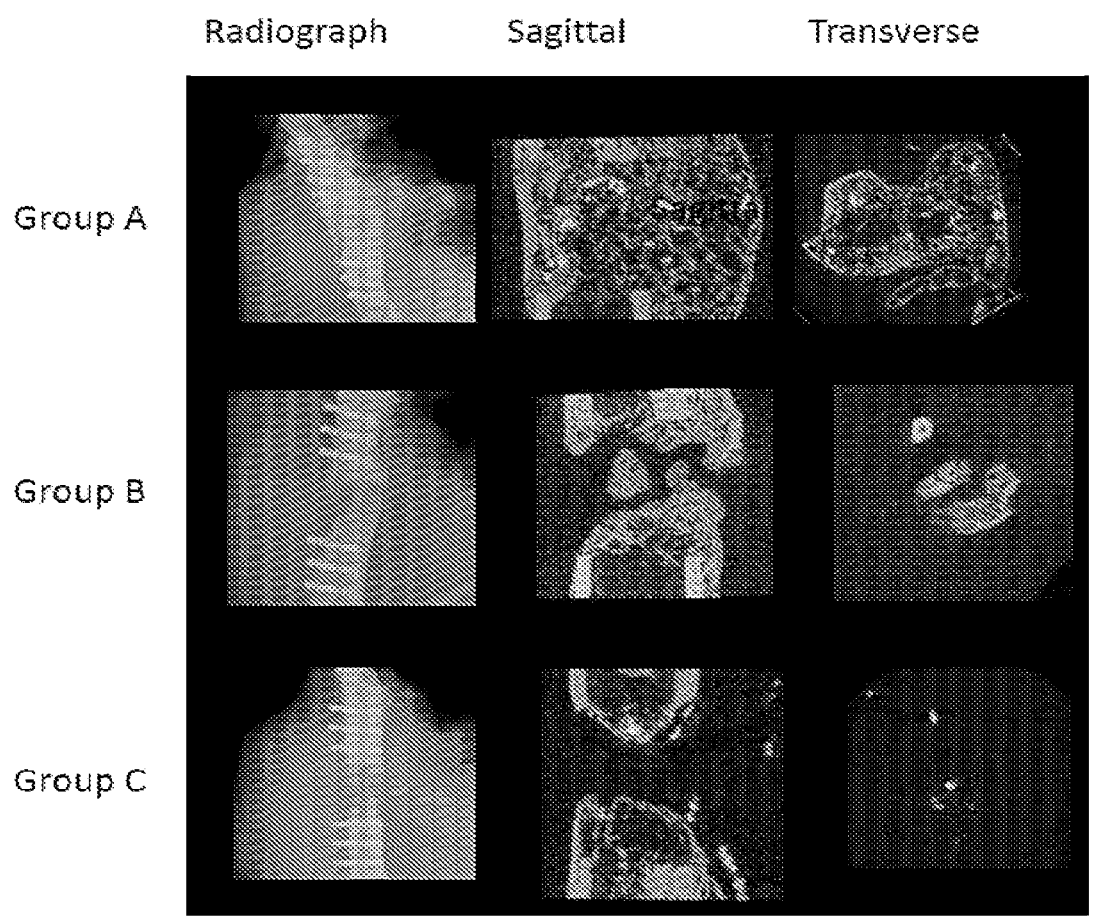
FIG. 3A are representative radiographs, sagittal, and transverse micro-CT images at 4-weeks post-operation from animals in Group A, B, or C.
Figure 3B:
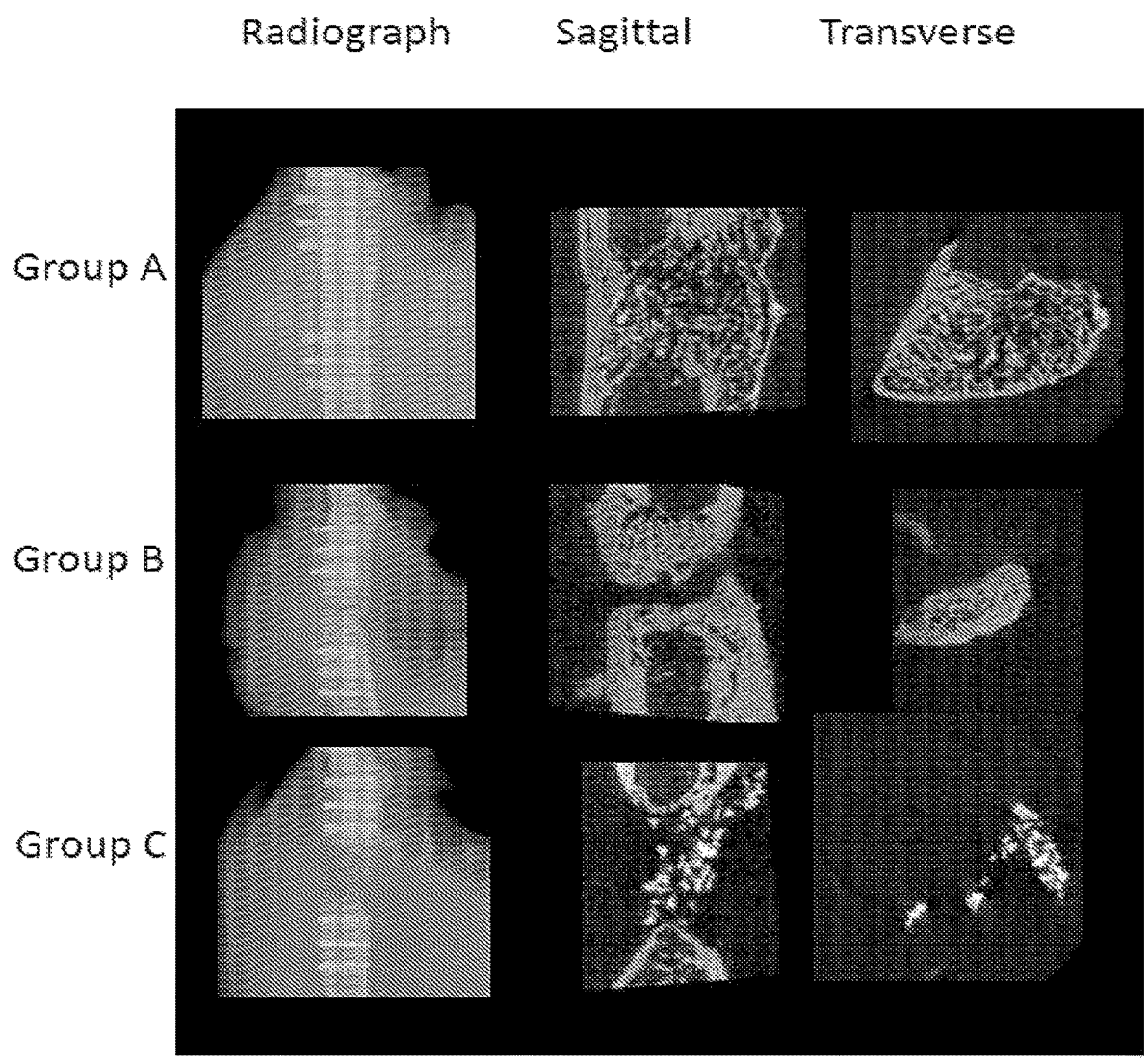
FIG. 3B are representative radiographs, sagittal, and transverse micro-CT images at 4-weeks post-operation from animals in Group A, B, or C.
Figure 4:
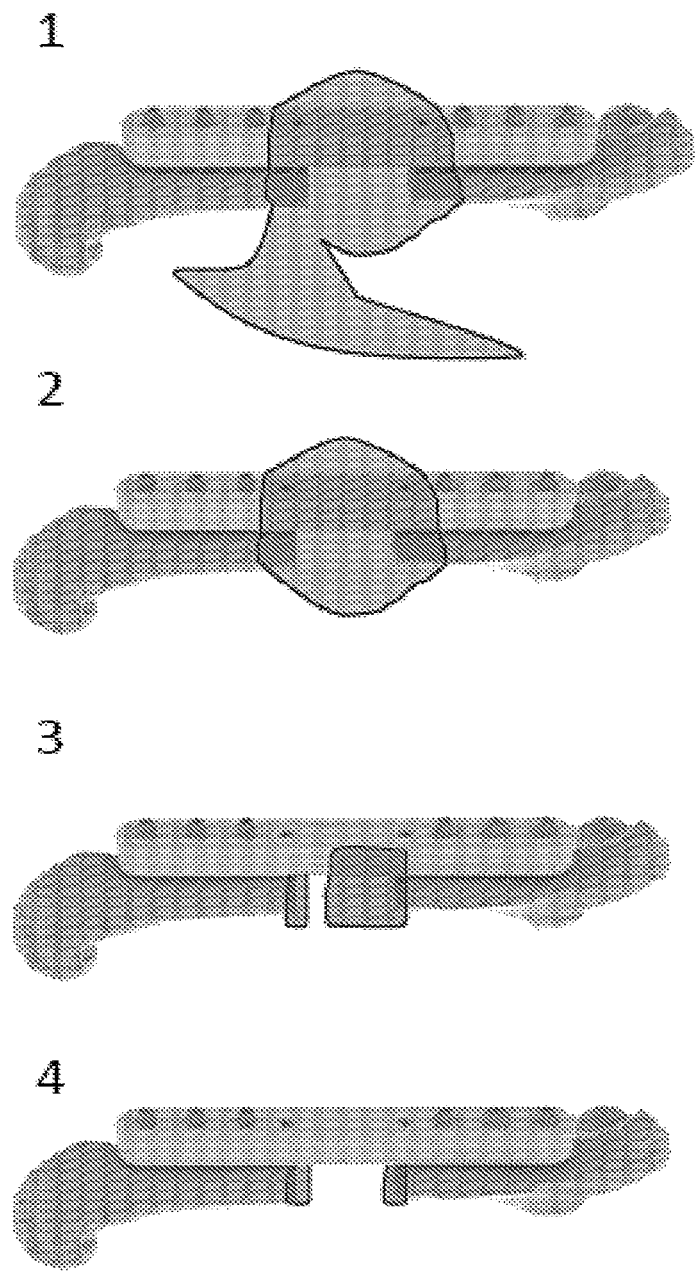
FIG. 4 is a schematic representation of the varied callus formation in animals from Group A, B, or C at 4 weeks post-surgery. The red-shaded area is an approximation of the mineralized callus volume.

At 4-weeks post-surgery, Group A routinely demonstrated bridging of the periosteal callus and frequently demonstrated mature callus with interfragmentary bridging (FIG. 3A). This as in clear contrast to Groups B and C where only callus tissue and little or no callus scores were observed respectively. At 8-weeks post-surgery, while there appears to be no significant radiographic change in the scoring of the mature callus, Group A remained advanced in the healing stage when compared to Group B and C, both of which only marginally improved their scores in the intervening 4 weeks (FIG. 3B). It is worth noting that in Group A, frequent larger boney callus volumes were observed intact but distal to the fracture site suggesting that the treatment in this group was not contained to the fracture region. Representative images from each group at 4- and 8-weeks post-surgery are located in FIGS. 3A and 3B. A schematic of the varied callus formations is represented in FIG. 4.

Micro-Computed Tomography

To quantify the total callus and bone mineral volumes, each specimen was scanned by high resolution μCT (Skyscan, Model 1174, Bruker microCT). Specimens were wrapped in PBS-soaked gauze and secured within a humidified tube prior to scanning. All scans were performed at 6.4 μm voxel resolution and X-ray tube potential of 50 kV and 800 μA. Images were acquired over 180 degrees with intervals of 0.8 degrees and frames were averaged from 2 images taken at each step. For each scan, the images were then reconstructed into a z-stack of images to represent the transverse plane of the femur (N-Recon software, Bruker microCT). All reconstructions used a modified Feldkamp cone-beam algorithm with a smoothing setting of 1, a ring artefact reduction level set to 12, a beam hardening level of 20% and a post-alignment value of no greater than ±1.0. Reconstructions of the callus region excluded the adjacent screws which secured the rat-fix plate, in order to remove the interfering signal of the titanium screws from subsequent analyses. Uniform realignment of datasets were performed using Dataviewer v. 1.5.1 (Bruker, BEL). Reconstructed z-stack images for each specimen were then analysed using CTan software (Bruker microCT). Analyses of bone volume in the fracture region were performed by three manually defined volumes of interest (VOI's). Prior to 3D analyses, all volumes of interest binarised using an adaptive thresholding technique using a specimen-specific hydroxyapatite standard control. 3D analyses were performed to establish total volume and bone volume fractions in each volume of interest.

During necropsy, all treated legs were removed, and placed in either 10% neutral-buffered formalin and kept at room temperature, or gauze-soaked saline and frozen at −20° C., for μCT imaging and mechanical strength testing. All legs were also X-rayed (Faxitron X-ray Imager) and the images graded as per Table 3 above. FIG. 4 shows a graphical representation of bridging of periosteal callus.

Moderate callus was observed in Group B samples, whereas Group C samples showed little or no callus.

Figure 5A:
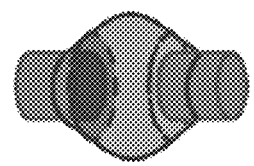
FIG. 5A is a representative graph of micro-CT analyses showing total callus volume in bone specimens obtained at 8 weeks post-surgery from animals in Group A (n=9), B (n=7), or C (n=8). The data are represented as Mean±SEM; *$P<0.01$ vs B, #$P<0.0.1$ vs C.
Figure 5A:
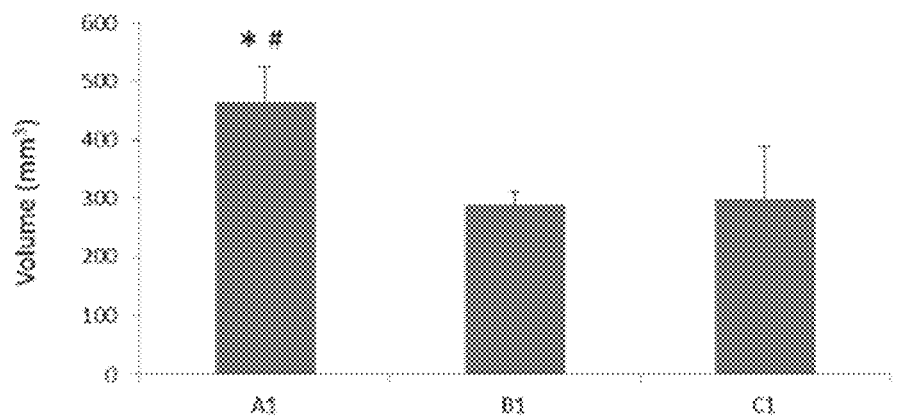
Figure 5B:
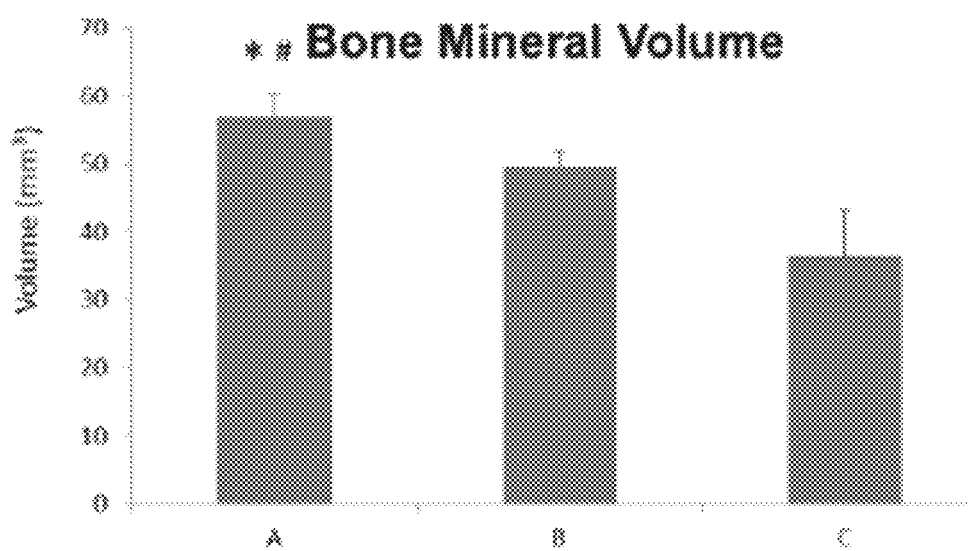
FIG. 5B is a representative graph of micro-CT analyses showing bone mineral volume in bone specimens obtained 8 weeks post-surgery from animals in Group A (n=9), B (n=7), or C (n=8). The data are represented as Mean±SEM; *$P<0.01$ vs B, #$P<0.0.1$ vs C.
Figure 6A:
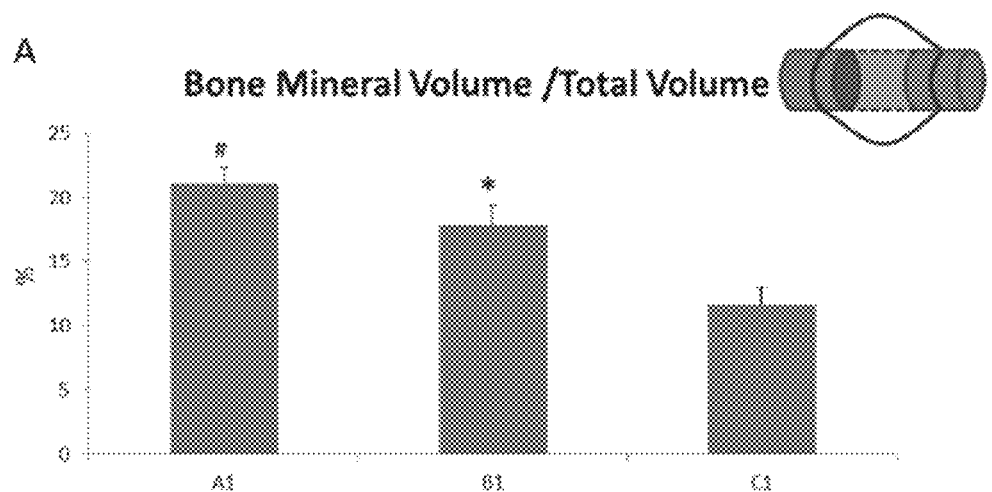
FIG. 6A is a representative graph of micro-CT analyses of the diaphyseal region volume of bone specimens obtained 4 weeks post-surgery in animals from Group A (n=10), B (n=8), or C (n=7). Bone mineral volume is expressed as the percentage of bone mineral volume to total volume. The data are represented as Mean±SEM; *$P<0.05$ vs B, #$P<0.0.5$ vs C. A1 vs B1; p=0.059.
Figure 6B:
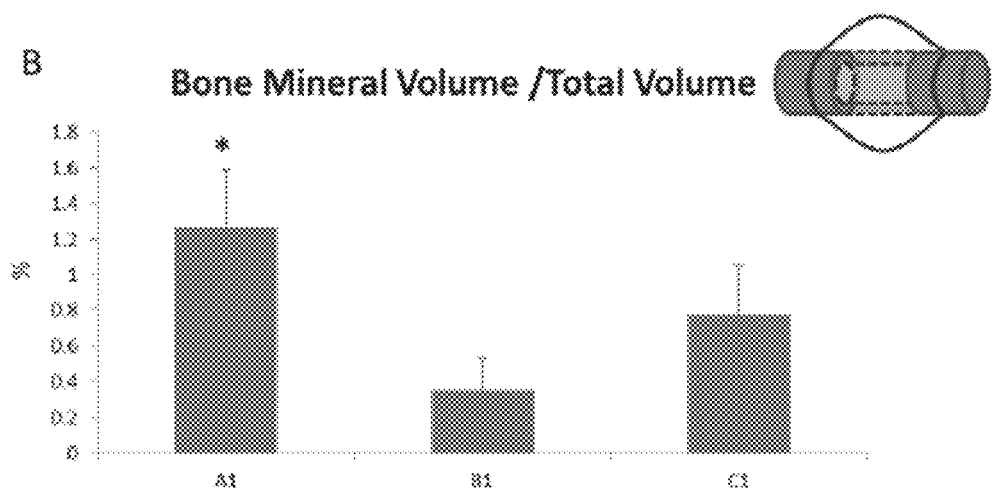
FIG. 6B is a representative graph of micro-CT analyses of the cortical bone volume of bone specimens obtained 4 weeks post-surgery in animals from Group A (n=10), B (n=8), or C (n=7). Bone mineral volume is expressed as the percentage of bone mineral volume to total volume. The data are represented as Mean±SEM; *P<0.05 vs B, #P<0.0.5 vs C.

Analyses of the μCT images for bone volume in the fracture region showed that the total callus volume and the bone mineral volume were significantly higher in Group A (tBMP+β-TCP putty-treated) animals than in either the β-TCP putty (Group C) or the rhBMP+ACS-treated animals ($p<0.01$ in both cases). There were no significant differences between the Group B and Group C animals for either total callus volume or bone mineral volume. These are shown in FIG. 5A and FIG. 5B. When restricting the region to the interpolated shaft region, in both Group A and Group B, the bone mineral volume as a percentage of the tissue volume (BV/TV) was approximately 2-fold greater than Group C ($P<0.05$). The BV/TV for Group A was trending to be increased by 15% when compared to Group B ($P=0.059$) (FIG. 6A). When restricting the region to the interpolated cortical bone region only, in Group A, the cortical bone mineral volume, in BV/TV terms, was 4-fold greater than levels in Group B ($P<0.05$) but not significantly greater than in Group C (FIG. 6B).

Figure 7A:
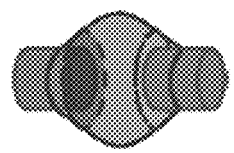
FIG. 7A is a representative graph of micro-CT analyses of total callus volume in bone specimens obtained 8 weeks post-surgery from animals in Group A (n=9), B (n=7), or C (n=8). The data are represented as Mean±SEM; *P<0.01 vs B, #P<0.0.1 vs C.
Figure 7A:
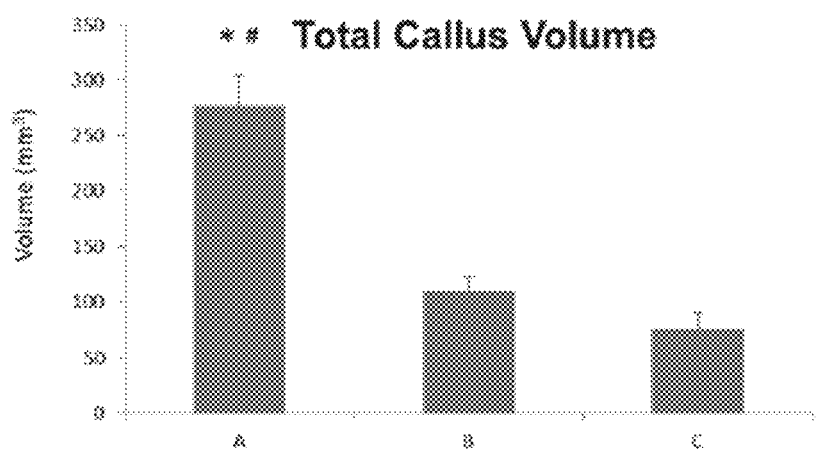
Figure 7B:
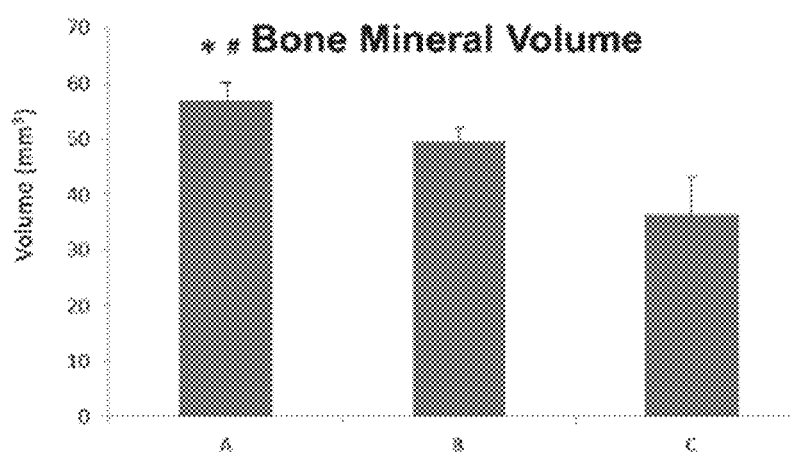
FIG. 7B is a representative graph of micro-CT analyses of bone mineral volume in bone specimens obtained 8 weeks post-surgery from animals in Group A (n=9), B (n=7), or C (n=8). The data are represented as Mean±SEM; *P<0.01 vs B, #P<0.0.1 vs C.

At 8-weeks post-surgery, TCB was markedly increased in Group A when compared to Groups B and C (FIG. 7A and FIG. 7B). However, BMV in Group A is not significantly increased when compared to Group B. These data suggested that while a larger bony callus existed in Group A, the density of bone mineral was more comparable to Group B.

Mechanical Strength Testing of Treated Femur

The mechanical strength testing of femoral callus was performed using 3 point bending method (5940 and BlueHill 3 software, v 3.25, Instron, MA, USA). Each specimen was stored in PBS-soaked gauze at −80° C. until ready for testing. Prior to testing, specimens were gradually thawed to 4° C. over three days to maintain tissue integrity. On the day of testing, samples were scanned by micro-CT in a humidified chamber and kept cool prior to allowing specimens to reach room temperature for mechanical testing. For each specimen, the rat-fix plate was cut immediately prior to testing using a slow speed rotary diamond tipped saw lubricated with cooled phosphate buffered saline. The mid-point of the rat-fix plate was cut to remove the support of the plate in the fracture stabilization. This cut was done so as to cause minimal disturbance to the surrounding callus. After cutting the plate, each bone was then loaded into the 3-point jig with the rat-fix plate in contact with the low anvils with a 10 mm span such that the upper anvil was positioned directly above the cut-point on the plate. The downward motion of the upper anvil tests the resistance, and thus the strength, of the callus. As the bone deforms during testing, the plate separates at the mid-point cut, minimizing the contribution of the plate to the measure of Ultimate Load to Failure (ULF). T Compression testing was performed by gradually increasing the force applied, at a rate of 0.01 mm per second. ULF was determined by the peak force immediately prior to the failure of callus as determined by the force-displacement curve.

Figure 8:
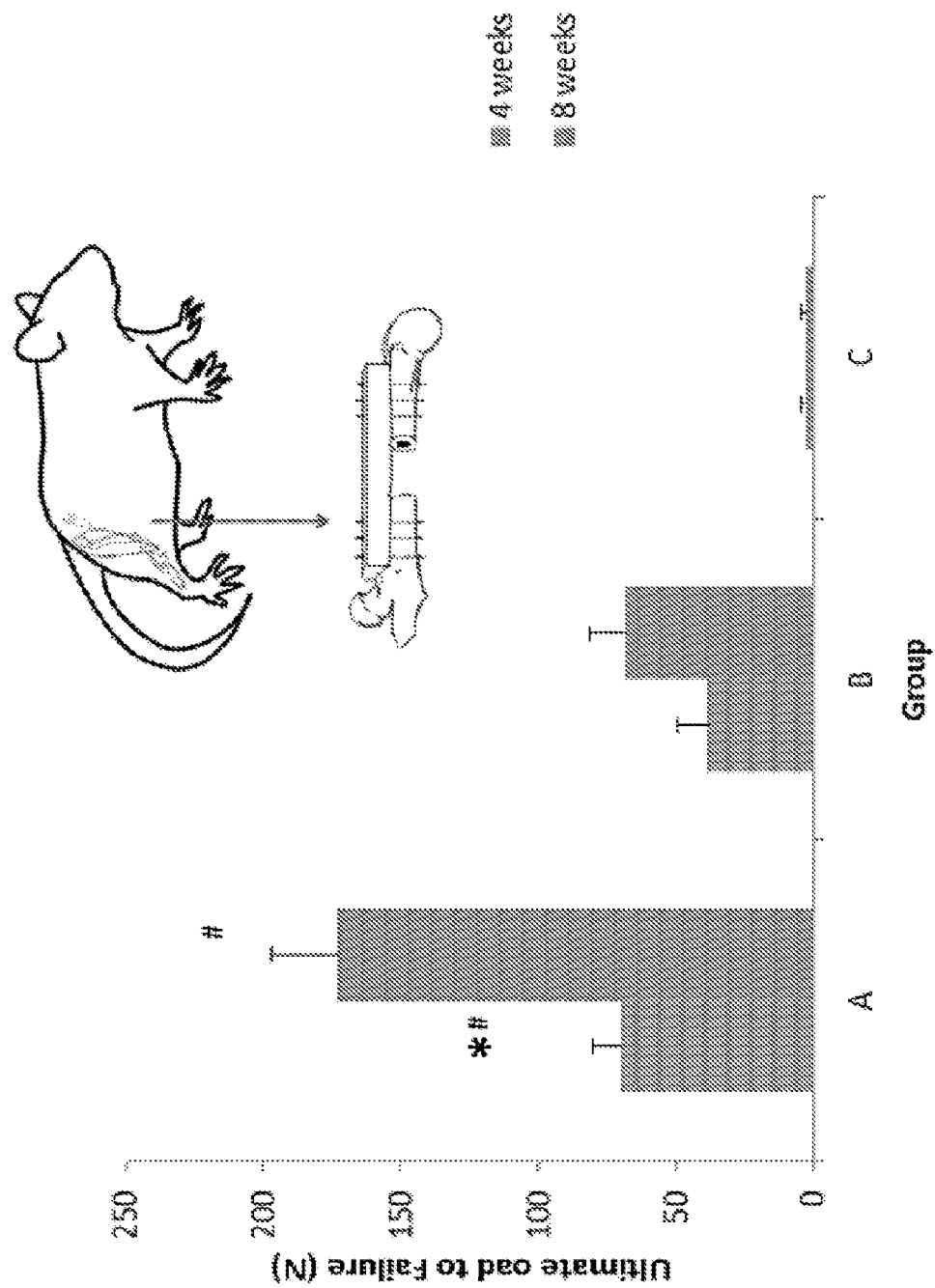
FIG. 8 is a representative graph of ultimate load to failure (ULF) at 4- and 8-weeks post-surgery for animals in Group A, B, or C (for each Group A-C, the bar on the left is 4 weeks and the bar on the right is 8 weeks). Data are represented as the mean+/–S.E.M. *P<0.05 vs 4-week groups; #P<0.01 vs 8-week groups.

The mechanical testing of femoral strength in each fracture specimen required that the contribution of the rat-fix plate be removed without disturbing the callus. Typically this would involve removing the rat-fix plate altogether. However, in numerous samples, in particular in Group A, the extent of callus enveloped the plate making removal impractical. Thus, the compromise was to cut the plate exactly at the mid-point such that it no longer contributed to femoral support. The cut was done in such a way as to only cause minimal damage to the callus. The downward motion of the upper anvil thus tests the resistance, and thus the strength, of the callus. Group A exhibited markedly increased ULF at 4 and 8 week post-surgery when compared to Groups B and C (FIG. 8). At 8 weeks post-surgery, Group A exhibited 2.5-fold increase in ULF when compared to Group B at the same time point ($P<0.001$). Group B demonstrated increased ULF when compared to Group C and both time points. At 8 weeks post-surgery, in Group B, a trend for increased ULF was observed when compared to 4 weeks post-surgery ($P=0.059$).

Histomorphometry of Treated Femur

At ten days prior to end-point, all animals were administered calcein green (25 mg/kg of 10 mg/mL), with the exception of Rat #6, 8, 9, 10, 18, 20, 23, 30 and 50, which were inadvertently administered 12.5 mg/Kg of 10 mg/mL solution. All rats received 100 mg/Kg of xylenol orange (100 mg/mL solution) at three days prior to end-point. All administrations were intraperitoneal.

Figure 9A:
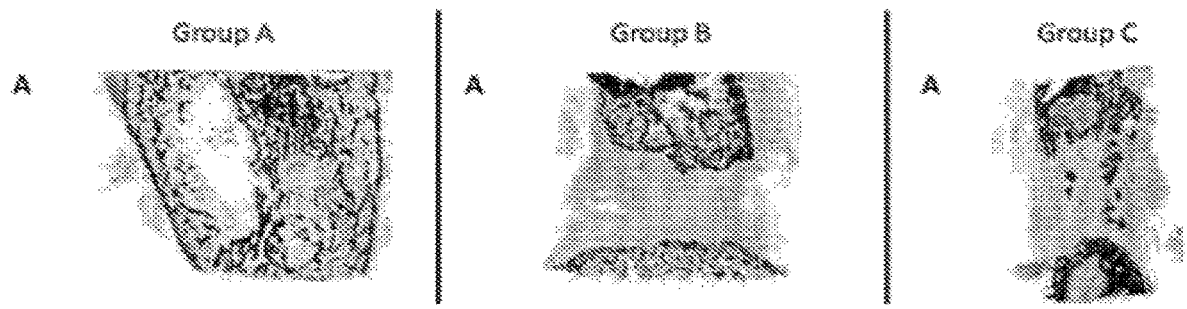
FIG. 9A are representative histological images of Von Kossa- and H&E-stained bone specimens obtained at 4 weeks post-surgery from animals in Group A, B, or C.
Figure 9B:
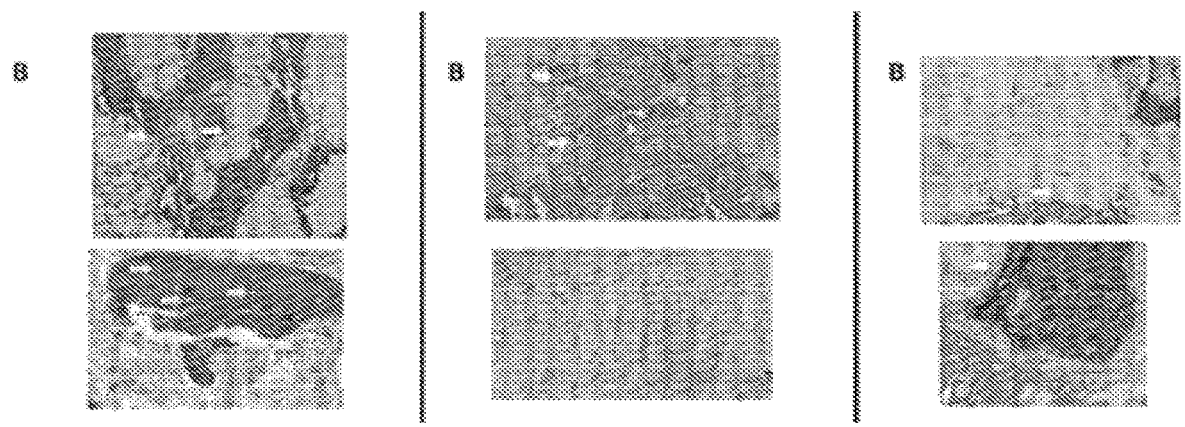
FIG. 9B are representative histological images of TRAP+ osteoclast-stained bone specimens obtained at 4 weeks post-surgery from animals in Groups A, B, or C (left, middle, and right panels, respectively). White arrows indicate osteoclasts, and yellow arrows indicate osteocytes.

At 4 weeks post-surgery, Group A exhibits extensive evidence of mineralization akin to mature trabecular bone (FIG. 9A). Significant remodelling of bone was observed by the presence of osteoclasts (FIG. 9B, white arrows), and the presence of osteocytes in Group A specimens (FIG. 9B, yellow arrows) which is indicative of mature mineralized bone. Osteoblastic activity was observed in the form of double-fluorochrome labelled mineral accretion. The osteoblastic bone formation was frequently observed as 'lines' colored green and red which are in association with each other (FIG. 9B, blue arrows). This represented the formation of lamella (mature) bone, rather than the ad-hoc mineralization of woven bone that occurs in early callus formation, a common observation in Group B. Furthermore, the presence of red-blood cells, and adipocytes indicated that an angiogenesis has occurred and suggested good infiltration of cells to most regions of the callus in Group A specimens.

In Group B, while bone mineral was observed, there were extensive regions of fibrous and cartilage tissue which was unmineralized within the callus region (FIG. 9A). Where new bone mineral occurs, double labels were observed indicating bone formation. However, these double labels were frequently disorganized and often occurred as single labels suggesting that woven bone formation (i.e. initial bone callus formation) was continuing to be formed at this time point (FIG. 9B). While not quantified, it appeared that osteoclasts predominantly existed in regions between the unmineralized and mineralized portions of the callus which suggested an earlier stage of callus development than what was observed for Group A animals.

In Group C, there was no evidence of mineralization, bone formation or bone remodelling. Indeed, there was no evidence of cartilage formation. A fibrous-like material with foreign mineralized spicules existed within the fracture site. There were some instances where osteoclasts as present on the surface of the foreign material, suggesting that this material could be resorbed (FIG. 9B).

Figure 10A:
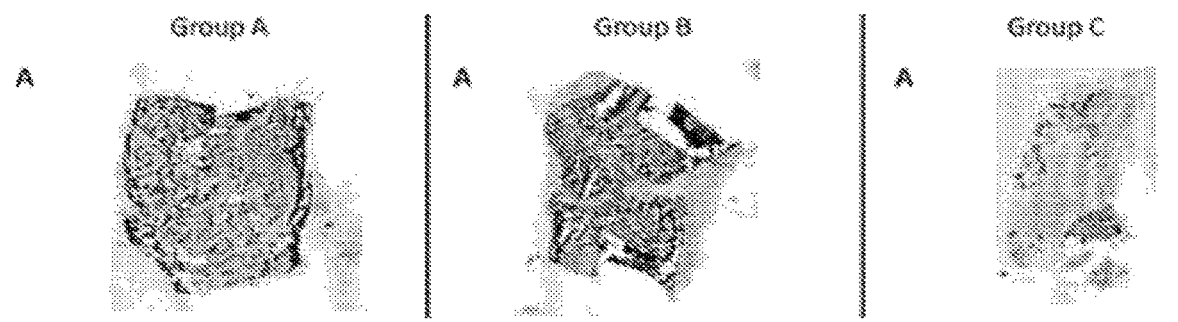
FIG. 10A are representative Von Kossa- and H&E-stained histological images of bone specimens obtained at 8 weeks post-surgery from animals in Group A, B, or C.
Figure 10B:
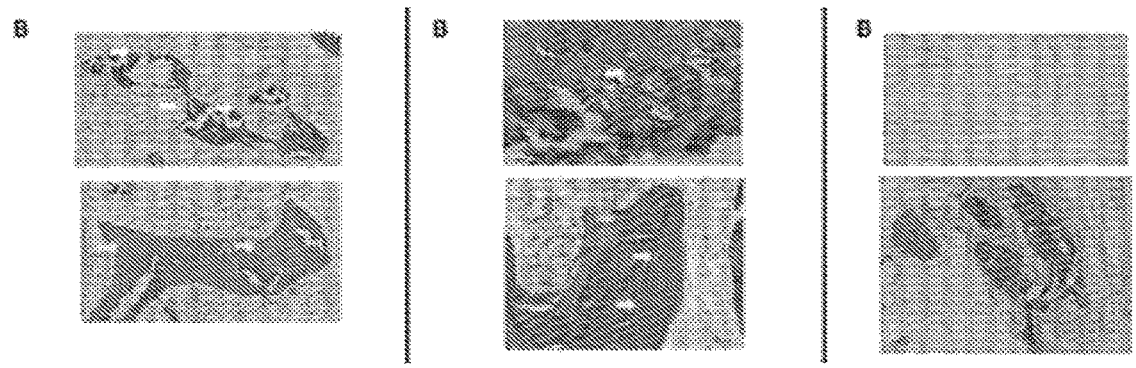
FIG. 10B are representative TRAP+ osteoclast-stained histological images of bone specimens obtained at 8 weeks post-surgery from animals in Group A, B, or C (left, middle, and right panels, respectively). White arrows indicate osteoclasts, and yellow arrows indicate osteocytes.

At 8 weeks post-surgery, the same pattern of activity between the groups was continued (FIG. 10A and FIG. 10B). Of note, however, in Group A, there appeared to be greater distribution of mature bone across all sections, consistent with μCT analyses. Also, a degree of intra-trabecular, or intra-cortical labelling of mineral (FIG. 10B, orange arrows) suggested a further maturing of bone consistent with late-stage bone healing. Also of note, Group B specimens appeared to exhibit all stages of callus formation and remodelling. That is, there was evidence of lack of periosteal bridging at times, the presence of cartilage, woven bone, lamellae bone, and evidence of remodelling as well. In Group C, the persistent lack of healing suggested that this group contained a treatment which was most comparable to a critical-sized defect model without any scaffold of healing agents.

In summary, sixty-one animals were successfully treated with one of three test items following surgical creation of a critical size defect in the right femur. The post-operative recovery was unremarkable in the majority of animals. The test items were all placed within the defects, but on X-ray, it could be seen that the compounds containing the β-TCP putty were spread out of the defect area and into the surrounding tissue. As the collagen sponge was not visible on X-ray, it was not possible to judge if the sponge had moved out of the defect area.

Most animals recovered from surgery well and in most cases were moving as per usual within 24 hours of surgery. A number of the animals were larger than the recommended weight for the plates, but the femurs were not so large that the screws of the internal fixator system were not going through the whole bone, so there should not have been loss of stability while new bone was forming at the site. Two animals had evidence of displaced bones on the two week radiographs, these animals were not heavier than others. One animal was in the rhBMP+ACS group, the other was in the β-TCP putty group. Another animal (Group C) had a broken screw and displaced bone at the six-week post-operative time point. There was no obvious reason why this had occurred.

There were no differences between any of the groups in any clinical pathology parameters or histological analyses of organs and tissues.

Radiographic and histological examination of the treated femurs showed that the Group A animals (tBMP-2+β-TCP putty) had the most evidence of formation of mature bone in the defect site compared to the other two groups. This was shown by bridging of the periosteal callus, increased mineralization, presence of osteocytes, active remodelling of the bone (as shown by the presence of osteoclasts) and evidence of angiogenesis (shown by the presence of red blood cells and adipocytes). Whilst some evidence of mineralization of callus is present in the Group B (rhBMP+ACS) samples, this appeared to be less developed than for Group A. Group C β-TCP putty) showed no evidence of mineralization, suggesting that having a scaffold alone could not induce new bone growth within eight weeks of application into a critical-sized defect.

Group A animals also had significantly stronger bones than either Group B or Group C animals as evidenced by ultimate load to failure tests. This was evident at both four and eight weeks post-treatment.

The differences in callus formation in the process of healing are distinct between all three groups, clearly indicating that there were unambiguous differences in the treatments of fracture in each group.

In Group C, a frank lack of periosteal bridging and minimal bony callus formation at both 4 and 8 weeks was associated with a lack of cellular activity within the fracture. These observations were consistent with the near complete absence of mechanical integrity at either time point.

In Group B, the mineralized callus was more extensive than the levels in Group C both 4 and 8 weeks post-surgery. This was evident in the radiographic and histomorphometric analyses. Furthermore, while periosteal bridging was observed only in some Group B specimens at 8 week post-surgery, there was a clear and overt difference in the histological assessment at both time points with regards to bone formation and cellular activity. Unlike in Group C, the presence of bone formation, frequently in the form of woven bone and occasionally as lamellae bone, was associated with increase in mechanical strength when compared to Group C. Interestingly, neither radiographic nor mechanical strength measures were significantly improved at 8 weeks when compared to 4 weeks post-surgery. This suggested that the majority of activity in callus formation and structural integrity occurred in the first 4 weeks.

Group A exhibited the most advanced healing when compared to the other groups. At 4 weeks post-surgery radiographic evidence of periosteal bridging was a measure that no samples achieved in Group C and often was not observed in Group B, even at 8 weeks post-surgery. Interestingly, while radiographic scores at 8 weeks post-surgery were comparable to 4 week scores, the mechanical strength of the callus was more than double the levels at 4 weeks post-surgery and at least 3-fold greater than levels in Group B, suggesting that considerable bone mineralization occurred within the callus region in the second 4 week period. This observation was consistent with high levels of lamellae bone formation in Group A at 4 and 8 weeks post-surgery, which was distinct from the weaker woven bone formation that occurred in Group B, even at 8 weeks post-surgery. It is important to note that callus volume at 8 weeks of age was lower than levels at 4 weeks post-surgery, suggesting that callus volume was being remodelled into a more compact callus at the site of fracture. In Group A, this was consistent with fewer observations of extraneous mineralized callus distal to the fracture site at 8 weeks post-surgery. With regards to the histological assessment of Group A specimens, observations of osteoclastic none resorption adjacent to regions of bone undergoing bone formation is entirely typical of bone undergoing remodelling which is known to be done to provide a stronger and more efficient structure for skeletal integrity. The additional observations of the presence of osteocytes as well as other cellular structures such as vascular structures and adipocytes clearly makes the bone often indistinguishable from endogenous trabecular micro-anatomy.

In conclusion, the bone specimens form the tBMP-2+β-TCP putty group clearly demonstrated vastly improved bone healing at 4- and 8-weeks post-surgery when compared to samples from animals in the rhBMP+ACS or the β-TCP putty alone treatment groups.

Example 3. Overview of Chimeric β-TCP Polypeptides

Figure 11:
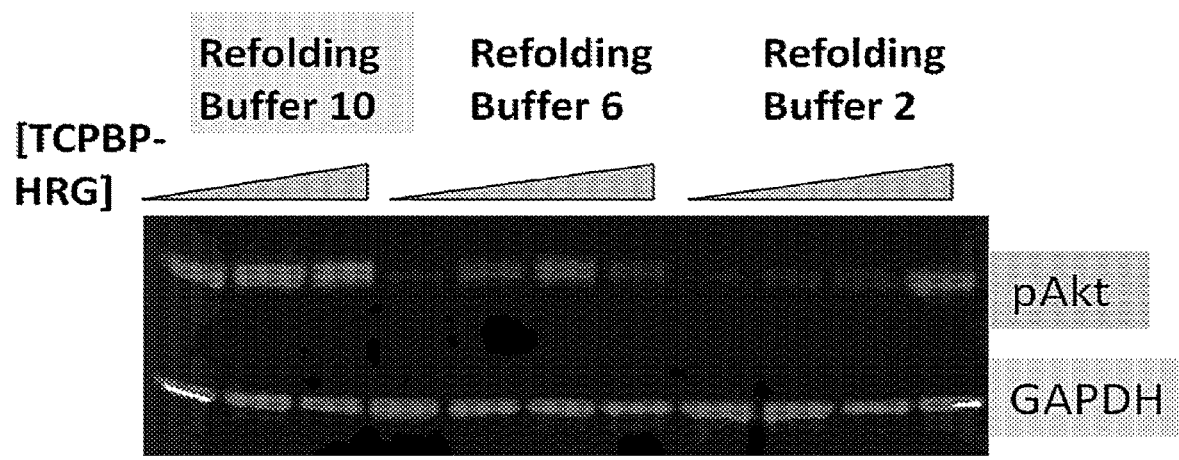
FIG. 11 is a representative immunoblot of MCF-7 cell lysate probed with an anti-P-Akt antibody, wherein the MCF-7 cells were incubated with β-TCBP-HRG.
Figure 12:
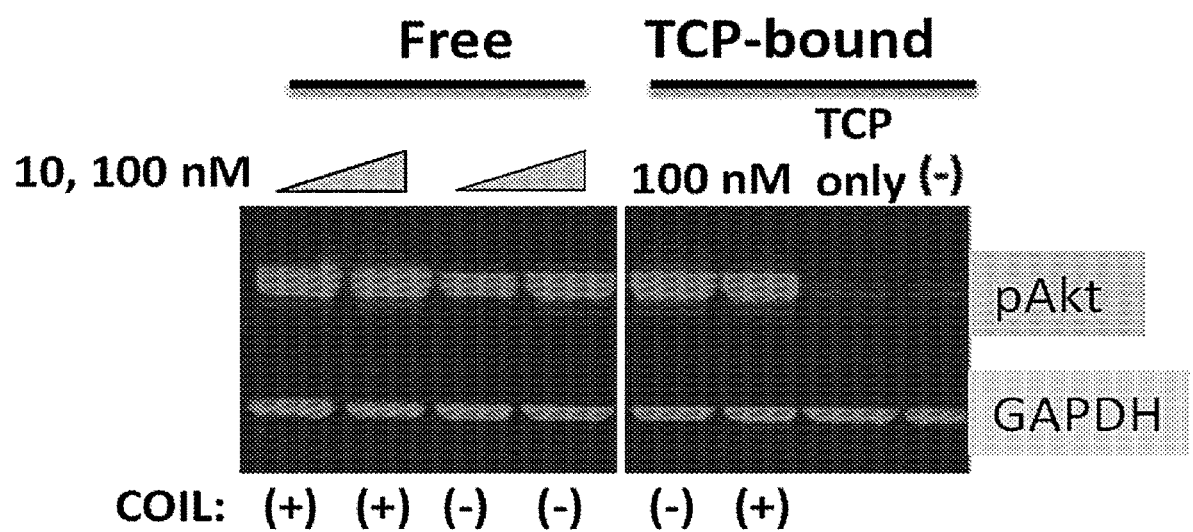
FIG. 12 is a representative immunoblot of MCF-7 lysate probed with an anti-P-Akt antibody, wherein the MCF-7 cells were incubated with β-TCBP-HRG (free) or β-TCBP-HRG (β-TCP-bound).

The present inventors found that chimeric polypeptides comprising a targeting polypeptide that binds to β-TCP maintained activity of the tethered protein (in this example, HRG). The chimeric polypeptide (10×β-TCP-histidine rich glycoprotein HRG) refolded at 22° C. in buffer 10, and following incubation of the chimeric polypeptide with MCF-7 breast cancer cells, Akt activity was detected (FIG. 11). This result indicated that the chimeric polypeptide stimulated signalling activity in the target cell and was able to cause Akt phosphorylation. Next, the Akt activity was determined in 10×β-TCP-HRG bound to a β-TCP peptide (FIG. 12). The β-TCP peptide on its own was unable to cause Akt phosphorylation in MCF-7 cells, however, incubation of MCF-7 cells with β-TCP peptide bound to 10×β-TCP-HRG led to Akt phosphorylation. Interestingly, the extent of Akt phosphorylation was not affected whether the chimeric polypeptide was bound to a β-TCP peptide or not.

Example 4. Binding Affinity of tBMP-2 to Various Substrate Materials

Binding assays were performed to quantify the affinity of tBMP-2 protein to various substrates, including commercially available bone graft materials, ceramic powders, 3D printable scaffold materials, and a plasma-sprayed hydroxyapatite coating. The tBMP-2 used in this study comprises MPIGSLLADTTHHRPWTVIGESTHHRPWSIIGESS-FIHKPFTGLGDTTHHRPWGILAESTHHKP WTASGAGGSEGGGSEGGTSGATGAGTSTSGG-GASTGGGTGQAKHKQRKRLKSSCKRHPLY VDFSDVGWNDWIVAPPGYHAFYCHGECPFP-LADHLNSTNHAIVQTLVNSVNSKIPKACCVPT ELSA-ISMLYLDENEKVVLKNYQDMVVEGCGCR (SEQ ID NO: 502). First, 10 mg of each material was washed with deionized water followed by acetate buffer. Then either a 150 μg or 250 μg load of tBMP-2 protein was applied to each material and allowed to bind under light agitation for 90-120 minutes. The flow through was aspirated (removing the tBMP-2 which did not bind to the substrate material), and a wash was conducted with acetate buffer. A subsequent overnight elution was done by immersing the substrate material in a sodium phosphate buffer (100 mM NaPhos, 4 M Urea, 1 M NaCl, 10% 1,6 Hexanediol, pH=8) to remove the bound protein from the substrate for measurement.

The bound tBMP-2 was quantified by either 1) running non-reducing SDS Page gel electrophoresis and comparing the eluted tBMP-2 band to the tBMP-2 load band with Image J Gel Analysis tool, or 2) conducting a Bradford assay (with a BSA standard curve) on the eluted tBMP-2 and tBMP-2 load. Dividing the eluted tBMP-2 quantity by the original tBMP-2 load quantity and multiplying by 100 gave the % of tBMP-2 load that was strongly tethered to the substrate after the binding incubation step.

Table 6 summarizes the materials that were evaluated as well as the % of tBMP-2 load which was effectively tethered to the substrate (% Bound).

TABLE 6

Summary of Binding Activity

| Product | Description | Manufacturer | Load tBMP2 Applied to Material | Method of measurement | % of tBMP2 load bound to material |
|---|---|---|---|---|---|
| Mastergraft Strip | Biphasic TCP (85% β-Tricalcium Phosphate: 15% Hydroxyapatite)/Type I bovine collagen composite | Medtronic | 15 ug tBMP2/mg material | Bradford Assay | 69% |
| Vitoss Foam Pack | β-Tricalcium Phosphate/Type I bovine collagen composite | Stryker | 15 ug tBMP2/mg material | Bradford Assay | 82% |
| chronOS Strip | β-Tricalcium Phosphate/poly (lactide co-ε-caprolactone) composite | DePuy Synthes | 15 ug tBMP2/mg material | Image J Gel Analysis Tool | 75% |
| Vitoss Micro-morsels | β-Tricalcium Phosphate granules (1 mm-2 mm) | Stryker | 15 ug tBMP2/mg material | Image J Gel Analysis Tool | 74% |
| Lifeink 500 | Calcium Phosphate Cement 3D printable ink | Advanced Biomatrix | 15 ug tBMP2/mg material | Image J Gel Analysis Tool | 87% |
| Hyperelastic Bone | Hydroxapatite/Poly(lactic-co-glycolic acid) 3D printable ink | Dimension Inx | 15 ug tBMP2/mg material | Image J Gel Analysis Tool | 58% |
| Bioactive Glass | Combeite 45S5 Bioactive Glass powder | Stryker | 25 ng tBMP2/mg material | Image J Gel Analysis Tool | 49% |
| Silicon Nitride Powder | $Si_3N_4$ powder, 99% purity | Chemsavers | 25 ng tBMP2/mg material | Image J Gel Analysis Tool | 54% |
| β-TCP Powder | β-Tricalcium Phosphate powder, 3-5 μm particle size | CaP Biomaterials | 25 ug tBMP2/mg material | Image J Gel Analysis Tool | 79% |
| β-TCP Spray Dried Powder | β-Tricalcium Phosphate spray dried powder, <38 μm particle size | CaP Biomaterials | 25 ug tBMP2/mg material | Image J Gel Analysis Tool | 78% |
| Hydroxyapatite Powder | Hydroxyapatite powder, 3-5 μm particle size | CaP Biomaterials | 25 ug tBMP2/mg material | Image J Gel Analysis Tool | 57% |
| HA-coated Bone Screw | Hydroxyapatite plasma spray-coated stainless steel bone screw | Citieffe | 25 ug tBMP2/mg material | Bradford Assay | 44% |

TABLE 6-continued

Summary of Binding Activity

| Product | Description | Manufacturer | Load tBMP2 Applied to Material | Method of measurement | % of tBMP2 load bound to material |
|---|---|---|---|---|---|
| P-TCP Granules | (6 mm dia × 5 mm long piece cut from screw) β-Tricalcium Phosphate granules, 250-1000 μm particle size | CaP Biomaterials | 15 ug tBMP2/mg material | Bradford Assay | 70% |
| Hydroxy-apatite Granules | Hydroxyapatite granules, 250-1000 μm particle size | CaP Biomaterials | 15 ug tBMP2/mg material | Bradford Assay | 52% |
| ReBOSSIS | Cotton-like bone void filler. Main ingredients are β-Tricalcium Phosphate, bioabsorbable polymer, and SiV (silicon-containing calcium carbonate) | Orthorebirth | 15 ug tBMP2/mg material | Bradford Assay | 83% |

Example 5. Generation of Ceramic-Binding Protein Variants

Ceramic-binding protein variants were generated by fusing targeting polypeptides that bind to ceramics such as calcium phosphate (Ca—PO4) and hydroxyapatite to protein biologics, including BMP2, BMP7, IGF1, FGF18, TGFβ3, EGF, and NRG1. The resulting protein variants (tBMP2, tBMP7, tIGF1, tFGF18, tTGFβ3, tEGF, and tNRG1, respectively) and the modification details are provided in Table 7. Dimeric binding motif refers to the presence of two binding domains due to the dimeric nature of the ligand.

TABLE 7

Modified Proteins

| Modified Protein | Total MW (kDa) | Terminal Modification | Dimeric Binding Motif | Ca-PO4 binding | Hydroxyapatite binding |
|---|---|---|---|---|---|
| tBMP2 | 22.8 | N-only | Y | Y | Y |
| tBMP7 | 23 | N-only | Y | Y | Y |
| tIGF1 | 17.6 | N- and/or C- | N | Y | Y |
| tFGF18 | 30.1 | N- and/or C- | N | Y | Y |
| tTGFβ3 | 22.6 | N-only | Y | Y | Y |
| tEGF | 16.1 | N- and/or C- | N | Y | Y |
| tNRG1-β1 | 17.4 | N- and/or C- | N | Y | Y |

Example 6. Safety and Efficacy of tBMP-2 on a Ceramic Carrier in a Challenging Caprine Critical Defect Model This example demonstrates that tBMP-2 accelerates bone repair in a rigorous and challenging segmental bone defect animal model (CCTDM).

Reconstruction of severe segmental bone loss remains a major challenge for treating wounded warriors and is frequently complicated by other conditions and concomitant injuries. In particular, there is an unmet need for precise tissue regeneration following trauma. Bone morphogenetic protein-2 (BMP-2) is the most effective osteoinductive agent identified to date and is used in clinical orthopaedic practice to actively promote bone formation. However, BMP-2 use is limited by cost and the need to control release and delivery.

To address this, a method for controlled, local delivery of BMP-2 activity has been engineered using a fusion protein that enables specific binding and retention of bioactive BMP-2 (tBMP-2) on beta-tricalcium phosphate ceramic substrates (CS). This example demonstrates the ability of CS-bound tBMP-2 to accelerate bone repair in a dose-responsive manner in the most rigorous bone defect model yet reported. tBMP-2 (SEQ ID NO: 502) was generated having a binding site that binds ceramic with high affinity and remains tightly bound under physiological conditions, thus reducing off-target effects. tBMP-2 behaves like a paint when applied to orthopaedic ceramics, thus reducing off-target effects. Targeted delivery of tBMP-2 can potentially improve the safety and efficacy of the current standard of care for bone repair.

Figure 13:
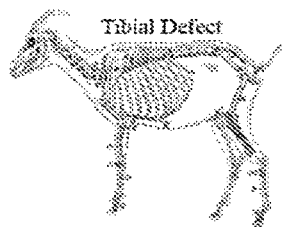
FIG. 13 outlines the procedure for generating a tibial defect in goats as described in Example 6.
Figure 13:
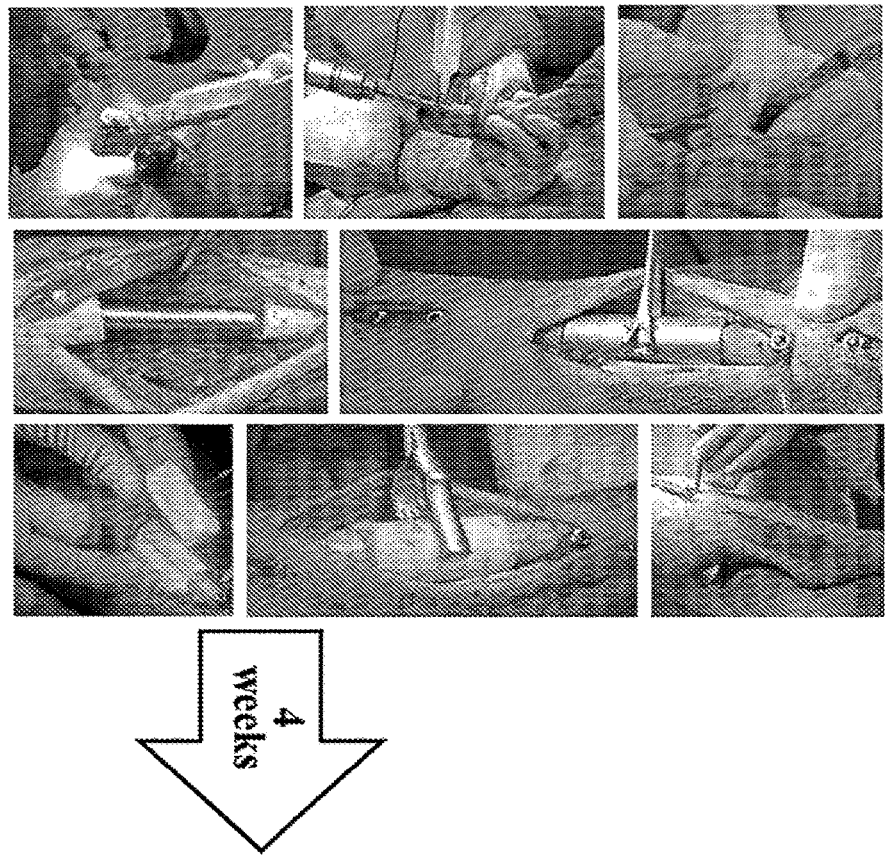
Figure 13:
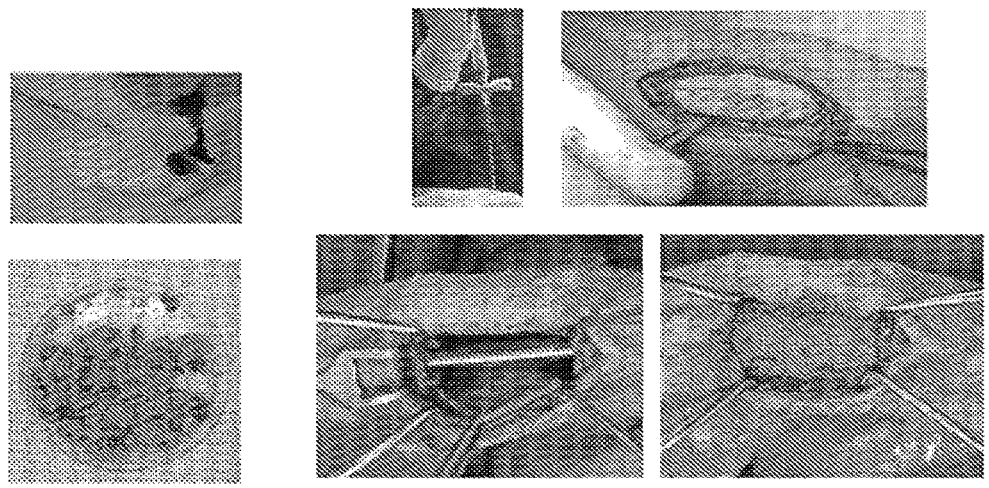

Briefly, twenty-four goats (female, 4-6 years; Body weight=43±9 kg) underwent the Caprine Chronic Tibial Defect Model (CCTDM) protocol after IACUC approval. As used in this example, tBMP-2=Ceramic scaffold composed of ß-TCP granules (CaP Biomaterials, East Troy, WI) and fibers (ORTHOReBIRTH, Georgetown, Texas). Treatment groups included group A=Ceramic substrate only (control) (n=4), group B=Low dose tBMP-2 added to the scaffold (0.214 mg/cc defect) (n=4), group C=Medium dose tBMP-2 added to the scaffold (2.15 mg/cc defect) (n=8), group H=High dose tBMP-2 (8 mg/cc defect) (n=8). The treatment procedures are outlined in FIG. 13. The Surgery 1 procedure included creating a 5-cm bone/periosteal defect in tibial diaphysis, stripping 2-cm periosteum from each segment, removing 10 cm$^3$ of cranial tibialis/gastrocnemius, placing 5-cm custom smooth or textured PMMA spacer, and stabilizing with interlocking intramedullary nail. Surgery 2, performed 4 weeks after Surgery 1, included aspirating 6 cc of sternal raw bone marrow and adding it to each graft, removal of the spacer while preserving the Induced Membrane (IM) using a bomb bay door opening, and placing the graft into the defect. The implant at each graft site was supplemented with 6 cc of bone marrow aspirated from the sternum to provide a source of osteogenic connective tissue progenitors in a marrow-derived clot. Follow up procedures were performed during the 12 weeks after Surgery 2, including anterior-posterior (AP) and mediolateral (ML) Radiographs every 4 weeks and physical examination (lameness). Twelve weeks after Surgery 2, tibia were harvested and fixed in Formalin. Outcomes measured included Micro CT (primary outcome), Radial % Bone Volume (BV) and Moment Angle plots, Total Bone Volume (mm3) in 2.5 cm central region, and 12-weeks radiographs (AP and ML views).

Figure 14A:
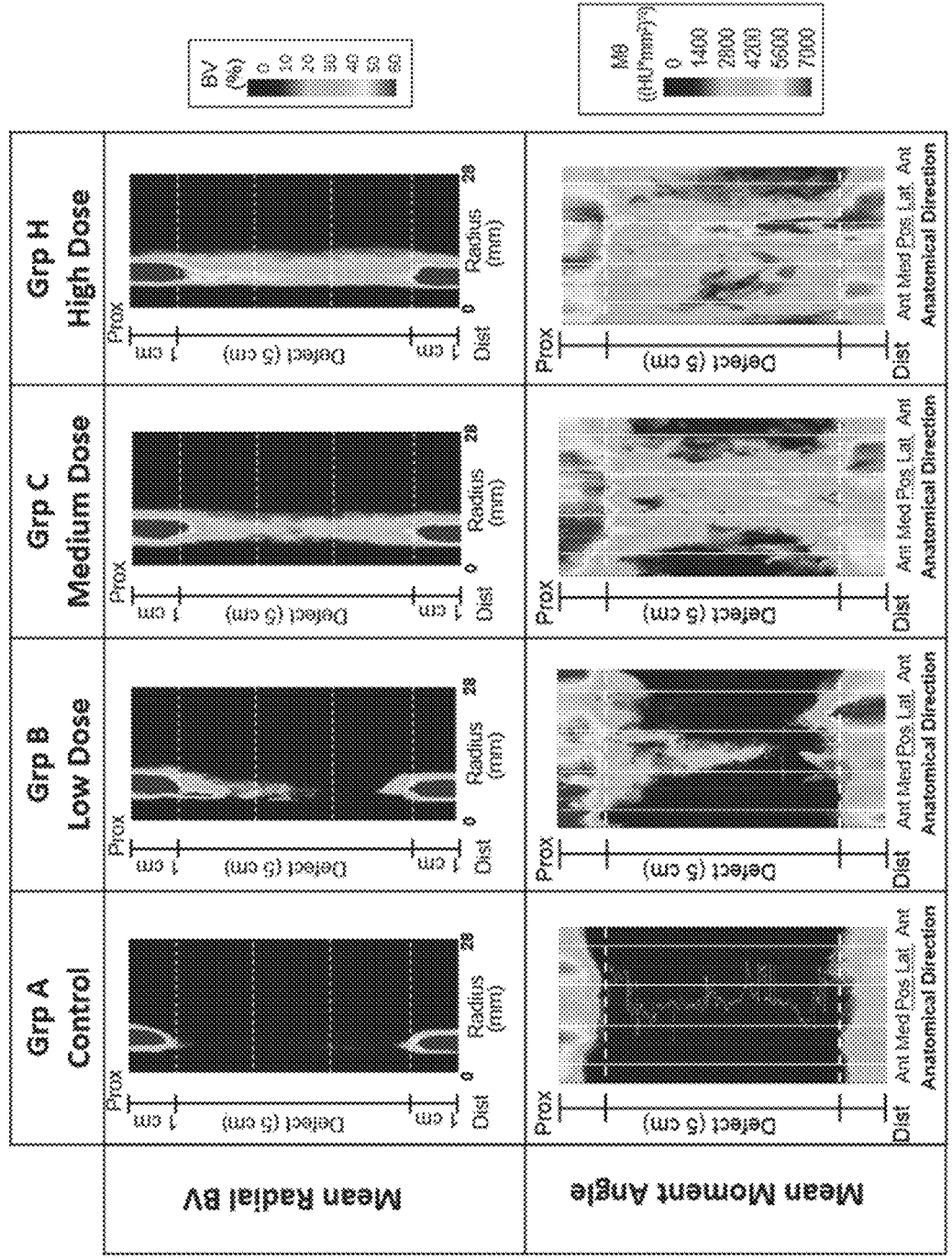
FIG. 14A are Mean Radial BV and Mean Moment Angle plots that illustrate the pattern and extent of new bone mineralization in the defect site for each treatment group.

The radiographic data (FIG. 14D) show that tBMP-2 demonstrates superior bone formation in a greater number of animals than the low dose and control conditions and the amount of new bone formed in both tBMP-2 groups was significantly higher than in the substrate-only group. Mean radial percent BV analysis illustrate a tendency for bone to form most readily in the medial-posterior aspect of the defect (FIG. 14A).

Figure 14B:
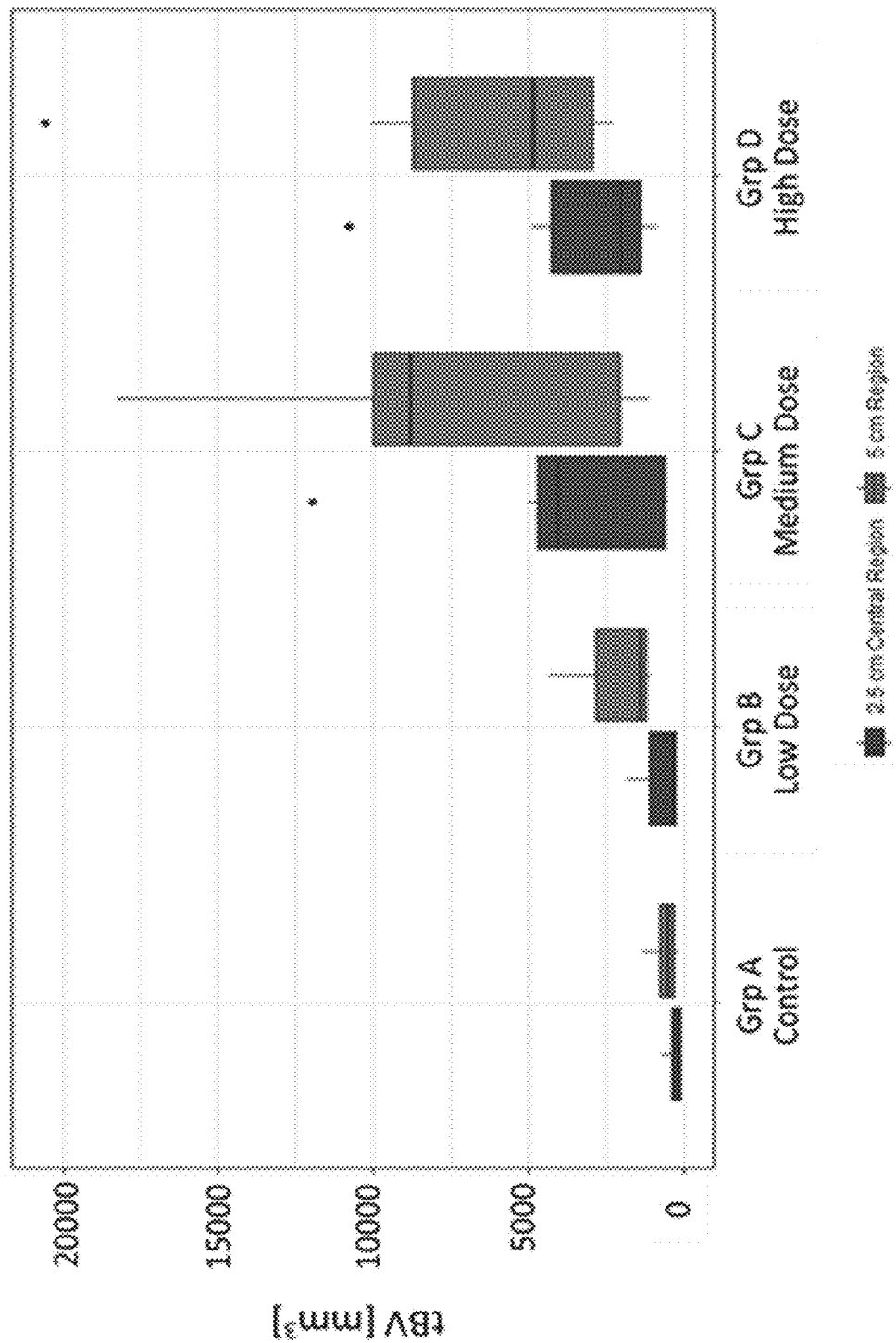
FIG. 14B are Total Bone Volume plots in the 2.5 cm central region and 5 cm full defect region. Variation of total new bone volume among goats within treatment group was measured. At medium dose and high doses, tBMP-2 demonstrated comparable bone formation that was superior to the low dose and substrate only groups. For each Group A-D, the bar on the left corresponds to the 2.5 cm central region, and the bar on the right corresponds to the 5 cm region.

The results show a statistically significant dose-response (FIG. 14C), with medium dose and high dose tBMP-2 demonstrating comparable bone formation that was superior to the carrier only group (FIG. 14B). Even the lowest dose elicited bone formation. No adverse effects were noted in any animals, including the highest dosed animals.

This study demonstrates that tBMP-2 delivered on a ceramic carrier can maintain local BMP-2 concentrations necessary to induce bone formation with high efficacy in a severely compromised tissue bed with a good safety margin, even when combined with autogenous bone marrow-derived cells. By binding tBMP-2 to resorbable substrates, the local concentration can be maintained over the time scales required to induce complete osteoinduction. In addition, the tBMP-2 technology tested in this study has demonstrated safety and efficacy in the most challenging large animal model that is available. It was notable that bioactivity remained only where the device was implanted. These data enable the selection of tBMP-2 dosing and formulation for subsequent preclinical model testing and future clinical trials. Improved materials and strategies for bone regeneration in compromised tissue beds will enable better outcomes for military and civilian patients suffering from large traumatic lower extremity injuries and reduce the need for amputation.

Example 7. Safety and Efficacy of tBMP-2 on a Ceramic Carrier in a Sheep Critical Defect Model This example demonstrates the effectiveness of tBMP-2 (SEQ ID NO: 502) in a challenging ovine critical tibial defect model (OCTDM) as compared to autograft, the current standard of care.

Figure 15:
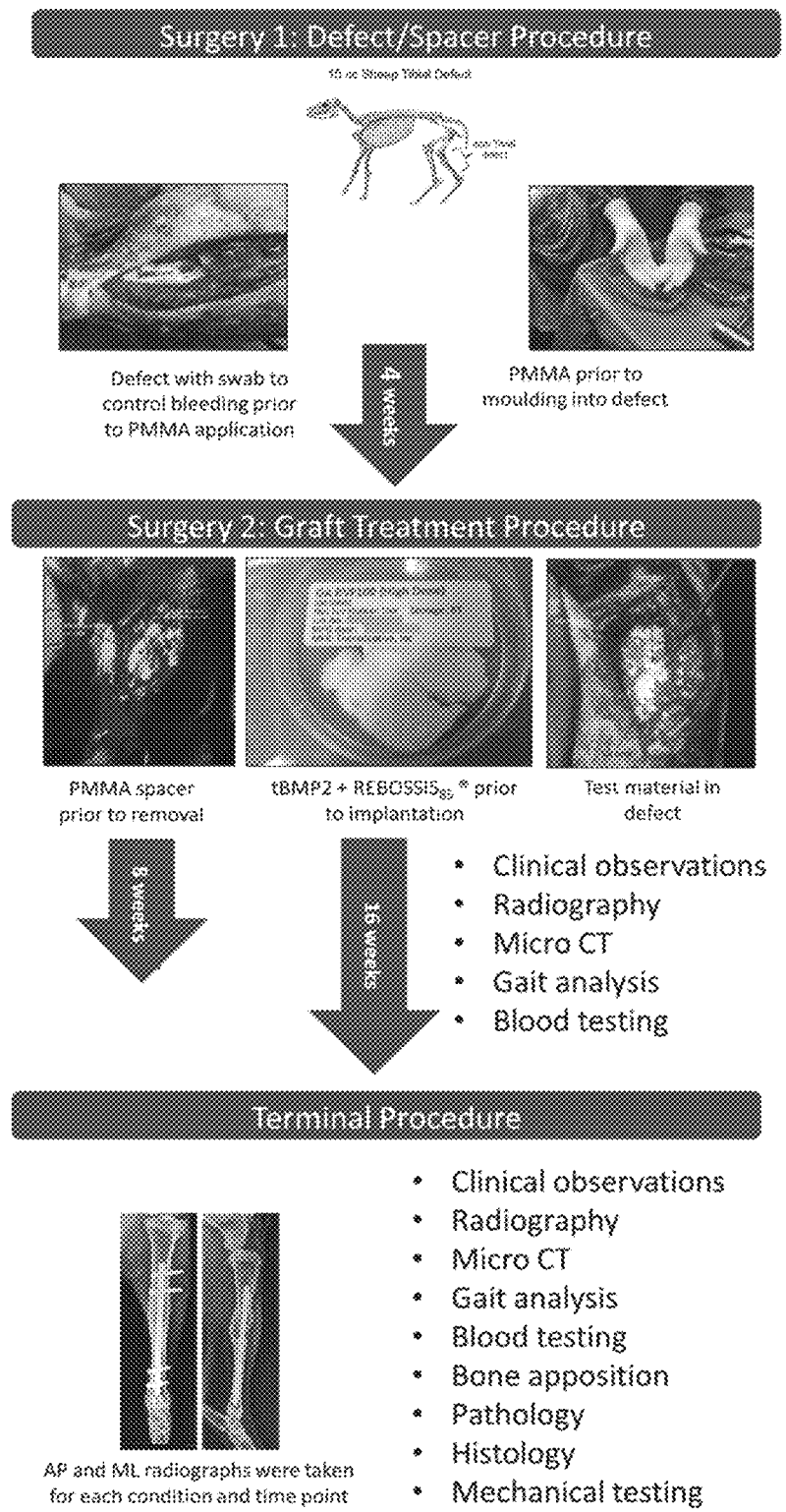
FIG. 15 outlines the procedure for generating and treating a tibial defect in sheep as described in Example 7.

Briefly, twenty-four male skeletally mature wethers (castrated sheep) underwent the two-surgical OCTDM procedures (using the Masquelet technique) under approved SAHMRI IACUC and ACURO protocols. FIG. 15 provides an outline of the first and second surgeries, Surgery 1 and Surgery 2, respectively. Surgery 1 included excision of 4 cm of the tibial diaphysis, reaming of the tibia if necessary, stabilization of the tibia with a stainless-steel intramedullary nail and two proximal and two distal cross-locking bolts, placing a polymethyl methacrylate (PMMA) spacer and molding such that it replicated the dimensions of the tibia and overlapped the ends of the osteotomy site by a few millimetres. Surgery 2 was performed 4 weeks after Surgery 1, where the spacer was removed and the defect (contained within an induced fibrous membrane) was filled with the test materials or control item. Treatment group 1 animals (n=8) received 2 mg tBMP-2 per cc of defect (CS, ReBOSSIS$_{85}$®), treatment group 2 animals (n=8) received 5 mg tBMP-2 per cc defect (CS), and treatment group 3 animals received autograft harvested from the iliac crest as a control.

Radiographs were taken immediately after each surgery and every two weeks following one month of post-graft recovery to evaluate bone formation, union and remodelling of the defect. The groups were divided between 8- and 16-week endpoints and the following methods were used for analysis: hematology, biochemistry, pathology, mechanical testing, micro computed tomography and bone histology. Two sheep were excluded from data analyses due to nail failure and two sheep presented with infection (not related to surgery or treatment) that may have impacted healing.

Figure 16A:
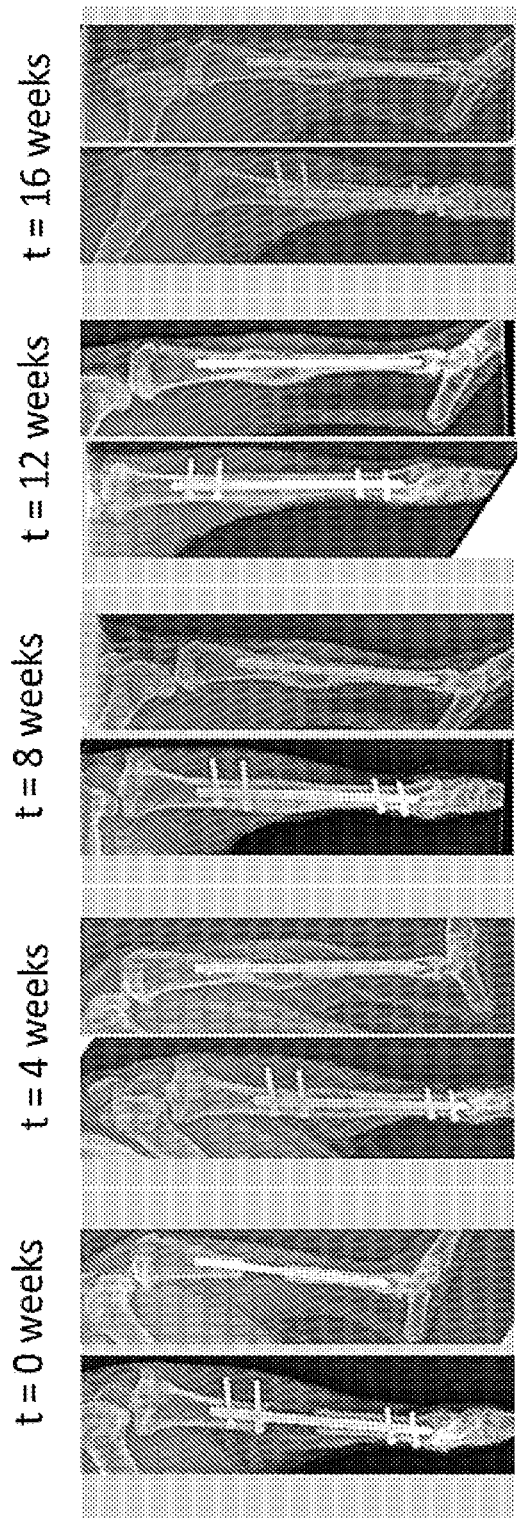
FIG. 16A are representative radiographs at each month of the study described in Example 7, in the treatment group receiving 2 mg tBMP-2 per cc defect volume.
Figure 16B:
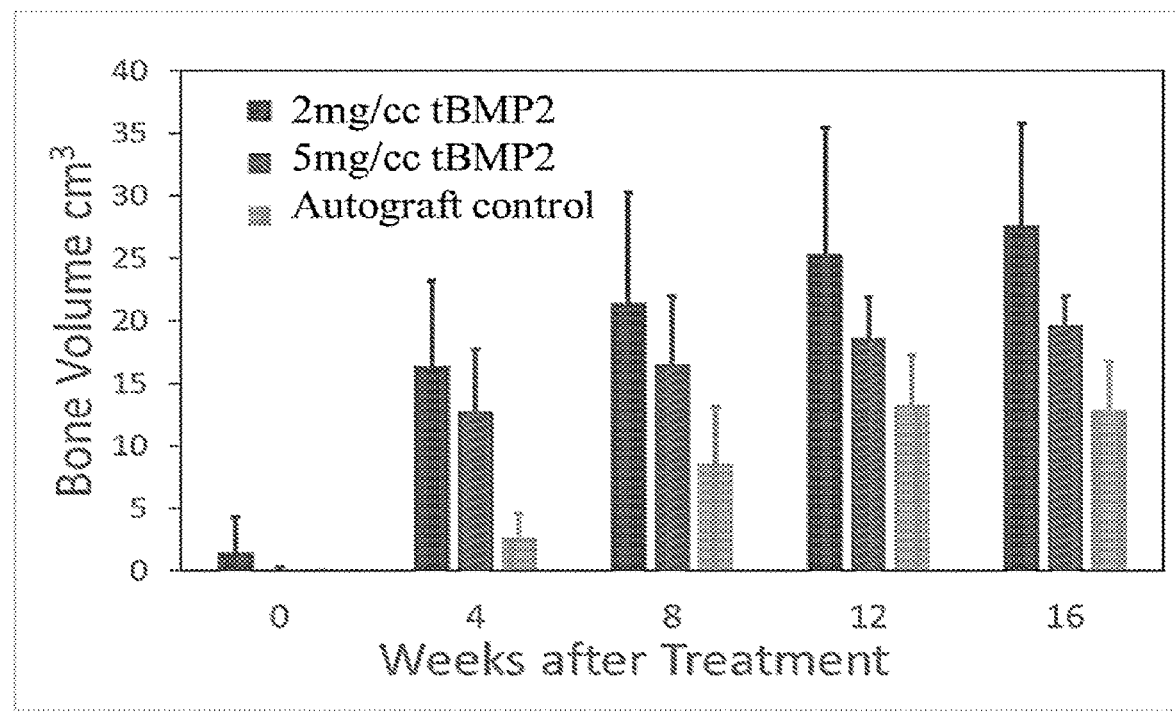
FIG. 16B is a graph of the mean±standard deviation bone volumes as measured from CT images for the study described in Example 7. For each week of treatment, the bars from left to right (dark to light shading) represent: 2 mg/cc tBMP2, 5 mg/cc tBMP2, and autograft control.
Figure 16C:
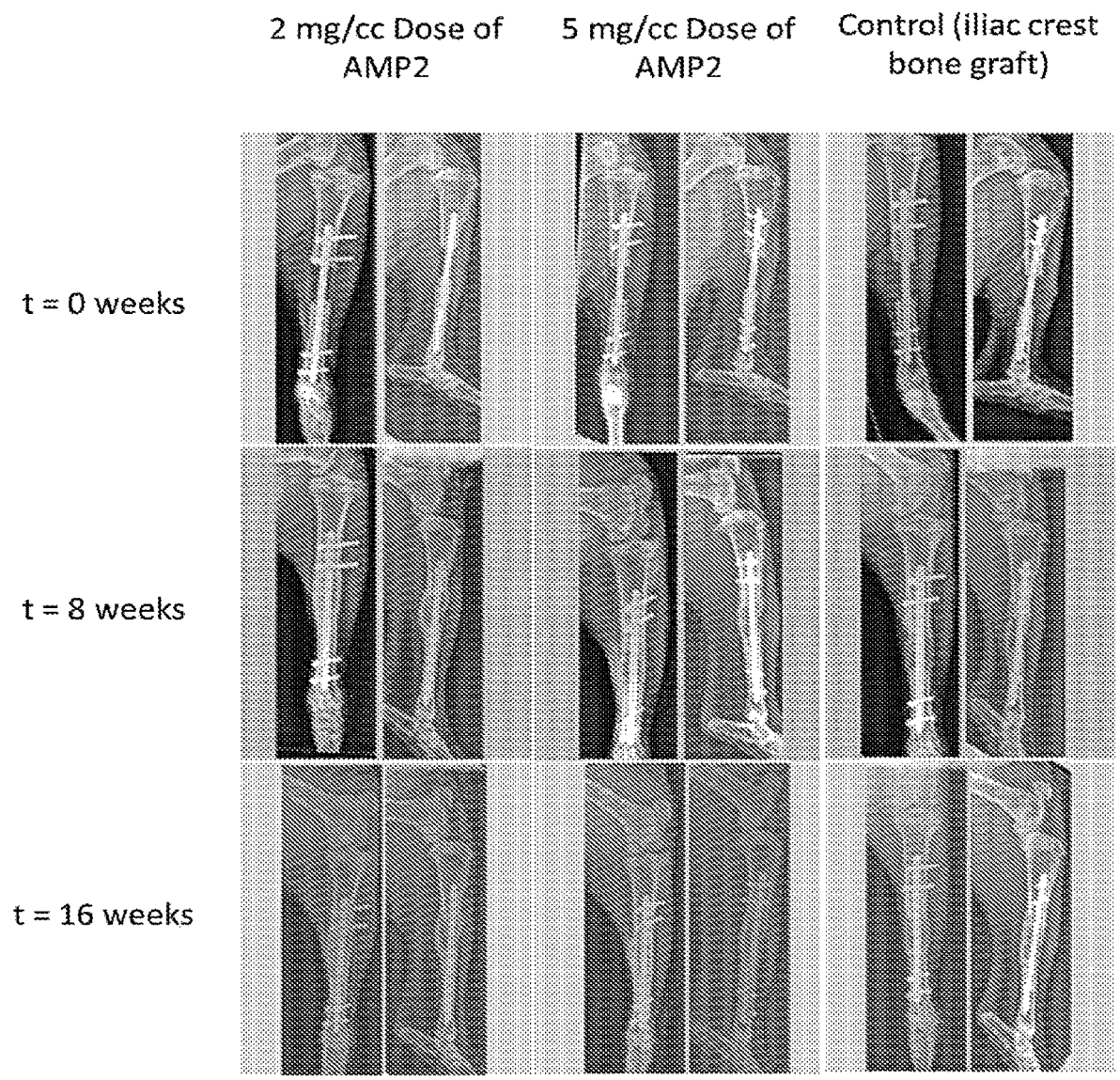
FIG. 16C are representative radiographs (AP and ML views) of the tibia defects in all conditions. 2 mg/cc dose groups resulted in significant bone growth, as did the 5 mg/cc and control conditions. Results were generally consistent across the multiple sheep tested.
Figure 16D:
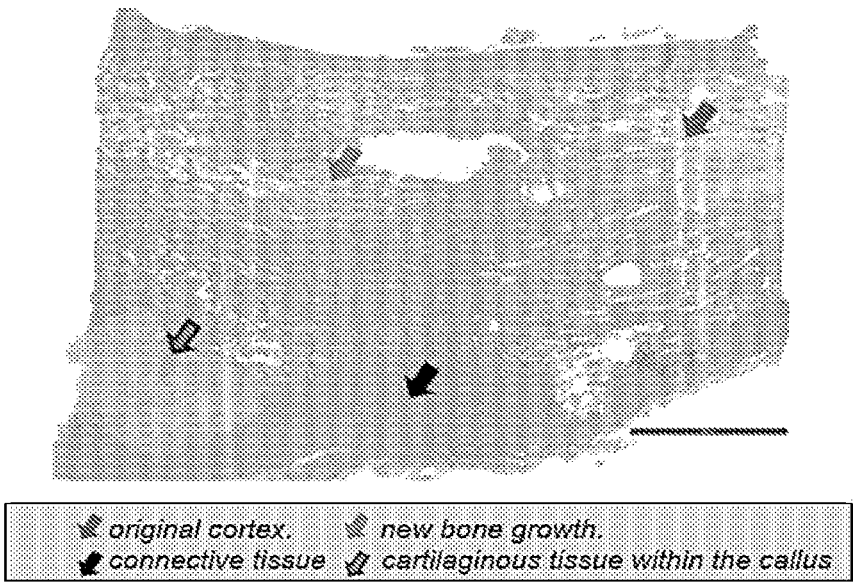
FIG. 16D is a representative H&E histology image from the 2 mg/cc group at 8 weeks showing normal bone formation adjacent to the cut ends of the original cortex. Arrows indicate cortex (blue, top right arrow), connective (black, bottom right arrow) and cartilaginous tissue (grey, bottom left arrow), and new bone growth (green, top left arrow).
Figure 16E:
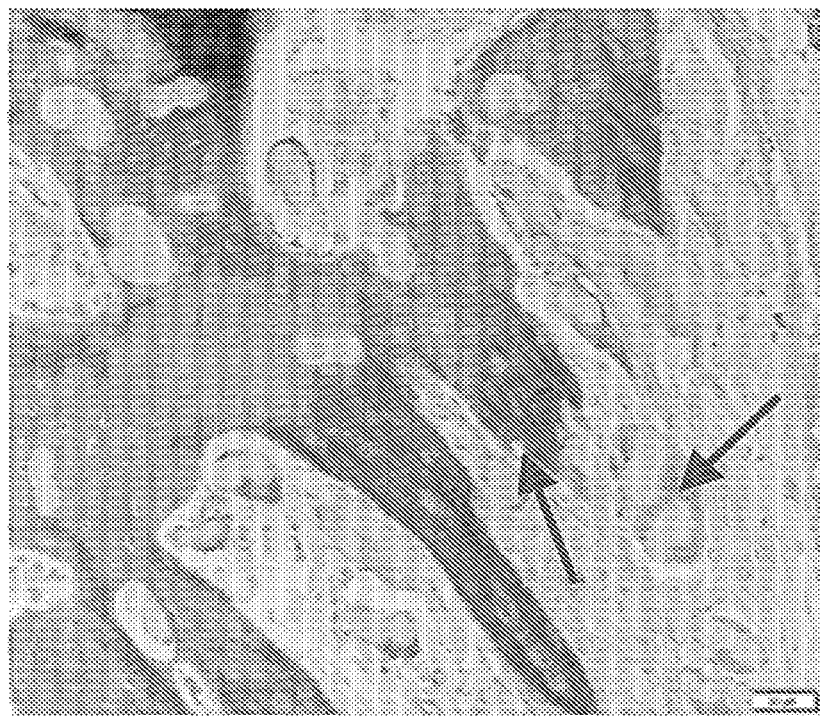
FIG. 16E is a tetrachrome histology image from the 2 mg/cc group. At 8 weeks, residual polymer fibers are visible. Some are surrounded by new bone growth and some are surrounded by connective tissue with multinucleated giant cells associated with the biological breakdown of the fibers.

All three groups showed significant bone formation throughout the time course of the study and the two tBMP-2 doses showed similar increases in new bone formation (FIGS. 16A-16E). tBMP-2 delivered by a cotton-like ceramic bone void filler provides an adequate osteoinductive signal to induce new bone formation comparable to autograft as demonstrated by radiographic (FIG. 16A) and CT (FIG. 16B) data, and it can maintain local BMP-2 concentrations necessary to induce bone formation with high efficacy in a severely compromised tissue bed with a good safety margin as shown in FIGS. 16D-16E.

No adverse clinical effects related to test or control item administration including heterotopic bone formation were seen in any group at either end-point time. No animals exhibited signs of illness in-life and all continued to eat and gain weight over the course of the study.

The tBMP-2 technology tested in this study demonstrated safety and efficacy in this challenging large animal model, enabling the selection of tBMP-2 formulation for future preclinical and clinical trials. Improved materials and strategies for bone regeneration in compromised tissue beds will enable better outcomes for military and civilian patients suffering from large traumatic lower extremity injuries and reduce the need for amputation.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A polypeptide composition comprising: a targeting polypeptide comprising a sequence at least 95% identical to SEQ ID NO: 22 (LLADTTHHRPWT VIGESTHHRPWS IIGESSHHKPFT GLGDTTHHRPWG ILAESTHHKPWT), connected to a therapeutic polypeptide comprising a sequence at least 95% identical to a sequence selected from the group consisting of SEQ ID NOs: 32, 55, 58, 59, 60, 61, 62, 64, 65 and 71, wherein the targeting polypeptide binds to calcium phosphate.

2. The polypeptide composition of claim 1, wherein the targeting polypeptide comprises the sequence of SEQ ID NO: 22.

3. The polypeptide composition of claim 1, wherein therapeutic polypeptide comprises the sequence of SEQ ID NO: 32, 55, 58, 59, 60, 61, 62, 64, 65 or 71.

4. The polypeptide composition of claim 1, wherein the therapeutic polypeptide comprises a sequence at least 95% identical to SEQ ID NO: 32.

5. The polypeptide composition of claim 4, wherein the therapeutic polypeptide comprises the sequence of SEQ ID NO: 32.

6. The polypeptide composition of claim 4, wherein the targeting polypeptide connected to the therapeutic polypeptide comprises a sequence at least 95% identical to SEQ ID NO: 502 or SEQ ID NO: 503.

7. The polypeptide composition of claim 6, wherein the targeting polypeptide connected to the therapeutic polypeptide comprises the sequence of SEQ ID NO: 502 or SEQ ID NO: 503.

8. The polypeptide composition of claim 1, wherein the therapeutic polypeptide comprises a sequence at least 95% identical to SEQ ID NO: 55.

9. The polypeptide composition of claim 1, wherein the therapeutic polypeptide comprises a sequence at least 95% identical to SEQ ID NO: 58.

10. The polypeptide composition of claim 1, wherein the therapeutic polypeptide comprises a sequence at least 95% identical to SEQ ID NO: 59.

11. The polypeptide composition of claim 1, wherein the therapeutic polypeptide comprises a sequence at least 95% identical to SEQ ID NO: 60.

12. The polypeptide composition of claim 1, wherein the therapeutic polypeptide comprises a sequence at least 95% identical to SEQ ID NO: 61.

13. The polypeptide composition of claim 1, wherein the therapeutic polypeptide comprises a sequence at least 95% identical to SEQ ID NO: 62.

14. The polypeptide composition of claim 1, wherein the therapeutic polypeptide comprises a sequence at least 95% identical to SEQ ID NO: 64.

15. The polypeptide composition of claim 1, wherein the therapeutic polypeptide comprises a sequence at least 95% identical to SEQ ID NO: 65.

16. The polypeptide composition of claim 1, wherein the therapeutic polypeptide comprises a sequence at least 95% identical to SEQ ID NO: 71.

17. The polypeptide composition of claim 1, wherein the therapeutic polypeptide has osteogenic activity.

18. A polypeptide composition comprising: a targeting polypeptide comprising a sequence at least 95% identical to SEQ ID NO: 22 (LLADTTHHRPWT VIGESTHHRPWS IIGESSHHKPFT GLGDTTHHRPWG ILAESTHHKPWT), connected to a therapeutic polypeptide comprising a sequence at least 95% identical to SEQ ID NO: 46, 47, 48, 49, 50, 53, 54 or 75, wherein the targeting polypeptide binds to calcium phosphate.

19. A polypeptide composition comprising: a targeting polypeptide comprising a sequence at least 95% identical to SEQ ID NO: 22 (LLADTTHHRPWT VIGESTHHRPWS IIGESSHHKPFT GLGDTTHHRPWG ILAESTHHKPWT), connected to a therapeutic polypeptide comprising a sequence at least 95% identical to a sequence selected from the group consisting of SEQ ID NOs: 82- 100, wherein the targeting polypeptide binds to calcium phosphate.

* * * * *

SEQUENCE LISTING

```
Sequence total quantity: 711
SEQ ID NO: 1              moltype = AA   length = 12
FEATURE                   Location/Qualifiers
REGION                    1..12
                          note = Description of Artificial Sequence: Synthetic peptide
source                    1..12
                          mol_type = protein
                          organism = synthetic construct
SEQUENCE: 1
LLADTTHHRP WT                                                                       12

SEQ ID NO: 2              moltype = AA   length = 12
FEATURE                   Location/Qualifiers
REGION                    1..12
                          note = Description of Artificial Sequence: Synthetic peptide
source                    1..12
                          mol_type = protein
                          organism = synthetic construct
SEQUENCE: 2
VIGESTHHRP WS                                                                       12

SEQ ID NO: 3              moltype = AA   length = 12
FEATURE                   Location/Qualifiers
REGION                    1..12
                          note = Description of Artificial Sequence: Synthetic peptide
source                    1..12
                          mol_type = protein
                          organism = synthetic construct
SEQUENCE: 3
LIADSTHHSP WT                                                                       12

SEQ ID NO: 4              moltype = AA   length = 12
FEATURE                   Location/Qualifiers
REGION                    1..12
                          note = Description of Artificial Sequence: Synthetic peptide
source                    1..12
                          mol_type = protein
                          organism = synthetic construct
SEQUENCE: 4
ILAESTHHKP WT                                                                       12

SEQ ID NO: 5              moltype = AA   length = 12
FEATURE                   Location/Qualifiers
REGION                    1..12
                          note = Description of Artificial Sequence: Synthetic peptide
source                    1..12
                          mol_type = protein
                          organism = synthetic construct
SEQUENCE: 5
ILAETTHHRP WS                                                                       12

SEQ ID NO: 6              moltype = AA   length = 12
FEATURE                   Location/Qualifiers
REGION                    1..12
                          note = Description of Artificial Sequence: Synthetic peptide
source                    1..12
                          mol_type = protein
                          organism = synthetic construct
SEQUENCE: 6
IIGESSHHKP FT                                                                       12

SEQ ID NO: 7              moltype = AA   length = 12
FEATURE                   Location/Qualifiers
REGION                    1..12
                          note = Description of Artificial Sequence: Synthetic peptide
source                    1..12
                          mol_type = protein
                          organism = synthetic construct
SEQUENCE: 7
GLGDTTHHRP WG                                                                       12

SEQ ID NO: 8              moltype = AA   length = 12
FEATURE                   Location/Qualifiers
REGION                    1..12
                          note = Description of Artificial Sequence: Synthetic peptide
source                    1..12
                          mol_type = protein
                          organism = synthetic construct
```

```
SEQUENCE: 8
VLGDTTHHKP WT                                                              12

SEQ ID NO: 9            moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 9
IVADSTHHRP WT                                                              12

SEQ ID NO: 10           moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 10
STADTSHHRP S                                                               11

SEQ ID NO: 11           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 11
TSGGESTHHR PS                                                              12

SEQ ID NO: 12           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 12
TSGGESSHHK PS                                                              12

SEQ ID NO: 13           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 13
TGSGDSSHHR PS                                                              12

SEQ ID NO: 14           moltype = AA  length = 13
FEATURE                 Location/Qualifiers
REGION                  1..13
                        note = Description of Artificial Sequence: Synthetic peptide
source                  1..13
                        mol_type = protein
                        organism = synthetic construct
SEQUENCE: 14
GSSGESTHHK PST                                                             13

SEQ ID NO: 15           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 15
VGADSTHHRP VT                                                              12

SEQ ID NO: 16           moltype = AA  length = 12
FEATURE                 Location/Qualifiers
REGION                  1..12
                        note = Description of Artificial Sequence: Synthetic peptide
source                  1..12
                        mol_type = protein
```

```
                        organism = synthetic construct
SEQUENCE: 16
GAADTTHHRP VT                                                            12

SEQ ID NO: 17           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 17
AGADTTHHRP VT                                                            12

SEQ ID NO: 18           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 18
GGADTTHHRP AT                                                            12

SEQ ID NO: 19           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 19
GGADTTHHRP GT                                                            12

SEQ ID NO: 20           moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 20
LLADTTHHRP WTVIGESTHH RPWS                                               24

SEQ ID NO: 21           moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 21
LLADTTHHRP WTVIGESTHH RPWSIIGESS HHKPFT                                  36

SEQ ID NO: 22           moltype = AA  length = 60
FEATURE                 Location/Qualifiers
REGION                  1..60
                        note = Description of Artificial Sequence: Synthetic
                         polypeptide
source                  1..60
                        mol_type = protein
                        organism = synthetic construct
SEQUENCE: 22
LLADTTHHRP WTVIGESTHH RPWSIIGESS HHKPFTGLGD TTHHRPWGIL AESTHHKPWT        60

SEQ ID NO: 23           moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 23
LLADTTHHRP WTILAESTHH KPWT                                               24

SEQ ID NO: 24           moltype = AA  length = 60
FEATURE                 Location/Qualifiers
REGION                  1..60
```

```
                        note = Description of Artificial Sequence: Synthetic
                         polypeptide
source                  1..60
                        mol_type = protein
                        organism = synthetic construct
SEQUENCE: 24
LLADTTHHRP WTILAESTHH KPWTLLADTT HHRPWTILAE STHHKPWTLL ADTTHHRPWT    60

SEQ ID NO: 25           moltype = AA  length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 25
LLADTTHHRP WTGLGDTTHH RPWG                                          24

SEQ ID NO: 26           moltype = AA  length = 36
FEATURE                 Location/Qualifiers
REGION                  1..36
                        note = Description of Artificial Sequence: Synthetic
                         polypeptide
source                  1..36
                        mol_type = protein
                        organism = synthetic construct
SEQUENCE: 26
LLADTTHHRP WTGLGDTTHH RPWGLLADTT HHRPWT                             36

SEQ ID NO: 27           moltype = AA  length = 60
FEATURE                 Location/Qualifiers
REGION                  1..60
                        note = Description of Artificial Sequence: Synthetic
                         polypeptide
source                  1..60
                        mol_type = protein
                        organism = synthetic construct
SEQUENCE: 27
LLADTTHHRP WTGLGDTTHH RPWGLLADTT HHRPWTGLGD TTHHRPWGLL ADTTHHRPWT    60

SEQ ID NO: 28           moltype = AA  length = 84
FEATURE                 Location/Qualifiers
REGION                  1..84
                        note = Description of Artificial Sequence: Synthetic
                         polypeptide
source                  1..84
                        mol_type = protein
                        organism = synthetic construct
SEQUENCE: 28
LLADTTHHRP WTGLGDTTHH RPWGLLADTT HHRPWTGLGD TTHHRPWGLL ADTTHHRPWT    60
GLGDTTHHRP WGLLADTTHH RPWT                                          84

SEQ ID NO: 29           moltype = AA  length = 60
FEATURE                 Location/Qualifiers
REGION                  1..60
                        note = Description of Artificial Sequence: Synthetic
                         polypeptide
source                  1..60
                        mol_type = protein
                        organism = synthetic construct
SEQUENCE: 29
STADTSHHRP STSGGESTHH RPSTSGGESS HHKPSTGSGD SSHHRPSGSS GESTHHKPST    60

SEQ ID NO: 30           moltype = AA  length = 60
FEATURE                 Location/Qualifiers
REGION                  1..60
                        note = Description of Artificial Sequence: Synthetic
                         polypeptide
source                  1..60
                        mol_type = protein
                        organism = synthetic construct
SEQUENCE: 30
VGADSTHHRP VTGAADTTHH RPVTAGADTT HHRPVTGGAD TTHHRPATGG ADTTHHRPGT    60

SEQ ID NO: 31           moltype = AA  length = 108
FEATURE                 Location/Qualifiers
REGION                  1..108
                        note = Description of Artificial Sequence: Synthetic
                         polypeptide
```

```
source                  1..108
                        mol_type = protein
                        organism = synthetic construct
SEQUENCE: 31
STADTSHHRP SLLADTTHHR PWTTSGGEST HHRPSVGADS THHRPVTTSG GESSHHKPSG    60
AADTTHHRPV TTGSGDSSHH RPSGSSGEST HHKPSTGGAD TTHHRPAT               108

SEQ ID NO: 32           moltype = AA  length = 114
FEATURE                 Location/Qualifiers
source                  1..114
                        mol_type = protein
                        organism = Homo sapiens
SEQUENCE: 32
QAKHKQRKRL KSSCKRHPLY VDFSDVGWND WIVAPPGYHA FYCHGECPFP LADHLNSTNH    60
AIVQTLVNSV NSKIPKACCV PTELSAISML YLDENEKVVL KNYQDMVVEG CGCR         114

SEQ ID NO: 33           moltype = AA  length = 37
FEATURE                 Location/Qualifiers
REGION                  1..37
                        note = Description of Artificial Sequence: Synthetic
                         polypeptide
source                  1..37
                        mol_type = protein
                        organism = synthetic construct
SEQUENCE: 33
TGGSGEGGTG ASTGGSAGTG GSGGTTSGEA GGSSGAG                             37

SEQ ID NO: 34           moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 34
GAGTG                                                                 5

SEQ ID NO: 35           moltype =     length =
SEQUENCE: 35
000

SEQ ID NO: 36           moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 36
AAADTTHHRP WT                                                        12

SEQ ID NO: 37           moltype = AA  length = 60
FEATURE                 Location/Qualifiers
REGION                  1..60
                        note = Description of Artificial Sequence: Synthetic
                         polypeptide
source                  1..60
                        mol_type = protein
                        organism = synthetic construct
SEQUENCE: 37
AAADTTHHRP WTAAADTTHH RPWTAAADTT HHRPWTAAAD TTHHRPWTAA ADTTHHRPWT    60

SEQ ID NO: 38           moltype = AA  length = 60
FEATURE                 Location/Qualifiers
REGION                  1..60
                        note = Description of Artificial Sequence: Synthetic
                         polypeptide
source                  1..60
                        mol_type = protein
                        organism = synthetic construct
SEQUENCE: 38
LLADAAHHRP WTLLADAAHH RPWTLLADAA HHRPWTLLAD AAHHRPWTLL ADAAHHRPWT    60

SEQ ID NO: 39           moltype = AA  length = 60
FEATURE                 Location/Qualifiers
REGION                  1..60
                        note = Description of Artificial Sequence: Synthetic
                         polypeptide
source                  1..60
```

```
                          mol_type = protein
                          organism = synthetic construct
SEQUENCE: 39
LLADTTAARP WTLLADTTAA RPWTLLADTT AARPWTLLAD TTAARPWTLL ADTTAARPWT    60

SEQ ID NO: 40             moltype = AA  length = 24
FEATURE                   Location/Qualifiers
REGION                    1..24
                          note = Description of Artificial Sequence: Synthetic peptide
source                    1..24
                          mol_type = protein
                          organism = synthetic construct
SEQUENCE: 40
LLADTTHHRP WTLLADTTHH RPWT                                           24

SEQ ID NO: 41             moltype = AA  length = 36
FEATURE                   Location/Qualifiers
REGION                    1..36
                          note = Description of Artificial Sequence: Synthetic
                           polypeptide
source                    1..36
                          mol_type = protein
                          organism = synthetic construct
SEQUENCE: 41
LLADTTHHRP WTLLADTTHH RPWTLLADTT HHRPWT                              36

SEQ ID NO: 42             moltype = AA  length = 60
FEATURE                   Location/Qualifiers
REGION                    1..60
                          note = Description of Artificial Sequence: Synthetic
                           polypeptide
source                    1..60
                          mol_type = protein
                          organism = synthetic construct
SEQUENCE: 42
LLADTTHHRP WTLLADTTHH RPWTLLADTT HHRPWTLLAD TTHHRPWTLL ADTTHHRPWT    60

SEQ ID NO: 43             moltype = AA  length = 120
FEATURE                   Location/Qualifiers
REGION                    1..120
                          note = Description of Artificial Sequence: Synthetic
                           polypeptide
source                    1..120
                          mol_type = protein
                          organism = synthetic construct
SEQUENCE: 43
STSGSTVIGE STHHRPWSLI ADSTHHSPWT ILAESTHHKP WTILAETTHH RPWSIIGESS    60
HHKPFTGLGD TTHHRPWGVL GDTTHHKPWT IVADSTHHRP WTGQVLPTTT PSSPSTTSGS   120

SEQ ID NO: 44             moltype = AA  length = 12
FEATURE                   Location/Qualifiers
REGION                    1..12
                          note = Description of Artificial Sequence: Synthetic peptide
source                    1..12
                          mol_type = protein
                          organism = synthetic construct
SEQUENCE: 44
GQVLPTTTPS SP                                                        12

SEQ ID NO: 45             moltype = AA  length = 6
FEATURE                   Location/Qualifiers
REGION                    1..6
                          note = Description of Artificial Sequence: Synthetic peptide
source                    1..6
                          mol_type = protein
                          organism = synthetic construct
SEQUENCE: 45
GSGATG                                                                6

SEQ ID NO: 46             moltype = AA  length = 53
FEATURE                   Location/Qualifiers
source                    1..53
                          mol_type = protein
                          organism = Homo sapiens
SEQUENCE: 46
NSDSECPLSH DGYCLHDGVC MYIEALDKYA CNCVVGYIGE RCQYRDLKWW ELR            53

SEQ ID NO: 47             moltype = AA  length = 66
FEATURE                   Location/Qualifiers
```

```
source                          1..66
                                mol_type = protein
                                organism = Homo sapiens
SEQUENCE: 47
EEAEIPREVI ERLARSQIHS IRDLQRLLEI DSVGSEDSLD TSLRAHGVHA TKHVPEKRPL    60
PIRRKR                                                              66

SEQ ID NO: 48                   moltype = AA  length = 70
FEATURE                         Location/Qualifiers
source                          1..70
                                mol_type = protein
                                organism = Homo sapiens
SEQUENCE: 48
GPETLCGAEL VDALQFVCGD RGFYFNKPTG YGSSSRRAPQ TGIVDECCFR SCDLRRLEMY    60
CAPLKPAKSA                                                          70

SEQ ID NO: 49                   moltype = AA  length = 140
FEATURE                         Location/Qualifiers
source                          1..140
                                mol_type = protein
                                organism = Homo sapiens
SEQUENCE: 49
FNLPPGNYKK PKLLYCSNGG HFLRILPDGT VDGTRDRSDQ HIQLQLSAES VGEVYIKSTE    60
TGQYLAMDTD GLLYGSQTPN EECLFLERLE ENHYNTYISK KHAEKNWFVG LKKNGSCKRG   120
PRTHYGQKAI LFLPLPVSSD                                              140

SEQ ID NO: 50                   moltype = AA  length = 146
FEATURE                         Location/Qualifiers
source                          1..146
                                mol_type = protein
                                organism = Homo sapiens
SEQUENCE: 50
PALPEDGGSG AFPPGHFKDP KRLYCKNGGF LRIHPDGRV DGVREKSDPH IKLQLQAEER    60
GVVSIKGVCA NRYLAMKEDG RLLASKCVTD ECFFFERLES NNYNTYRSRK YTSWYVALKR   120
TGQYKLGSKT GPGQKAILFL PMSAKS                                       146

SEQ ID NO: 51                   moltype = AA  length = 180
FEATURE                         Location/Qualifiers
source                          1..180
                                mol_type = protein
                                organism = Homo sapiens
SEQUENCE: 51
EENVDFRIHV ENQTRARDDV SRKQLRLYQL YSRTSGKHIQ VLGRRISARG EDGDKYAQLL    60
VETDTFGSQV RIKGKETEFY LCMNRKGKLV GKPDGTSKEC VFIEKVLENN YTALMSAKYS   120
GWYVGFTKKG RPRKGPKTRE NQQDVHFMKR YPKGQPELQK PFKYTTVTKR SRRIRPTHPA   180

SEQ ID NO: 52                   moltype = AA  length = 137
FEATURE                         Location/Qualifiers
source                          1..137
                                mol_type = protein
                                organism = Homo sapiens
SEQUENCE: 52
ENSTSPLSAD PPVAAAVVSH FNDCPDSHTQ FCFHGTCRFL VQEDKPACVC HSGYVGARCE    60
HADLLAVVAA SQKKQAITAL VVVSIVALAV LIITCVLIHC CQVRKHCEWC RALICRHEKP   120
SALLKGRTAC CHSETVV                                                 137

SEQ ID NO: 53                   moltype = AA  length = 112
FEATURE                         Location/Qualifiers
source                          1..112
                                mol_type = protein
                                organism = Homo sapiens
SEQUENCE: 53
ALDTNYCFSS TEKNCCVRQL YIDFRKDLGW KWIHEPKGYH ANFCLGPCPY IWSLDTQYSK    60
VLALYNQHNP GASAAPCCVP QALEPLPIVY YVGRKPKVEQ LSNMIVRSCK CS           112

SEQ ID NO: 54                   moltype = AA  length = 112
FEATURE                         Location/Qualifiers
source                          1..112
                                mol_type = protein
                                organism = Homo sapiens
SEQUENCE: 54
ALDTNYCFRN LEENCCVRPL YIDFRQDLGW KWVHEPKGYY ANFCSGPCPY LRSADTTHST    60
VLGLYNTLNP EASASPCCVP QDLEPLTILY YVGRTPKVEQ LSNMVVKSCK CS           112

SEQ ID NO: 55                   moltype = AA  length = 139
FEATURE                         Location/Qualifiers
source                          1..139
                                mol_type = protein
                                organism = Homo sapiens
```

```
SEQUENCE: 55
AVRPLRRRQP KKSNELPQAN RLPGIFDDVH GSHGRQVCRR HELYVSFQDL GWLDWVIAPQ    60
GYSAYYCEGE CSFPLDSCMN ATNHAILQSL VHLMMPDAVP KACCAPTKLS ATSVLYYDSS   120
NNVILRKHRN MVVKACGCH                                                139

SEQ ID NO: 56           moltype = AA  length = 139
FEATURE                 Location/Qualifiers
source                  1..139
                        mol_type = protein
                        organism = Homo sapiens
SEQUENCE: 56
AVRPLRRRQP KKSNELPQAN RLPGIFDDVR GSHGRQVCRR HELYVSFQDL GWLDWVIAPQ    60
GYSAYYCEGE CSFPLDSCMN ATNHAILQSL VHLMKPNAVP KACCAPTKLS ATSVLYYDSS   120
NNVILRKHRN MVVKACGCH                                                139

SEQ ID NO: 57           moltype = AA  length = 110
FEATURE                 Location/Qualifiers
source                  1..110
                        mol_type = protein
                        organism = Homo sapiens
SEQUENCE: 57
QWIEPRNCAR RYLKVDFADI GWSEWIISPK SFDAYYCSGA CQFPMPKSLK PSNHATIQSI    60
VRAVGVVPGI PEPCCVPEKM SSLSILFFDE NKNVVLKVYP NMTVESCACR              110

SEQ ID NO: 58           moltype = AA  length = 116
FEATURE                 Location/Qualifiers
source                  1..116
                        mol_type = protein
                        organism = Homo sapiens
SEQUENCE: 58
SPKHHSQRAR KKNKNCRRHS LYVDFSDVGW NDWIVAPPGY QAFYCHGDCP FPLADHLNST    60
NHAIVQTLVN SVNSSIPKAC CVPTELSAIS MLYLDEYDKV VLKNYQEMVV EGCGCR       116

SEQ ID NO: 59           moltype = AA  length = 138
FEATURE                 Location/Qualifiers
source                  1..138
                        mol_type = protein
                        organism = Homo sapiens
SEQUENCE: 59
AANKRKQNR NKSSSHQDSS RMSSVGDYNT SEQKQACKKH ELYVSFRDLG WQDWIIAPEG     60
YAAFYCDGEC SFPLNAHMNA TNHAIVQTLV HLMFPDHVPK PCCAPTKLNA ISVLYFDDSS   120
NVILKKYRNM VVRSCGCH                                                 138

SEQ ID NO: 60           moltype = AA  length = 139
FEATURE                 Location/Qualifiers
source                  1..139
                        mol_type = protein
                        organism = Homo sapiens
SEQUENCE: 60
SASSRRRQQS RNRSTQSQDV ARVSSASDYN SSELKTACRK HELYVSFQDL GWQDWIIAPK    60
GYAANYCDGE CSFPLNAHMN ATNHAIVQTL VHLMNPEYVP KPCCAPTKLN AISVLYFDDN   120
SNVILKKYRN MVVRACGCH                                                139

SEQ ID NO: 61           moltype = AA  length = 139
FEATURE                 Location/Qualifiers
source                  1..139
                        mol_type = protein
                        organism = Homo sapiens
SEQUENCE: 61
STGSKQRSQN RSKTPKNQEA LRMANVAENS SSDQRQACKK HELYVSFRDL GWQDWIIAPE    60
GYAAYYCEGE CAFPLNSYMN ATNHAIVQTL VHFINPETVP KPCCAPTQLN AISVLYFDDS   120
SNVILKKYRN MVVRACGCH                                                139

SEQ ID NO: 62           moltype = AA  length = 110
FEATURE                 Location/Qualifiers
source                  1..110
                        mol_type = protein
                        organism = Homo sapiens
SEQUENCE: 62
SAGAGSHCQK TSLRVNFEDI GWDSWIIAPK EYEAYECKGG CFFPLADDVT PTKHAIVQTL    60
VHLKFPTKVG KACCVPTKLS PISVLYKDDM GVPTLKYHYE GMSVAECGCR              110

SEQ ID NO: 63           moltype = AA  length = 108
FEATURE                 Location/Qualifiers
source                  1..108
                        mol_type = protein
                        organism = Homo sapiens
SEQUENCE: 63
NAKGNYCKRT PLYIDFKEIG WDSWIIAPPG YEAYECRGVC NYPLAEHLTP TKHAIIQALV    60
```

```
HLKNSQKASK ACCVPTKLEP ISILYLDKGV VTYKFKYEGM AVSECGCR          108

SEQ ID NO: 64          moltype = AA   length = 109
FEATURE                Location/Qualifiers
source                 1..109
                       mol_type = protein
                       organism = Homo sapiens
SEQUENCE: 64
NLGLDCDEHS SESRCCRYPL TVDFEAFGWD WIIAPKRYKA NYCSGQCEYM FMQKYPHTHL   60
VQQANPRGSA GPCCTPTKMS PINMLYFNDK QQIIYGKIPG MVVDRCGCS             109

SEQ ID NO: 65          moltype = AA   length = 129
FEATURE                Location/Qualifiers
source                 1..129
                       mol_type = protein
                       organism = Homo sapiens
SEQUENCE: 65
TALAGTRTAQ GSGGGAGRGH GRRGRSRCSR KPLHVDFKEL GWDDWIIAPL DYEAYHCEGL   60
CDFPLRSHLE PTNHAIIQTL LNSMAPDAAP ASCCVPARLS PISILYIDAA NNVVYKQYED  120
MVVEACGCR                                                         129

SEQ ID NO: 66          moltype = AA   length = 120
FEATURE                Location/Qualifiers
source                 1..120
                       mol_type = protein
                       organism = Homo sapiens
SEQUENCE: 66
TAFASRHGKR HGKKSRLRCS KKPLHVNFKE LGWDDWIIAP LEYEAYHCEG VCDFPLRSHL   60
EPTNHAIIQT LMNSMDPGST PPSCCVPTKL TPISILYIDA GNNVVYKQYE DMVVESCGCR  120

SEQ ID NO: 67          moltype = AA   length = 125
FEATURE                Location/Qualifiers
source                 1..125
                       mol_type = protein
                       organism = Homo sapiens
SEQUENCE: 67
QADGISAEVT ASSSKHSGPE NNQCSLHPFQ ISFRQLGWDH WIIAPPFYTP NYCKGTCLRV   60
LRDGLNSPNH AIIQNLINQL VDQSVPRPSC VPYKYVPISV LMIEANGSIL YKEYEGMIAE  120
SCTCR                                                             125

SEQ ID NO: 68          moltype = AA   length = 447
FEATURE                Location/Qualifiers
source                 1..447
                       mol_type = protein
                       organism = Homo sapiens
SEQUENCE: 68
IPVPQSKPLE RHVEKSMNLH LLARSNVSVQ DELNASGTIK ESGVLVHEGD RGRQENTQDG   60
HKGEGNGSKW AEVGGKSFST YSTLANEEGN IEGWNGDTGK AETYGHDGIH GKEENITANG  120
IQGQVSIIDN AGATNRSNTN GNTDKNTQNG DVGDAGHNED VAVVQEDGPQ VAGSNNSTDN  180
EDEIIENSCR NEGNTSEITP QINSKRNGTK EAEVTPGTGE DAGLDNSDGS PSGNGADEDE  240
DEGSGDEDEE EAGNGKDSSN NSKGQEGQDH GKEDDHDSSI GQNSDSKEYY DPEGKEDPHN  300
EVDGDKTSKS EENSAGIPED NGSQRIEDTQ KLNHRESKRV ENRITKESET HAVGKSQDKG  360
IEIKGPSSGN RNITKEVGKG NEGKEDKGQH GMILGKGNVK TQGEVVNIEG PGQKSEPGNK  420
VGHSNTGSDS NSDGYDSYDF DDKSMQG                                     447

SEQ ID NO: 69          moltype = AA   length = 119
FEATURE                Location/Qualifiers
source                 1..119
                       mol_type = protein
                       organism = Homo sapiens
SEQUENCE: 69
DAEPVLGGGP GGACRARRLY VSFREVGWHR WVIAPRGFLA NYCQGQCALP VALSGSGGPP   60
ALNHAVLRAL MHAAAPGAAD LPCCVPARLS PISVLFFDNS DNVVLRQYED MVVDECGCR   119

SEQ ID NO: 70          moltype = AA   length = 114
FEATURE                Location/Qualifiers
source                 1..114
                       mol_type = protein
                       organism = Homo sapiens
SEQUENCE: 70
AAIPVPKLSC KNLCHRHQLF INFRDLGWHK WIIAPKGFMA NYCHGECPFS LTISLNSSNY   60
AFMQALMHAV DPEIPQAVCI PTKLSPISML YQDNNDNVIL RHYEDMVVDE CGCG        114

SEQ ID NO: 71          moltype = AA   length = 120
FEATURE                Location/Qualifiers
source                 1..120
                       mol_type = protein
                       organism = Homo sapiens
SEQUENCE: 71
```

```
APLATRQGKR PSKNLKARCS RKALHVNFKD MGWDDWIIAP LEYEAFHCEG LCEFPLRSHL   60
EPTNHAVIQT LMNSMDPEST PPTCCVPTRL SPISILFIDS ANNVVYKQYE DMVVESCGCR  120

SEQ ID NO: 72            moltype =     length =
SEQUENCE: 72
000

SEQ ID NO: 73            moltype = AA   length = 109
FEATURE                  Location/Qualifiers
source                   1..109
                         mol_type = protein
                         organism = Homo sapiens
SEQUENCE: 73
DFGLDCDEHS TESRCCRYPL TVDFEAFGWD WIIAPKRYKA NYCSGECEFV FLQKYPHTHL   60
VHQANPRGSA GPCCTPTKMS PINMLYFNGK EQIIYGKIPA MVVDRCGCS              109

SEQ ID NO: 74            moltype = AA   length = 114
FEATURE                  Location/Qualifiers
source                   1..114
                         mol_type = protein
                         organism = Homo sapiens
SEQUENCE: 74
ARARNGDHCP LGPGRCCRLH TVRASLEDLG WADWVLSPRE VQVTMCIGAC PSQFRAANMH   60
AQIKTSLHRL KPDTVPAPCC VPASYNPMVL IQKTDTGVSL QTYDDLLAKD CHCI        114

SEQ ID NO: 75            moltype = AA   length = 206
FEATURE                  Location/Qualifiers
source                   1..206
                         mol_type = protein
                         organism = Homo sapiens
SEQUENCE: 75
APMAEGGGQN HHEVVKFMDV YQRSYCHPIE TLVDIFQEYP DEIEYIFKPS CVPLMRCGGC   60
CNDEGLECVP TEESNITMQI MRIKPHQGQH IGEMSFLQHN KCECRPKKDR ARQEKKSVRG  120
KGKGQKRKRK KSRYKSWSVY VGARCCLMPW SLPGPHPCGP CSERRKHLFV QDPQTCKCSC  180
KNTDSRCKAR QLELNERTCR CDKPRR                                      206

SEQ ID NO: 76            moltype = AA   length = 290
FEATURE                  Location/Qualifiers
source                   1..290
                         mol_type = protein
                         organism = Homo sapiens
SEQUENCE: 76
FSLMSLLESL DPDWTPDQYD YSYEDYNQEE NTSSTLTHAE NPDWYYTEDQ ADPCQPNPCE   60
HGGDCLVHGS TFTCSCLAPF SGNKCQKVQN TCKDNPCGRG QCLITQSPPY YRCVCKHPYT  120
GPSCSQVVPV CRPNPCQNGA TCSRHKRRSK FTCACPDQFK GKFCEIGSDD CYVGDGYSYR  180
GKMNRTVNQH ACLYWNSHLL LQENYNMFME DAETHGIGEH NFCRNPDADE KPWCFIKVTN  240
DKVKWEYCDV SACSAQDVAY PEESPTEPST KLPGFDSCGK TEIAERKIKR            290

SEQ ID NO: 77            moltype = AA   length = 400
FEATURE                  Location/Qualifiers
source                   1..400
                         mol_type = protein
                         organism = Homo sapiens
SEQUENCE: 77
AEVKKPAAAA APGTAEKLSP KAATLAERSA GLAFSLYQAM AKDQAVENIL VSPVVVASSL   60
GLVSLGGKAT TASQAKAVLS AEQLRDEEVH AGLGELLRSL SNSTARNVTW KLGSRLYGPS  120
SVSFADDFVR SSKQHYNCEH SKINFRDKRS ALQSINEWAA QTTDGKLPEV TKDVERTDGA  180
LLVNAMFFKP HWDEKFHHKM VDNRGFMVTR SYTVGVMMMH RTGLYNYYDD EKEKLQIVEM  240
PLAHKLSSLI ILMPHHVEPL ERLEKLLTKE QLKIWMGKMQ KKAVAISLPK GVVEVTHDLQ  300
KHLAGLGLTE AIDKNKADLS RMSGKKDLYL ASVFHATAFE LDTDGNPFDQ DIYGREELRS  360
PKLFYADHPF IFLVRDTQSG SLLFIGRLVR PKGDKMRDEL                       400

SEQ ID NO: 78            moltype =     length =
SEQUENCE: 78
000

SEQ ID NO: 79            moltype = AA   length = 163
FEATURE                  Location/Qualifiers
source                   1..163
                         mol_type = protein
                         organism = Homo sapiens
SEQUENCE: 79
CNDMTPEQMA TNVNCSSPER HTRSYDYMEG GDIRVRRLFC RTQWYLRIDK RGKVKGTQEM   60
KNNYNIMEIR TVAVGIVAIK GVESEFYLAM NKEGKLYAKK ECNEDCNFKE LILENHYNTY  120
ASAKWTHNGG EMFVALNQKG IPVRGKKTKK EQKTAHFLPM AIT                   163

SEQ ID NO: 80            moltype = AA   length = 177
FEATURE                  Location/Qualifiers
source                   1..177
```

```
                            mol_type = protein
                            organism = Homo sapiens
SEQUENCE: 80
GPQREEFPRD LSLISPLAQA VRSSSRTPSD KPVAHVVANP QAEGQLQWLN RRANALLANG    60
VELRDNQLVV PSEGLYLIYS QVLFKGQGCP STHVLLTHTI SRIAVSYQTK VNLLSAIKSP   120
CQRETPEGAE AKPWYEPIYL GGVFQLEKGD RLSAEINRPD YLDFAESGQV YFGIIAL      177

SEQ ID NO: 81               moltype = AA  length = 243
FEATURE                     Location/Qualifiers
source                      1..243
                            mol_type = protein
                            organism = Homo sapiens
SEQUENCE: 81
TNELKQMQDK YSKSGIACFL KEDDSYWDPN DEESMNSPCW QVKWQLRQLV RKMILRTSEE    60
TISTVQEKQQ NISPLVRERG PQRVAAHITG TRGRSNTLSS PNSKNEKALG RKINSWESSR   120
SGHSFLSNLH LRNGELVIHE KGFYYIYSQT YFRFQEEIKE NTKNDKQMVQ YIYKYTSYPD   180
PILLMKSARN SCWSKDAEYG LYSIYQGGIF ELKENDRIFV SVTNEHLIDM DHEASFFGAF   240
LVG                                                                 243

SEQ ID NO: 82               moltype = AA  length = 343
FEATURE                     Location/Qualifiers
source                      1..343
                            mol_type = protein
                            organism = Homo sapiens
SEQUENCE: 82
ANSSGRWWGI VNVASSTNLL TDSKSLQLVL EPSLQLLSRK QRRLIRQNPG ILHSVSGGLQ    60
SAVRECKWQF RNRRWNCPTA PGPHLFGKIV NRGCRETAFI FAITSAGVTH SVARSCSEGS   120
IESCTCDYRR RGPGGPDWHW GGCSDNIDFG RLFGREFVDS GEKGRDLRFL MNLHNNEAGR   180
TTVFSEMRQE CKCHGMSGSC TVRTCWMRLP TLRAVGDVLR DRFDGASRVL YGNRGSNRAS   240
RAELLRLEPE DPAHKPPSPH DLVYFEKSPN FCTYSGRLGT AGTAGRACNS SSPALDGCEL   300
LCCGRGHRTR TQRVTERCNC TFHWCCHVSC RNCTHTRVLH ECL                     343

SEQ ID NO: 83               moltype = AA  length = 335
FEATURE                     Location/Qualifiers
source                      1..335
                            mol_type = protein
                            organism = Homo sapiens
SEQUENCE: 83
SWWYMRATGG SSRVMCDNVP GLVSSQRQLC HRHPDVMRAI SQGVAEWTAE CQHQFRQHRW    60
NCNTLDRDHS LFGRVLLRSS RESAFVYAIS SAGVVFAITR ACSQGEVKSC SCDPKKMGSA   120
KDSKGIFDWG GCSDNIDYGI KFARAFVDAK ERKGKDARAL MNLHNNRAGR KAVKRFLKQE   180
CKCHGVSGSC TLRTCWLAMA DFRKTGDYLW RKYNGAIQVV MNQDGTGFTV ANERFKKPTK   240
NDLVYFENSP DYCIRDREAG SLGTAGRVCN LTSRGMDSCE VMCCGRGYDT SHVTRMTKCG   300
CKFHWCCAVR CQDCLEALDV HTCKAPKNAD WTTAT                              335

SEQ ID NO: 84               moltype = AA  length = 333
FEATURE                     Location/Qualifiers
source                      1..333
                            mol_type = protein
                            organism = Homo sapiens
SEQUENCE: 84
SWWYIGALGA RVICDNIPGL VSRQRQLCQR YPDIMRSVGE GAREWIRECQ HQFRHHRWNC    60
TTLDRDHTVF GRVMLRSSRE AAFVYAISSA GVVHAITRAC SQGELSVCSC DPYTRGRHHD   120
QRGDFDWGGC SDNIHYGVRF AKAFVDAKEK RLKDARALMN LHNNRCGRTA VRRFLKLECK   180
CHGVSGSCTL RTCWRALSDF RRTGDYLRRR YDGAVQVMAT QDGANFTAAR QGYRRATRTD   240
LVYFDNSPDY CVLDKAAGSL GTAGRVCSKT SKGTDGCEIM CCGRGYDTTR VTRVTQCECK   300
FHWCCAVRCK ECRNTVDVHT CKAPKKAEWL DQT                                333

SEQ ID NO: 85               moltype = AA  length = 334
FEATURE                     Location/Qualifiers
source                      1..334
                            mol_type = protein
                            organism = Homo sapiens
SEQUENCE: 85
GYPIWWSLAL GQQYTSLGSQ PLLCGSIPGL VPKQLRFCRN YIEIMPSVAE GVKLGIQECQ    60
HQFRGRRWNC TTIDDSLAIF GPVLDKATRE SAFVHAIASA GVAFAVTRSC AEGTSTICGC   120
DSHHKGPPGE GWKWGGCSED ADFGVLVSRE FADARENRPD ARSAMNKHNN EAGRTTILDH   180
MHLKCKCHGL SGSCEVKTCW WAQPDFRAIG DFLKDKYDSA SEMVVEKHRE SRGWVETLRA   240
KYSLFKPPTE RDLVYYENSP NFCEPNPETG SFGTRDRTCN VTSHGIDGCD LLCCGRGHNT   300
RTEKRKEKCH CIFHWCCYVS CQECIRIYDV HTCK                               334

SEQ ID NO: 86               moltype = AA  length = 334
FEATURE                     Location/Qualifiers
source                      1..334
                            mol_type = protein
                            organism = Homo sapiens
SEQUENCE: 86
SYPIWWSLAV GPQYSSLGSQ PILCASIPGL VPKQLRFCRN YVEIMPSVAE GIKIGIQECQ    60
HQFRGRRWNC TTVHDSLAIF GPVLDKATRE SAFVHAIASA GVAFAVTRSC AEGTAAICGC   120
```

```
SSRHQGSPGK GWKWGGCSED IEFGGMVSRE FADARENRPD ARSAMNRHNN EAGRQAIASH   180
MHLKCKCHGL SGSCEVKTCW WSQPDFRAIG DFLKDKYDSA SEMVVEKHRE SRGWVETLRP   240
RYTYFKVPTE RDLVYYEASP NFCEPNPETG SFGTRDRTCN VSSHGIDGCD LLCCGRGHNA   300
RAERRREKCR CVFHWCCYVS CQECTRVYDV HTCK                              334

SEQ ID NO: 87              moltype = AA   length = 329
FEATURE                    Location/Qualifiers
source                     1..329
                           mol_type = protein
                           organism = Homo sapiens
SEQUENCE: 87
SNWLYLAKLS SVGSISEEET CEKLKGLIQR QVQMCKRNLE VMDSVRRGAQ LAIEECQYQF    60
RNRRWNCSTL DSLPVFGKVV TQGTREAAFV YAISSAGVAF AVTRACSSGE LEKCGCDRTV   120
HGVSPQGFQW SGCSDNIAYG VAFSQSFVDV RERSKGASSS RALMNLHNNE AGRKAILTHM   180
RVECKCHGVS GSCEVKTCWR AVPPFRQVGH ALKEKFDGAT EVEPRRVGSS RALVPRNAQF   240
KPHTDEDLVY LEPSPDFCEQ DMRSGVLGTR GRTCNKTSKA IDGCELLCCG RGFHTAQVEL   300
AERCSCKFHW CCFVKCRQCQ RLVELHTCR                                    329

SEQ ID NO: 88              moltype = AA   length = 319
FEATURE                    Location/Qualifiers
source                     1..319
                           mol_type = protein
                           organism = Homo sapiens
SEQUENCE: 88
IIGAQPLCSQ LAGLSQGQKK LCHLYQDHMQ YIGEGAKTGI KECQYQFRHR RWNCSTVDNT    60
SVFGRVMQIG SRETAFTYAV SAAGVVNAMS RACREGELST CGCSRAARPK DLPRDWLWGG   120
CGDNIDYGYR FAKEFVDARE RERIHAKGSY ESARILMNLH NNEAGRRTVY NLADVACKCH   180
GVSGSCSLKT CWLQLADFRK VGDALKEKYD SAAAMRLNSR GKLVQVNSRF NSPTTQDLVY   240
IDPSPDYCVR NESTGSLGTQ GRLCNKTSEG MDGCELMCCG RGYDQFKTVQ TERCHCKFHW   300
CCYVKCKKCT EIVDQFVCK                                               319

SEQ ID NO: 89              moltype = AA   length = 342
FEATURE                    Location/Qualifiers
source                     1..342
                           mol_type = protein
                           organism = Homo sapiens
SEQUENCE: 89
QLLTDANSWW SLALNPVQRP EMFIIGAQPV CSQLPGLSPG QRKLCQLYQE HMAYIGEGAK    60
TGIKECQHQF RQRRWNCSTA DNASVFGRVM QIGSRETAFT HAVSAAGVVN AISRACREGE   120
LSTCGCSRTA RPKDLPRDWL WGGCGDNVEY GYRFAKEFVD ARERKNFAK GSEEQGRVLM   180
NLQNNEAGRR AVYKMADVAC KCHGVSGSCS LKTCWLQLAE FRKVGDRLKE KYDSAAAMRV   240
TRKGRLELVN SRFTQPTPED LVYVDPSPDY CLRNESTGSL GTQGRLCNKT SEGMDGCELM   300
CCGRGYNQFK SVQVERCHCK FHWCCFVRCK KCTEIVDQYI CK                     342

SEQ ID NO: 90              moltype = AA   length = 341
FEATURE                    Location/Qualifiers
source                     1..341
                           mol_type = protein
                           organism = Homo sapiens
SEQUENCE: 90
LWWAVGSPLV MDPTSICRKA RRLAGRQAEL CQAEPEVVAE LARGARLGVR ECQFQFRFRR    60
WNCSSHSKAF GRILQQDIRE TAFVFAITAA GASHAVTQAC SMGELLQCGC QAPRGRAPPR   120
PSGLPGTPGP PGPAGSPEGS AAWEWGGCGD DVDFGDEKSR LFMDARHKRG RGDIRALVQL   180
HNNEAGRLAV RSHTRTECKC HGLSGSCALR TCWQKLPPFR EVGARLLERF HGASRVMGTN   240
DGKALLPAVR TLKPPGRADL LYAADSPDFC APNRRTGSPG TRGRACNSSA PDLSGCDLLC   300
CGRGHRQESV QLEENCLCRF HWCCVVQCHR CRVRKELSLC L                      341

SEQ ID NO: 91              moltype = AA   length = 318
FEATURE                    Location/Qualifiers
source                     1..318
                           mol_type = protein
                           organism = Homo sapiens
SEQUENCE: 91
LGASIICNKI PGLAPRQRAI CQSRPDAIIV IGEGSQMGLD ECQFQFRNGR WNCSALGERT    60
VFGKELKVGS REAAFTYAII AAGVAHAITA ACTQGNLSDC GCDKEKQGQY HRDEGWKWGG   120
CSADIRYGIG FAKVFDARE IKQNARTLMN LHNNEAGRKI LEENMKLECK CHGVSGSCTT   180
KTCWTTLPQF RELGYVLKDK YNEAVHVEPV RASRNKRPTF LKIKKPLSYR KPMDTDLVYI   240
EKSPNYCEED PVTGSVGTQG RACNKTAPQA SGCDLMCCGR GYNTHQYARV WQCNCKFHWC   300
CYVKCNTCSE RTEMYTCK                                                318

SEQ ID NO: 92              moltype = AA   length = 325
FEATURE                    Location/Qualifiers
source                     1..325
                           mol_type = protein
                           organism = Homo sapiens
SEQUENCE: 92
ALSSVVALGA NIICNKIPGL APRQRAICQS RPDAIIVIGE GAQMGINECQ YQFRFGRWNC    60
SALGEKTVFG QELRVGSREA AFTYAITAAG VAHAVTAACS QGNLSNCGCD REKQGYYNQA   120
EGWKWGGCSA DVRYGIDFSR RFVDAREIKK NARRLMNLHN NEAGRKVLED RMQLECKCHG   180
```

```
VSGSCTTKTC WTTLPKFREV GHLLKEKYNA AVQVEVVRAS RLRQPTFLRI KQLRSYQKPM    240
ETDLVYIEKS PNYCEEDAAT GSVGTQGRLC NRTSPGADGC DTMCCGRGYN THQYTKVWQC    300
NCKFHWCCFV KCNTCSERTE VFTCK                                          325

SEQ ID NO: 93             moltype = AA   length = 327
FEATURE                   Location/Qualifiers
source                    1..327
                          mol_type = protein
                          organism = Homo sapiens
SEQUENCE: 93
VNNFLITGPK AYLTYTTSVA LGAQSGIEEC KFQFAWERWN CPENALQLST HNRLRSATRE    60
TSFIHAISSA GVMYIITKNC SMGDFENCGC DGSNNGKTGG HGWIWGGCSD NVEFGERISK    120
LFVDSLEKGK DARALMNLHN NRAGRLAVRA TMKRTCKCHG ISGSCSIQTC WLQLAEFREM    180
GDYLKAKYDQ ALKIEMDKRQ LRAGNSAEGH WVPAEAFLPS AEAELIFLEE SPDYCTCNSS    240
LGIYGTEGRE CLQNSHNTSR WERRSCGRLC TECGLQVEER KTEVISSCNC KFQWCCTVKC    300
DQCRHVVSKY YCARSPGSAQ SLGKGSA                                        327

SEQ ID NO: 94             moltype = AA   length = 329
FEATURE                   Location/Qualifiers
source                    1..329
                          mol_type = protein
                          organism = Homo sapiens
SEQUENCE: 94
WSVNNFLMTG PKAYLIYSSS VAAGAQSGIE ECKYQFAWDR WNCPERALQL SSHGGLRSAN    60
RETAFVHAIS SAGVMYTLTR NCSLGDFDNC GCDDSRNGQL GGQGWLWGGC SDNVGFGEAI    120
SKQFVDALET GQDARAAMNL HNNEAGRKAV KGTMKRTCKC HGVSGSCTTQ TCWLQLPEFR    180
EVGAHLKEKY HAALKVDLLQ GAGNSAAGRG AIADTFRSIS TRELVHLEDS PDYCLENKTL    240
GLLGTEGREC LRRGRALGRW ERRSCRRLCG DCGLAVEERR AETVSSCNCK FHWCCAVRCE    300
QCRRRVTKYF CSRAERPRGG AAHKPGRKP                                      329

SEQ ID NO: 95             moltype = AA   length = 336
FEATURE                   Location/Qualifiers
source                    1..336
                          mol_type = protein
                          organism = Homo sapiens
SEQUENCE: 95
YFGLTGSEPL TILPLTLEPE AAAQAHYKAC DRLKLERKQR RMCRRDPGVA ETLVEAVSMS    60
ALECQFQFRF ERWNCTLEGR YRASLLKRGF KETAFLYAIS SAGLTHALAK ACSAGRMERC    120
TCDEAPDLEN REAWQWGGCG DNLKYSSKFV KEFLGRRSSK DLRARVDFHN NLVGVKVIKA    180
GVETTCKCHG VSGSCTVRTC WRQLAPFHEV GKHLKHKYET ALKVGSTTNE AAGEAGAISP    240
PRGRASGAGG SDPLPRTPEL VHLDDSPSFC LAGRFSPGTA GRRCHREKNC ESICCGRGHN    300
TQSRVVTRPC QCQVRWCCYV ECRQCTQREE VYTCKG                              336

SEQ ID NO: 96             moltype = AA   length = 335
FEATURE                   Location/Qualifiers
source                    1..335
                          mol_type = protein
                          organism = Homo sapiens
SEQUENCE: 96
SYFGLTGREV LTPFPGLGTA AAPAQGGAHL KQCDLLKLSR RQKQLCRREP GLAETLRDAA    60
HLGLLECQFQ FRHERWNCSL EGRMGLLKRG FKETAFLYAV SSAALTHTLA RACSAGRMER    120
CTCDDSPGLE SRQAWQWGVC GDNLKYSTKF LSNFLGSKRG NKDLRARADA HNTHVGIKAV    180
KSGLRTTCKC HGVSGSCAVR TCWKQLSPFR ETGQVLKLRY DSAVKVSSAT NEALGRLELW    240
APARQGSLTK GLAPRSGDLV YMEDSPSFCR PSKYSPGTAG RVCSREASCS SLCCGRGYDT    300
QSRLVAFSCH CQVQWCCYVE CQQCVQEELV YTCKH                               335

SEQ ID NO: 97             moltype = AA   length = 382
FEATURE                   Location/Qualifiers
source                    1..382
                          mol_type = protein
                          organism = Homo sapiens
SEQUENCE: 97
MPRSAPNDIL DLRLPPEPVL NANTVCLTLP GLSRRQMEVC VRHPDVAASA IQGIQIAIHE    60
CQHQFRDQRW NCSSLETRNK IPYESPIFSR GFRESAFAYA IAAAGVVHAV SNACALGKLK    120
ACGCDASRRG DEEAFRRKLH RLQLDALQRG KGLSHGVPEH PALPTASPGL QDSWEWGGCS    180
PDMGFGERFS KDFLDSREPH RDIHARMRLH NNRVGRQAVM ENMRRKCKCH GTSGSCQLKT    240
CWQVTPEFRT VGALLRSRFH RATLIRPHNR NGGQLEPGPA GAPSPAPGAP GPRRRASPAD    300
LVYFEKSPDF CEREPRLDSA GTVGRLCNKS SAGSDGCGSM CCGRGHNILR QTRSERCHCR    360
FHWCCFVVCE ECRITEWVSV CK                                             382

SEQ ID NO: 98             moltype = AA   length = 361
FEATURE                   Location/Qualifiers
source                    1..361
                          mol_type = protein
                          organism = Homo sapiens
SEQUENCE: 98
NEILGLKLPG EPPLTANTVC LTLSGLSKRQ LGLCLRNPDV TASALQGLHI AVHECQHQLR    60
DQRWNCSALE GGGRLPHHSA ILKRGFRESA FSFSMLAAGV MHAVATACSL GKLVSCGCGW    120
KGSGEQDRLR AKLLQLQALS RGKSFPHSLP SPGPGSSPSP GPQDTWEWGG CNHDMDFGEK    180
```

```
FSRDFLDSRE APRDIQARMR IHNNRVGRQV VTENLKRKCK CHGTSGSCQF KTCWRAAPEF      240
RAVGAALRER LGRAIFIDTH NRNSGAFQPR LRPRRLSGEL VYFEKSPDFC ERDPTMGSPG      300
TRGRACNKTS RLLDGCGSLC CGRGHNVLRQ TRVERCHCRF HWCCYVLCDE CKVTEWVNVC      360
K                                                                     361

SEQ ID NO: 99            moltype = AA  length = 330
FEATURE                  Location/Qualifiers
source                   1..330
                         mol_type = protein
                         organism = Homo sapiens
SEQUENCE: 99
IKWLALSKTP SALALNQTQH CKQLEGLVSA QVQLCRSNLE LMHTVVHAAR EVMKACRRAF       60
ADMRWNCSSI ELAPNYLLDL ERGTRESAFV YALSAAAISH AIARACTSGD LPGCSCGPVP      120
GEPPGPGNRW GGCADNLSYG LLMGAKFSDA PMKVKKTGSQ ANKLMRLHNS EVGRQALRAS      180
LEMKCKCHGV SGSCSIRTCW KGLQELQDVA ADLKTRYLSA TKVVHRPMGT RKHLVPKDLD      240
IRPVKDSELV YLQSSPDFCM KNEKVGSHGT QDRQCNKTSN GSDSCDLMCC GRGYNPYTDR      300
VVERCHCKYH WCCYVTCRRC ERTVERYVCK                                      330

SEQ ID NO: 100           moltype = AA  length = 336
FEATURE                  Location/Qualifiers
source                   1..336
                         mol_type = protein
                         organism = Homo sapiens
SEQUENCE: 100
NWMWLGIASF GVPEKLGCAN LPLNSRQKEL CKRKPYLLPS IREGARLGIQ ECGSQFRHER       60
WNCMITAAAT TAPMGASPLF GYELSSGTKE TAFIYAVMAA GLVHSVTRSC SAGNMTECSC      120
DTTLQNGGSA SEGWHWGGCS DDVQYGMWFS RKFLDFPIGN TTGKENKVLL AMNLHNNEAG      180
RQAVAKLMSV DCRCHGVSGS CAVKTCWKTM SSFEKIGHLL KDKYENSIQI SDKTKRKMRR      240
REKDQRKIPI HKDDLLYVNK SPNYCVEDKK LGIPGTQGRE CNRTSEGADG CNLLCCGRGY      300
NTHVVRHVER CECKFIWCCY VRCRRCESMT DVHTCK                               336

SEQ ID NO: 101           moltype = AA  length = 65
FEATURE                  Location/Qualifiers
source                   1..65
                         mol_type = protein
                         organism = Homo sapiens
SEQUENCE: 101
SHLVKCAEKE KTFCVNGGEC FMVKDLSNPS RYLCKCPNEF TGDRCQNYVM ASFYKHLGIE       60
FMEAE                                                                  65

SEQ ID NO: 102           moltype =     length =
SEQUENCE: 102
000

SEQ ID NO: 103           moltype =     length =
SEQUENCE: 103
000

SEQ ID NO: 104           moltype =     length =
SEQUENCE: 104
000

SEQ ID NO: 105           moltype =     length =
SEQUENCE: 105
000

SEQ ID NO: 106           moltype =     length =
SEQUENCE: 106
000

SEQ ID NO: 107           moltype =     length =
SEQUENCE: 107
000

SEQ ID NO: 108           moltype =     length =
SEQUENCE: 108
000

SEQ ID NO: 109           moltype =     length =
SEQUENCE: 109
000

SEQ ID NO: 110           moltype =     length =
SEQUENCE: 110
000

SEQ ID NO: 111           moltype =     length =
SEQUENCE: 111
000
```

| | | |
|---|---|---|
| SEQ ID NO: 112 SEQUENCE: 112 000 | moltype = | length = |
| SEQ ID NO: 113 SEQUENCE: 113 000 | moltype = | length = |
| SEQ ID NO: 114 SEQUENCE: 114 000 | moltype = | length = |
| SEQ ID NO: 115 SEQUENCE: 115 000 | moltype = | length = |
| SEQ ID NO: 116 SEQUENCE: 116 000 | moltype = | length = |
| SEQ ID NO: 117 SEQUENCE: 117 000 | moltype = | length = |
| SEQ ID NO: 118 SEQUENCE: 118 000 | moltype = | length = |
| SEQ ID NO: 119 SEQUENCE: 119 000 | moltype = | length = |
| SEQ ID NO: 120 SEQUENCE: 120 000 | moltype = | length = |
| SEQ ID NO: 121 SEQUENCE: 121 000 | moltype = | length = |
| SEQ ID NO: 122 SEQUENCE: 122 000 | moltype = | length = |
| SEQ ID NO: 123 SEQUENCE: 123 000 | moltype = | length = |
| SEQ ID NO: 124 SEQUENCE: 124 000 | moltype = | length = |
| SEQ ID NO: 125 SEQUENCE: 125 000 | moltype = | length = |
| SEQ ID NO: 126 SEQUENCE: 126 000 | moltype = | length = |
| SEQ ID NO: 127 SEQUENCE: 127 000 | moltype = | length = |
| SEQ ID NO: 128 SEQUENCE: 128 000 | moltype = | length = |
| SEQ ID NO: 129 SEQUENCE: 129 000 | moltype = | length = |
| SEQ ID NO: 130 SEQUENCE: 130 000 | moltype = | length = |
| SEQ ID NO: 131 SEQUENCE: 131 | moltype = | length = |

-continued

000

SEQ ID NO: 132           moltype =    length =
SEQUENCE: 132
000

SEQ ID NO: 133           moltype =    length =
SEQUENCE: 133
000

SEQ ID NO: 134           moltype =    length =
SEQUENCE: 134
000

SEQ ID NO: 135           moltype =    length =
SEQUENCE: 135
000

SEQ ID NO: 136           moltype =    length =
SEQUENCE: 136
000

SEQ ID NO: 137           moltype =    length =
SEQUENCE: 137
000

SEQ ID NO: 138           moltype =    length =
SEQUENCE: 138
000

SEQ ID NO: 139           moltype =    length =
SEQUENCE: 139
000

SEQ ID NO: 140           moltype =    length =
SEQUENCE: 140
000

SEQ ID NO: 141           moltype =    length =
SEQUENCE: 141
000

SEQ ID NO: 142           moltype =    length =
SEQUENCE: 142
000

SEQ ID NO: 143           moltype =    length =
SEQUENCE: 143
000

SEQ ID NO: 144           moltype =    length =
SEQUENCE: 144
000

SEQ ID NO: 145           moltype =    length =
SEQUENCE: 145
000

SEQ ID NO: 146           moltype =    length =
SEQUENCE: 146
000

SEQ ID NO: 147           moltype =    length =
SEQUENCE: 147
000

SEQ ID NO: 148           moltype =    length =
SEQUENCE: 148
000

SEQ ID NO: 149           moltype =    length =
SEQUENCE: 149
000

SEQ ID NO: 150           moltype =    length =
SEQUENCE: 150
000

SEQ ID NO: 151           moltype =    length =

```
SEQUENCE: 151
000

SEQ ID NO: 152          moltype = AA  length = 50
FEATURE                 Location/Qualifiers
source                  1..50
                        mol_type = protein
                        organism = Homo sapiens
SEQUENCE: 152
VVSHFNDCPD SHTQFCFHGT CRFLVQEDKP ACVCHSGYVG ARCEHADLLA              50

SEQ ID NO: 153          moltype =    length =
SEQUENCE: 153
000

SEQ ID NO: 154          moltype =    length =
SEQUENCE: 154
000

SEQ ID NO: 155          moltype =    length =
SEQUENCE: 155
000

SEQ ID NO: 156          moltype =    length =
SEQUENCE: 156
000

SEQ ID NO: 157          moltype =    length =
SEQUENCE: 157
000

SEQ ID NO: 158          moltype =    length =
SEQUENCE: 158
000

SEQ ID NO: 159          moltype =    length =
SEQUENCE: 159
000

SEQ ID NO: 160          moltype =    length =
SEQUENCE: 160
000

SEQ ID NO: 161          moltype =    length =
SEQUENCE: 161
000

SEQ ID NO: 162          moltype =    length =
SEQUENCE: 162
000

SEQ ID NO: 163          moltype =    length =
SEQUENCE: 163
000

SEQ ID NO: 164          moltype =    length =
SEQUENCE: 164
000

SEQ ID NO: 165          moltype =    length =
SEQUENCE: 165
000

SEQ ID NO: 166          moltype =    length =
SEQUENCE: 166
000

SEQ ID NO: 167          moltype =    length =
SEQUENCE: 167
000

SEQ ID NO: 168          moltype = AA  length = 1286
FEATURE                 Location/Qualifiers
source                  1..1286
                        mol_type = protein
                        organism = Homo sapiens
SEQUENCE: 168
IPVPQSKPLE RHVEKSMNLH LLARSNVSVQ DELNASGTIK ESGVLVHEGD RGRQENTQDG    60
HKGEGNGSKW AEVGGKSFST YSTLANEEGN IEGWNGDTGK AETYGHDGIH GKEENITANG   120
```

```
IQGQVSIIDN AGATNRSNTN GNTDKNTQNG DVGDAGHNED VAVVQEDGPQ VAGSNNSTDN    180
EDEIIENSCR NEGNTSEITP QINSKRNGTK EAEVTPGTGE DAGLDNSDGS PSGNGADEDE    240
DEGSGDDEDE EAGNGKDSSN NSKGQEGQDH GKEDDHDSSI GQNSDSKEYY DPEGKEDPHN    300
EVDGDKTSKS EENSAGIPED NGSQRIEDTQ KLNHRESKRV ENRITKESET HAVGKSQDKG    360
IEIKGPSSGN RNITKEVGKG NEGKEDKGQH GMILGKGNVK TQGEVVNIEG PGQKSEPGNK    420
VGHSNTGSDS NSDGYDSYDF DDKSMQGDDP NSSDESNGND DANSESDNNS SSRGDASYNS    480
DESKDNGNGS DSKGAEDDDS DSTSDTNNSD SNGNGNNGND DNDKSDSGKG KSDSSDSDSS    540
DSSNSSDSSD SSDSDSSDSN SSSDSDSSDS DSSDSSDSDS SDSSNSSDSS DSSDSSDSSD    600
SSDSSDSKSD SSKSESDSSD SDSKDSSDS NSSDSSDNSD SDSSNSSNS SDSSDSSDS      660
DSSSSSDSSN SSDSSDSSDS SNSSESSDSS DSSDSDSSDS SDSSNSSSD SDSSNSSDSS     720
DSSNSSDSSD SSDSSNSSDS SDSSDSSNSS DSSDSSDSSD SDSSNSSDS NDSSNSSDSS     780
DSSNSSDSSN SSDSSDSSDS SDSDSSNSSD SSNSSDSSDS SNSSDSSDSS DSSDGSDSDS    840
SNRSDSSNSS DSSDSSDSSN SSDSSDSSDS NESSNSSDSS DSSDSSDSS SSDSSDSSDSS     900
DSSNSSDSSE SSNSSDNSNS SDSSNSSDSS DSSDSSNSSD SSNSSDSSNS SDSSDSNSSD    960
SSDSSNSSDS SDSSDSSDSS DSSDSSNSSD SSDSSNSSDS SNSSDSSNSS DSSNSSDSSD    1020
SSDSSDSSDS SDSSDSSDSS NSSDSSDSSD SDSSDSSSDS SDSDSSESS DSSDSSNSSD     1080
SSDSSDSSDS SDSSDSSDSS DSSDSSNSSD SSDSSDSSDS SDSSNSSDSS DSSESSDSSD    1140
SSDSSDSSDS SDSSDSSDSS DSSDSSDSSD SDSSDSSDSS DSSDSSDSSD SDSSDSSDSS    1200
SSDSSDSSDS SDSDSNESS DSSDSSDSSD SSNSSDSSDS SDSSDSTSDS NDESDSQSKS    1260
GNGNNNGSDS DSDSEGSDSN HSTSDD                                        1286

SEQ ID NO: 169         moltype =    length =
SEQUENCE: 169
000

SEQ ID NO: 170         moltype =    length =
SEQUENCE: 170
000

SEQ ID NO: 171         moltype =    length =
SEQUENCE: 171
000

SEQ ID NO: 172         moltype =    length =
SEQUENCE: 172
000

SEQ ID NO: 173         moltype =    length =
SEQUENCE: 173
000

SEQ ID NO: 174         moltype =    length =
SEQUENCE: 174
000

SEQ ID NO: 175         moltype =    length =
SEQUENCE: 175
000

SEQ ID NO: 176         moltype = AA   length = 247
FEATURE                Location/Qualifiers
source                 1..247
                       mol_type = protein
                       organism = Homo sapiens
SEQUENCE: 176
IYGGFKSTAG KHPWQASLQS SLPLTISMPQ GHFCGGALIH PCWVLTAAHC TDIKTRHLKV     60
VLGDQDLKKE EFHEQSFRVE KIFKYSHYNE RDEIPHNDIA LLKLKPVDGH CALESKYVKT    120
VCLPDGSFPS GSECHISGWG VTETGKGSRQ LLDAKVKLIA NTLCNSRQLY DHMIDDSMIC    180
AGNLQKPGQD TCQGDSGGPL TCEKDGTYYV YGIVSWGLEC GKRPGVYTQV TKFLNWIKAT    240
IKSESGF                                                             247

SEQ ID NO: 177         moltype =    length =
SEQUENCE: 177
000

SEQ ID NO: 178         moltype =    length =
SEQUENCE: 178
000

SEQ ID NO: 179         moltype =    length =
SEQUENCE: 179
000

SEQ ID NO: 180         moltype =    length =
SEQUENCE: 180
000

SEQ ID NO: 181         moltype =    length =
SEQUENCE: 181
```

000

SEQ ID NO: 182          moltype =       length =
SEQUENCE: 182
000

SEQ ID NO: 183          moltype =       length =
SEQUENCE: 183
000

SEQ ID NO: 184          moltype =       length =
SEQUENCE: 184
000

SEQ ID NO: 185          moltype =       length =
SEQUENCE: 185
000

SEQ ID NO: 186          moltype =       length =
SEQUENCE: 186
000

SEQ ID NO: 187          moltype =       length =
SEQUENCE: 187
000

SEQ ID NO: 188          moltype =       length =
SEQUENCE: 188
000

SEQ ID NO: 189          moltype =       length =
SEQUENCE: 189
000

SEQ ID NO: 190          moltype =       length =
SEQUENCE: 190
000

SEQ ID NO: 191          moltype =       length =
SEQUENCE: 191
000

SEQ ID NO: 192          moltype =       length =
SEQUENCE: 192
000

SEQ ID NO: 193          moltype =       length =
SEQUENCE: 193
000

SEQ ID NO: 194          moltype =       length =
SEQUENCE: 194
000

SEQ ID NO: 195          moltype =       length =
SEQUENCE: 195
000

SEQ ID NO: 196          moltype =       length =
SEQUENCE: 196
000

SEQ ID NO: 197          moltype =       length =
SEQUENCE: 197
000

SEQ ID NO: 198          moltype =       length =
SEQUENCE: 198
000

SEQ ID NO: 199          moltype =       length =
SEQUENCE: 199
000

SEQ ID NO: 200          moltype =       length =
SEQUENCE: 200
000

SEQ ID NO: 201          moltype =       length =

```
SEQUENCE: 201
000

SEQ ID NO: 202           moltype =    length =
SEQUENCE: 202
000

SEQ ID NO: 203           moltype =    length =
SEQUENCE: 203
000

SEQ ID NO: 204           moltype =    length =
SEQUENCE: 204
000

SEQ ID NO: 205           moltype =    length =
SEQUENCE: 205
000

SEQ ID NO: 206           moltype =    length =
SEQUENCE: 206
000

SEQ ID NO: 207           moltype =    length =
SEQUENCE: 207
000

SEQ ID NO: 208           moltype =    length =
SEQUENCE: 208
000

SEQ ID NO: 209           moltype =    length =
SEQUENCE: 209
000

SEQ ID NO: 210           moltype =    length =
SEQUENCE: 210
000

SEQ ID NO: 211           moltype =    length =
SEQUENCE: 211
000

SEQ ID NO: 212           moltype =    length =
SEQUENCE: 212
000

SEQ ID NO: 213           moltype =    length =
SEQUENCE: 213
000

SEQ ID NO: 214           moltype =    length =
SEQUENCE: 214
000

SEQ ID NO: 215           moltype =    length =
SEQUENCE: 215
000

SEQ ID NO: 216           moltype =    length =
SEQUENCE: 216
000

SEQ ID NO: 217           moltype =    length =
SEQUENCE: 217
000

SEQ ID NO: 218           moltype =    length =
SEQUENCE: 218
000

SEQ ID NO: 219           moltype =    length =
SEQUENCE: 219
000

SEQ ID NO: 220           moltype =    length =
SEQUENCE: 220
000
```

| | | |
|---|---|---|
| SEQ ID NO: 221<br>SEQUENCE: 221<br>000 | moltype = | length = |
| SEQ ID NO: 222<br>SEQUENCE: 222<br>000 | moltype = | length = |
| SEQ ID NO: 223<br>SEQUENCE: 223<br>000 | moltype = | length = |
| SEQ ID NO: 224<br>SEQUENCE: 224<br>000 | moltype = | length = |
| SEQ ID NO: 225<br>SEQUENCE: 225<br>000 | moltype = | length = |
| SEQ ID NO: 226<br>SEQUENCE: 226<br>000 | moltype = | length = |
| SEQ ID NO: 227<br>SEQUENCE: 227<br>000 | moltype = | length = |
| SEQ ID NO: 228<br>SEQUENCE: 228<br>000 | moltype = | length = |
| SEQ ID NO: 229<br>SEQUENCE: 229<br>000 | moltype = | length = |
| SEQ ID NO: 230<br>SEQUENCE: 230<br>000 | moltype = | length = |
| SEQ ID NO: 231<br>SEQUENCE: 231<br>000 | moltype = | length = |
| SEQ ID NO: 232<br>SEQUENCE: 232<br>000 | moltype = | length = |
| SEQ ID NO: 233<br>SEQUENCE: 233<br>000 | moltype = | length = |
| SEQ ID NO: 234<br>SEQUENCE: 234<br>000 | moltype = | length = |
| SEQ ID NO: 235<br>SEQUENCE: 235<br>000 | moltype = | length = |
| SEQ ID NO: 236<br>SEQUENCE: 236<br>000 | moltype = | length = |
| SEQ ID NO: 237<br>SEQUENCE: 237<br>000 | moltype = | length = |
| SEQ ID NO: 238<br>SEQUENCE: 238<br>000 | moltype = | length = |
| SEQ ID NO: 239<br>SEQUENCE: 239<br>000 | moltype = | length = |
| SEQ ID NO: 240<br>SEQUENCE: 240<br>000 | moltype = | length = |

| | | |
|---|---|---|
| SEQ ID NO: 241<br>SEQUENCE: 241<br>000 | moltype = | length = |
| SEQ ID NO: 242<br>SEQUENCE: 242<br>000 | moltype = | length = |
| SEQ ID NO: 243<br>SEQUENCE: 243<br>000 | moltype = | length = |
| SEQ ID NO: 244<br>SEQUENCE: 244<br>000 | moltype = | length = |
| SEQ ID NO: 245<br>SEQUENCE: 245<br>000 | moltype = | length = |
| SEQ ID NO: 246<br>SEQUENCE: 246<br>000 | moltype = | length = |
| SEQ ID NO: 247<br>SEQUENCE: 247<br>000 | moltype = | length = |
| SEQ ID NO: 248<br>SEQUENCE: 248<br>000 | moltype = | length = |
| SEQ ID NO: 249<br>SEQUENCE: 249<br>000 | moltype = | length = |
| SEQ ID NO: 250<br>SEQUENCE: 250<br>000 | moltype = | length = |
| SEQ ID NO: 251<br>SEQUENCE: 251<br>000 | moltype = | length = |
| SEQ ID NO: 252<br>SEQUENCE: 252<br>000 | moltype = | length = |
| SEQ ID NO: 253<br>SEQUENCE: 253<br>000 | moltype = | length = |
| SEQ ID NO: 254<br>SEQUENCE: 254<br>000 | moltype = | length = |
| SEQ ID NO: 255<br>SEQUENCE: 255<br>000 | moltype = | length = |
| SEQ ID NO: 256<br>SEQUENCE: 256<br>000 | moltype = | length = |
| SEQ ID NO: 257<br>SEQUENCE: 257<br>000 | moltype = | length = |
| SEQ ID NO: 258<br>SEQUENCE: 258<br>000 | moltype = | length = |
| SEQ ID NO: 259<br>SEQUENCE: 259<br>000 | moltype = | length = |
| SEQ ID NO: 260<br>SEQUENCE: 260 | moltype = | length = |

```
SEQ ID NO: 261          moltype =    length =
SEQUENCE: 261
000

SEQ ID NO: 262          moltype =    length =
SEQUENCE: 262
000

SEQ ID NO: 263          moltype =    length =
SEQUENCE: 263
000

SEQ ID NO: 264          moltype =    length =
SEQUENCE: 264
000

SEQ ID NO: 265          moltype =    length =
SEQUENCE: 265
000

SEQ ID NO: 266          moltype =    length =
SEQUENCE: 266
000

SEQ ID NO: 267          moltype =    length =
SEQUENCE: 267
000

SEQ ID NO: 268          moltype = AA  length = 839
FEATURE                 Location/Qualifiers
source                  1..839
                        mol_type = protein
                        organism = Homo sapiens
SEQUENCE: 268
DDPNSSDESN GNDDANSESD NNSSSRGDAS YNSDESKDNG NGSDSKGAED DDSDSTSDTN    60
NSDSNGNGNN GNDDNDKSDS GKGKSDSSDS DSSDSSNSSD SSDSSDSDSS DSNSSSDSDS   120
SDSDSSDSSD SDSSDSSNSS DSSDSSDSSD SSDSSDSSDS KSDSSKSESD SSDSDSKSDS   180
SDSNSSDSSD NSDSSDSSNS SNSSDSSDSS DSSDSSSSSD SSNSSDSSDS SDSSNSSESS   240
DSSDSSDSDS SDSSDSSNSN SSDSDSSNSS DSSDSSNSSD SSDSSDSSNS SDSSDSSDSS   300
NSSDSSDSSD SSDSSDSSNS SDSNDSSNSS DSSDSSDSSD SSNSSDSSDS SDSSDSDSSN   360
SSDSSNSSDS SDSSNSSDSS DSSDSSDGSD SDSSNRSDSS NSSDSDSSD SSNSSDSSDS    420
SDSNESSNSS DSSDSSNSSD SDSSDSSNSS DSSDSSNSSD SSESSNSSDN SNSSDSSNSS   480
DSSDSSDSSN SSDSSNSSDS SNSSDSSDSN SSDSSDSSNS SDSSDSSDSS DSSDSSDSSN   540
SSDSSDSSDS SDSSNSSDSS NSSDSSNSSD SSDSSDSSDS SDSSDSSDSS DSSNSSDSSD   600
SSDSSDSDSS SDSSDSSDSS ESSDSSDSSN SSDSSDSSDS DSSDSSDSSD DSSDSSDSSN   660
SSDSSDSSDS SDSSDSSNSS DSSDSSESSD SSDSSDSSDS DSSDSSDSSS DSSDSSNSSD   720
SSDSSDSDS SDSSDSSDSS DSSDSSDSSD SSDSSDSSDS SDSSDSSDSN ESSDSSDSSD    780
SSDSSNSSDS SDSSDSSDST SDSNDESDSQ SKSGNGNNNG SDSDSDSEGS DSNHSTSDD    839

SEQ ID NO: 269          moltype =    length =
SEQUENCE: 269
000

SEQ ID NO: 270          moltype =    length =
SEQUENCE: 270
000

SEQ ID NO: 271          moltype =    length =
SEQUENCE: 271
000

SEQ ID NO: 272          moltype =    length =
SEQUENCE: 272
000

SEQ ID NO: 273          moltype =    length =
SEQUENCE: 273
000

SEQ ID NO: 274          moltype =    length =
SEQUENCE: 274
000

SEQ ID NO: 275          moltype =    length =
SEQUENCE: 275
000
```

| | | |
|---|---|---|
| SEQ ID NO: 276<br>SEQUENCE: 276<br>000 | moltype = | length = |
| SEQ ID NO: 277<br>SEQUENCE: 277<br>000 | moltype = | length = |
| SEQ ID NO: 278<br>SEQUENCE: 278<br>000 | moltype = | length = |
| SEQ ID NO: 279<br>SEQUENCE: 279<br>000 | moltype = | length = |
| SEQ ID NO: 280<br>SEQUENCE: 280<br>000 | moltype = | length = |
| SEQ ID NO: 281<br>SEQUENCE: 281<br>000 | moltype = | length = |
| SEQ ID NO: 282<br>SEQUENCE: 282<br>000 | moltype = | length = |
| SEQ ID NO: 283<br>SEQUENCE: 283<br>000 | moltype = | length = |
| SEQ ID NO: 284<br>SEQUENCE: 284<br>000 | moltype = | length = |
| SEQ ID NO: 285<br>SEQUENCE: 285<br>000 | moltype = | length = |
| SEQ ID NO: 286<br>SEQUENCE: 286<br>000 | moltype = | length = |
| SEQ ID NO: 287<br>SEQUENCE: 287<br>000 | moltype = | length = |
| SEQ ID NO: 288<br>SEQUENCE: 288<br>000 | moltype = | length = |
| SEQ ID NO: 289<br>SEQUENCE: 289<br>000 | moltype = | length = |
| SEQ ID NO: 290<br>SEQUENCE: 290<br>000 | moltype = | length = |
| SEQ ID NO: 291<br>SEQUENCE: 291<br>000 | moltype = | length = |
| SEQ ID NO: 292<br>SEQUENCE: 292<br>000 | moltype = | length = |
| SEQ ID NO: 293<br>SEQUENCE: 293<br>000 | moltype = | length = |
| SEQ ID NO: 294<br>SEQUENCE: 294<br>000 | moltype = | length = |
| SEQ ID NO: 295<br>SEQUENCE: 295<br>000 | moltype = | length = |

| | | |
|---|---|---|
| SEQ ID NO: 296<br>SEQUENCE: 296<br>000 | moltype = | length = |
| SEQ ID NO: 297<br>SEQUENCE: 297<br>000 | moltype = | length = |
| SEQ ID NO: 298<br>SEQUENCE: 298<br>000 | moltype = | length = |
| SEQ ID NO: 299<br>SEQUENCE: 299<br>000 | moltype = | length = |
| SEQ ID NO: 300<br>SEQUENCE: 300<br>000 | moltype = | length = |
| SEQ ID NO: 301<br>SEQUENCE: 301<br>000 | moltype = | length = |
| SEQ ID NO: 302<br>SEQUENCE: 302<br>000 | moltype = | length = |
| SEQ ID NO: 303<br>SEQUENCE: 303<br>000 | moltype = | length = |
| SEQ ID NO: 304<br>SEQUENCE: 304<br>000 | moltype = | length = |
| SEQ ID NO: 305<br>SEQUENCE: 305<br>000 | moltype = | length = |
| SEQ ID NO: 306<br>SEQUENCE: 306<br>000 | moltype = | length = |
| SEQ ID NO: 307<br>SEQUENCE: 307<br>000 | moltype = | length = |
| SEQ ID NO: 308<br>SEQUENCE: 308<br>000 | moltype = | length = |
| SEQ ID NO: 309<br>SEQUENCE: 309<br>000 | moltype = | length = |
| SEQ ID NO: 310<br>SEQUENCE: 310<br>000 | moltype = | length = |
| SEQ ID NO: 311<br>SEQUENCE: 311<br>000 | moltype = | length = |
| SEQ ID NO: 312<br>SEQUENCE: 312<br>000 | moltype = | length = |
| SEQ ID NO: 313<br>SEQUENCE: 313<br>000 | moltype = | length = |
| SEQ ID NO: 314<br>SEQUENCE: 314<br>000 | moltype = | length = |
| SEQ ID NO: 315<br>SEQUENCE: 315 | moltype = | length = |

000

SEQ ID NO: 316          moltype =     length =
SEQUENCE: 316
000

SEQ ID NO: 317          moltype =     length =
SEQUENCE: 317
000

SEQ ID NO: 318          moltype =     length =
SEQUENCE: 318
000

SEQ ID NO: 319          moltype =     length =
SEQUENCE: 319
000

SEQ ID NO: 320          moltype =     length =
SEQUENCE: 320
000

SEQ ID NO: 321          moltype =     length =
SEQUENCE: 321
000

SEQ ID NO: 322          moltype =     length =
SEQUENCE: 322
000

SEQ ID NO: 323          moltype =     length =
SEQUENCE: 323
000

SEQ ID NO: 324          moltype =     length =
SEQUENCE: 324
000

SEQ ID NO: 325          moltype =     length =
SEQUENCE: 325
000

SEQ ID NO: 326          moltype =     length =
SEQUENCE: 326
000

SEQ ID NO: 327          moltype =     length =
SEQUENCE: 327
000

SEQ ID NO: 328          moltype =     length =
SEQUENCE: 328
000

SEQ ID NO: 329          moltype =     length =
SEQUENCE: 329
000

SEQ ID NO: 330          moltype =     length =
SEQUENCE: 330
000

SEQ ID NO: 331          moltype =     length =
SEQUENCE: 331
000

SEQ ID NO: 332          moltype =     length =
SEQUENCE: 332
000

SEQ ID NO: 333          moltype =     length =
SEQUENCE: 333
000

SEQ ID NO: 334          moltype =     length =
SEQUENCE: 334
000

SEQ ID NO: 335          moltype =     length =

| | | |
|---|---|---|
| SEQUENCE: 335 000 | | |
| SEQ ID NO: 336 SEQUENCE: 336 000 | moltype = | length = |
| SEQ ID NO: 337 SEQUENCE: 337 000 | moltype = | length = |
| SEQ ID NO: 338 SEQUENCE: 338 000 | moltype = | length = |
| SEQ ID NO: 339 SEQUENCE: 339 000 | moltype = | length = |
| SEQ ID NO: 340 SEQUENCE: 340 000 | moltype = | length = |
| SEQ ID NO: 341 SEQUENCE: 341 000 | moltype = | length = |
| SEQ ID NO: 342 SEQUENCE: 342 000 | moltype = | length = |
| SEQ ID NO: 343 SEQUENCE: 343 000 | moltype = | length = |
| SEQ ID NO: 344 SEQUENCE: 344 000 | moltype = | length = |
| SEQ ID NO: 345 SEQUENCE: 345 000 | moltype = | length = |
| SEQ ID NO: 346 SEQUENCE: 346 000 | moltype = | length = |
| SEQ ID NO: 347 SEQUENCE: 347 000 | moltype = | length = |
| SEQ ID NO: 348 SEQUENCE: 348 000 | moltype = | length = |
| SEQ ID NO: 349 SEQUENCE: 349 000 | moltype = | length = |
| SEQ ID NO: 350 SEQUENCE: 350 000 | moltype = | length = |
| SEQ ID NO: 351 SEQUENCE: 351 000 | moltype = | length = |
| SEQ ID NO: 352 SEQUENCE: 352 000 | moltype = | length = |
| SEQ ID NO: 353 SEQUENCE: 353 000 | moltype = | length = |
| SEQ ID NO: 354 SEQUENCE: 354 000 | moltype = | length = |

| | | |
|---|---|---|
| SEQ ID NO: 355　SEQUENCE: 355 | moltype = | length = 000 |
| SEQ ID NO: 356　SEQUENCE: 356 | moltype = | length = 000 |
| SEQ ID NO: 357　SEQUENCE: 357 | moltype = | length = 000 |
| SEQ ID NO: 358　SEQUENCE: 358 | moltype = | length = 000 |
| SEQ ID NO: 359　SEQUENCE: 359 | moltype = | length = 000 |
| SEQ ID NO: 360　SEQUENCE: 360 | moltype = | length = 000 |
| SEQ ID NO: 361　SEQUENCE: 361 | moltype = | length = 000 |
| SEQ ID NO: 362　SEQUENCE: 362 | moltype = | length = 000 |
| SEQ ID NO: 363　SEQUENCE: 363 | moltype = | length = 000 |
| SEQ ID NO: 364　SEQUENCE: 364 | moltype = | length = 000 |
| SEQ ID NO: 365　SEQUENCE: 365 | moltype = | length = 000 |
| SEQ ID NO: 366　SEQUENCE: 366 | moltype = | length = 000 |
| SEQ ID NO: 367　SEQUENCE: 367 | moltype = | length = 000 |
| SEQ ID NO: 368　SEQUENCE: 368 | moltype = | length = 000 |
| SEQ ID NO: 369　SEQUENCE: 369 | moltype = | length = 000 |
| SEQ ID NO: 370　SEQUENCE: 370 | moltype = | length = 000 |
| SEQ ID NO: 371　SEQUENCE: 371 | moltype = | length = 000 |
| SEQ ID NO: 372　SEQUENCE: 372 | moltype = | length = 000 |
| SEQ ID NO: 373　SEQUENCE: 373 | moltype = | length = 000 |
| SEQ ID NO: 374　SEQUENCE: 374 | moltype = | length = 000 |

| | | |
|---|---|---|
| SEQ ID NO: 375<br>SEQUENCE: 375<br>000 | moltype = | length = |
| SEQ ID NO: 376<br>SEQUENCE: 376<br>000 | moltype = | length = |
| SEQ ID NO: 377<br>SEQUENCE: 377<br>000 | moltype = | length = |
| SEQ ID NO: 378<br>SEQUENCE: 378<br>000 | moltype = | length = |
| SEQ ID NO: 379<br>SEQUENCE: 379<br>000 | moltype = | length = |
| SEQ ID NO: 380<br>SEQUENCE: 380<br>000 | moltype = | length = |
| SEQ ID NO: 381<br>SEQUENCE: 381<br>000 | moltype = | length = |
| SEQ ID NO: 382<br>SEQUENCE: 382<br>000 | moltype = | length = |
| SEQ ID NO: 383<br>SEQUENCE: 383<br>000 | moltype = | length = |
| SEQ ID NO: 384<br>SEQUENCE: 384<br>000 | moltype = | length = |
| SEQ ID NO: 385<br>SEQUENCE: 385<br>000 | moltype = | length = |
| SEQ ID NO: 386<br>SEQUENCE: 386<br>000 | moltype = | length = |
| SEQ ID NO: 387<br>SEQUENCE: 387<br>000 | moltype = | length = |
| SEQ ID NO: 388<br>SEQUENCE: 388<br>000 | moltype = | length = |
| SEQ ID NO: 389<br>SEQUENCE: 389<br>000 | moltype = | length = |
| SEQ ID NO: 390<br>SEQUENCE: 390<br>000 | moltype = | length = |
| SEQ ID NO: 391<br>SEQUENCE: 391<br>000 | moltype = | length = |
| SEQ ID NO: 392<br>SEQUENCE: 392<br>000 | moltype = | length = |
| SEQ ID NO: 393<br>SEQUENCE: 393<br>000 | moltype = | length = |
| SEQ ID NO: 394<br>SEQUENCE: 394 | moltype = | length = |

```
000

SEQ ID NO: 395          moltype =    length =
SEQUENCE: 395
000

SEQ ID NO: 396          moltype =    length =
SEQUENCE: 396
000

SEQ ID NO: 397          moltype =    length =
SEQUENCE: 397
000

SEQ ID NO: 398          moltype =    length =
SEQUENCE: 398
000

SEQ ID NO: 399          moltype =    length =
SEQUENCE: 399
000

SEQ ID NO: 400          moltype =    length =
SEQUENCE: 400
000

SEQ ID NO: 401          moltype = AA  length = 48
FEATURE                 Location/Qualifiers
REGION                  1..48
                        note = Description of Artificial Sequence: Synthetic
                         polypeptide
source                  1..48
                        mol_type = protein
                        organism = synthetic construct
SEQUENCE: 401
LLADTTHHRP WTVIGESTHH RPWSIIGESS HHKPFTGLGD TTHHRPWG                    48

SEQ ID NO: 402          moltype = AA  length = 48
FEATURE                 Location/Qualifiers
REGION                  1..48
                        note = Description of Artificial Sequence: Synthetic
                         polypeptide
source                  1..48
                        mol_type = protein
                        organism = synthetic construct
SEQUENCE: 402
VIGESTHHRP WSIIGESSHH KPFTGLGDTT HHRPWGILAE STHHKPWT                    48

SEQ ID NO: 403          moltype = AA  length = 1416
FEATURE                 Location/Qualifiers
REGION                  1..1416
                        note = Description of Artificial Sequence: Synthetic
                         polypeptide
MOD_RES                 13..1416
                        note = This region may encompass one or more of the
                         following sequences: "LLADTTHHRPWT" or "VIGESTHHRPWS" or
                         "LIADSTHHSPWT" or "ILAESTHHKPWT" or "ILAETTHHRPWS" or
                         "IIGESSHHKPFT" or "GLGDTTHHRPWG" or "VLGDTTHHKPWT" or
                         "IVADSTHHRPWT" or
MOD_RES                 13..1416
                        note = CONT. FROM ABOVE: "STADTSHHRPS" or "TSGGESTHHRPS" or
                         "TSGGESSHHKPS" or "TGSGDSSHHRPS" or "GSSGESTHHKPST" or
                         "VGADSTHHRPVT" or "GAADTTHHRPVT" or "AGADTTHHRPVT" or
                         "GGADTTHHRPAT" or "GGADTTHHRPGT" or
                         "LLADTTHHRPWTVIGESTHHRPWS"
MOD_RES                 13..1416
                        note = CONT. FROM ABOVE: or
                         "LLADTTHHRPWTVIGESTHHRPWSIIGESSHHKPFT" or
                         "LLADTTHHRPWTVIGESTHHRPWSIIGESSHHKPFTGLGDTTHHRPWGILAESTHHKP
                         WT" or "LLADTTHHRPWTILAESTHHKPWT" or
                         "LLADTTHHRPWTILAESTHHKPWTLLAD
                         TTHHRPWTILAESTHHKPWTLLADTTHHRPWT" or
                         "LLADTTHHRPWTGLGDTTHHRPWG"
MOD_RES                 13..1416
                        note = CONT. FROM ABOVE: or
                         "LLADTTHHRPWTGLGDTTHHRPWGLLADTTHHRPWT" or
                         "LLADTTHHRPWTGLGDTTHHRPWGLLADTTHHRPWTGLGDTTHHRPWGLLADTTHHRP
                         WT" or
                         "LLADTTHHRPWTGLGDTTHHRPWGLLADTTHHRPWTGLGDTTHHRPWGLLADTTHHRP
```

```
                         WTGLGDTTHHRPWGLLADTTHHRPWT" or
                        "STADTSHHRPSTSGGESTHHRPSTSGGESS
MOD_RES                 13..1416
                        note = CONT. FROM ABOVE: HHKPSTGSGDSSHHRPSGSSGESTHHKPST" or
                         "VGADSTHHR
                         PVTGAADTTHHRPVTAGADTTHHRPVTGGADTTHHRPATGGADTTHHRPGT" or
                         "STADTS
                         HHRPSLLADTTHHRPWTTSGGESTHHRPSVGADSTHHRPVTTSGGESSHHKPSGAADTT
                         HHRP VTTGSGDSSHHRPSGSSGESTHHKPSTGGADTTHHRPAT" or
                         "XXXXXXXXXXXX" or
MOD_RES                 13..1416
                        note = CONT. FROM ABOVE: "AAADTTHHRPWT" or
                         "AAADTTHHRPWTAAADTTHHRPWTAA
                         ADTTHHRPWTAAADTTHHRPWTAAADTTHHRPWT" or
                         "LLADAAHHRPWTLLADAAHHRPW
                         TLLADAAHHRPWTLLADAAHHRPWTLLADAAHHRPWT" or
                         "LLADTTAARPWTLLADTTAA
                         RPWTLLADTTAARPWTLLADTTAARPWTLLADTTAARPWT" or
                         "LLADTTHHRPWTLLADT
MOD_RES                 13..1416
                        note = CONT. FROM ABOVE: THHRPWT" or
                         "LLADTTHHRPWTLLADTTHHRPWTLLADTTHH RPWT" or
                         "LLADTTHHRPWTLLADTTHHRPWTLLADTTHHRPWTLLADTTHHRPWTLLADT
                         THHRPWT" or
                         "STSGSTVIGESTHHRPWSLIADSTHHSPWTILAESTHHKPWTILAETTHH
                         RPWSIIGESSHHKPFTGLGDTTHHRPWGVLGDTTHHKPWTIVADSTHHRPWTGQVLPTT
                         TPSS
MOD_RES                 13..1416
                        note = CONT. FROM ABOVE: PSTTSGS" or
                         "LLADTTHHRPWTVIGESTHHRPWSIIGESSHH KPFTGLGDTTHHRPWG" or
                         "VIGESTHHRPWSIIGESSHHKPFTGLGDTTHHRPWGILAE STHHKPWT" and
                         wherein X's respectively = V, L, I, G, S, T or A; I, L, V,
                         Q, T, S, G or A; G, A, V or S; E, D, L or G; S, T, P
MOD_RES                 13..1416
                        note = CONT. FROM ABOVE: T, E or D; T or S; H, T or S; H or
                         T; R, S, K, P or H; P, S, R or K; W, F, S, P, V, A or G;
                         and absent, S, T G, or A
REGION                  1..1416
                        note = See specification as filed for detailed description
                         of substitutions and preferred embodiments
source                  1..1416
                        mol_type = protein
                        organism = synthetic construct
SEQUENCE: 403
LLADTTHHRP WTXXXXXXXX XXXXXXXXXX XXXXXXXXXX XXXXXXXXXX XXXXXXXXXX   60
XXXXXXXXXX XXXXXXXXXX XXXXXXXXXX XXXXXXXXXX XXXXXXXXXX XXXXXXXXXX   120
XXXXXXXXXX XXXXXXXXXX XXXXXXXXXX XXXXXXXXXX XXXXXXXXXX XXXXXXXXXX   180
XXXXXXXXXX XXXXXXXXXX XXXXXXXXXX XXXXXXXXXX XXXXXXXXXX XXXXXXXXXX   240
XXXXXXXXXX XXXXXXXXXX XXXXXXXXXX XXXXXXXXXX XXXXXXXXXX XXXXXXXXXX   300
XXXXXXXXXX XXXXXXXXXX XXXXXXXXXX XXXXXXXXXX XXXXXXXXXX XXXXXXXXXX   360
XXXXXXXXXX XXXXXXXXXX XXXXXXXXXX XXXXXXXXXX XXXXXXXXXX XXXXXXXXXX   420
XXXXXXXXXX XXXXXXXXXX XXXXXXXXXX XXXXXXXXXX XXXXXXXXXX XXXXXXXXXX   480
XXXXXXXXXX XXXXXXXXXX XXXXXXXXXX XXXXXXXXXX XXXXXXXXXX XXXXXXXXXX   540
XXXXXXXXXX XXXXXXXXXX XXXXXXXXXX XXXXXXXXXX XXXXXXXXXX XXXXXXXXXX   600
XXXXXXXXXX XXXXXXXXXX XXXXXXXXXX XXXXXXXXXX XXXXXXXXXX XXXXXXXXXX   660
XXXXXXXXXX XXXXXXXXXX XXXXXXXXXX XXXXXXXXXX XXXXXXXXXX XXXXXXXXXX   720
XXXXXXXXXX XXXXXXXXXX XXXXXXXXXX XXXXXXXXXX XXXXXXXXXX XXXXXXXXXX   780
XXXXXXXXXX XXXXXXXXXX XXXXXXXXXX XXXXXXXXXX XXXXXXXXXX XXXXXXXXXX   840
XXXXXXXXXX XXXXXXXXXX XXXXXXXXXX XXXXXXXXXX XXXXXXXXXX XXXXXXXXXX   900
XXXXXXXXXX XXXXXXXXXX XXXXXXXXXX XXXXXXXXXX XXXXXXXXXX XXXXXXXXXX   960
XXXXXXXXXX XXXXXXXXXX XXXXXXXXXX XXXXXXXXXX XXXXXXXXXX XXXXXXXXXX   1020
XXXXXXXXXX XXXXXXXXXX XXXXXXXXXX XXXXXXXXXX XXXXXXXXXX XXXXXXXXXX   1080
XXXXXXXXXX XXXXXXXXXX XXXXXXXXXX XXXXXXXXXX XXXXXXXXXX XXXXXXXXXX   1140
XXXXXXXXXX XXXXXXXXXX XXXXXXXXXX XXXXXXXXXX XXXXXXXXXX XXXXXXXXXX   1200
XXXXXXXXXX XXXXXXXXXX XXXXXXXXXX XXXXXXXXXX XXXXXXXXXX XXXXXXXXXX   1260
XXXXXXXXXX XXXXXXXXXX XXXXXXXXXX XXXXXXXXXX XXXXXXXXXX XXXXXXXXXX   1320
XXXXXXXXXX XXXXXXXXXX XXXXXXXXXX XXXXXXXXXX XXXXXXXXXX XXXXXXXXXX   1380
XXXXXXXXXX XXXXXXXXXX XXXXXXXXXX XXXXXX                             1416

SEQ ID NO: 404          moltype = AA  length = 1416
FEATURE                 Location/Qualifiers
REGION                  1..1416
                        note = Description of Artificial Sequence: Synthetic
                         polypeptide
MOD_RES                 13..1416
                        note = This region may encompass one or more of the
                         following sequences: "LLADTTHHRPWT" or "VIGESTHHRPWS" or
                         "LIADSTHHSPWT" or "ILAESTHHKPWT" or "ILAETTHHRPWS" or
                         "IIGESSHHKPFT" or "GLGDTTHHRPWG" or "VLGDTTHHKPWT" or
```

```
                          "IVADSTHHRPWT" or
MOD_RES                   13..1416
                          note = CONT. FROM ABOVE: "STADTSHHRPS" or "TSGGESTHHRPS" or
                           "TSGGESSHHKPS" or "TGSGDSSHHRPS" or "GSSGESTHHKPST" or
                           "VGADSTHHRPVT" or "GAADTTHHRPVT" or "AGADTTHHRPVT" or
                           "GGADTTHHRPAT" or "GGADTTHHRPGT" or
                           "LLADTTHHRPWTVIGESTHHRPWS"
MOD_RES                   13..1416
                          note = CONT. FROM ABOVE: or
                           "LLADTTHHRPWTVIGESTHHRPWSIIGESSHHKPFT" or
                           "LLADTTHHRPWTVIGESTHHRPWSIIGESSHHKPFTGLGDTTHHRPWGILAESTHHKP
                           WT" or "LLADTTHHRPWTILAESTHHKPWT" or
                           "LLADTTHHRPWTILAESTHHKPWTLLAD
                           TTHHRPWTILAESTHHKPWTLLADTTHHRPWT" or
                           "LLADTTHHRPWTGLGDTTHHRPWG"
MOD_RES                   13..1416
                          note = CONT. FROM ABOVE: or
                           "LLADTTHHRPWTGLGDTTHHRPWGLLADTTHHRPWT" or
                           "LLADTTHHRPWTGLGDTTHHRPWGLLADTTHHRPWTGLGDTTHHRPWGLLADTTHHRP
                           WT" or
                           "LLADTTHHRPWTGLGDTTHHRPWGLLADTTHHRPWTGLGDTTHHRPWGLLADTTHHRP
                            WTGLGDTTHHRPWGLLADTTHHRPWT" or
                           "STADTSHHRPSTSGGESTHHRPSTSGGESS
MOD_RES                   13..1416
                          note = CONT. FROM ABOVE: HHKPSTGSGDSSHHRPSGSSGESTHHKPST" or
                           "VGADSTHHR
                           PVTGAADTTHHRPVTAGADTTHHRPVTGGADTTHHRPATGGADTTHHRPGT" or
                           "STADTS
                           HHRPSLLADTTHHRPWTTSGGESTHHRPSVGADSTHHRPVTTSGGESSHHKPSGAADTT
                           HHRP VTTGSGDSSHHRPSGSSGESTHHKPSTGGADTTHHRPAT" or
                           "XXXXXXXXXXXX" or
MOD_RES                   13..1416
                          note = CONT. FROM ABOVE: "AAADTTHHRPWT" or
                           "AAADTTHHRPWTAAADTTHHRPWTAA
                           ADTTHHRPWTAAADTTHHRPWTAAADTTHHRPWT" or
                           "LLADAAHHRPWTLLADAAHHRPW
                           TLLADAAHHRPWTLLADAAHHRPWTLLADAAHHRPWT" or
                           "LLADTTAARPWTLLADTTAA
                           RPWTLLADTTAARPWTLLADTTAARPWTLLADTTAARPWT" or
                           "LLADTTHHRPWTLLADT
MOD_RES                   13..1416
                          note = CONT. FROM ABOVE: THHRPWT" or
                           "LLADTTHHRPWTLLADTTHHRPWTLLADTTHH RPWT" or
                           "LLADTTHHRPWTLLADTTHHRPWTLLADTTHHRPWTLLADTTHHRPWTLLADT
                           THHRPWT" or
                           "STSGSTVIGESTHHRPWSLIADSTHHSPWTILAESTHHKPWTILAETTHH
                           RPWSIIGESSHHKPFTGLGDTTHHRPWGVLGDTTHHKPWTIVADSTHHRPWTGQVLPTT
                           TPSS
MOD_RES                   13..1416
                          note = CONT. FROM ABOVE: PSTTSGS" or
                           "LLADTTHHRPWTVIGESTHHRPWSIIGESSHH KPFTGLGDTTHHRPWG" or
                           "VIGESTHHRPWSIIGESSHHKPFTGLGDTTHHRPWGILAE STHHKPWT" and
                           wherein X's respectively = V, L, I, G, S, T or A; I, L, V,
                           Q, T, S, G or A; G, A, V or S; E, D, L or G; S, T, P
MOD_RES                   13..1416
                          note = CONT. FROM ABOVE: T, E or D; T or S; H, T or S; H or
                           T; R, S, K, P or H; P, S, R or K; W, F, S, P, V, A or G;
                           and absent, S, T G, or A
REGION                    1..1416
                          note = See specification as filed for detailed description
                           of substitutions and preferred embodiments
source                    1..1416
                          mol_type = protein
                          organism = synthetic construct
SEQUENCE: 404
VIGESTHHRP WSXXXXXXXX XXXXXXXXXX XXXXXXXXXX XXXXXXXXXX XXXXXXXXXX  60
XXXXXXXXXX XXXXXXXXXX XXXXXXXXXX XXXXXXXXXX XXXXXXXXXX XXXXXXXXXX  120
XXXXXXXXXX XXXXXXXXXX XXXXXXXXXX XXXXXXXXXX XXXXXXXXXX XXXXXXXXXX  180
XXXXXXXXXX XXXXXXXXXX XXXXXXXXXX XXXXXXXXXX XXXXXXXXXX XXXXXXXXXX  240
XXXXXXXXXX XXXXXXXXXX XXXXXXXXXX XXXXXXXXXX XXXXXXXXXX XXXXXXXXXX  300
XXXXXXXXXX XXXXXXXXXX XXXXXXXXXX XXXXXXXXXX XXXXXXXXXX XXXXXXXXXX  360
XXXXXXXXXX XXXXXXXXXX XXXXXXXXXX XXXXXXXXXX XXXXXXXXXX XXXXXXXXXX  420
XXXXXXXXXX XXXXXXXXXX XXXXXXXXXX XXXXXXXXXX XXXXXXXXXX XXXXXXXXXX  480
XXXXXXXXXX XXXXXXXXXX XXXXXXXXXX XXXXXXXXXX XXXXXXXXXX XXXXXXXXXX  540
XXXXXXXXXX XXXXXXXXXX XXXXXXXXXX XXXXXXXXXX XXXXXXXXXX XXXXXXXXXX  600
XXXXXXXXXX XXXXXXXXXX XXXXXXXXXX XXXXXXXXXX XXXXXXXXXX XXXXXXXXXX  660
XXXXXXXXXX XXXXXXXXXX XXXXXXXXXX XXXXXXXXXX XXXXXXXXXX XXXXXXXXXX  720
XXXXXXXXXX XXXXXXXXXX XXXXXXXXXX XXXXXXXXXX XXXXXXXXXX XXXXXXXXXX  780
XXXXXXXXXX XXXXXXXXXX XXXXXXXXXX XXXXXXXXXX XXXXXXXXXX XXXXXXXXXX  840
```

| | | |
|---|---|---|
| XXXXXXXXXX XXXXXXXXXX XXXXXXXXXX XXXXXXXXXX XXXXXXXXXX XXXXXXXXXX | | 900 |
| XXXXXXXXXX XXXXXXXXXX XXXXXXXXXX XXXXXXXXXX XXXXXXXXXX XXXXXXXXXX | | 960 |
| XXXXXXXXXX XXXXXXXXXX XXXXXXXXXX XXXXXXXXXX XXXXXXXXXX XXXXXXXXXX | | 1020 |
| XXXXXXXXXX XXXXXXXXXX XXXXXXXXXX XXXXXXXXXX XXXXXXXXXX XXXXXXXXXX | | 1080 |
| XXXXXXXXXX XXXXXXXXXX XXXXXXXXXX XXXXXXXXXX XXXXXXXXXX XXXXXXXXXX | | 1140 |
| XXXXXXXXXX XXXXXXXXXX XXXXXXXXXX XXXXXXXXXX XXXXXXXXXX XXXXXXXXXX | | 1200 |
| XXXXXXXXXX XXXXXXXXXX XXXXXXXXXX XXXXXXXXXX XXXXXXXXXX XXXXXXXXXX | | 1260 |
| XXXXXXXXXX XXXXXXXXXX XXXXXXXXXX XXXXXXXXXX XXXXXXXXXX XXXXXXXXXX | | 1320 |
| XXXXXXXXXX XXXXXXXXXX XXXXXXXXXX XXXXXXXXXX XXXXXXXXXX XXXXXXXXXX | | 1380 |
| XXXXXXXXXX XXXXXXXXXX XXXXXXXXXX XXXXXX | | 1416 |

```
SEQ ID NO: 405        moltype = AA  length = 1416
FEATURE               Location/Qualifiers
REGION                1..1416
                      note = Description of Artificial Sequence: Synthetic
                      polypeptide
MOD_RES               13..1416
                      note = This region may encompass one or more of the
                      following sequences: "LLADTTHHRPWT" or "VIGESTHHRPWS" or
                      "LIADSTHHSPWT" or "ILAESTHHKPWT" or "ILAETTHHRPWS" or
                      "IIGESSHHKPFT" or "GLGDTTHHRPWG" or "VLGDTTHHKPWT" or
                      "IVADSTHHRPWT" or
MOD_RES               13..1416
                      note = CONT. FROM ABOVE: "STADTSHHRPS" or "TSGGESTHHRPS" or
                      "TSGGESSHHKPS" or "TGSGDSSHHRPS" or "GSSGESTHHKPST" or
                      "VGADSTHHRPVT" or "GAADTTHHRPVT" or "AGADTTHHRPVT" or
                      "GGADTTHHRPAT" or "GGADTTHHRPGT" or
                      "LLADTTHHRPWTVIGESTHHRPWS"
MOD_RES               13..1416
                      note = CONT. FROM ABOVE: or
                      "LLADTTHHRPWTVIGESTHHRPWSIIGESSHHKPFT" or
                      "LLADTTHHRPWTVIGESTHHRPWSIIGESSHHKPFTGLGDTTHHRPWGILAESTHHKP
                      WT" or "LLADTTHHRPWTILAESTHHKPWT" or
                      "LLADTTHHRPWTILAESTHHKPWTLLAD
                      TTHHRPWTILAESTHHKPWTLLADTTHHRPWT" or
                      "LLADTTHHRPWTGLGDTTHHRPWG"
MOD_RES               13..1416
                      note = CONT. FROM ABOVE: or
                      "LLADTTHHRPWTGLGDTTHHRPWGLLADTTHHRPWT" or
                      "LLADTTHHRPWTGLGDTTHHRPWGLLADTTHHRPWTGLGDTTHHRPWGLLADTTHHRP
                      WT" or
                      "LLADTTHHRPWTGLGDTTHHRPWGLLADTTHHRPWTGLGDTTHHRPWGLLADTTHHRP
                       WTGLGDTTHHRPWGLLADTTHHRPWT" or
                      "STADTSHHRPSTSGGESTHHRPSTSGGESS
MOD_RES               13..1416
                      note = CONT. FROM ABOVE: HHKPSTGSGDSSHHRPSGSSGESTHHKPST" or
                      "VGADSTHHR
                      PVTGAADTTHHRPVTAGADTTHHRPVTGGADTTHHRPATGGADTTHHRPGT" or
                      "STADTS
                      HHRPSLLADTTHHRPWTTSGGESTHHRPSVGADSTHHRPVTTSGGESSHHKPSGAADTT
                      HHRP VTTGSGDSSHHRPSGSSGESTHHKPSTGGADTTHHRPAT" or
                      "XXXXXXXXXXXX" or
MOD_RES               13..1416
                      note = CONT. FROM ABOVE: "AAADTTHHRPWT" or
                      "AAADTTHHRPWTAAADTTHHRPWTAA
                      ADTTHHRPWTAAADTTHHRPWTAAADTTHHRPWT" or
                      "LLADAAHHRPWTLLADAAHHRPW
                      TLLADAAHHRPWTLLADAAHHRPWTLLADAAHHRPWT" or
                      "LLADTTAARPWTLLADTTAA
                      RPWTLLADTTAARPWTLLADTTAARPWTLLADTTAARPWT" or
                      "LLADTTHHRPWTLLADT
MOD_RES               13..1416
                      note = CONT. FROM ABOVE: THHRPWT" or
                      "LLADTTHHRPWTLLADTTHHRPWTLLADTTHH RPWT" or
                      "LLADTTHHRPWTLLADTTHHRPWTLLADTTHHRPWTLLADTTHHRPWTLLADT
                      THHRPWT" or
                      "STSGSTVIGESTHHRPWSLIADSTHHSPWTILAESTHHKPWTILAETTHH
                      RPWSIIGESSHHKPFTGLGDTTHHRPWGVLGDTTHHKPWTIVADSTHHRPWTGQVLPTT
                      TPSS
MOD_RES               13..1416
                      note = CONT. FROM ABOVE: PSTTSGS" or
                      "LLADTTHHRPWTVIGESTHHRPWSIIGESSHH KPFTGLGDTTHHRPWG" or
                      "VIGESTHHRPWSIIGESSHHKPFTGLGDTTHHRPWGILAE STHHKPWT" and
                      wherein X's respectively = V, L, I, G, S, T or A; I, L, V,
                      Q, T, S, G or A; G, A, V or S; E, D, L or G; S, T, P
MOD_RES               13..1416
                      note = CONT. FROM ABOVE: T, E or D; T or S; H, T or S; H or
                      T; R, S, K, P or H; P, S, R or K; W, F, S, P, V, A or G;
                      and absent, S, T G, or A
```

| | | |
|---|---|---|
| REGION | 1..1416<br>note = See specification as filed for detailed description of substitutions and preferred embodiments | |
| source | 1..1416<br>mol_type = protein<br>organism = synthetic construct | |

SEQUENCE: 405

```
ILAESTHHKP WTXXXXXXXX XXXXXXXXXX XXXXXXXXXX XXXXXXXXXX XXXXXXXXXX    60
XXXXXXXXXX XXXXXXXXXX XXXXXXXXXX XXXXXXXXXX XXXXXXXXXX XXXXXXXXXX   120
XXXXXXXXXX XXXXXXXXXX XXXXXXXXXX XXXXXXXXXX XXXXXXXXXX XXXXXXXXXX   180
XXXXXXXXXX XXXXXXXXXX XXXXXXXXXX XXXXXXXXXX XXXXXXXXXX XXXXXXXXXX   240
XXXXXXXXXX XXXXXXXXXX XXXXXXXXXX XXXXXXXXXX XXXXXXXXXX XXXXXXXXXX   300
XXXXXXXXXX XXXXXXXXXX XXXXXXXXXX XXXXXXXXXX XXXXXXXXXX XXXXXXXXXX   360
XXXXXXXXXX XXXXXXXXXX XXXXXXXXXX XXXXXXXXXX XXXXXXXXXX XXXXXXXXXX   420
XXXXXXXXXX XXXXXXXXXX XXXXXXXXXX XXXXXXXXXX XXXXXXXXXX XXXXXXXXXX   480
XXXXXXXXXX XXXXXXXXXX XXXXXXXXXX XXXXXXXXXX XXXXXXXXXX XXXXXXXXXX   540
XXXXXXXXXX XXXXXXXXXX XXXXXXXXXX XXXXXXXXXX XXXXXXXXXX XXXXXXXXXX   600
XXXXXXXXXX XXXXXXXXXX XXXXXXXXXX XXXXXXXXXX XXXXXXXXXX XXXXXXXXXX   660
XXXXXXXXXX XXXXXXXXXX XXXXXXXXXX XXXXXXXXXX XXXXXXXXXX XXXXXXXXXX   720
XXXXXXXXXX XXXXXXXXXX XXXXXXXXXX XXXXXXXXXX XXXXXXXXXX XXXXXXXXXX   780
XXXXXXXXXX XXXXXXXXXX XXXXXXXXXX XXXXXXXXXX XXXXXXXXXX XXXXXXXXXX   840
XXXXXXXXXX XXXXXXXXXX XXXXXXXXXX XXXXXXXXXX XXXXXXXXXX XXXXXXXXXX   900
XXXXXXXXXX XXXXXXXXXX XXXXXXXXXX XXXXXXXXXX XXXXXXXXXX XXXXXXXXXX   960
XXXXXXXXXX XXXXXXXXXX XXXXXXXXXX XXXXXXXXXX XXXXXXXXXX XXXXXXXXXX  1020
XXXXXXXXXX XXXXXXXXXX XXXXXXXXXX XXXXXXXXXX XXXXXXXXXX XXXXXXXXXX  1080
XXXXXXXXXX XXXXXXXXXX XXXXXXXXXX XXXXXXXXXX XXXXXXXXXX XXXXXXXXXX  1140
XXXXXXXXXX XXXXXXXXXX XXXXXXXXXX XXXXXXXXXX XXXXXXXXXX XXXXXXXXXX  1200
XXXXXXXXXX XXXXXXXXXX XXXXXXXXXX XXXXXXXXXX XXXXXXXXXX XXXXXXXXXX  1260
XXXXXXXXXX XXXXXXXXXX XXXXXXXXXX XXXXXXXXXX XXXXXXXXXX XXXXXXXXXX  1320
XXXXXXXXXX XXXXXXXXXX XXXXXXXXXX XXXXXXXXXX XXXXXXXXXX XXXXXXXXXX  1380
XXXXXXXXXX XXXXXXXXXX XXXXXXXXXX XXXXX                              1416
```

| | | |
|---|---|---|
| SEQ ID NO: 406 | moltype = AA length = 1416 | |
| FEATURE | Location/Qualifiers | |
| REGION | 1..1416<br>note = Description of Artificial Sequence: Synthetic polypeptide | |
| MOD_RES | 13..1416<br>note = This region may encompass one or more of the following sequences: "LLADTTHHRPWT" or "VIGESTHHRPWS" or "LIADSTHHSPWT" or "ILAESTHHKPWT" or "ILAETTHHRPWS" or "IIGESSHHKPFT" or "GLGDTTHHRPWG" or "VLGDTTHHKPWT" or "IVADSTHHRPWT" or | |
| MOD_RES | 13..1416<br>note = CONT. FROM ABOVE: "STADTSHHRPS" or "TSGGESTHHRPS" or "TSGGESSHHKPS" or "TGSGDSSHHRPS" or "GSSGESTHHKPST" or "VGADSTHHRPVT" or "GAADTTHHRPVT" or "AGADTTHHRPVT" or "GGADTTHHRPAT" or "GGADTTHHRPGT" or "LLADTTHHRPWTVIGESTHHRPWS" | |
| MOD_RES | 13..1416<br>note = CONT. FROM ABOVE: or "LLADTTHHRPWTVIGESTHHRPWSIIGESSHHKPFT" or "LLADTTHHRPWTVIGESTHHRPWSIIGESSHHKPFTGLGDTTHHRPWGILAESTHHKPWT" or "LLADTTHHRPWTILAESTHHKPWT" or "LLADTTHHRPWTILAESTHHKPWTLLADTTHHRPWTILAESTHHKPWTLLADTTHHRPWT" or "LLADTTHHRPWTGLGDTTHHRPWG" | |
| MOD_RES | 13..1416<br>note = CONT. FROM ABOVE: or "LLADTTHHRPWTGLGDTTHHRPWGLLADTTHHRPWT" or "LLADTTHHRPWTGLGDTTHHRPWGLLADTTHHRPWTGLGDTTHHRPWGLLADTTHHRPWT" or "LLADTTHHRPWTGLGDTTHHRPWGLLADTTHHRPWTGLGDTTHHRPWGLLADTTHHRPWTGLGDTTHHRPWGLLADTTHHRPWT" or "STADTSHHRPSTSGGESTHHRPSTSGGESS | |
| MOD_RES | 13..1416<br>note = CONT. FROM ABOVE: HHKPSTGSGDSSHHRPSGSSGESTHHKPST" or "VGADSTHHR PVTGAADTTHHRPVTAGADTTHHRPVTGGADTTHHRPATGGADTTHHRPGT" or "STADTS HHRPSLLADTTHHRPWTTSGGESTHHRPSVGADSTHHRPVTTSGGESSHHKPSGAADTT HHRP VTTGSGDSSHHRPSGSSGESTHHKPSTGGADTTHHRPAT" or "XXXXXXXXXXXX" or | |
| MOD_RES | 13..1416<br>note = CONT. FROM ABOVE: "AAADTTHHRPWT" or "AAADTTHHRPWTAAADTTHHRPWTAA ADTTHHRPWTAAADTTHHRPWTAAADTTHHRPWT" or "LLADAAHHRPWTLLADAAHHRPW TLLADAAHHRPWTLLADAAHHRPWTLLADAAHHRPWT" or | |

```
                              "LLADTTAARPWTLLADTTAA
                              RPWTLLADTTAARPWTLLADTTAARPWTLLADTTAARPWT" or
                              "LLADTTHHRPWTLLADT
MOD_RES                       13..1416
                              note = CONT. FROM ABOVE: THHRPWT" or
                              "LLADTTHHRPWTLLADTTHHRPWTLLADTTHH RPWT" or
                              "LLADTTHHRPWTLLADTTHHRPWTLLADTTHHRPWTLLADTTHHRPWTLLADT
                              THHRPWT" or
                              "STSGSTVIGESTHHRPWSLIADSTHHSPWTILAESTHHKPWTILAETTHH
                              RPWSIIGESSHHKPFTGLGDTTHHRPWGVLGDTTHHKPWTIVADSTHHRPWTGQVLPTT
                              TPSS
MOD_RES                       13..1416
                              note = CONT. FROM ABOVE: PSTTSGS" or
                              "LLADTTHHRPWTVIGESTHHRPWSIIGESSHH KPFTGLGDTTHHRPWG" or
                              "VIGESTHHRPWSIIGESSHHKPFTGLGDTTHHRPWGILAE STHHKPWT" and
                              wherein X's respectively = V, L, I, G, S, T or A; I, L, V,
                              Q, T, S, G or A; G, A, V or S; E, D, L or G; S, T, P
MOD_RES                       13..1416
                              note = CONT. FROM ABOVE: T, E or D; T or S; H, T or S; H or
                              T; R, S, K, P or H; P, S, R or K; W, F, S, P, V, A or G;
                              and absent, S, T G, or A
REGION                        1..1416
                              note = See specification as filed for detailed description
                              of substitutions and preferred embodiments
source                        1..1416
                              mol_type = protein
                              organism = synthetic construct
SEQUENCE: 406
IIGESSHHKP FTXXXXXXXX XXXXXXXXXX XXXXXXXXXX XXXXXXXXXX XXXXXXXXXX    60
XXXXXXXXXX XXXXXXXXXX XXXXXXXXXX XXXXXXXXXX XXXXXXXXXX XXXXXXXXXX   120
XXXXXXXXXX XXXXXXXXXX XXXXXXXXXX XXXXXXXXXX XXXXXXXXXX XXXXXXXXXX   180
XXXXXXXXXX XXXXXXXXXX XXXXXXXXXX XXXXXXXXXX XXXXXXXXXX XXXXXXXXXX   240
XXXXXXXXXX XXXXXXXXXX XXXXXXXXXX XXXXXXXXXX XXXXXXXXXX XXXXXXXXXX   300
XXXXXXXXXX XXXXXXXXXX XXXXXXXXXX XXXXXXXXXX XXXXXXXXXX XXXXXXXXXX   360
XXXXXXXXXX XXXXXXXXXX XXXXXXXXXX XXXXXXXXXX XXXXXXXXXX XXXXXXXXXX   420
XXXXXXXXXX XXXXXXXXXX XXXXXXXXXX XXXXXXXXXX XXXXXXXXXX XXXXXXXXXX   480
XXXXXXXXXX XXXXXXXXXX XXXXXXXXXX XXXXXXXXXX XXXXXXXXXX XXXXXXXXXX   540
XXXXXXXXXX XXXXXXXXXX XXXXXXXXXX XXXXXXXXXX XXXXXXXXXX XXXXXXXXXX   600
XXXXXXXXXX XXXXXXXXXX XXXXXXXXXX XXXXXXXXXX XXXXXXXXXX XXXXXXXXXX   660
XXXXXXXXXX XXXXXXXXXX XXXXXXXXXX XXXXXXXXXX XXXXXXXXXX XXXXXXXXXX   720
XXXXXXXXXX XXXXXXXXXX XXXXXXXXXX XXXXXXXXXX XXXXXXXXXX XXXXXXXXXX   780
XXXXXXXXXX XXXXXXXXXX XXXXXXXXXX XXXXXXXXXX XXXXXXXXXX XXXXXXXXXX   840
XXXXXXXXXX XXXXXXXXXX XXXXXXXXXX XXXXXXXXXX XXXXXXXXXX XXXXXXXXXX   900
XXXXXXXXXX XXXXXXXXXX XXXXXXXXXX XXXXXXXXXX XXXXXXXXXX XXXXXXXXXX   960
XXXXXXXXXX XXXXXXXXXX XXXXXXXXXX XXXXXXXXXX XXXXXXXXXX XXXXXXXXXX  1020
XXXXXXXXXX XXXXXXXXXX XXXXXXXXXX XXXXXXXXXX XXXXXXXXXX XXXXXXXXXX  1080
XXXXXXXXXX XXXXXXXXXX XXXXXXXXXX XXXXXXXXXX XXXXXXXXXX XXXXXXXXXX  1140
XXXXXXXXXX XXXXXXXXXX XXXXXXXXXX XXXXXXXXXX XXXXXXXXXX XXXXXXXXXX  1200
XXXXXXXXXX XXXXXXXXXX XXXXXXXXXX XXXXXXXXXX XXXXXXXXXX XXXXXXXXXX  1260
XXXXXXXXXX XXXXXXXXXX XXXXXXXXXX XXXXXXXXXX XXXXXXXXXX XXXXXXXXXX  1320
XXXXXXXXXX XXXXXXXXXX XXXXXXXXXX XXXXXXXXXX XXXXXXXXXX XXXXXXXXXX  1380
XXXXXXXXXX XXXXXXXXXX XXXXXXXXXX XXXXX                             1416

SEQ ID NO: 407                moltype = AA  length = 1416
FEATURE                       Location/Qualifiers
REGION                        1..1416
                              note = Description of Artificial Sequence: Synthetic
                              polypeptide
MOD_RES                       13..1416
                              note = This region may encompass one or more of the
                              following sequences: "LLADTTHHRPWT" or "VIGESTHHRPWS" or
                              "LIADSTHHSPWT" or "ILAESTHHKPWT" or "ILAETTHHRPWS" or
                              "IIGESSHHKPFT" or "GLGDTTHHRPWG" or "VLGDTTHHKPWT" or
                              "IVADSTHHRPWT" or
MOD_RES                       13..1416
                              note = CONT. FROM ABOVE: "STADTSHHRPS" or "TSGGESTHHRPS" or
                              "TSGGESSHHKPS" or "TGSGDSSHHRPS" or "GSSGESTHHKPST" or
                              "VGADSTHHRPVT" or "GAADTTHHRPVT" or "AGADTTHHRPVT" or
                              "GGADTTHHRPAT" or "GGADTTHHRPGT" or
                              "LLADTTHHRPWTVIGESTHHRPWS"
MOD_RES                       13..1416
                              note = CONT. FROM ABOVE: or
                              "LLADTTHHRPWTVIGESTHHRPWSIIGESSHHKPFT" or
                              "LLADTTHHRPWTVIGESTHHRPWSIIGESSHHKPFTGLGDTTHHRPWGILAESTHHKP
                              WT" or "LLADTTHHRPWTILAESTHHKPWT" or
                              "LLADTTHHRPWTILAESTHHKPWTLLAD
                              TTHHRPWTILAESTHHKPWTLLADTTHHRPWT" or
                              "LLADTTHHRPWTGLGDTTHHRPWG"
MOD_RES                       13..1416
```

|                | |
|---|---|
| | note = CONT. FROM ABOVE: or<br>"LLADTTHHHRPWTGLGDTTHHHRPWGLLADTTHHHRPWT" or<br>"LLADTTHHHRPWTGLGDTTHHHRPWGLLADTTHHHRPWTGLGDTTHHHRPWGLLADTTHHHRPWT" or<br>"LLADTTHHHRPWTGLGDTTHHHRPWGLLADTTHHHRPWTGLGDTTHHHRPWGLLADTTHHHRPWTGLGDTTHHHRPWGLLADTTHHHRPWT" or<br>"STADTSHHRPSTSGGESTHHRPSTSGGESS |
| MOD_RES | 13..1416<br>note = CONT. FROM ABOVE: HHKPSTGSGDSSHHRPSGSSGESTHHKPST" or<br>"VGADSTHHR<br>PVTGAADTTHHHRPVTAGADTTHHHRPVTGGADTTHHHRPATGGADTTHHHRPGT" or<br>"STADTS<br>HHRPSLLADTTHHHRPWTTSGGESTHHHRPSVGADSTHHHRPVTTSGGESSHHKPSGAADTT<br>HHHRP VTTGSGDSSHHRPSGSSGESTHHKPSTGGADTTHHHRPAT" or<br>"XXXXXXXXXXX" or |
| MOD_RES | 13..1416<br>note = CONT. FROM ABOVE: "AAADTTHHHRPWT" or<br>"AAADTTHHHRPWTAAADTTHHHRPWTAA<br>ADTTHHHRPWTAAADTTHHHRPWTAAADTTHHHRPWT" or<br>"LLADAAHHRPWTLLADAAHHRPW<br>TLLADAAHHRPWTLLADAAHHRPWTLLADAAHHRPWT" or<br>"LLADTTAARPWTLLADTTAA<br>RPWTLLADTTAARPWTLLADTTAARPWTLLADTTAARPWT" or<br>"LLADTTHHHRPWTLLADT |
| MOD_RES | 13..1416<br>note = CONT. FROM ABOVE: THHRPWT" or<br>"LLADTTHHHRPWTLLADTTHHHRPWTLLADTTHH RPWT" or<br>"LLADTTHHHRPWTLLADTTHHHRPWTLLADTTHHHRPWTLLADTTHHHRPWTLLADT<br>THHRPWT" or<br>"STSGSTVIGESTHHRPWSLIADSTHHSPWTILAESTHHKPWTILAETTHH<br>RPWSIIGESSHHKPFTGLGDTTHHHRPWGVLGDTTHHKPWTIVADSTHHHRPWTGQVLPTT<br>TPSS |
| MOD_RES | 13..1416<br>note = CONT. FROM ABOVE: PSTTSGS" or<br>"LLADTTHHHRPWTVIGESTHHHRPWSIIGESSHH KPFTGLGDTTHHHRPWG" or<br>"VIGESTHHHRPWSIIGESSHHKPFTGLGDTTHHHRPWGILAE STHHKPWT" and<br>wherein X's respectively = V, L, I, G, S, T or A; I, L, V,<br>Q, T, S, G or A; G, A, V or S; E, D, L or G; S, T, P |
| MOD_RES | 13..1416<br>note = CONT. FROM ABOVE: T, E or D; T or S; H, T or S; H or<br>T; R, S, K, P or H; P, S, R or K; W, F, S, P, V, A or G;<br>and absent, S, T G, or A |
| REGION | 1..1416<br>note = See specification as filed for detailed description<br>of substitutions and preferred embodiments |
| source | 1..1416<br>mol_type = protein<br>organism = synthetic construct |

SEQUENCE: 407
```
GLGDTTHHRP WGXXXXXXXX XXXXXXXXXX XXXXXXXXXX XXXXXXXXXX XXXXXXXXXX    60
XXXXXXXXXX XXXXXXXXXX XXXXXXXXXX XXXXXXXXXX XXXXXXXXXX XXXXXXXXXX   120
XXXXXXXXXX XXXXXXXXXX XXXXXXXXXX XXXXXXXXXX XXXXXXXXXX XXXXXXXXXX   180
XXXXXXXXXX XXXXXXXXXX XXXXXXXXXX XXXXXXXXXX XXXXXXXXXX XXXXXXXXXX   240
XXXXXXXXXX XXXXXXXXXX XXXXXXXXXX XXXXXXXXXX XXXXXXXXXX XXXXXXXXXX   300
XXXXXXXXXX XXXXXXXXXX XXXXXXXXXX XXXXXXXXXX XXXXXXXXXX XXXXXXXXXX   360
XXXXXXXXXX XXXXXXXXXX XXXXXXXXXX XXXXXXXXXX XXXXXXXXXX XXXXXXXXXX   420
XXXXXXXXXX XXXXXXXXXX XXXXXXXXXX XXXXXXXXXX XXXXXXXXXX XXXXXXXXXX   480
XXXXXXXXXX XXXXXXXXXX XXXXXXXXXX XXXXXXXXXX XXXXXXXXXX XXXXXXXXXX   540
XXXXXXXXXX XXXXXXXXXX XXXXXXXXXX XXXXXXXXXX XXXXXXXXXX XXXXXXXXXX   600
XXXXXXXXXX XXXXXXXXXX XXXXXXXXXX XXXXXXXXXX XXXXXXXXXX XXXXXXXXXX   660
XXXXXXXXXX XXXXXXXXXX XXXXXXXXXX XXXXXXXXXX XXXXXXXXXX XXXXXXXXXX   720
XXXXXXXXXX XXXXXXXXXX XXXXXXXXXX XXXXXXXXXX XXXXXXXXXX XXXXXXXXXX   780
XXXXXXXXXX XXXXXXXXXX XXXXXXXXXX XXXXXXXXXX XXXXXXXXXX XXXXXXXXXX   840
XXXXXXXXXX XXXXXXXXXX XXXXXXXXXX XXXXXXXXXX XXXXXXXXXX XXXXXXXXXX   900
XXXXXXXXXX XXXXXXXXXX XXXXXXXXXX XXXXXXXXXX XXXXXXXXXX XXXXXXXXXX   960
XXXXXXXXXX XXXXXXXXXX XXXXXXXXXX XXXXXXXXXX XXXXXXXXXX XXXXXXXXXX  1020
XXXXXXXXXX XXXXXXXXXX XXXXXXXXXX XXXXXXXXXX XXXXXXXXXX XXXXXXXXXX  1080
XXXXXXXXXX XXXXXXXXXX XXXXXXXXXX XXXXXXXXXX XXXXXXXXXX XXXXXXXXXX  1140
XXXXXXXXXX XXXXXXXXXX XXXXXXXXXX XXXXXXXXXX XXXXXXXXXX XXXXXXXXXX  1200
XXXXXXXXXX XXXXXXXXXX XXXXXXXXXX XXXXXXXXXX XXXXXXXXXX XXXXXXXXXX  1260
XXXXXXXXXX XXXXXXXXXX XXXXXXXXXX XXXXXXXXXX XXXXXXXXXX XXXXXXXXXX  1320
XXXXXXXXXX XXXXXXXXXX XXXXXXXXXX XXXXXXXXXX XXXXXXXXXX XXXXXXXXXX  1380
XXXXXXXXXX XXXXXXXXXX XXXXXXXXXX XXXXX                             1416
```

|                | |
|---|---|
| SEQ ID NO: 408 | moltype = AA  length = 60 |
| FEATURE | Location/Qualifiers |
| REGION | 1..60<br>note = Description of Artificial Sequence: Synthetic<br>polypeptide |

```
MOD_RES              13..60
                     note = This region may encompass one or more of the
                      following sequences: "VIGESTHHRPWS" or "ILAESTHHKPWT" or
                      "IIGESSHHKPFT" or "GLGDTTHHRPWG"
REGION               1..60
                     note = See specification as filed for detailed description
                      of substitutions and preferred embodiments
source               1..60
                     mol_type = protein
                     organism = synthetic construct
SEQUENCE: 408
LLADTTHHRP WTXXXXXXXX XXXXXXXXX XXXXXXXXXX XXXXXXXXXX XXXXXXXXXX   60

SEQ ID NO: 409       moltype = AA  length = 60
FEATURE              Location/Qualifiers
REGION               1..60
                     note = Description of Artificial Sequence: Synthetic
                      polypeptide
MOD_RES              13..60
                     note = This region may encompass one or more of the
                      following sequences: "LLADTTHHRPWT" or "ILAESTHHKPWT" or
                      "IIGESSHHKPFT" or "GLGDTTHHRPWG"
REGION               1..60
                     note = See specification as filed for detailed description
                      of substitutions and preferred embodiments
source               1..60
                     mol_type = protein
                     organism = synthetic construct
SEQUENCE: 409
VIGESTHHRP WSXXXXXXXX XXXXXXXXXX XXXXXXXXXX XXXXXXXXXX XXXXXXXXXX   60

SEQ ID NO: 410       moltype = AA  length = 60
FEATURE              Location/Qualifiers
REGION               1..60
                     note = Description of Artificial Sequence: Synthetic
                      polypeptide
MOD_RES              13..60
                     note = This region may encompass one or more of the
                      following sequences: "LLADTTHHRPWT" or "VIGESTHHRPWS" or
                      "IIGESSHHKPFT" or "GLGDTTHHRPWG"
REGION               1..60
                     note = See specification as filed for detailed description
                      of substitutions and preferred embodiments
source               1..60
                     mol_type = protein
                     organism = synthetic construct
SEQUENCE: 410
ILAESTHHKP WTXXXXXXXX XXXXXXXXXX XXXXXXXXXX XXXXXXXXXX XXXXXXXXXX   60

SEQ ID NO: 411       moltype = AA  length = 60
FEATURE              Location/Qualifiers
REGION               1..60
                     note = Description of Artificial Sequence: Synthetic
                      polypeptide
MOD_RES              13..60
                     note = This region may encompass one or more of the
                      following sequences: "LLADTTHHRPWT" or "ILAESTHHKPWT" or
                      "VIGESTHHRPWS" or "GLGDTTHHRPWG"
REGION               1..60
                     note = See specification as filed for detailed description
                      of substitutions and preferred embodiments
source               1..60
                     mol_type = protein
                     organism = synthetic construct
SEQUENCE: 411
IIGESSHHKP FTXXXXXXXX XXXXXXXXXX XXXXXXXXXX XXXXXXXXXX XXXXXXXXXX   60

SEQ ID NO: 412       moltype = AA  length = 60
FEATURE              Location/Qualifiers
REGION               1..60
                     note = Description of Artificial Sequence: Synthetic
                      polypeptide
MOD_RES              13..60
                     note = This region may encompass one or more of the
                      following sequences: "LLADTTHHRPWT" or "ILAESTHHKPWT" or
                      "IIGESSHHKPFT" or "VIGESTHHRPWS"
REGION               1..60
                     note = See specification as filed for detailed description
                      of substitutions and preferred embodiments
```

```
                        source          1..60
                                        mol_type = protein
                                        organism = synthetic construct
SEQUENCE: 412
GLGDTTHHRP WGXXXXXXXX XXXXXXXXXX XXXXXXXXXX XXXXXXXXXX XXXXXXXXXX   60

SEQ ID NO: 413          moltype = AA  length = 60
FEATURE                 Location/Qualifiers
REGION                  1..60
                        note = Description of Artificial Sequence: Synthetic
                         polypeptide
MOD_RES                 13..60
                        note = This region may encompass two or more of the
                         following sequences: "VIGESTHHRPWS" or "ILAESTHHKPWT" or
                         "IIGESSHHKPFT" or "GLGDTTHHRPWG"
REGION                  1..60
                        note = See specification as filed for detailed description
                         of substitutions and preferred embodiments
source                  1..60
                        mol_type = protein
                        organism = synthetic construct
SEQUENCE: 413
LLADTTHHRP WTXXXXXXXX XXXXXXXXXX XXXXXXXXXX XXXXXXXXXX XXXXXXXXXX   60

SEQ ID NO: 414          moltype = AA  length = 60
FEATURE                 Location/Qualifiers
REGION                  1..60
                        note = Description of Artificial Sequence: Synthetic
                         polypeptide
MOD_RES                 13..60
                        note = This region may encompass two or more of the
                         following sequences: "LLADTTHHRPWT" or "ILAESTHHKPWT" or
                         "IIGESSHHKPFT" or "GLGDTTHHRPWG"
REGION                  1..60
                        note = See specification as filed for detailed description
                         of substitutions and preferred embodiments
source                  1..60
                        mol_type = protein
                        organism = synthetic construct
SEQUENCE: 414
VIGESTHHRP WSXXXXXXXX XXXXXXXXXX XXXXXXXXXX XXXXXXXXXX XXXXXXXXXX   60

SEQ ID NO: 415          moltype = AA  length = 60
FEATURE                 Location/Qualifiers
REGION                  1..60
                        note = Description of Artificial Sequence: Synthetic
                         polypeptide
MOD_RES                 13..60
                        note = This region may encompass two or more of the
                         following sequences: "LLADTTHHRPWT" or "VIGESTHHRPWS" or
                         "IIGESSHHKPFT" or "GLGDTTHHRPWG"
REGION                  1..60
                        note = See specification as filed for detailed description
                         of substitutions and preferred embodiments
source                  1..60
                        mol_type = protein
                        organism = synthetic construct
SEQUENCE: 415
ILAESTHHKP WTXXXXXXXX XXXXXXXXXX XXXXXXXXXX XXXXXXXXXX XXXXXXXXXX   60

SEQ ID NO: 416          moltype = AA  length = 60
FEATURE                 Location/Qualifiers
REGION                  1..60
                        note = Description of Artificial Sequence: Synthetic
                         polypeptide
MOD_RES                 13..60
                        note = This region may encompass two or more of the
                         following sequences: "LLADTTHHRPWT" or "ILAESTHHKPWT" or
                         "VIGESTHHRPWS" or "GLGDTTHHRPWG"
REGION                  1..60
                        note = See specification as filed for detailed description
                         of substitutions and preferred embodiments
source                  1..60
                        mol_type = protein
                        organism = synthetic construct
SEQUENCE: 416
IIGESSHHKP FTXXXXXXXX XXXXXXXXXX XXXXXXXXXX XXXXXXXXXX XXXXXXXXXX   60

SEQ ID NO: 417          moltype = AA  length = 60
```

```
FEATURE                 Location/Qualifiers
REGION                  1..60
                        note = Description of Artificial Sequence: Synthetic
                        polypeptide
MOD_RES                 13..60
                        note = This region may encompass two or more of the
                        following sequences: "LLADTTHHRPWT" or "ILAESTHHKPWT" or
                        "IIGESSHHKPFT" or "VIGESTHHRPWS"
REGION                  1..60
                        note = See specification as filed for detailed description
                        of substitutions and preferred embodiments
source                  1..60
                        mol_type = protein
                        organism = synthetic construct
SEQUENCE: 417
GLGDTTHHRP WGXXXXXXXX XXXXXXXXX XXXXXXXXXX XXXXXXXXXX XXXXXXXXXX    60

SEQ ID NO: 418          moltype = AA  length = 60
FEATURE                 Location/Qualifiers
REGION                  1..60
                        note = Description of Artificial Sequence: Synthetic
                        polypeptide
MOD_RES                 13..60
                        note = This region may encompass three or more of the
                        following sequences: "VIGESTHHRPWS" or "ILAESTHHKPWT" or
                        "IIGESSHHKPFT" or "GLGDTTHHRPWG"
REGION                  1..60
                        note = See specification as filed for detailed description
                        of substitutions and preferred embodiments
source                  1..60
                        mol_type = protein
                        organism = synthetic construct
SEQUENCE: 418
LLADTTHHRP WTXXXXXXXX XXXXXXXXXX XXXXXXXXXX XXXXXXXXXX XXXXXXXXXX    60

SEQ ID NO: 419          moltype = AA  length = 60
FEATURE                 Location/Qualifiers
REGION                  1..60
                        note = Description of Artificial Sequence: Synthetic
                        polypeptide
MOD_RES                 13..60
                        note = This region may encompass three or more of the
                        following sequences: "LLADTTHHRPWT" or "ILAESTHHKPWT" or
                        "IIGESSHHKPFT" or "GLGDTTHHRPWG"
REGION                  1..60
                        note = See specification as filed for detailed description
                        of substitutions and preferred embodiments
source                  1..60
                        mol_type = protein
                        organism = synthetic construct
SEQUENCE: 419
VIGESTHHRP WSXXXXXXXX XXXXXXXXXX XXXXXXXXXX XXXXXXXXXX XXXXXXXXXX    60

SEQ ID NO: 420          moltype = AA  length = 60
FEATURE                 Location/Qualifiers
REGION                  1..60
                        note = Description of Artificial Sequence: Synthetic
                        polypeptide
MOD_RES                 13..60
                        note = This region may encompass three or more of the
                        following sequences: "LLADTTHHRPWT" or "VIGESTHHRPWS" or
                        "IIGESSHHKPFT" or "GLGDTTHHRPWG"
REGION                  1..60
                        note = See specification as filed for detailed description
                        of substitutions and preferred embodiments
source                  1..60
                        mol_type = protein
                        organism = synthetic construct
SEQUENCE: 420
ILAESTHHKP WTXXXXXXXX XXXXXXXXXX XXXXXXXXXX XXXXXXXXXX XXXXXXXXXX    60

SEQ ID NO: 421          moltype = AA  length = 60
FEATURE                 Location/Qualifiers
REGION                  1..60
                        note = Description of Artificial Sequence: Synthetic
                        polypeptide
MOD_RES                 13..60
                        note = This region may encompass three or more of the
                        following sequences: "LLADTTHHRPWT" or "ILAESTHHKPWT" or
```

|  |  |
|---|---|
| REGION | "VIGESTHHRPWS" or "GLGDTTHHRPWG"<br>1..60<br>note = See specification as filed for detailed description of substitutions and preferred embodiments |
| source | 1..60<br>mol_type = protein<br>organism = synthetic construct |

SEQUENCE: 421

IIGESSHHKP FTXXXXXXXX XXXXXXXXXX XXXXXXXXXX XXXXXXXXXX XXXXXXXXXX   60

|  |  |
|---|---|
| SEQ ID NO: 422 | moltype = AA  length = 60 |
| FEATURE | Location/Qualifiers |
| REGION | 1..60<br>note = Description of Artificial Sequence: Synthetic polypeptide |
| MOD_RES | 13..60<br>note = This region may encompass three or more of the following sequences: "LLADTTHHRPWT" or "ILAESTHHKPWT" or "IIGESSHHKPFT" or "VIGESTHHRPWS" |
| REGION | 1..60<br>note = See specification as filed for detailed description of substitutions and preferred embodiments |
| source | 1..60<br>mol_type = protein<br>organism = synthetic construct |

SEQUENCE: 422

GLGDTTHHRP WGXXXXXXXX XXXXXXXXXX XXXXXXXXXX XXXXXXXXXX XXXXXXXXXX   60

SEQ ID NO: 423          moltype =    length =
SEQUENCE: 423
000

SEQ ID NO: 424          moltype =    length =
SEQUENCE: 424
000

SEQ ID NO: 425          moltype =    length =
SEQUENCE: 425
000

SEQ ID NO: 426          moltype =    length =
SEQUENCE: 426
000

SEQ ID NO: 427          moltype =    length =
SEQUENCE: 427
000

SEQ ID NO: 428          moltype =    length =
SEQUENCE: 428
000

SEQ ID NO: 429          moltype =    length =
SEQUENCE: 429
000

SEQ ID NO: 430          moltype =    length =
SEQUENCE: 430
000

SEQ ID NO: 431          moltype =    length =
SEQUENCE: 431
000

SEQ ID NO: 432          moltype =    length =
SEQUENCE: 432
000

SEQ ID NO: 433          moltype =    length =
SEQUENCE: 433
000

SEQ ID NO: 434          moltype =    length =
SEQUENCE: 434
000

SEQ ID NO: 435          moltype =    length =
SEQUENCE: 435
000

| | | |
|---|---|---|
| SEQ ID NO: 436<br>SEQUENCE: 436<br>000 | moltype = | length = |
| SEQ ID NO: 437<br>SEQUENCE: 437<br>000 | moltype = | length = |
| SEQ ID NO: 438<br>SEQUENCE: 438<br>000 | moltype = | length = |
| SEQ ID NO: 439<br>SEQUENCE: 439<br>000 | moltype = | length = |
| SEQ ID NO: 440<br>SEQUENCE: 440<br>000 | moltype = | length = |
| SEQ ID NO: 441<br>SEQUENCE: 441<br>000 | moltype = | length = |
| SEQ ID NO: 442<br>SEQUENCE: 442<br>000 | moltype = | length = |
| SEQ ID NO: 443<br>SEQUENCE: 443<br>000 | moltype = | length = |
| SEQ ID NO: 444<br>SEQUENCE: 444<br>000 | moltype = | length = |
| SEQ ID NO: 445<br>SEQUENCE: 445<br>000 | moltype = | length = |
| SEQ ID NO: 446<br>SEQUENCE: 446<br>000 | moltype = | length = |
| SEQ ID NO: 447<br>SEQUENCE: 447<br>000 | moltype = | length = |
| SEQ ID NO: 448<br>SEQUENCE: 448<br>000 | moltype = | length = |
| SEQ ID NO: 449<br>SEQUENCE: 449<br>000 | moltype = | length = |
| SEQ ID NO: 450<br>SEQUENCE: 450<br>000 | moltype = | length = |
| SEQ ID NO: 451<br>SEQUENCE: 451<br>000 | moltype = | length = |
| SEQ ID NO: 452<br>SEQUENCE: 452<br>000 | moltype = | length = |
| SEQ ID NO: 453<br>SEQUENCE: 453<br>000 | moltype = | length = |
| SEQ ID NO: 454<br>SEQUENCE: 454<br>000 | moltype = | length = |
| SEQ ID NO: 455<br>SEQUENCE: 455 | moltype = | length = |

SEQ ID NO: 456    moltype =    length =
SEQUENCE: 456
000

SEQ ID NO: 457    moltype =    length =
SEQUENCE: 457
000

SEQ ID NO: 458    moltype =    length =
SEQUENCE: 458
000

SEQ ID NO: 459    moltype =    length =
SEQUENCE: 459
000

SEQ ID NO: 460    moltype =    length =
SEQUENCE: 460
000

SEQ ID NO: 461    moltype =    length =
SEQUENCE: 461
000

SEQ ID NO: 462    moltype =    length =
SEQUENCE: 462
000

SEQ ID NO: 463    moltype =    length =
SEQUENCE: 463
000

SEQ ID NO: 464    moltype =    length =
SEQUENCE: 464
000

SEQ ID NO: 465    moltype =    length =
SEQUENCE: 465
000

SEQ ID NO: 466    moltype =    length =
SEQUENCE: 466
000

SEQ ID NO: 467    moltype =    length =
SEQUENCE: 467
000

SEQ ID NO: 468    moltype =    length =
SEQUENCE: 468
000

SEQ ID NO: 469    moltype =    length =
SEQUENCE: 469
000

SEQ ID NO: 470    moltype =    length =
SEQUENCE: 470
000

SEQ ID NO: 471    moltype =    length =
SEQUENCE: 471
000

SEQ ID NO: 472    moltype =    length =
SEQUENCE: 472
000

SEQ ID NO: 473    moltype =    length =
SEQUENCE: 473
000

SEQ ID NO: 474    moltype =    length =
SEQUENCE: 474
000

SEQ ID NO: 475    moltype =    length =

| | | |
|---|---|---|
| SEQUENCE: 475 000 | | |
| SEQ ID NO: 476 SEQUENCE: 476 000 | moltype = | length = |
| SEQ ID NO: 477 SEQUENCE: 477 000 | moltype = | length = |
| SEQ ID NO: 478 SEQUENCE: 478 000 | moltype = | length = |
| SEQ ID NO: 479 SEQUENCE: 479 000 | moltype = | length = |
| SEQ ID NO: 480 SEQUENCE: 480 000 | moltype = | length = |
| SEQ ID NO: 481 SEQUENCE: 481 000 | moltype = | length = |
| SEQ ID NO: 482 SEQUENCE: 482 000 | moltype = | length = |
| SEQ ID NO: 483 SEQUENCE: 483 000 | moltype = | length = |
| SEQ ID NO: 484 SEQUENCE: 484 000 | moltype = | length = |
| SEQ ID NO: 485 SEQUENCE: 485 000 | moltype = | length = |
| SEQ ID NO: 486 SEQUENCE: 486 000 | moltype = | length = |
| SEQ ID NO: 487 SEQUENCE: 487 000 | moltype = | length = |
| SEQ ID NO: 488 SEQUENCE: 488 000 | moltype = | length = |
| SEQ ID NO: 489 SEQUENCE: 489 000 | moltype = | length = |
| SEQ ID NO: 490 SEQUENCE: 490 000 | moltype = | length = |
| SEQ ID NO: 491 SEQUENCE: 491 000 | moltype = | length = |
| SEQ ID NO: 492 SEQUENCE: 492 000 | moltype = | length = |
| SEQ ID NO: 493 SEQUENCE: 493 000 | moltype = | length = |
| SEQ ID NO: 494 SEQUENCE: 494 000 | moltype = | length = |

```
SEQ ID NO: 495          moltype =    length =
SEQUENCE: 495
000

SEQ ID NO: 496          moltype =    length =
SEQUENCE: 496
000

SEQ ID NO: 497          moltype =    length =
SEQUENCE: 497
000

SEQ ID NO: 498          moltype =    length =
SEQUENCE: 498
000

SEQ ID NO: 499          moltype =    length =
SEQUENCE: 499
000

SEQ ID NO: 500          moltype =    length =
SEQUENCE: 500
000

SEQ ID NO: 501          moltype = AA   length = 152
FEATURE                 Location/Qualifiers
REGION                  1..152
                        note = Description of Artificial Sequence: Synthetic
                         polypeptide
source                  1..152
                        mol_type = protein
                        organism = synthetic construct
SEQUENCE: 501
ASGAGGSEGG GSEGGTSGAT GAGTSTSGGG ASTGGGTGQA KHKQRKRLKS SCKRHPLYVD   60
FSDVGWNDWI VAPPGYHAFY CHGECPFPLA DHLNSTNHAI VQTLVNSVNS KIPKACCVPT  120
ELSAISMLYL DENEKVVLKN YQDMVVEGCG CR                                152

SEQ ID NO: 502          moltype = AA   length = 217
FEATURE                 Location/Qualifiers
REGION                  1..217
                        note = Description of Artificial Sequence: Synthetic
                         polypeptide
source                  1..217
                        mol_type = protein
                        organism = synthetic construct
SEQUENCE: 502
MPIGSLLADT THHRPWTVIG ESTHHRPWSI IGESSHHKPF TGLGDTTHHR PWGILAESTH   60
HKPWTASGAG GSEGGGSEGG TSGATGAGTS TSGGGASTGG GTGQAKHKQR KRLKSSCKRH  120
PLYVDFSDVG WNDWIVAPPG YHAFYCHGEC PFPLADHLNS TNHAIVQTLV NSVNSKIPKA  180
CCVPTELSAI SMLYLDENEK VVLKNYQDMV VEGCGCR                           217

SEQ ID NO: 503          moltype = AA   length = 212
FEATURE                 Location/Qualifiers
REGION                  1..212
                        note = Description of Artificial Sequence: Synthetic
                         polypeptide
source                  1..212
                        mol_type = protein
                        organism = synthetic construct
SEQUENCE: 503
LLADTTHHRP WTVIGESTHH RPWSIIGESS HHKPFTGLGD TTHHRPWGIL AESTHHKPWT   60
ASGAGGSEGG GSEGGTSGAT GAGTSTSGGG ASTGGGTGQA KHKQRKRLKS SCKRHPLYVD  120
FSDVGWNDWI VAPPGYHAFY CHGECPFPLA DHLNSTNHAI VQTLVNSVNS KIPKACCVPT  180
ELSAISMLYL DENEKVVLKN YQDMVVEGCG CR                                212

SEQ ID NO: 504          moltype = AA   length = 200
FEATURE                 Location/Qualifiers
REGION                  1..200
                        note = Description of Artificial Sequence: Synthetic
                         polypeptide
source                  1..200
                        mol_type = protein
                        organism = synthetic construct
SEQUENCE: 504
VIGESTHHRP WSIIGESSHH KPFTGLGDTT HHRPWGILAE STHHKPWTAS GAGGSEGGGS   60
EGGTSGATGA GTSTSGGGAS TGGGTGQAKH KQRKRLKSSC KRHPLYVDFS DVGWNDWIVA  120
PPGYHAFYCH GECPFPLADH LNSTNHAIVQ TLVNSVNSKI PKACCVPTEL SAISMLYLDE  180
NEKVVLKNYQ DMVVEGCGCR                                              200
```

-continued

```
SEQ ID NO: 505          moltype = AA  length = 188
FEATURE                 Location/Qualifiers
REGION                  1..188
                        note = Description of Artificial Sequence: Synthetic
                         polypeptide
source                  1..188
                        mol_type = protein
                        organism = synthetic construct
SEQUENCE: 505
IIGESSHHKP FTGLGDTTHH RPWGILAEST HHKPWTASGA GGSEGGGSEG GTSGATGAGT   60
STSGGGASTG GGTGQAKHKQ RKRLKSSCKR HPLYVDFSDV GWNDWIVAPP GYHAFYCHGE  120
CPFPLADHLN STNHAIVQTL VNSVNSKIPK ACCVPTELSA ISMLYLDENE KVVLKNYQDM  180
VVEGCGCR                                                          188

SEQ ID NO: 506          moltype = AA  length = 176
FEATURE                 Location/Qualifiers
REGION                  1..176
                        note = Description of Artificial Sequence: Synthetic
                         polypeptide
source                  1..176
                        mol_type = protein
                        organism = synthetic construct
SEQUENCE: 506
GLGDTTHHRP WGILAESTHH KPWTASGAGG SEGGGSEGGT SGATGAGTST SGGGASTGGG   60
TGQAKHKQRK RLKSSCKRHP LYVDFSDVGW NDWIVAPPGY HAFYCHGECP FPLADHLNST  120
NHAIVQTLVN SVNSKIPKAC CVPTELSAIS MLYLDENEKV VLKNYQDMVV EGCGCR      176

SEQ ID NO: 507          moltype = AA  length = 164
FEATURE                 Location/Qualifiers
REGION                  1..164
                        note = Description of Artificial Sequence: Synthetic
                         polypeptide
source                  1..164
                        mol_type = protein
                        organism = synthetic construct
SEQUENCE: 507
ILAESTHHKP WTASGAGGSE GGGSEGGTSG ATGAGTSTSG GGASTGGGTG QAKHKQRKRL   60
KSSCKRHPLY VDFSDVGWND WIVAPPGYHA FYCHGECPFP LADHLNSTNH AIVQTLVNSV  120
NSKIPKACCV PTELSAISML YLDENEKVVL KNYQDMVVEG CGCR                   164

SEQ ID NO: 508          moltype = AA  length = 126
FEATURE                 Location/Qualifiers
REGION                  1..126
                        note = Description of Artificial Sequence: Synthetic
                         polypeptide
MOD_RES                 1
                        note = V, L, I, G, S, T or A
MOD_RES                 2
                        note = I, L, V, Q, T, S, G or A
MOD_RES                 3
                        note = G, A, V or S
MOD_RES                 4
                        note = E, D, L or G
MOD_RES                 5
                        note = S, T, P T, E or D
MOD_RES                 6
                        note = T or S
MOD_RES                 7
                        note = H, T or S
MOD_RES                 8
                        note = H or T
MOD_RES                 9
                        note = R, S, K, P or H
MOD_RES                 10
                        note = P, S, R or K
MOD_RES                 11
                        note = W, F, S, P, V, A or G
MOD_RES                 12
                        note = absent or is S, T G, or A
REGION                  12..13
                        note = NON_CONS - Residues at these positions can be
                         separated by a linker of unknown length
source                  1..126
                        mol_type = protein
                        organism = synthetic construct
SEQUENCE: 508
XXXXXXXXXX XXQAKHKQRK RLKSSCKRHP LYVDFSDVGW NDWIVAPPGY HAFYCHGECP   60
FPLADHLNST NHAIVQTLVN SVNSKIPKAC CVPTELSAIS MLYLDENEKV VLKNYQDMVV  120
EGCGCR                                                            126
```

```
SEQ ID NO: 509           moltype = AA   length = 164
FEATURE                  Location/Qualifiers
REGION                   1..164
                         note = Description of Artificial Sequence: Synthetic
                          polypeptide
MOD_RES                  1
                         note = V, L, I, G, S, T or A
MOD_RES                  2
                         note = I, L, V, Q, T, S, G or A
MOD_RES                  3
                         note = G, A, V or S
MOD_RES                  4
                         note = E, D, L or G
MOD_RES                  5
                         note = S, T, P T, E or D
MOD_RES                  6
                         note = T or S
MOD_RES                  7
                         note = H, T or S
MOD_RES                  8
                         note = H or T
MOD_RES                  9
                         note = R, S, K, P or H
MOD_RES                  10
                         note = P, S, R or K
MOD_RES                  11
                         note = W, F, S, P, V, A or G
MOD_RES                  12
                         note = absent or is S, T G, or A
source                   1..164
                         mol_type = protein
                         organism = synthetic construct
SEQUENCE: 509
XXXXXXXXXX XXASGAGGSE GGGSEGGTSG ATGAGTSTSG GGASTGGGTG QAKHKQRKRL    60
KSSCKRHPLY VDFSDVGWND WIVAPPGYHA FYCHGECPFP LADHLNSTNH AIVQTLVNSV   120
NSKIPKACCV PTELSAISML YLDENEKVVL KNYQDMVVEG CGCR                   164

SEQ ID NO: 510           moltype = AA   length = 126
FEATURE                  Location/Qualifiers
REGION                   1..126
                         note = Description of Artificial Sequence: Synthetic
                          polypeptide
REGION                   12..13
                         note = NON_CONS - Residues at these positions can be
                          separated by a linker of unknown length
source                   1..126
                         mol_type = protein
                         organism = synthetic construct
SEQUENCE: 510
LLADTTHHRP WTQAKHKQRK RLKSSCKRHP LYVDFSDVGW NDWIVAPPGY HAFYCHGECP    60
FPLADHLNST NHAIVQTLVN SVNSKIPKAC CVPTELSAIS MLYLDENEKV VLKNYQDMVV   120
EGCGCR                                                             126

SEQ ID NO: 511           moltype = AA   length = 164
FEATURE                  Location/Qualifiers
REGION                   1..164
                         note = Description of Artificial Sequence: Synthetic
                          polypeptide
source                   1..164
                         mol_type = protein
                         organism = synthetic construct
SEQUENCE: 511
LLADTTHHRP WTASGAGGSE GGGSEGGTSG ATGAGTSTSG GGASTGGGTG QAKHKQRKRL    60
KSSCKRHPLY VDFSDVGWND WIVAPPGYHA FYCHGECPFP LADHLNSTNH AIVQTLVNSV   120
NSKIPKACCV PTELSAISML YLDENEKVVL KNYQDMVVEG CGCR                   164

SEQ ID NO: 512           moltype = AA   length = 164
FEATURE                  Location/Qualifiers
REGION                   1..164
                         note = Description of Artificial Sequence: Synthetic
                          polypeptide
source                   1..164
                         mol_type = protein
                         organism = synthetic construct
SEQUENCE: 512
VIGESTHHRP WSASGAGGSE GGGSEGGTSG ATGAGTSTSG GGASTGGGTG QAKHKQRKRL    60
KSSCKRHPLY VDFSDVGWND WIVAPPGYHA FYCHGECPFP LADHLNSTNH AIVQTLVNSV   120
NSKIPKACCV PTELSAISML YLDENEKVVL KNYQDMVVEG CGCR                   164
```

```
SEQ ID NO: 513          moltype = AA  length = 126
FEATURE                 Location/Qualifiers
REGION                  1..126
                        note = Description of Artificial Sequence: Synthetic
                         polypeptide
REGION                  12..13
                        note = NON_CONS - Residues at these positions can be
                         separated by a linker of unknown length
source                  1..126
                        mol_type = protein
                        organism = synthetic construct
SEQUENCE: 513
LIADSTHHSP WTQAKHKQRK RLKSSCKRHP LYVDFSDVGW NDWIVAPPGY HAFYCHGECP   60
FPLADHLNST NHAIVQTLVN SVNSKIPKAC CVPTELSAIS MLYLDENEKV VLKNYQDMVV  120
EGCGCR                                                             126

SEQ ID NO: 514          moltype = AA  length = 164
FEATURE                 Location/Qualifiers
REGION                  1..164
                        note = Description of Artificial Sequence: Synthetic
                         polypeptide
source                  1..164
                        mol_type = protein
                        organism = synthetic construct
SEQUENCE: 514
LIADSTHHSP WTASGAGGSE GGGSEGGTSG ATGAGTSTSG GGASTGGGTG QAKHKQRKRL   60
KSSCKRHPLY VDFSDVGWND WIVAPPGYHA FYCHGECPFP LADHLNSTNH AIVQTLVNSV  120
NSKIPKACCV PTELSAISML YLDENEKVVL KNYQDMVVEG CGCR                   164

SEQ ID NO: 515          moltype = AA  length = 126
FEATURE                 Location/Qualifiers
REGION                  1..126
                        note = Description of Artificial Sequence: Synthetic
                         polypeptide
REGION                  12..13
                        note = NON_CONS - Residues at these positions can be
                         separated by a linker of unknown length
source                  1..126
                        mol_type = protein
                        organism = synthetic construct
SEQUENCE: 515
ILAESTHHKP WTQAKHKQRK RLKSSCKRHP LYVDFSDVGW NDWIVAPPGY HAFYCHGECP   60
FPLADHLNST NHAIVQTLVN SVNSKIPKAC CVPTELSAIS MLYLDENEKV VLKNYQDMVV  120
EGCGCR                                                             126

SEQ ID NO: 516          moltype = AA  length = 164
FEATURE                 Location/Qualifiers
REGION                  1..164
                        note = Description of Artificial Sequence: Synthetic
                         polypeptide
source                  1..164
                        mol_type = protein
                        organism = synthetic construct
SEQUENCE: 516
ILAESTHHKP WTASGAGGSE GGGSEGGTSG ATGAGTSTSG GGASTGGGTG QAKHKQRKRL   60
KSSCKRHPLY VDFSDVGWND WIVAPPGYHA FYCHGECPFP LADHLNSTNH AIVQTLVNSV  120
NSKIPKACCV PTELSAISML YLDENEKVVL KNYQDMVVEG CGCR                   164

SEQ ID NO: 517          moltype = AA  length = 126
FEATURE                 Location/Qualifiers
REGION                  1..126
                        note = Description of Artificial Sequence: Synthetic
                         polypeptide
REGION                  12..13
                        note = NON_CONS - Residues at these positions can be
                         separated by a linker of unknown length
source                  1..126
                        mol_type = protein
                        organism = synthetic construct
SEQUENCE: 517
ILAETTHHRP WSQAKHKQRK RLKSSCKRHP LYVDFSDVGW NDWIVAPPGY HAFYCHGECP   60
FPLADHLNST NHAIVQTLVN SVNSKIPKAC CVPTELSAIS MLYLDENEKV VLKNYQDMVV  120
EGCGCR                                                             126

SEQ ID NO: 518          moltype = AA  length = 164
FEATURE                 Location/Qualifiers
REGION                  1..164
                        note = Description of Artificial Sequence: Synthetic
```

```
                        polypeptide
source                  1..164
                        mol_type = protein
                        organism = synthetic construct
SEQUENCE: 518
ILAETTHHRP WSASGAGGSE GGGSEGGTSG ATGAGTSTSG GGASTGGGTG QAKHKQRKRL    60
KSSCKRHPLY VDFSDVGWND WIVAPPGYHA FYCHGECPFP LADHLNSTNH AIVQTLVNSV   120
NSKIPKACCV PTELSAISML YLDENEKVVL KNYQDMVVEG CGCR                    164

SEQ ID NO: 519          moltype = AA   length = 126
FEATURE                 Location/Qualifiers
REGION                  1..126
                        note = Description of Artificial Sequence: Synthetic
                        polypeptide
REGION                  12..13
                        note = NON_CONS - Residues at these positions can be
                        separated by a linker of unknown length
source                  1..126
                        mol_type = protein
                        organism = synthetic construct
SEQUENCE: 519
IIGESSHHKP FTQAKHKQRK RLKSSCKRHP LYVDFSDVGW NDWIVAPPGY HAFYCHGECP    60
FPLADHLNST NHAIVQTLVN SVNSKIPKAC CVPTELSAIS MLYLDENEKV VLKNYQDMVV   120
EGCGCR                                                              126

SEQ ID NO: 520          moltype = AA   length = 164
FEATURE                 Location/Qualifiers
REGION                  1..164
                        note = Description of Artificial Sequence: Synthetic
                        polypeptide
source                  1..164
                        mol_type = protein
                        organism = synthetic construct
SEQUENCE: 520
IIGESSHHKP FTASGAGGSE GGGSEGGTSG ATGAGTSTSG GGASTGGGTG QAKHKQRKRL    60
KSSCKRHPLY VDFSDVGWND WIVAPPGYHA FYCHGECPFP LADHLNSTNH AIVQTLVNSV   120
NSKIPKACCV PTELSAISML YLDENEKVVL KNYQDMVVEG CGCR                    164

SEQ ID NO: 521          moltype = AA   length = 126
FEATURE                 Location/Qualifiers
REGION                  1..126
                        note = Description of Artificial Sequence: Synthetic
                        polypeptide
REGION                  12..13
                        note = NON_CONS - Residues at these positions can be
                        separated by a linker of unknown length
source                  1..126
                        mol_type = protein
                        organism = synthetic construct
SEQUENCE: 521
GLGDTTHHRP WGQAKHKQRK RLKSSCKRHP LYVDFSDVGW NDWIVAPPGY HAFYCHGECP    60
FPLADHLNST NHAIVQTLVN SVNSKIPKAC CVPTELSAIS MLYLDENEKV VLKNYQDMVV   120
EGCGCR                                                              126

SEQ ID NO: 522          moltype = AA   length = 164
FEATURE                 Location/Qualifiers
REGION                  1..164
                        note = Description of Artificial Sequence: Synthetic
                        polypeptide
source                  1..164
                        mol_type = protein
                        organism = synthetic construct
SEQUENCE: 522
GLGDTTHHRP WGASGAGGSE GGGSEGGTSG ATGAGTSTSG GGASTGGGTG QAKHKQRKRL    60
KSSCKRHPLY VDFSDVGWND WIVAPPGYHA FYCHGECPFP LADHLNSTNH AIVQTLVNSV   120
NSKIPKACCV PTELSAISML YLDENEKVVL KNYQDMVVEG CGCR                    164

SEQ ID NO: 523          moltype = AA   length = 126
FEATURE                 Location/Qualifiers
REGION                  1..126
                        note = Description of Artificial Sequence: Synthetic
                        polypeptide
REGION                  12..13
                        note = NON_CONS - Residues at these positions can be
                        separated by a linker of unknown length
source                  1..126
                        mol_type = protein
                        organism = synthetic construct
SEQUENCE: 523
```

```
VLGDTTHHKP WTQAKHKQRK RLKSSCKRHP LYVDFSDVGW NDWIVAPPGY HAFYCHGECP    60
FPLADHLNST NHAIVQTLVN SVNSKIPKAC CVPTELSAIS MLYLDENEKV VLKNYQDMVV   120
EGCGCR                                                             126

SEQ ID NO: 524           moltype = AA   length = 164
FEATURE                  Location/Qualifiers
REGION                   1..164
                         note = Description of Artificial Sequence: Synthetic
                          polypeptide
source                   1..164
                         mol_type = protein
                         organism = synthetic construct
SEQUENCE: 524
VLGDTTHHKP WTASGAGGSE GGGSEGGTSG ATGAGTSTSG GGASTGGGTG QAKHKQRKRL    60
KSSCKRHPLY VDFSDVGWND WIVAPPGYHA FYCHGECPFP LADHLNSTNH AIVQTLVNSV   120
NSKIPKACCV PTELSAISML YLDENEKVVL KNYQDMVVEG CGCR                    164

SEQ ID NO: 525           moltype = AA   length = 126
FEATURE                  Location/Qualifiers
REGION                   1..126
                         note = Description of Artificial Sequence: Synthetic
                          polypeptide
REGION                   12..13
                         note = NON_CONS - Residues at these positions can be
                          separated by a linker of unknown length
source                   1..126
                         mol_type = protein
                         organism = synthetic construct
SEQUENCE: 525
IVADSTHHRP WTQAKHKQRK RLKSSCKRHP LYVDFSDVGW NDWIVAPPGY HAFYCHGECP    60
FPLADHLNST NHAIVQTLVN SVNSKIPKAC CVPTELSAIS MLYLDENEKV VLKNYQDMVV   120
EGCGCR                                                             126

SEQ ID NO: 526           moltype = AA   length = 164
FEATURE                  Location/Qualifiers
REGION                   1..164
                         note = Description of Artificial Sequence: Synthetic
                          polypeptide
source                   1..164
                         mol_type = protein
                         organism = synthetic construct
SEQUENCE: 526
IVADSTHHRP WTASGAGGSE GGGSEGGTSG ATGAGTSTSG GGASTGGGTG QAKHKQRKRL    60
KSSCKRHPLY VDFSDVGWND WIVAPPGYHA FYCHGECPFP LADHLNSTNH AIVQTLVNSV   120
NSKIPKACCV PTELSAISML YLDENEKVVL KNYQDMVVEG CGCR                    164

SEQ ID NO: 527           moltype = AA   length = 125
FEATURE                  Location/Qualifiers
REGION                   1..125
                         note = Description of Artificial Sequence: Synthetic
                          polypeptide
REGION                   11..12
                         note = NON_CONS - Residues at these positions can be
                          separated by a linker of unknown length
source                   1..125
                         mol_type = protein
                         organism = synthetic construct
SEQUENCE: 527
STADTSHHRP SQAKHKQRKR LKSSCKRHPL YVDFSDVGWN DWIVAPPGYH AFYCHGECPF    60
PLADHLNSTN HAIVQTLVNS VNSKIPKACC VPTELSAISM LYLDENEKVV LKNYQDMVVE   120
GCGCR                                                              125

SEQ ID NO: 528           moltype = AA   length = 163
FEATURE                  Location/Qualifiers
REGION                   1..163
                         note = Description of Artificial Sequence: Synthetic
                          polypeptide
source                   1..163
                         mol_type = protein
                         organism = synthetic construct
SEQUENCE: 528
STADTSHHRP SASGAGGSEG GGSEGGTSGA TGAGTSTSGG GASTGGGTGQ AKHKQRKRLK    60
SSCKRHPLYV DFSDVGWNDW IVAPPGYHAF YCHGECPFPL ADHLNSTNHA IVQTLVNSVN   120
SKIPKACCVP TELSAISMLY LDENEKVVLK NYQDMVVEGC GCR                     163

SEQ ID NO: 529           moltype = AA   length = 126
FEATURE                  Location/Qualifiers
REGION                   1..126
                         note = Description of Artificial Sequence: Synthetic
```

```
                              polypeptide
REGION                        12..13
                              note = NON_CONS - Residues at these positions can be
                              separated by a linker of unknown length
source                        1..126
                              mol_type = protein
                              organism = synthetic construct
SEQUENCE: 529
TSGGESTHHR PSQAKHKQRK RLKSSCKRHP LYVDFSDVGW NDWIVAPPGY HAFYCHGECP    60
FPLADHLNST NHAIVQTLVN SVNSKIPKAC CVPTELSAIS MLYLDENEKV VLKNYQDMVV   120
EGCGCR                                                              126

SEQ ID NO: 530                moltype = AA   length = 164
FEATURE                       Location/Qualifiers
REGION                        1..164
                              note = Description of Artificial Sequence: Synthetic
                              polypeptide
source                        1..164
                              mol_type = protein
                              organism = synthetic construct
SEQUENCE: 530
TSGGESTHHR PSASGAGGSE GGGSEGGTSG ATGAGTSTSG GGASTGGGTG QAKHKQRKRL    60
KSSCKRHPLY VDFSDVGWND WIVAPPGYHA FYCHGECPFP LADHLNSTNH AIVQTLVNSV   120
NSKIPKACCV PTELSAISML YLDENEKVVL KNYQDMVVEG CGCR                    164

SEQ ID NO: 531                moltype = AA   length = 126
FEATURE                       Location/Qualifiers
REGION                        1..126
                              note = Description of Artificial Sequence: Synthetic
                              polypeptide
REGION                        12..13
                              note = NON_CONS - Residues at these positions can be
                              separated by a linker of unknown length
source                        1..126
                              mol_type = protein
                              organism = synthetic construct
SEQUENCE: 531
TSGGESSHHK PSQAKHKQRK RLKSSCKRHP LYVDFSDVGW NDWIVAPPGY HAFYCHGECP    60
FPLADHLNST NHAIVQTLVN SVNSKIPKAC CVPTELSAIS MLYLDENEKV VLKNYQDMVV   120
EGCGCR                                                              126

SEQ ID NO: 532                moltype = AA   length = 164
FEATURE                       Location/Qualifiers
REGION                        1..164
                              note = Description of Artificial Sequence: Synthetic
                              polypeptide
source                        1..164
                              mol_type = protein
                              organism = synthetic construct
SEQUENCE: 532
TSGGESSHHK PSASGAGGSE GGGSEGGTSG ATGAGTSTSG GGASTGGGTG QAKHKQRKRL    60
KSSCKRHPLY VDFSDVGWND WIVAPPGYHA FYCHGECPFP LADHLNSTNH AIVQTLVNSV   120
NSKIPKACCV PTELSAISML YLDENEKVVL KNYQDMVVEG CGCR                    164

SEQ ID NO: 533                moltype = AA   length = 126
FEATURE                       Location/Qualifiers
REGION                        1..126
                              note = Description of Artificial Sequence: Synthetic
                              polypeptide
REGION                        12..13
                              note = NON_CONS - Residues at these positions can be
                              separated by a linker of unknown length
source                        1..126
                              mol_type = protein
                              organism = synthetic construct
SEQUENCE: 533
TGSGDSSHHR PSQAKHKQRK RLKSSCKRHP LYVDFSDVGW NDWIVAPPGY HAFYCHGECP    60
FPLADHLNST NHAIVQTLVN SVNSKIPKAC CVPTELSAIS MLYLDENEKV VLKNYQDMVV   120
EGCGCR                                                              126

SEQ ID NO: 534                moltype = AA   length = 164
FEATURE                       Location/Qualifiers
REGION                        1..164
                              note = Description of Artificial Sequence: Synthetic
                              polypeptide
source                        1..164
                              mol_type = protein
                              organism = synthetic construct
SEQUENCE: 534
```

```
TGSGDSSHHR PSASGAGGSE GGGSEGGTSG ATGAGTSTSG GGASTGGGTG QAKHKQRKRL    60
KSSCKRHPLY VDFSDVGWND WIVAPPGYHA FYCHGECPFP LADHLNSTNH AIVQTLVNSV   120
NSKIPKACCV PTELSAISML YLDENEKVVL KNYQDMVVEG CGCR                   164

SEQ ID NO: 535          moltype = AA   length = 127
FEATURE                 Location/Qualifiers
REGION                  1..127
                        note = Description of Artificial Sequence: Synthetic
                        polypeptide
REGION                  13..14
                        note = NON_CONS - Residues at these positions can be
                        separated by a linker of unknown length
source                  1..127
                        mol_type = protein
                        organism = synthetic construct
SEQUENCE: 535
GSSGESTHHK PSTQAKHKQR KRLKSSCKRH PLYVDFSDVG WNDWIVAPPG YHAFYCHGEC    60
PFPLADHLNS TNHAIVQTLV NSVNSKIPKA CCVPTELSAI SMLYLDENEK VVLKNYQDMV   120
VEGCGCR                                                            127

SEQ ID NO: 536          moltype = AA   length = 165
FEATURE                 Location/Qualifiers
REGION                  1..165
                        note = Description of Artificial Sequence: Synthetic
                        polypeptide
source                  1..165
                        mol_type = protein
                        organism = synthetic construct
SEQUENCE: 536
GSSGESTHHK PSTASGAGGS EGGGSEGGTS GATGAGTSTS GGGASTGGGT GQAKHKQRKR    60
LKSSCKRHPL YVDFSDVGWN DWIVAPPGYH AFYCHGECPF PLADHLNSTN HAIVQTLVNS   120
VNSKIPKACC VPTELSAISM LYLDENEKVV LKNYQDMVVE GCGCR                  165

SEQ ID NO: 537          moltype = AA   length = 126
FEATURE                 Location/Qualifiers
REGION                  1..126
                        note = Description of Artificial Sequence: Synthetic
                        polypeptide
REGION                  12..13
                        note = NON_CONS - Residues at these positions can be
                        separated by a linker of unknown length
source                  1..126
                        mol_type = protein
                        organism = synthetic construct
SEQUENCE: 537
VGADSTHHRP VTQAKHKQRK RLKSSCKRHP LYVDFSDVGW NDWIVAPPGY HAFYCHGECP    60
FPLADHLNST NHAIVQTLVN SVNSKIPKAC CVPTELSAIS MLYLDENEKV VLKNYQDMVV   120
EGCGCR                                                             126

SEQ ID NO: 538          moltype = AA   length = 164
FEATURE                 Location/Qualifiers
REGION                  1..164
                        note = Description of Artificial Sequence: Synthetic
                        polypeptide
source                  1..164
                        mol_type = protein
                        organism = synthetic construct
SEQUENCE: 538
VGADSTHHRP VTASGAGGSE GGGSEGGTSG ATGAGTSTSG GGASTGGGTG QAKHKQRKRL    60
KSSCKRHPLY VDFSDVGWND WIVAPPGYHA FYCHGECPFP LADHLNSTNH AIVQTLVNSV   120
NSKIPKACCV PTELSAISML YLDENEKVVL KNYQDMVVEG CGCR                   164

SEQ ID NO: 539          moltype = AA   length = 126
FEATURE                 Location/Qualifiers
REGION                  1..126
                        note = Description of Artificial Sequence: Synthetic
                        polypeptide
REGION                  12..13
                        note = NON_CONS - Residues at these positions can be
                        separated by a linker of unknown length
source                  1..126
                        mol_type = protein
                        organism = synthetic construct
SEQUENCE: 539
GAADTTHHRP VTQAKHKQRK RLKSSCKRHP LYVDFSDVGW NDWIVAPPGY HAFYCHGECP    60
FPLADHLNST NHAIVQTLVN SVNSKIPKAC CVPTELSAIS MLYLDENEKV VLKNYQDMVV   120
EGCGCR                                                             126

SEQ ID NO: 540          moltype = AA   length = 164
```

```
FEATURE            Location/Qualifiers
REGION             1..164
                   note = Description of Artificial Sequence: Synthetic
                   polypeptide
source             1..164
                   mol_type = protein
                   organism = synthetic construct
SEQUENCE: 540
GAADTTHHRP VTASGAGGSE GGGSEGGTSG ATGAGTSTSG GGASTGGGTG QAKHKQRKRL    60
KSSCKRHPLY VDFSDVGWND WIVAPPGYHA FYCHGECPFP LADHLNSTNH AIVQTLVNSV   120
NSKIPKACCV PTELSAISML YLDENEKVVL KNYQDMVVEG CGCR                   164

SEQ ID NO: 541     moltype = AA  length = 126
FEATURE            Location/Qualifiers
REGION             1..126
                   note = Description of Artificial Sequence: Synthetic
                   polypeptide
REGION             12..13
                   note = NON_CONS - Residues at these positions can be
                   separated by a linker of unknown length
source             1..126
                   mol_type = protein
                   organism = synthetic construct
SEQUENCE: 541
AGADTTHHRP VTQAKHKQRK RLKSSCKRHP LYVDFSDVGW NDWIVAPPGY HAFYCHGECP    60
FPLADHLNST NHAIVQTLVN SVNSKIPKAC CVPTELSAIS MLYLDENEKV VLKNYQDMVV   120
EGCGCR                                                             126

SEQ ID NO: 542     moltype = AA  length = 164
FEATURE            Location/Qualifiers
REGION             1..164
                   note = Description of Artificial Sequence: Synthetic
                   polypeptide
source             1..164
                   mol_type = protein
                   organism = synthetic construct
SEQUENCE: 542
AGADTTHHRP VTASGAGGSE GGGSEGGTSG ATGAGTSTSG GGASTGGGTG QAKHKQRKRL    60
KSSCKRHPLY VDFSDVGWND WIVAPPGYHA FYCHGECPFP LADHLNSTNH AIVQTLVNSV   120
NSKIPKACCV PTELSAISML YLDENEKVVL KNYQDMVVEG CGCR                   164

SEQ ID NO: 543     moltype = AA  length = 126
FEATURE            Location/Qualifiers
REGION             1..126
                   note = Description of Artificial Sequence: Synthetic
                   polypeptide
REGION             12..13
                   note = NON_CONS - Residues at these positions can be
                   separated by a linker of unknown length
source             1..126
                   mol_type = protein
                   organism = synthetic construct
SEQUENCE: 543
GGADTTHHRP ATQAKHKQRK RLKSSCKRHP LYVDFSDVGW NDWIVAPPGY HAFYCHGECP    60
FPLADHLNST NHAIVQTLVN SVNSKIPKAC CVPTELSAIS MLYLDENEKV VLKNYQDMVV   120
EGCGCR                                                             126

SEQ ID NO: 544     moltype = AA  length = 164
FEATURE            Location/Qualifiers
REGION             1..164
                   note = Description of Artificial Sequence: Synthetic
                   polypeptide
source             1..164
                   mol_type = protein
                   organism = synthetic construct
SEQUENCE: 544
GGADTTHHRP ATASGAGGSE GGGSEGGTSG ATGAGTSTSG GGASTGGGTG QAKHKQRKRL    60
KSSCKRHPLY VDFSDVGWND WIVAPPGYHA FYCHGECPFP LADHLNSTNH AIVQTLVNSV   120
NSKIPKACCV PTELSAISML YLDENEKVVL KNYQDMVVEG CGCR                   164

SEQ ID NO: 545     moltype = AA  length = 126
FEATURE            Location/Qualifiers
REGION             1..126
                   note = Description of Artificial Sequence: Synthetic
                   polypeptide
REGION             12..13
                   note = NON_CONS - Residues at these positions can be
                   separated by a linker of unknown length
source             1..126
```

```
                            mol_type = protein
                            organism = synthetic construct
SEQUENCE: 545
GGADTTHHRP GTQAKHKQRK RLKSSCKRHP LYVDFSDVGW NDWIVAPPGY HAFYCHGECP      60
FPLADHLNST NHAIVQTLVN SVNSKIPKAC CVPTELSAIS MLYLDENEKV VLKNYQDMVV      120
EGCGCR                                                                 126

SEQ ID NO: 546              moltype = AA  length = 164
FEATURE                     Location/Qualifiers
REGION                      1..164
                            note = Description of Artificial Sequence: Synthetic
                              polypeptide
source                      1..164
                            mol_type = protein
                            organism = synthetic construct
SEQUENCE: 546
GGADTTHHRP GTASGAGGSE GGGSEGGTSG ATGAGTSTSG GGASTGGGTG QAKHKQRKRL      60
KSSCKRHPLY VDFSDVGWND WIVAPPGYHA FYCHGECPFP LADHLNSTNH AIVQTLVNSV      120
NSKIPKACCV PTELSAISML YLDENEKVVL KNYQDMVVEG CGCR                       164

SEQ ID NO: 547              moltype = AA  length = 138
FEATURE                     Location/Qualifiers
REGION                      1..138
                            note = Description of Artificial Sequence: Synthetic
                              polypeptide
REGION                      24..25
                            note = NON_CONS - Residues at these positions can be
                              separated by a linker of unknown length
source                      1..138
                            mol_type = protein
                            organism = synthetic construct
SEQUENCE: 547
LLADTTHHRP WTVIGESTHH RPWSQAKHKQ RKRLKSSCKR HPLYVDFSDV GWNDWIVAPP      60
GYHAFYCHGE CPFPLADHLN STNHAIVQTL VNSVNSKIPK ACCVPTELSA ISMLYLDENE      120
KVVLKNYQDM VVEGCGCR                                                    138

SEQ ID NO: 548              moltype = AA  length = 176
FEATURE                     Location/Qualifiers
REGION                      1..176
                            note = Description of Artificial Sequence: Synthetic
                              polypeptide
source                      1..176
                            mol_type = protein
                            organism = synthetic construct
SEQUENCE: 548
LLADTTHHRP WTVIGESTHH RPWSASGAGG SEGGGSEGGT SGATGAGTST SGGGASTGGG      60
TGQAKHKQRK RLKSSCKRHP LYVDFSDVGW NDWIVAPPGY HAFYCHGECP FPLADHLNST      120
NHAIVQTLVN SVNSKIPKAC CVPTELSAIS MLYLDENEKV VLKNYQDMVV EGCGCR          176

SEQ ID NO: 549              moltype = AA  length = 150
FEATURE                     Location/Qualifiers
REGION                      1..150
                            note = Description of Artificial Sequence: Synthetic
                              polypeptide
REGION                      36..37
                            note = NON_CONS - Residues at these positions can be
                              separated by a linker of unknown length
source                      1..150
                            mol_type = protein
                            organism = synthetic construct
SEQUENCE: 549
LLADTTHHRP WTVIGESTHH RPWSIIGESS HHKPFTQAKH KQRKRLKSSC KRHPLYVDFS      60
DVGWNDWIVA PPGYHAFYCH GECPFPLADH LNSTNHAIVQ TLVNSVNSKI PKACCVPTEL      120
SAISMLYLDE NEKVVLKNYQ DMVVEGCGCR                                       150

SEQ ID NO: 550              moltype = AA  length = 188
FEATURE                     Location/Qualifiers
REGION                      1..188
                            note = Description of Artificial Sequence: Synthetic
                              polypeptide
source                      1..188
                            mol_type = protein
                            organism = synthetic construct
SEQUENCE: 550
LLADTTHHRP WTVIGESTHH RPWSIIGESS HHKPFTASGA GGSEGGGSEG GTSGATGAGT      60
STSGGGASTG GGTGQAKHKQ RKRLKSSCKR HPLYVDFSDV GWNDWIVAPP GYHAFYCHGE      120
CPFPLADHLN STNHAIVQTL VNSVNSKIPK ACCVPTELSA ISMLYLDENE KVVLKNYQDM      180
VVEGCGCR                                                               188
```

```
SEQ ID NO: 551            moltype = AA  length = 174
FEATURE                   Location/Qualifiers
REGION                    1..174
                          note = Description of Artificial Sequence: Synthetic
                          polypeptide
REGION                    60..61
                          note = NON_CONS - Residues at these positions can be
                          separated by a linker of unknown length
source                    1..174
                          mol_type = protein
                          organism = synthetic construct
SEQUENCE: 551
LLADTTHHRP WTVIGESTHH RPWSIIGESS HHKPFTGLGD TTHHRPWGIL AESTHHKPWT    60
QAKHKQRKRL KSSCKRHPLY VDFSDVGWND WIVAPPGYHA FYCHGECPFP LADHLNSTNH   120
AIVQTLVNSV NSKIPKACCV PTELSAISML YLDENEKVVL KNYQDMVVEG CGCR          174

SEQ ID NO: 552            moltype = AA  length = 212
FEATURE                   Location/Qualifiers
REGION                    1..212
                          note = Description of Artificial Sequence: Synthetic
                          polypeptide
source                    1..212
                          mol_type = protein
                          organism = synthetic construct
SEQUENCE: 552
LLADTTHHRP WTVIGESTHH RPWSIIGESS HHKPFTGLGD TTHHRPWGIL AESTHHKPWT    60
ASGAGGSEGG GSEGGTSGAT GAGTSTSGGG ASTGGGTGQA KHKQRKRLKS SCKRHPLYVD   120
FSDVGWNDWI VAPPGYHAFY CHGECPFPLA DHLNSTNHAI VQTLVNSVNS KIPKACCVPT   180
ELSAISMLYL DENEKVVLKN YQDMVVEGCG CR                                 212

SEQ ID NO: 553            moltype = AA  length = 138
FEATURE                   Location/Qualifiers
REGION                    1..138
                          note = Description of Artificial Sequence: Synthetic
                          polypeptide
REGION                    24..25
                          note = NON_CONS - Residues at these positions can be
                          separated by a linker of unknown length
source                    1..138
                          mol_type = protein
                          organism = synthetic construct
SEQUENCE: 553
LLADTTHHRP WTILAESTHH KPWTQAKHKQ RKRLKSSCKR HPLYVDFSDV GWNDWIVAPP    60
GYHAFYCHGE CPFPLADHLN STNHAIVQTL VNSVNSKIPK ACCVPTELSA ISMLYLDENE   120
KVVLKNYQDM VVEGCGCR                                                 138

SEQ ID NO: 554            moltype = AA  length = 176
FEATURE                   Location/Qualifiers
REGION                    1..176
                          note = Description of Artificial Sequence: Synthetic
                          polypeptide
source                    1..176
                          mol_type = protein
                          organism = synthetic construct
SEQUENCE: 554
LLADTTHHRP WTILAESTHH KPWTASGAGG SEGGGSEGGT SGATGAGTST SGGGASTGGG    60
TGQAKHKQRK RLKSSCKRHP LYVDFSDVGW NDWIVAPPGY HAFYCHGECP PPLADHLNST   120
NHAIVQTLVN SVNSKIPKAC CVPTELSAIS MLYLDENEKV VLKNYQDMVV EGCGCR        176

SEQ ID NO: 555            moltype = AA  length = 174
FEATURE                   Location/Qualifiers
REGION                    1..174
                          note = Description of Artificial Sequence: Synthetic
                          polypeptide
REGION                    60..61
                          note = NON_CONS - Residues at these positions can be
                          separated by a linker of unknown length
source                    1..174
                          mol_type = protein
                          organism = synthetic construct
SEQUENCE: 555
LLADTTHHRP WTILAESTHH KPWTLLADTT HHRPWTILAE STHHKPWTLL ADTTHHRPWT    60
QAKHKQRKRL KSSCKRHPLY VDFSDVGWND WIVAPPGYHA FYCHGECPFP LADHLNSTNH   120
AIVQTLVNSV NSKIPKACCV PTELSAISML YLDENEKVVL KNYQDMVVEG CGCR          174

SEQ ID NO: 556            moltype = AA  length = 212
FEATURE                   Location/Qualifiers
REGION                    1..212
                          note = Description of Artificial Sequence: Synthetic
```

```
                            polypeptide
source                      1..212
                            mol_type = protein
                            organism = synthetic construct
SEQUENCE: 556
LLADTTHHRP WTILAESTHH KPWTLLADTT HHRPWTILAE STHHKPWTLL ADTTHHRPWT    60
ASGAGGSEGG GSEGGTSGAT GAGTSTSGGG ASTGGGTGQA KHKQRKRLKS SCKRHPLYVD   120
FSDVGWNDWI VAPPGYHAFY CHGECPFPLA DHLNSTNHAI VQTLVNSVNS KIPKACCVPT   180
ELSAISMLYL DENEKVVLKN YQDMVVEGCG CR                                 212

SEQ ID NO: 557              moltype = AA  length = 138
FEATURE                     Location/Qualifiers
REGION                      1..138
                            note = Description of Artificial Sequence: Synthetic
                             polypeptide
REGION                      24..25
                            note = NON_CONS - Residues at these positions can be
                             separated by a linker of unknown length
source                      1..138
                            mol_type = protein
                            organism = synthetic construct
SEQUENCE: 557
LLADTTHHRP WTGLGDTTHH RPWGQAKHKQ RKRLKSSCKR HPLYVDFSDV GWNDWIVAPP    60
GYHAFYCHGE CPFPLADHLN STNHAIVQTL VNSVNSKIPK ACCVPTELSA ISMLYLDENE   120
KVVLKNYQDM VVEGCGCR                                                 138

SEQ ID NO: 558              moltype = AA  length = 176
FEATURE                     Location/Qualifiers
REGION                      1..176
                            note = Description of Artificial Sequence: Synthetic
                             polypeptide
source                      1..176
                            mol_type = protein
                            organism = synthetic construct
SEQUENCE: 558
LLADTTHHRP WTGLGDTTHH RPWGASGAGG SEGGGSEGGT SGATGAGTST SGGGASTGGG    60
TGQAKHKQRK RLKSSCKRHP LYVDFSDVGW NDWIVAPPGY HAFYCHGECP FPLADHLNST   120
NHAIVQTLVN SVNSKIPKAC CVPTELSAIS MLYLDENEKV VLKNYQDMVV EGCGCR       176

SEQ ID NO: 559              moltype = AA  length = 150
FEATURE                     Location/Qualifiers
REGION                      1..150
                            note = Description of Artificial Sequence: Synthetic
                             polypeptide
REGION                      36..37
                            note = NON_CONS - Residues at these positions can be
                             separated by a linker of unknown length
source                      1..150
                            mol_type = protein
                            organism = synthetic construct
SEQUENCE: 559
LLADTTHHRP WTGLGDTTHH RPWGLLADTT HHRPWTQAKH KQRKRLKSSC KRHPLYVDFS    60
DVGWNDWIVA PPGYHAFYCH GECPFPLADH LNSTNHAIVQ TLVNSVNSKI PKACCVPTEL   120
SAISMLYLDE NEKVVLKNYQ DMVVEGCGCR                                    150

SEQ ID NO: 560              moltype = AA  length = 188
FEATURE                     Location/Qualifiers
REGION                      1..188
                            note = Description of Artificial Sequence: Synthetic
                             polypeptide
source                      1..188
                            mol_type = protein
                            organism = synthetic construct
SEQUENCE: 560
LLADTTHHRP WTGLGDTTHH RPWGLLADTT HHRPWTASGA GGSEGGGSEG GTSGATGAGT    60
STSGGGASTG GGTGQAKHKQ RKRLKSSCKR HPLYVDFSDV GWNDWIVAPP GYHAFYCHGE   120
CPFPLADHLN STNHAIVQTL VNSVNSKIPK ACCVPTELSA ISMLYLDENE KVVLKNYQDM   180
VVEGCGCR                                                            188

SEQ ID NO: 561              moltype = AA  length = 174
FEATURE                     Location/Qualifiers
REGION                      1..174
                            note = Description of Artificial Sequence: Synthetic
                             polypeptide
REGION                      60..61
                            note = NON_CONS - Residues at these positions can be
                             separated by a linker of unknown length
source                      1..174
                            mol_type = protein
```

```
                    organism = synthetic construct
SEQUENCE: 561
LLADTTHHRP WTGLGDTTHH RPWGLLADTT HHRPWTGLGD TTHHRPWGLL ADTTHHRPWT    60
QAKHKQRKRL KSSCKRHPLY VDFSDVGWND WIVAPPGYHA FYCHGECPFP LADHLNSTNH   120
AIVQTLVNSV NSKIPKACCV PTELSAISML YLDENEKVVL KNYQDMVVEG CGCR         174

SEQ ID NO: 562           moltype = AA  length = 212
FEATURE                  Location/Qualifiers
REGION                   1..212
                         note = Description of Artificial Sequence: Synthetic
                           polypeptide
source                   1..212
                         mol_type = protein
                         organism = synthetic construct
SEQUENCE: 562
LLADTTHHRP WTGLGDTTHH RPWGLLADTT HHRPWTGLGD TTHHRPWGLL ADTTHHRPWT    60
ASGAGGSEGG GSEGGTSGAT GAGTSTSGGG ASTGGGTGQA KHKQRKRLKS SCKRHPLYVD   120
FSDVGWNDWI VAPPGYHAFY CHGECPFPLA DHLNSTNHAI VQTLVNSVNS KIPKACCVPT   180
ELSAISMLYL DENEKVVLKN YQDMVVEGCG CR                                 212

SEQ ID NO: 563           moltype = AA  length = 198
FEATURE                  Location/Qualifiers
REGION                   1..198
                         note = Description of Artificial Sequence: Synthetic
                           polypeptide
REGION                   84..85
                         note = NON_CONS - Residues at these positions can be
                           separated by a linker of unknown length
source                   1..198
                         mol_type = protein
                         organism = synthetic construct
SEQUENCE: 563
LLADTTHHRP WTGLGDTTHH RPWGLLADTT HHRPWTGLGD TTHHRPWGLL ADTTHHRPWT    60
GLGDTTHHRP WGLLADTTHH RPWTQAKHKQ RKRLKSSCKR HPLYVDFSDV GWNDWIVAPP   120
GYHAFYCHGE CPFPLADHLN STNHAIVQTL VNSVNSKIPK ACCVPTELSA ISMLYLDENE   180
KVVLKNYQDM VVEGCGCR                                                 198

SEQ ID NO: 564           moltype = AA  length = 236
FEATURE                  Location/Qualifiers
REGION                   1..236
                         note = Description of Artificial Sequence: Synthetic
                           polypeptide
source                   1..236
                         mol_type = protein
                         organism = synthetic construct
SEQUENCE: 564
LLADTTHHRP WTGLGDTTHH RPWGLLADTT HHRPWTGLGD TTHHRPWGLL ADTTHHRPWT    60
GLGDTTHHRP WGLLADTTHH RPWTASGAGG SEGGGSEGGT SGATGAGTST SGGGASTGGG   120
TGQAKHKQRK RLKSSCKRHP LYVDFSDVGW NDWIVAPPGY HAFYCHGECP FPLADHLNST   180
NHAIVQTLVN SVNSKIPKAC CVPTELSAIS MLYLDENEKV VLKNYQDMVV EGCGCR       236

SEQ ID NO: 565           moltype = AA  length = 174
FEATURE                  Location/Qualifiers
REGION                   1..174
                         note = Description of Artificial Sequence: Synthetic
                           polypeptide
REGION                   60..61
                         note = NON_CONS - Residues at these positions can be
                           separated by a linker of unknown length
source                   1..174
                         mol_type = protein
                         organism = synthetic construct
SEQUENCE: 565
STADTSHHRP STSGGESTHH RPSTSGGESS HHKPSTGSGD SSHHRPSGSS GESTHHKPST    60
QAKHKQRKRL KSSCKRHPLY VDFSDVGWND WIVAPPGYHA FYCHGECPFP LADHLNSTNH   120
AIVQTLVNSV NSKIPKACCV PTELSAISML YLDENEKVVL KNYQDMVVEG CGCR         174

SEQ ID NO: 566           moltype = AA  length = 212
FEATURE                  Location/Qualifiers
REGION                   1..212
                         note = Description of Artificial Sequence: Synthetic
                           polypeptide
source                   1..212
                         mol_type = protein
                         organism = synthetic construct
SEQUENCE: 566
STADTSHHRP STSGGESTHH RPSTSGGESS HHKPSTGSGD SSHHRPSGSS GESTHHKPST    60
ASGAGGSEGG GSEGGTSGAT GAGTSTSGGG ASTGGGTGQA KHKQRKRLKS SCKRHPLYVD   120
FSDVGWNDWI VAPPGYHAFY CHGECPFPLA DHLNSTNHAI VQTLVNSVNS KIPKACCVPT   180
```

```
ELSAISMLYL DENEKVVLKN YQDMVVEGCG CR                                        212

SEQ ID NO: 567            moltype = AA   length = 174
FEATURE                   Location/Qualifiers
REGION                    1..174
                          note = Description of Artificial Sequence: Synthetic
                            polypeptide
REGION                    60..61
                          note = NON_CONS - Residues at these positions can be
                            separated by a linker of unknown length
source                    1..174
                          mol_type = protein
                          organism = synthetic construct
SEQUENCE: 567
VGADSTHHRP VTGAADTTHH RPVTAGADTT HHRPVTGGAD TTHHRPATGG ADTTHHRPGT    60
QAKHKQRKRL KSSCKRHPLY VDFSDVGWND WIVAPPGYHA FYCHGECPFP LADHLNSTNH   120
AIVQTLVNSV NSKIPKACCV PTELSAISML YLDENEKVVL KNYQDMVVEG CGCR         174

SEQ ID NO: 568            moltype = AA   length = 212
FEATURE                   Location/Qualifiers
REGION                    1..212
                          note = Description of Artificial Sequence: Synthetic
                            polypeptide
source                    1..212
                          mol_type = protein
                          organism = synthetic construct
SEQUENCE: 568
VGADSTHHRP VTGAADTTHH RPVTAGADTT HHRPVTGGAD TTHHRPATGG ADTTHHRPGT    60
ASGAGGSEGG GSEGGTSGAT GAGTSTSGGG ASTGGGTGQA KHKQRKRLKS SCKRHPLYVD   120
FSDVGWNDWI VAPPGYHAFY CHGECPFPLA DHLNSTNHAI VQTLVNSVNS KIPKACCVPT   180
ELSAISMLYL DENEKVVLKN YQDMVVEGCG CR                                 212

SEQ ID NO: 569            moltype = AA   length = 222
FEATURE                   Location/Qualifiers
REGION                    1..222
                          note = Description of Artificial Sequence: Synthetic
                            polypeptide
REGION                    108..109
                          note = NON_CONS - Residues at these positions can be
                            separated by a linker of unknown length
source                    1..222
                          mol_type = protein
                          organism = synthetic construct
SEQUENCE: 569
STADTSHHRP SLLADTTHHR PWTTSGGEST HHRPSVGADS THHRPVTTSG GESSHHKPSG    60
AADTTHHRPV TTGSGDSSHH RPSGSSGEST HHKPSTGGAD TTHHRPATQA KHKQRKRLKS   120
SCKRHPLYVD FSDVGWNDWI VAPPGYHAFY CHGECPFPLA DHLNSTNHAI VQTLVNSVNS   180
KIPKACCVPT ELSAISMLYL DENEKVVLKN YQDMVVEGCG CR                      222

SEQ ID NO: 570            moltype = AA   length = 260
FEATURE                   Location/Qualifiers
REGION                    1..260
                          note = Description of Artificial Sequence: Synthetic
                            polypeptide
source                    1..260
                          mol_type = protein
                          organism = synthetic construct
SEQUENCE: 570
STADTSHHRP SLLADTTHHR PWTTSGGEST HHRPSVGADS THHRPVTTSG GESSHHKPSG    60
AADTTHHRPV TTGSGDSSHH RPSGSSGEST HHKPSTGGAD TTHHRPATAS GAGGSEGGGS   120
EGGTSGATGA GTSTSGGGAS TGGGTGQAKH KQRKRLKSSC KRHPLYVDFS DVGWNDWIVA   180
PPGYHAFYCH GECPFPLADH LNSTNHAIVQ TLVNSVNSKI PKACCVPTEL SAISMLYLDE   240
NEKVVLKNYQ DMVVEGCGCR                                               260

SEQ ID NO: 571            moltype = AA   length = 228
FEATURE                   Location/Qualifiers
REGION                    1..228
                          note = Description of Artificial Sequence: Synthetic
                            polypeptide
REGION                    114..115
                          note = NON_CONS - Residues at these positions can be
                            separated by a linker of unknown length
source                    1..228
                          mol_type = protein
                          organism = synthetic construct
SEQUENCE: 571
QAKHKQRKRL KSSCKRHPLY VDFSDVGWND WIVAPPGYHA FYCHGECPFP LADHLNSTNH    60
AIVQTLVNSV NSKIPKACCV PTELSAISML YLDENEKVVL KNYQDMVVEG CGCRQAKHKQ   120
RKRLKSSCKR HPLYVDFSDV GWNDWIVAPP GYHAFYCHGE CPFPLADHLN STNHAIVQTL   180
```

```
VNSVNSKIPK ACCVPTELSA ISMLYLDENE KVVLKNYQDM VVEGCGCR              228

SEQ ID NO: 572         moltype = AA  length = 266
FEATURE                Location/Qualifiers
REGION                 1..266
                       note = Description of Artificial Sequence: Synthetic
                        polypeptide
source                 1..266
                       mol_type = protein
                       organism = synthetic construct
SEQUENCE: 572
QAKHKQRKRL KSSCKRHPLY VDFSDVGWND WIVAPPGYHA FYCHGECPFP LADHLNSTNH  60
AIVQTLVNSV NSKIPKACCV PTELSAISML YLDENEKVVL KNYQDMVVEG CGCRASGAGG  120
SEGGGSEGGT SGATGAGTST SGGGASTGGG TGQAKHKQRK RLKSSCKRHP LYVDFSDVGW  180
NDWIVAPPGY HAFYCHGECP FPLADHLNST NHAIVQTLVN SVNSKIPKAC CVPTELSAIS  240
MLYLDENEKV VLKNYQDMVV EGCGCR                                      266

SEQ ID NO: 573         moltype = AA  length = 151
FEATURE                Location/Qualifiers
REGION                 1..151
                       note = Description of Artificial Sequence: Synthetic
                        polypeptide
REGION                 37..38
                       note = NON_CONS - Residues at these positions can be
                        separated by a linker of unknown length
source                 1..151
                       mol_type = protein
                       organism = synthetic construct
SEQUENCE: 573
TGGSGEGGTG ASTGGSAGTG GSGGTTSGEA GGSSGAGQAK HKQRKRLKSS CKRHPLYVDF  60
SDVGWNDWIV APPGYHAFYC HGECPFPLAD HLNSTNHAIV QTLVNSVNSK IPKACCVPTE  120
LSAISMLYLD ENEKVVLKNY QDMVVEGCGC R                                151

SEQ ID NO: 574         moltype = AA  length = 189
FEATURE                Location/Qualifiers
REGION                 1..189
                       note = Description of Artificial Sequence: Synthetic
                        polypeptide
source                 1..189
                       mol_type = protein
                       organism = synthetic construct
SEQUENCE: 574
TGGSGEGGTG ASTGGSAGTG GSGGTTSGEA GGSSGAGASG AGGSEGGGSE GGTSGATGAG  60
TSTSGGGAST GGGTGQAKHK QRKRLKSSCK RHPLYVDFSD VGWNDWIVAP PGYHAFYCHG  120
ECPFPLADHL NSTNHAIVQT LVNSVNSKIP KACCVPTELS AISMLYLDEN EKVVLKNYQD  180
MVVEGCGCR                                                         189

SEQ ID NO: 575         moltype = AA  length = 119
FEATURE                Location/Qualifiers
REGION                 1..119
                       note = Description of Artificial Sequence: Synthetic
                        polypeptide
REGION                 5..6
                       note = NON_CONS - Residues at these positions can be
                        separated by a linker of unknown length
source                 1..119
                       mol_type = protein
                       organism = synthetic construct
SEQUENCE: 575
GAGTGQAKHK QRKRLKSSCK RHPLYVDFSD VGWNDWIVAP PGYHAFYCHG ECPFPLADHL  60
NSTNHAIVQT LVNSVNSKIP KACCVPTELS AISMLYLDEN EKVVLKNYQD MVVEGCGCR   119

SEQ ID NO: 576         moltype = AA  length = 157
FEATURE                Location/Qualifiers
REGION                 1..157
                       note = Description of Artificial Sequence: Synthetic
                        polypeptide
source                 1..157
                       mol_type = protein
                       organism = synthetic construct
SEQUENCE: 576
GAGTGASGAG GSEGGGSEGG TSGATGAGTS TSGGGASTGG GTGQAKHKQR KRLKSSCKRH  60
PLYVDFSDVG WNDWIVAPPG YHAFYCHGEC PFPLADHLNS TNHAIVQTLV NSVNSKIPKA  120
CCVPTELSAI SMLYLDENEK VVLKNYQDMV VEGCGCR                          157

SEQ ID NO: 577         moltype = AA  length = 126
FEATURE                Location/Qualifiers
REGION                 1..126
                       note = Description of Artificial Sequence: Synthetic
```

```
                          polypeptide
MOD_RES                   1
                          note = V, L, I, G, S, T or A
MOD_RES                   2
                          note = I, L, V, Q, T, S, G or A
MOD_RES                   3
                          note = G, A, V or S
MOD_RES                   4
                          note = E, D, L or G
MOD_RES                   5
                          note = S, T, P T, E or D
MOD_RES                   6
                          note = T or S
MOD_RES                   7
                          note = H, T or S
MOD_RES                   8
                          note = H or T
MOD_RES                   9
                          note = R, S, K, P or H
MOD_RES                   10
                          note = P, S, R or K
MOD_RES                   11
                          note = W, F, S, P, V, A or G
MOD_RES                   12
                          note = absent or is S, T G, or A
REGION                    12..13
                          note = NON_CONS - Residues at these positions can be
                           separated by a linker of unknown length
source                    1..126
                          mol_type = protein
                          organism = synthetic construct
SEQUENCE: 577
XXXXXXXXXX XXQAKHKQRK RLKSSCKRHP LYVDFSDVGW NDWIVAPPGY HAFYCHGECP   60
FPLADHLNST NHAIVQTLVN SVNSKIPKAC CVPTELSAIS MLYLDENEKV VLKNYQDMVV   120
EGCGCR                                                             126

SEQ ID NO: 578            moltype = AA  length = 164
FEATURE                   Location/Qualifiers
REGION                    1..164
                          note = Description of Artificial Sequence: Synthetic
                           polypeptide
MOD_RES                   1
                          note = V, L, I, G, S, T or A
MOD_RES                   2
                          note = I, L, V, Q, T, S, G or A
MOD_RES                   3
                          note = G, A, V or S
MOD_RES                   4
                          note = E, D, L or G
MOD_RES                   5
                          note = S, T, P T, E or D
MOD_RES                   6
                          note = T or S
MOD_RES                   7
                          note = H, T or S
MOD_RES                   8
                          note = H or T
MOD_RES                   9
                          note = R, S, K, P or H
MOD_RES                   10
                          note = P, S, R or K
MOD_RES                   11
                          note = W, F, S, P, V, A or G
MOD_RES                   12
                          note = absent or is S, T G, or A
source                    1..164
                          mol_type = protein
                          organism = synthetic construct
SEQUENCE: 578
XXXXXXXXXX XXASGAGGSE GGGSEGGTSG ATGAGTSTSG GGASTGGGTG QAKHKQRKRL   60
KSSCKRHPLY VDFSDVGWND WIVAPPGYHA FYCHGECPFP LADHLNSTNH AIVQTLVNSV   120
NSKIPKACCV PTELSAISML YLDENEKVVL KNYQDMVVEG CGCR                   164

SEQ ID NO: 579            moltype = AA  length = 126
FEATURE                   Location/Qualifiers
REGION                    1..126
                          note = Description of Artificial Sequence: Synthetic
                           polypeptide
REGION                    12..13
```

```
                        note = NON_CONS - Residues at these positions can be
                           separated by a linker of unknown length
source                  1..126
                        mol_type = protein
                        organism = synthetic construct
SEQUENCE: 579
AAADTTHHRP WTQAKHKQRK RLKSSCKRHP LYVDFSDVGW NDWIVAPPGY HAFYCHGECP     60
FPLADHLNST NHAIVQTLVN SVNSKIPKAC CVPTELSAIS MLYLDENEKV VLKNYQDMVV    120
EGCGCR                                                               126

SEQ ID NO: 580          moltype = AA   length = 164
FEATURE                 Location/Qualifiers
REGION                  1..164
                        note = Description of Artificial Sequence: Synthetic
                           polypeptide
source                  1..164
                        mol_type = protein
                        organism = synthetic construct
SEQUENCE: 580
AAADTTHHRP WTASGAGGSE GGGSEGGTSG ATGAGTSTSG GGASTGGGTG QAKHKQRKRL     60
KSSCKRHPLY VDFSDVGWND WIVAPPGYHA FYCHGECPFP LADHLNSTNH AIVQTLVNSV    120
NSKIPKACCV PTELSAISML YLDENEKVVL KNYQDMVVEG CGCR                     164

SEQ ID NO: 581          moltype = AA   length = 174
FEATURE                 Location/Qualifiers
REGION                  1..174
                        note = Description of Artificial Sequence: Synthetic
                           polypeptide
REGION                  60..61
                        note = NON_CONS - Residues at these positions can be
                           separated by a linker of unknown length
source                  1..174
                        mol_type = protein
                        organism = synthetic construct
SEQUENCE: 581
AAADTTHHRP WTAAADTTHH RPWTAAADTT HHRPWTAAAD TTHHRPWTAA ADTTHHRPWT     60
QAKHKQRKRL KSSCKRHPLY VDFSDVGWND WIVAPPGYHA FYCHGECPFP LADHLNSTNH    120
AIVQTLVNSV NSKIPKACCV PTELSAISML YLDENEKVVL KNYQDMVVEG CGCR          174

SEQ ID NO: 582          moltype = AA   length = 212
FEATURE                 Location/Qualifiers
REGION                  1..212
                        note = Description of Artificial Sequence: Synthetic
                           polypeptide
source                  1..212
                        mol_type = protein
                        organism = synthetic construct
SEQUENCE: 582
AAADTTHHRP WTAAADTTHH RPWTAAADTT HHRPWTAAAD TTHHRPWTAA ADTTHHRPWT     60
ASGAGGSEGG GSEGGTSGAT GAGTSTSGGG ASTGGGTGQA KHKQRKRLKS SCKRHPLYVD    120
FSDVGWNDWI VAPPGYHAFY CHGECPFPLA DHLNSTNHAI VQTLVNSVNS KIPKACCVPT    180
ELSAISMLYL DENEKVVLKN YQDMVVEGCG CR                                  212

SEQ ID NO: 583          moltype = AA   length = 174
FEATURE                 Location/Qualifiers
REGION                  1..174
                        note = Description of Artificial Sequence: Synthetic
                           polypeptide
REGION                  60..61
                        note = NON_CONS - Residues at these positions can be
                           separated by a linker of unknown length
source                  1..174
                        mol_type = protein
                        organism = synthetic construct
SEQUENCE: 583
LLADAAHHRP WTLLADAAHH RPWTLLADAA HHRPWTLLAD AAHHRPWTLL ADAAHHRPWT     60
QAKHKQRKRL KSSCKRHPLY VDFSDVGWND WIVAPPGYHA FYCHGECPFP LADHLNSTNH    120
AIVQTLVNSV NSKIPKACCV PTELSAISML YLDENEKVVL KNYQDMVVEG CGCR          174

SEQ ID NO: 584          moltype = AA   length = 212
FEATURE                 Location/Qualifiers
REGION                  1..212
                        note = Description of Artificial Sequence: Synthetic
                           polypeptide
source                  1..212
                        mol_type = protein
                        organism = synthetic construct
SEQUENCE: 584
LLADAAHHRP WTLLADAAHH RPWTLLADAA HHRPWTLLAD AAHHRPWTLL ADAAHHRPWT     60
```

```
ASGAGGSEGG GSEGGTSGAT GAGTSTSGGG ASTGGGTGQA KHKQRKRLKS SCKRHPLYVD    120
FSDVGWNDWI VAPPGYHAFY CHGECPFPLA DHLNSTNHAI VQTLVNSVNS KIPKACCVPT    180
ELSAISMLYL DENEKVVLKN YQDMVVEGCG CR                                  212

SEQ ID NO: 585          moltype = AA   length = 174
FEATURE                 Location/Qualifiers
REGION                  1..174
                        note = Description of Artificial Sequence: Synthetic
                        polypeptide
REGION                  60..61
                        note = NON_CONS - Residues at these positions can be
                        separated by a linker of unknown length
source                  1..174
                        mol_type = protein
                        organism = synthetic construct
SEQUENCE: 585
LLADTTAARP WTLLADTTAA RPWTLLADTT AARPWTLLAD TTAARPWTLL ADTTAARPWT    60
QAKHKQRKRL KSSCKRHPLY VDFSDVGWND WIVAPPGYHA FYCHGECPFP LADHLNSTNH    120
AIVQTLVNSV NSKIPKACCV PTELSAISML YLDENEKVVL KNYQDMVVEG CGCR          174

SEQ ID NO: 586          moltype = AA   length = 212
FEATURE                 Location/Qualifiers
REGION                  1..212
                        note = Description of Artificial Sequence: Synthetic
                        polypeptide
source                  1..212
                        mol_type = protein
                        organism = synthetic construct
SEQUENCE: 586
LLADTTAARP WTLLADTTAA RPWTLLADTT AARPWTLLAD TTAARPWTLL ADTTAARPWT    60
ASGAGGSEGG GSEGGTSGAT GAGTSTSGGG ASTGGGTGQA KHKQRKRLKS SCKRHPLYVD    120
FSDVGWNDWI VAPPGYHAFY CHGECPFPLA DHLNSTNHAI VQTLVNSVNS KIPKACCVPT    180
ELSAISMLYL DENEKVVLKN YQDMVVEGCG CR                                  212

SEQ ID NO: 587          moltype = AA   length = 138
FEATURE                 Location/Qualifiers
REGION                  1..138
                        note = Description of Artificial Sequence: Synthetic
                        polypeptide
REGION                  24..25
                        note = NON_CONS - Residues at these positions can be
                        separated by a linker of unknown length
source                  1..138
                        mol_type = protein
                        organism = synthetic construct
SEQUENCE: 587
LLADTTHHRP WTLLADTTHH RPWTQAKHKQ RKRLKSSCKR HPLYVDFSDV GWNDWIVAPP    60
GYHAFYCHGE CPFPLADHLN STNHAIVQTL VNSVNSKIPK ACCVPTELSA ISMLYLDENE    120
KVVLKNYQDM VVEGCGCR                                                  138

SEQ ID NO: 588          moltype = AA   length = 176
FEATURE                 Location/Qualifiers
REGION                  1..176
                        note = Description of Artificial Sequence: Synthetic
                        polypeptide
source                  1..176
                        mol_type = protein
                        organism = synthetic construct
SEQUENCE: 588
LLADTTHHRP WTLLADTTHH RPWTASGAGG SEGGGSEGGT SGATGAGTST SGGGASTGGG    60
TGQAKHKQRK RLKSSCKRHP LYVDFSDVGW NDWIVAPPGY HAFYCHGECP FPLADHLNST    120
NHAIVQTLVN SVNSKIPKAC CVPTELSAIS MLYLDENEKV VLKNYQDMVV EGCGCR        176

SEQ ID NO: 589          moltype = AA   length = 150
FEATURE                 Location/Qualifiers
REGION                  1..150
                        note = Description of Artificial Sequence: Synthetic
                        polypeptide
REGION                  36..37
                        note = NON_CONS - Residues at these positions can be
                        separated by a linker of unknown length
source                  1..150
                        mol_type = protein
                        organism = synthetic construct
SEQUENCE: 589
LLADTTHHRP WTLLADTTHH RPWTLLADTT HHRPWTQAKH KQRKRLKSSC KRHPLYVDFS    60
DVGWNDWIVA PPGYHAFYCH GECPFPLADH LNSTNHAIVQ TLVNSVNSKI PKACCVPTEL    120
SAISMLYLDE NEKVVLKNYQ DMVVEGCGCR                                     150
```

```
SEQ ID NO: 590            moltype = AA  length = 188
FEATURE                   Location/Qualifiers
REGION                    1..188
                          note = Description of Artificial Sequence: Synthetic
                          polypeptide
source                    1..188
                          mol_type = protein
                          organism = synthetic construct
SEQUENCE: 590
LLADTTHHRP WTLLADTTHH RPWTLLADTT HHRPWTASGA GGSEGGGSEG GTSGATGAGT      60
STSGGGASTG GGTGQAKHKQ RKRLKSSCKR HPLYVDFSDV GWNDWIVAPP GYHAFYCHGE     120
CPFPLADHLN STNHAIVQTL VNSVNSKIPK ACCVPTELSA ISMLYLDENE KVVLKNYQDM     180
VVEGCGCR                                                              188

SEQ ID NO: 591            moltype = AA  length = 174
FEATURE                   Location/Qualifiers
REGION                    1..174
                          note = Description of Artificial Sequence: Synthetic
                          polypeptide
REGION                    60..61
                          note = NON_CONS - Residues at these positions can be
                          separated by a linker of unknown length
source                    1..174
                          mol_type = protein
                          organism = synthetic construct
SEQUENCE: 591
LLADTTHHRP WTLLADTTHH RPWTLLADTT HHRPWTLLAD TTHHRPWTLL ADTTHHRPWT      60
QAKHKQRKRL KSSCKRHPLY VDFSDVGWND WIVAPPGYHA FYCHGECPFP LADHLNSTNH     120
AIVQTLVNSV NSKIPKACCV PTELSAISML YLDENEKVVL KNYQDMVVEG CGCR            174

SEQ ID NO: 592            moltype = AA  length = 212
FEATURE                   Location/Qualifiers
REGION                    1..212
                          note = Description of Artificial Sequence: Synthetic
                          polypeptide
source                    1..212
                          mol_type = protein
                          organism = synthetic construct
SEQUENCE: 592
LLADTTHHRP WTLLADTTHH RPWTLLADTT HHRPWTLLAD TTHHRPWTLL ADTTHHRPWT      60
ASGAGGSEGG GSEGGTSGAT GAGTSTSGGG ASTGGGTGQA KHKQRKRLKS SCKRHPLYVD     120
FSDVGWNDWI VAPPGYHAFY CHGECPFPLA DHLNSTNHAI VQTLVNSVNS KIPKACCVPT     180
ELSAISMLYL DENEKVVLKN YQDMVVEGCG CR                                   212

SEQ ID NO: 593            moltype = AA  length = 234
FEATURE                   Location/Qualifiers
REGION                    1..234
                          note = Description of Artificial Sequence: Synthetic
                          polypeptide
REGION                    120..121
                          note = NON_CONS - Residues at these positions can be
                          separated by a linker of unknown length
source                    1..234
                          mol_type = protein
                          organism = synthetic construct
SEQUENCE: 593
STSGSTVIGE STHHRPWSLI ADSTHHSPWT ILAESTHHKP WTILAETTHH RPWSIIGESS      60
HHKPFTGLGD TTHHRPWGVL GDTTHHKPWT IVADSTHHRP WTGQVLPTTT PSSPSTTSGS     120
QAKHKQRKRL KSSCKRHPLY VDFSDVGWND WIVAPPGYHA FYCHGECPFP LADHLNSTNH     180
AIVQTLVNSV NSKIPKACCV PTELSAISML YLDENEKVVL KNYQDMVVEG CGCR            234

SEQ ID NO: 594            moltype = AA  length = 272
FEATURE                   Location/Qualifiers
REGION                    1..272
                          note = Description of Artificial Sequence: Synthetic
                          polypeptide
source                    1..272
                          mol_type = protein
                          organism = synthetic construct
SEQUENCE: 594
STSGSTVIGE STHHRPWSLI ADSTHHSPWT ILAESTHHKP WTILAETTHH RPWSIIGESS      60
HHKPFTGLGD TTHHRPWGVL GDTTHHKPWT IVADSTHHRP WTGQVLPTTT PSSPSTTSGS     120
ASGAGGSEGG GSEGGTSGAT GAGTSTSGGG ASTGGGTGQA KHKQRKRLKS SCKRHPLYVD     180
FSDVGWNDWI VAPPGYHAFY CHGECPFPLA DHLNSTNHAI VQTLVNSVNS KIPKACCVPT     240
ELSAISMLYL DENEKVVLKN YQDMVVEGCG CR                                   272

SEQ ID NO: 595            moltype = AA  length = 162
FEATURE                   Location/Qualifiers
REGION                    1..162
```

```
                        note = Description of Artificial Sequence: Synthetic
                            polypeptide
REGION                  48..49
                        note = NON_CONS - Residues at these positions can be
                            separated by a linker of unknown length
source                  1..162
                        mol_type = protein
                        organism = synthetic construct
SEQUENCE: 595
LLADTTHHRP WTVIGESTHH RPWSIIGESS HHKPFTGLGD TTHHRPWGQA KHKQRKRLKS    60
SCKRHPLYVD FSDVGWNDWI VAPPGYHAFY CHGECPFPLA DHLNSTNHAI VQTLVNSVNS   120
KIPKACCVPT ELSAISMLYL DENEKVVLKN YQDMVVEGCG CR                     162

SEQ ID NO: 596          moltype = AA   length = 200
FEATURE                 Location/Qualifiers
REGION                  1..200
                        note = Description of Artificial Sequence: Synthetic
                            polypeptide
source                  1..200
                        mol_type = protein
                        organism = synthetic construct
SEQUENCE: 596
LLADTTHHRP WTVIGESTHH RPWSIIGESS HHKPFTGLGD TTHHRPWGAS GAGGSEGGGS    60
EGGTSGATGA GTSTSGGGAS TGGGTGQAKH KQRKRLKSSC KRHPLYVDFS DVGWNDWIVA   120
PPGYHAFYCH GECPFPLADH LNSTNHAIVQ TLVNSVNSKI PKACCVPTEL SAISMLYLDE   180
NEKVVLKNYQ DMVVEGCGCR                                              200

SEQ ID NO: 597          moltype = AA   length = 162
FEATURE                 Location/Qualifiers
REGION                  1..162
                        note = Description of Artificial Sequence: Synthetic
                            polypeptide
REGION                  48..49
                        note = NON_CONS - Residues at these positions can be
                            separated by a linker of unknown length
source                  1..162
                        mol_type = protein
                        organism = synthetic construct
SEQUENCE: 597
VIGESTHHRP WSIIGESSHH KPFTGLGDTT HHRPWGILAE STHHKPWTQA KHKQRKRLKS    60
SCKRHPLYVD FSDVGWNDWI VAPPGYHAFY CHGECPFPLA DHLNSTNHAI VQTLVNSVNS   120
KIPKACCVPT ELSAISMLYL DENEKVVLKN YQDMVVEGCG CR                     162

SEQ ID NO: 598          moltype = AA   length = 200
FEATURE                 Location/Qualifiers
REGION                  1..200
                        note = Description of Artificial Sequence: Synthetic
                            polypeptide
source                  1..200
                        mol_type = protein
                        organism = synthetic construct
SEQUENCE: 598
VIGESTHHRP WSIIGESSHH KPFTGLGDTT HHRPWGILAE STHHKPWTAS GAGGSEGGGS    60
EGGTSGATGA GTSTSGGGAS TGGGTGQAKH KQRKRLKSSC KRHPLYVDFS DVGWNDWIVA   120
PPGYHAFYCH GECPFPLADH LNSTNHAIVQ TLVNSVNSKI PKACCVPTEL SAISMLYLDE   180
NEKVVLKNYQ DMVVEGCGCR                                              200

SEQ ID NO: 599          moltype = AA   length = 1530
FEATURE                 Location/Qualifiers
REGION                  1..1530
                        note = Description of Artificial Sequence: Synthetic
                            polypeptide
MOD_RES                 13..1416
                        note = This region may encompass one or more of the
                            following sequences: "LLADTTHHRPWT" or "VIGESTHHRPWS" or
                            "LIADSTHHSPWT" or "ILAESTHHKPWT" or "ILAETTHHRPWS" or
                            "IIGESSHHKPFT" or "GLGDTTHHRPWG" or "VLGDTTHHKPWT" or
                            "IVADSTHHRPWT" or
MOD_RES                 13..1416
                        note = CONT. FROM ABOVE: "STADTSHHRPS" or "TSGGESTHHRPS" or
                            "TSGGESSHHKPS" or "TGSGDSSHHRPS" or "GSSGESTHHKPST" or
                            "VGADSTHHRPVT" or "GAADTTHHRPVT" or "AGADTTHHRPVT" or
                            "GGADTTHHRPAT" or "GGADTTHHRPGT" or
                            "LLADTTHHRPWTVIGESTHHRPWS"
MOD_RES                 13..1416
                        note = CONT. FROM ABOVE: or
                            "LLADTTHHRPWTVIGESTHHRPWSIIGESSHHKPFT" or
                            "LLADTTHHRPWTVIGESTHHRPWSIIGESSHHKPFTGLGDTTHHRPWGILAESTHHKP
                            WT" or "LLADTTHHRPWTILAESTHHKPWT" or
```

|  |  |
|---|---|
| | "LLADTTHHRPWTILAESTHHKPWTLLAD<br>TTHHRPWTILAESTHHKPWTLLADTTHHRPWT" or<br>"LLADTTHHRPWTGLGDTTHHRPWG" |
| MOD_RES | 13..1416<br>note = CONT. FROM ABOVE: or<br>"LLADTTHHRPWTGLGDTTHHRPWGLLADTTHHRPWT" or<br>"LLADTTHHRPWTGLGDTTHHRPWGLLADTTHHRPWTGLGDTTHHRPWGLLADTTHHRP<br>WT" or<br>"LLADTTHHRPWTGLGDTTHHRPWGLLADTTHHRPWTGLGDTTHHRPWGLLADTTHHRP<br>WTGLGDTTHHRPWGLLADTTHHRPWT" or<br>"STADTSHHRPSTSGGESTHHRPSTSGGESS |
| MOD_RES | 13..1416<br>note = CONT. FROM ABOVE: HHKPSTGSGDSSHHRPSGSSGESTHHKPST" or<br>"VGADSTHHR<br>PVTGAADTTHHRPVTAGADTTHHRPVTGGADTTHHRPATGGADTTHHRPGT" or<br>"STADTS<br>HHRPSLLADTTHHRPWTTSGGESTHHRPSVGADSTHHRPVTTSGGESSHHKPSGAADTT<br>HHRP VTTGSGDSSHHRPSGSSGESTHHKPSTGGADTTHHRPAT" or<br>"XXXXXXXXXXX" or |
| MOD_RES | 13..1416<br>note = CONT. FROM ABOVE: "AAADTTHHRPWT" or<br>"AAADTTHHRPWTAAADTTHHRPWTAA<br>ADTTHHRPWTAAADTTHHRPWTAAADTTHHRPWT" or<br>"LLADAAHHRPWTLLADAAHHRPW<br>TLLADAAHHRPWTLLADAAHHRPWTLLADAAHHRPWT" or<br>"LLADTTAARPWTLLADTTAA<br>RPWTLLADTTAARPWTLLADTTAARPWTLLADTTAARPWT" or<br>"LLADTTHHRPWTLLADT |
| MOD_RES | 13..1416<br>note = CONT. FROM ABOVE: THHRPWT" or<br>"LLADTTHHRPWTLLADTTHHRPWTLLADTTHH RPWT" or<br>"LLADTTHHRPWTLLADTTHHRPWTLLADTTHHRPWTLLADTTHHRPWTLLADT<br>THHRPWT" or<br>"STSGSTVIGESTHHRPWSLIADSTHHSPWTILAESTHHKPWTILAETTHH<br>RPWSIIGESSHHKPFTGLGDTTHHRPWGVLGDTTHHKPWTIVADSTHHRPWTGQVLPTT<br>TPSS |
| MOD_RES | 13..1416<br>note = CONT. FROM ABOVE: PSTTSGS" or<br>"LLADTTHHRPWTVIGESTHHRPWSIIGESSHH KPFTGLGDTTHHRPWG" or<br>"VIGESTHHRPWSIIGESSHHKPFTGLGDTTHHRPWGILAE STHHKPWT" and<br>wherein X's respectively = V, L, I, G, S, T or A; I, L, V,<br>Q, T, S, G or A; G, A, V or S; E, D, L or G; S, T, P |
| MOD_RES | 13..1416<br>note = CONT. FROM ABOVE: T, E or D; T or S; H, T or S; H or<br>T; R, S, K, P or H; P, S, R or K; W, F, S, P, V, A or G;<br>and absent, S, T G, or A |
| REGION | 1416..1417<br>note = NON_CONS - Residues at these positions can be<br>separated by a linker of unknown length |
| REGION | 1..1530<br>note = See specification as filed for detailed description<br>of substitutions and preferred embodiments |
| source | 1..1530<br>mol_type = protein<br>organism = synthetic construct |

SEQUENCE: 599

```
LLADTTHHRP WTXXXXXXXX XXXXXXXXX XXXXXXXXX XXXXXXXXX XXXXXXXXX   60
XXXXXXXXX XXXXXXXXX XXXXXXXXX XXXXXXXXX XXXXXXXXX XXXXXXXXX  120
XXXXXXXXX XXXXXXXXX XXXXXXXXX XXXXXXXXX XXXXXXXXX XXXXXXXXX  180
XXXXXXXXX XXXXXXXXX XXXXXXXXX XXXXXXXXX XXXXXXXXX XXXXXXXXX  240
XXXXXXXXX XXXXXXXXX XXXXXXXXX XXXXXXXXX XXXXXXXXX XXXXXXXXX  300
XXXXXXXXX XXXXXXXXX XXXXXXXXX XXXXXXXXX XXXXXXXXX XXXXXXXXX  360
XXXXXXXXX XXXXXXXXX XXXXXXXXX XXXXXXXXX XXXXXXXXX XXXXXXXXX  420
XXXXXXXXX XXXXXXXXX XXXXXXXXX XXXXXXXXX XXXXXXXXX XXXXXXXXX  480
XXXXXXXXX XXXXXXXXX XXXXXXXXX XXXXXXXXX XXXXXXXXX XXXXXXXXX  540
XXXXXXXXX XXXXXXXXX XXXXXXXXX XXXXXXXXX XXXXXXXXX XXXXXXXXX  600
XXXXXXXXX XXXXXXXXX XXXXXXXXX XXXXXXXXX XXXXXXXXX XXXXXXXXX  660
XXXXXXXXX XXXXXXXXX XXXXXXXXX XXXXXXXXX XXXXXXXXX XXXXXXXXX  720
XXXXXXXXX XXXXXXXXX XXXXXXXXX XXXXXXXXX XXXXXXXXX XXXXXXXXX  780
XXXXXXXXX XXXXXXXXX XXXXXXXXX XXXXXXXXX XXXXXXXXX XXXXXXXXX  840
XXXXXXXXX XXXXXXXXX XXXXXXXXX XXXXXXXXX XXXXXXXXX XXXXXXXXX  900
XXXXXXXXX XXXXXXXXX XXXXXXXXX XXXXXXXXX XXXXXXXXX XXXXXXXXX  960
XXXXXXXXX XXXXXXXXX XXXXXXXXX XXXXXXXXX XXXXXXXXX XXXXXXXXX 1020
XXXXXXXXX XXXXXXXXX XXXXXXXXX XXXXXXXXX XXXXXXXXX XXXXXXXXX 1080
XXXXXXXXX XXXXXXXXX XXXXXXXXX XXXXXXXXX XXXXXXXXX XXXXXXXXX 1140
XXXXXXXXX XXXXXXXXX XXXXXXXXX XXXXXXXXX XXXXXXXXX XXXXXXXXX 1200
XXXXXXXXX XXXXXXXXX XXXXXXXXX XXXXXXXXX XXXXXXXXX XXXXXXXXX 1260
XXXXXXXXX XXXXXXXXX XXXXXXXXX XXXXXXXXX XXXXXXXXX XXXXXXXXX 1320
XXXXXXXXX XXXXXXXXX XXXXXXXXX XXXXXXXXX XXXXXXXXX XXXXXXXXX 1380
```

```
XXXXXXXXXX XXXXXXXXXX XXXXXXXXXX XXXXXXQAKH KQRKRLKSSC KRHPLYVDFS   1440
DVGWNDWIVA PPGYHAFYCH GECPFPLADH LNSTNHAIVQ TLVNSVNSKI PKACCVPTEL   1500
SAISMLYLDE NEKVVLKNYQ DMVVEGCGCR                                   1530

SEQ ID NO: 600            moltype = AA  length = 1568
FEATURE                   Location/Qualifiers
REGION                    1..1568
                          note = Description of Artificial Sequence: Synthetic
                          polypeptide
MOD_RES                   13..1416
                          note = This region may encompass one or more of the
                          following sequences: "LLADTTHHRPWT" or "VIGESTHHRPWS" or
                          "LIADSTHHSPWT" or "ILAESTHHKPWT" or "ILAETTHHRPWS" or
                          "IIGESSHHKPFT" or "GLGDTTHHRPWG" or "VLGDTTHHKPWT" or
                          "IVADSTHHRPWT" or
MOD_RES                   13..1416
                          note = CONT. FROM ABOVE: "STADTSHHRPS" or "TSGGESTHHRPS" or
                          "TSGGESSHHKPS" or "TSGDSSHHRPS" or "GSSGESTHHKPST" or
                          "VGADSTHHRPVT" or "GAADTTHHRPVT" or "AGADTTHHRPVT" or
                          "GGADTTHHRPAT" or "GGADTTHHRPGT" or
                          "LLADTTHHRPWTVIGESTHHRPWS"
MOD_RES                   13..1416
                          note = CONT. FROM ABOVE: or
                          "LLADTTHHRPWTVIGESTHHRPWSIIGESSHHKPFT" or
                          "LLADTTHHRPWTVIGESTHHRPWSIIGESSHHKPFTGLGDTTHHRPWGILAESTHHKP
                          WT" or "LLADTTHHRPWTILAESTHHKPWT" or
                          "LLADTTHHRPWTILAESTHHKPWTLLAD
                          TTHHRPWTILAESTHHKPWTLLADTTHHRPWT" or
                          "LLADTTHHRPWTGLGDTTHHRPWG"
MOD_RES                   13..1416
                          note = CONT. FROM ABOVE: or
                          "LLADTTHHRPWTGLGDTTHHRPWGLLADTTHHRPWT" or
                          "LLADTTHHRPWTGLGDTTHHRPWGLLADTTHHRPWTGLGDTTHHRPWGLLADTTHHRP
                          WT" or
                          "LLADTTHHRPWTGLGDTTHHRPWGLLADTTHHRPWTGLGDTTHHRPWGLLADTTHHRP
                          WTGLGDTTHHRPWGLLADTTHHRPWT" or
                          "STADTSHHRPSTSGGESTHHRPSTSGGESS
MOD_RES                   13..1416
                          note = CONT. FROM ABOVE: HHKPSTGSGDSSHHRPSGSSGESTHHKPST" or
                          "VGADSTHHR
                          PVTGAADTTHHRPVTAGADTTHHRPVTGGADTTHHRPATGGADTTHHRPGT" or
                          "STADTS
                          HHRPSLLADTTHHRPWTTSGGESTHHRPSVGADSTHHRPVTTSGGESSHHKPSGAADTT
                          HHRP VTTGSGDSSHHRPSGSSGESTHHKPSTGGADTTHHRPAT" or
                          "XXXXXXXXXXXX" or
MOD_RES                   13..1416
                          note = CONT. FROM ABOVE: "AAADTTHHRPWT" or
                          "AAADTTHHRPWTAAADTTHHRPWTAA
                          ADTTHHRPWTAAADTTHHRPWTAAADTTHHRPWT" or
                          "LLADAAHHRPWTLLADAAHHRPW
                          TLLADAAHHRPWTLLADAAHHRPWTLLADAAHHRPWT" or
                          "LLADTTAARPWTLLADTTAA
                          RPWTLLADTTAARPWTLLADTTAARPWTLLADTTAARPWT" or
                          "LLADTTHHRPWTLLADT
MOD_RES                   13..1416
                          note = CONT. FROM ABOVE: THHRPWT" or
                          "LLADTTHHRPWTLLADTTHHRPWTLLADTTHH RPWT" or
                          "LLADTTHHRPWTLLADTTHHRPWTLLADTTHHRPWTLLADTTHHRPWTLLADT
                          THHRPWT" or
                          "STSGSTVIGESTHHRPWSLIADSTHHSPWTILAESTHHKPWTILAETTHH
                          RPWSIIGESSHHKPFTGLGDTTHHRPWGVLGDTTHHKPWTIVADSTHHRPWTGQVLPTT
                          TPSS
MOD_RES                   13..1416
                          note = CONT. FROM ABOVE: PSTTSGS" or
                          "LLADTTHHRPWTVIGESTHHRPWSIIGESSHH KPFTGLGDTTHHRPWG" or
                          "VIGESTHHRPWSIIGESSHHKPFTGLGDTTHHRPWGILAE STHHKPWT" and
                          wherein X's respectively = V, L, I, G, S, T or A; I, L, V,
                          Q, T, S, G or A; G, A, V or S; E, D, L or G; S, T, P
MOD_RES                   13..1416
                          note = CONT. FROM ABOVE: T, E or D; T or S; H, T or S; H or
                          T; R, S, K, P or H; P, S, R or K; W, F, S, P, V, A or G;
                          and absent, S, T G, or A
REGION                    1..1568
                          note = See specification as filed for detailed description
                          of substitutions and preferred embodiments
source                    1..1568
                          mol_type = protein
                          organism = synthetic construct
SEQUENCE: 600
```

```
LLADTTHHRP WTXXXXXXXX XXXXXXXXX XXXXXXXXX XXXXXXXXX XXXXXXXXX   60
XXXXXXXXX XXXXXXXXX XXXXXXXXX XXXXXXXXX XXXXXXXXX XXXXXXXXX   120
XXXXXXXXX XXXXXXXXX XXXXXXXXX XXXXXXXXX XXXXXXXXX XXXXXXXXX   180
XXXXXXXXX XXXXXXXXX XXXXXXXXX XXXXXXXXX XXXXXXXXX XXXXXXXXX   240
XXXXXXXXX XXXXXXXXX XXXXXXXXX XXXXXXXXX XXXXXXXXX XXXXXXXXX   300
XXXXXXXXX XXXXXXXXX XXXXXXXXX XXXXXXXXX XXXXXXXXX XXXXXXXXX   360
XXXXXXXXX XXXXXXXXX XXXXXXXXX XXXXXXXXX XXXXXXXXX XXXXXXXXX   420
XXXXXXXXX XXXXXXXXX XXXXXXXXX XXXXXXXXX XXXXXXXXX XXXXXXXXX   480
XXXXXXXXX XXXXXXXXX XXXXXXXXX XXXXXXXXX XXXXXXXXX XXXXXXXXX   540
XXXXXXXXX XXXXXXXXX XXXXXXXXX XXXXXXXXX XXXXXXXXX XXXXXXXXX   600
XXXXXXXXX XXXXXXXXX XXXXXXXXX XXXXXXXXX XXXXXXXXX XXXXXXXXX   660
XXXXXXXXX XXXXXXXXX XXXXXXXXX XXXXXXXXX XXXXXXXXX XXXXXXXXX   720
XXXXXXXXX XXXXXXXXX XXXXXXXXX XXXXXXXXX XXXXXXXXX XXXXXXXXX   780
XXXXXXXXX XXXXXXXXX XXXXXXXXX XXXXXXXXX XXXXXXXXX XXXXXXXXX   840
XXXXXXXXX XXXXXXXXX XXXXXXXXX XXXXXXXXX XXXXXXXXX XXXXXXXXX   900
XXXXXXXXX XXXXXXXXX XXXXXXXXX XXXXXXXXX XXXXXXXXX XXXXXXXXX   960
XXXXXXXXX XXXXXXXXX XXXXXXXXX XXXXXXXXX XXXXXXXXX XXXXXXXXX  1020
XXXXXXXXX XXXXXXXXX XXXXXXXXX XXXXXXXXX XXXXXXXXX XXXXXXXXX  1080
XXXXXXXXX XXXXXXXXX XXXXXXXXX XXXXXXXXX XXXXXXXXX XXXXXXXXX  1140
XXXXXXXXX XXXXXXXXX XXXXXXXXX XXXXXXXXX XXXXXXXXX XXXXXXXXX  1200
XXXXXXXXX XXXXXXXXX XXXXXXXXX XXXXXXXXX XXXXXXXXX XXXXXXXXX  1260
XXXXXXXXX XXXXXXXXX XXXXXXXXX XXXXXXXXX XXXXXXXXX XXXXXXXXX  1320
XXXXXXXXX XXXXXXXXX XXXXXXXXX XXXXXXXXX XXXXXXXXX XXXXXXXXX  1380
XXXXXXXXX XXXXXXXXX XXXXXXXXX XXXXXXASGA GGSEGGGSEG GTSGATGAGT 1440
STSGGGASTG GGTGQAKHKQ RKRLKSSCKR HPLYVDFSDV GWNDWIVAPP GYHAFYCHGE 1500
CPFPLADHLN STNHAIVQTL VNSVNSKIPK ACCVPTELSA ISMLYLDENE KVVLKNYQDM 1560
VVEGCGCR                                                     1568

SEQ ID NO: 601         moltype = AA  length = 1530
FEATURE                Location/Qualifiers
REGION                 1..1530
                       note = Description of Artificial Sequence: Synthetic
                       polypeptide
MOD_RES                13..1416
                       note = This region may encompass one or more of the
                       following sequences: "LLADTTHHRPWT" or "VIGESTHHRPWS" or
                       "LIADSTHHSPWT" or "ILAESTHHKPWT" or "ILAETTHHRPWS" or
                       "IIGESSHHKPFT" or "GLGDTTHHRPWG" or "VLGDTTHHKPWT" or
                       "IVADSTHHRPWT" or
MOD_RES                13..1416
                       note = CONT. FROM ABOVE: "STADTSHHRPS" or "TSGGESTHHRPS" or
                       "TSGGESSHHKPS" or "TGSGDSSHHRPS" or "GSSGESTHHKPST" or
                       "VGADSTHHRPVT" or "GAADTTHHRPVT" or "AGADTTHHRPVT" or
                       "GGADTTHHRPAT" or "GGADTTHHRPGT" or
                       "LLADTTHHRPWTVIGESTHHRPWS"
MOD_RES                13..1416
                       note = CONT. FROM ABOVE: or
                       "LLADTTHHRPWTVIGESTHHRPWSIIGESSHHKPFT" or
                       "LLADTTHHRPWTVIGESTHHRPWSIIGESSHHKPFTGLGDTTHHRPWGILAESTHHKP
                       WT" or "LLADTTHHRPWTILAESTHHKPWT" or
                       "LLADTTHHRPWTILAESTHHKPWTLLAD
                       TTHHRPWTILAESTHHKPWTLLADTTHHRPWT" or
                       "LLADTTHHRPWTGLGDTTHHRPWG"
MOD_RES                13..1416
                       note = CONT. FROM ABOVE: or
                       "LLADTTHHRPWTGLGDTTHHRPWGLLADTTHHRPWT" or
                       "LLADTTHHRPWTGLGDTTHHRPWGLLADTTHHRPWTGLGDTTHHRPWGLLADTTHHRP
                       WT" or
                       "LLADTTHHRPWTGLGDTTHHRPWGLLADTTHHRPWTGLGDTTHHRPWGLLADTTHHRP
                         WTGLGDTTHHRPWGLLADTTHHRPWT" or
                       "STADTSHHRPSTSGGESTHHRPSTSGGESS
MOD_RES                13..1416
                       note = CONT. FROM ABOVE: HHKPSTGSGDSSHHRPSGSSGESTHHKPST" or
                       "VGADSTHHR
                       PVTGAADTTHHRPVTAGADTTHHRPVTGGADTTHHRPATGGADTTHHRPGT" or
                       "STADTS
                       HHRPSLLADTTHHRPWTTSGGESTHHRPSVGADSTHHRPVTTSGGESSHHKPSGAADTT
                       HHRP VTTGSGDSSHHRPSGSSGESTHHKPSTGGADTTHHRPAT" or
                       "XXXXXXXXXXXX" or
MOD_RES                13..1416
                       note = CONT. FROM ABOVE: "AAADTTHHRPWT" or
                       "AAADTTHHRPWTAAADTTHHRPWTAA
                       ADTTHHRPWTAAADTTHHRPWTAAADTTHHRPWT" or
                       "LLADAAHHRPWTLLADAAHHRPW
                       TLLADAAHHRPWTLLADAAHHRPWTLLADAAHHRPWT" or
                       "LLADTTAARPWTLLADTTAA
                       RPWTLLADTTAARPWTLLADTTAARPWTLLADTTAARPWT" or
                       "LLADTTHHRPWTLLADT
MOD_RES                13..1416
```

|  |  |
|---|---|
|  | note = CONT. FROM ABOVE: THHRPWT" or<br>"LLADTTHHRPWTLLADTTHHRPWTLLADTTHH RPWT" or<br>"LLADTTHHRPWTLLADTTHHRPWTLLADTTHHRPWTLLADT<br>THHRPWT" or<br>"STSGSTVIGESTHHRPWSLIADSTHHSPWTILAESTHHKPWTILAETTHH<br>RPWSIIGESSHHKPFTGLGDTTHHRPWGVLGDTTHHKPWTIVADSTHHRPWTGQVLPTT<br>TPSS |
| MOD_RES | 13..1416 |
|  | note = CONT. FROM ABOVE: PSTTSGS" or<br>"LLADTTHHRPWTVIGESTHHRPWSIIGESSHH KPFTGLGDTTHHRPWG" or<br>"VIGESTHHRPWSIIGESSHHKPFTGLGDTTHHRPWGILAE STHHKPWT" and<br>wherein X's respectively = V, L, I, G, S, T or A; I, L, V,<br>Q, T, S, G or A; G, A, V or S; E, D, L or G; S, T, P |
| MOD_RES | 13..1416 |
|  | note = CONT. FROM ABOVE: T, E or D; T or S; H, T or S; H or<br>T; R, S, K, P or H; P, S, R or K; W, F, S, P, V, A or G;<br>and absent, S, T G, or A |
| REGION | 1416..1417 |
|  | note = NON_CONS - Residues at these positions can be<br>separated by a linker of unknown length |
| REGION | 1..1530 |
|  | note = See specification as filed for detailed description<br>of substitutions and preferred embodiments |
| source | 1..1530<br>mol_type = protein<br>organism = synthetic construct |

SEQUENCE: 601
```
VIGESTHHRP WSXXXXXXXX XXXXXXXXXX XXXXXXXXXX XXXXXXXXXX XXXXXXXXXX    60
XXXXXXXXXX XXXXXXXXXX XXXXXXXXXX XXXXXXXXXX XXXXXXXXXX XXXXXXXXXX   120
XXXXXXXXXX XXXXXXXXXX XXXXXXXXXX XXXXXXXXXX XXXXXXXXXX XXXXXXXXXX   180
XXXXXXXXXX XXXXXXXXXX XXXXXXXXXX XXXXXXXXXX XXXXXXXXXX XXXXXXXXXX   240
XXXXXXXXXX XXXXXXXXXX XXXXXXXXXX XXXXXXXXXX XXXXXXXXXX XXXXXXXXXX   300
XXXXXXXXXX XXXXXXXXXX XXXXXXXXXX XXXXXXXXXX XXXXXXXXXX XXXXXXXXXX   360
XXXXXXXXXX XXXXXXXXXX XXXXXXXXXX XXXXXXXXXX XXXXXXXXXX XXXXXXXXXX   420
XXXXXXXXXX XXXXXXXXXX XXXXXXXXXX XXXXXXXXXX XXXXXXXXXX XXXXXXXXXX   480
XXXXXXXXXX XXXXXXXXXX XXXXXXXXXX XXXXXXXXXX XXXXXXXXXX XXXXXXXXXX   540
XXXXXXXXXX XXXXXXXXXX XXXXXXXXXX XXXXXXXXXX XXXXXXXXXX XXXXXXXXXX   600
XXXXXXXXXX XXXXXXXXXX XXXXXXXXXX XXXXXXXXXX XXXXXXXXXX XXXXXXXXXX   660
XXXXXXXXXX XXXXXXXXXX XXXXXXXXXX XXXXXXXXXX XXXXXXXXXX XXXXXXXXXX   720
XXXXXXXXXX XXXXXXXXXX XXXXXXXXXX XXXXXXXXXX XXXXXXXXXX XXXXXXXXXX   780
XXXXXXXXXX XXXXXXXXXX XXXXXXXXXX XXXXXXXXXX XXXXXXXXXX XXXXXXXXXX   840
XXXXXXXXXX XXXXXXXXXX XXXXXXXXXX XXXXXXXXXX XXXXXXXXXX XXXXXXXXXX   900
XXXXXXXXXX XXXXXXXXXX XXXXXXXXXX XXXXXXXXXX XXXXXXXXXX XXXXXXXXXX   960
XXXXXXXXXX XXXXXXXXXX XXXXXXXXXX XXXXXXXXXX XXXXXXXXXX XXXXXXXXXX  1020
XXXXXXXXXX XXXXXXXXXX XXXXXXXXXX XXXXXXXXXX XXXXXXXXXX XXXXXXXXXX  1080
XXXXXXXXXX XXXXXXXXXX XXXXXXXXXX XXXXXXXXXX XXXXXXXXXX XXXXXXXXXX  1140
XXXXXXXXXX XXXXXXXXXX XXXXXXXXXX XXXXXXXXXX XXXXXXXXXX XXXXXXXXXX  1200
XXXXXXXXXX XXXXXXXXXX XXXXXXXXXX XXXXXXXXXX XXXXXXXXXX XXXXXXXXXX  1260
XXXXXXXXXX XXXXXXXXXX XXXXXXXXXX XXXXXXXXXX XXXXXXXXXX XXXXXXXXXX  1320
XXXXXXXXXX XXXXXXXXXX XXXXXXXXXX XXXXXXXXXX XXXXXXXXXX XXXXXXXXXX  1380
XXXXXXXXXX XXXXXXXXXX XXXXXXXXXX XXXXXXQAKH KQRKRLKSSC KRHPLYVDFS  1440
DVGWNDWIVA PPGYHAFYCH GECPFPLADH LNSTNHAIVQ TLVNSVNSKI PKACCVPTEL  1500
SAISMLYLDE NEKVVLKNYQ DMVVEGCGCR                                   1530
```

|  |  |
|---|---|
| SEQ ID NO: 602<br>FEATURE<br>REGION | moltype = AA   length = 1568<br>Location/Qualifiers<br>1..1568 |
|  | note = Description of Artificial Sequence: Synthetic<br>polypeptide |
| MOD_RES | 13..1416 |
|  | note = This region may encompass one or more of the<br>following sequences: "LLADTTHHRPWT" or "VIGESTHHRPWS" or<br>"LIADSTHHSPWT" or "ILAESTHHKPWT" or "ILAETTHHRPWS" or<br>"IIGESSHHKPFT" or "GLGDTTHHRPWG" or "VLGDTTHHKPWT" or<br>"IVADSTHHRPWT" or |
| MOD_RES | 13..1416 |
|  | note = CONT. FROM ABOVE: "STADTSHHRPS" or "TSGGESTHHRPS" or<br>"TSGGESSHHKPS" or "TGSGDSSHHRPS" or "GSSGESTHHKPST" or<br>"VGADSTHHRPVT" or "GAADTTHHRPVT" or "AGADTTHHRPVT" or<br>"GGADTTHHRPAT" or "GGADTTHHRPGT" or<br>"LLADTTHHRPWTVIGESTHHRPWS" |
| MOD_RES | 13..1416 |
|  | note = CONT. FROM ABOVE: or<br>"LLADTTHHRPWTVIGESTHHRPWSIIGESSHHKPFT" or<br>"LLADTTHHRPWTVIGESTHHRPWSIIGESSHHKPFTGLGDTTHHRPWGILAESTHHKP<br>WT" or "LLADTTHHRPWTILAESTHHKPWT" or<br>"LLADTTHHRPWTILAESTHHKPWTLLAD<br>TTHHRPWTILAESTHHKPWTLLADTTHHRPWT" or<br>"LLADTTHHRPWTGLGDTTHHRPWG" |

| | | |
|---|---|---|
| MOD_RES | 13..1416 | |
| | note = CONT. FROM ABOVE: or "LLADTTHHRPWTGLGDTTHHRPWGLLADTTHHRPWT" or "LLADTTHHRPWTGLGDTTHHRPWGLLADTTHHRPWTGLGDTTHHRPWGLLADTTHHRPWT" or "LLADTTHHRPWTGLGDTTHHRPWGLLADTTHHRPWTGLGDTTHHRPWGLLADTTHHRPWTGLGDTTHHRPWGLLADTTHHRPWT" or "STADTSHHRPSTSGGESTHHRPSTSGGESS | |
| MOD_RES | 13..1416 | |
| | note = CONT. FROM ABOVE: HHKPSTGSGDSSHHRPSGSSGESTHHKPST" or "VGADSTHHR PVTGAADTTHHRPVTAGADTTHHRPVTGGADTTHHRPATGGADTTHHRPGT" or "STADTS HHRPSLLADTTHHRPWTTSGGESTHHRPSVGADSTHHRPVTTSGGESSHHKPSGAADTT HHRP VTTGSGDSSHHRPSGSSGESTHHKPSTGGADTTHHRPAT" or "XXXXXXXXXXX" or | |
| MOD_RES | 13..1416 | |
| | note = CONT. FROM ABOVE: "AAADTTHHRPWT" or "AAADTTHHRPWTAAADTTHHRPWTAA ADTTHHRPWTAAADTTHHRPWTAAADTTHHRPWT" or "LLADAAHHRPWTLLADAAHHRPW TLLADAAHHRPWTLLADAAHHRPWTLLADAAHHRPWT" or "LLADTTAARPWTLLADTTAA RPWTLLADTTAARPWTLLADTTAARPWTLLADTTAARPWT" or "LLADTTHHRPWTLLADT | |
| MOD_RES | 13..1416 | |
| | note = CONT. FROM ABOVE: THHRPWT" or "LLADTTHHRPWTLLADTTHHRPWTLLADTTHH RPWT" or "LLADTTHHRPWTLLADTTHHRPWTLLADTTHHRPWTLLADTTHHRPWTLLADT THHRPWT" or "STSGSTVIGESTHHRPWSLIADSTHHSPWTILAESTHHKPWTILAETTHH RPWSIIGESSHHKPFTGLGDTTHHRPWGVLGDTTHHKPWTIVADSTHHRPWTGQVLPTT T

```
FEATURE                 Location/Qualifiers
REGION                  1..1530
                        note = Description of Artificial Sequence: Synthetic
                        polypeptide
MOD_RES                 13..1416
                        note = This region may encompass one or more of the
                        following sequences: "LLADTTHHRPWT" or "VIGESTHHRPWS" or
                        "LIADSTHHSPWT" or "ILAESTHHKPWT" or "ILAETTHHRPWS" or
                        "IIGESSHHKPFT" or "GLGDTTHHRPWG" or "VLGDTTHHKPWT" or
                        "IVADSTHHRPWT" or
MOD_RES                 13..1416
                        note = CONT. FROM ABOVE: "STADTSHHRPS" or "TSGGESTHHRPS" or
                        "TSGGESSHHKPS" or "TGSGDSSHHRPS" or "GSSGESTHHKPST" or
                        "VGADSTHHRPVT" or "GAADTTHHRPVT" or "AGADTTHHRPVT" or
                        "GGADTTHHRPAT" or "GGADTTHHRPGT" or
                        "LLADTTHHRPWTVIGESTHHRPWS"
MOD_RES                 13..1416
                        note = CONT. FROM ABOVE: or
                        "LLADTTHHRPWTVIGESTHHRPWSIIGESSHHKPFT" or
                        "LLADTTHHRPWTVIGESTHHRPWSIIGESSHHKPFTGLGDTTHHRPWGILAESTHHKP
                        WT" or "LLADTTHHRPWTILAESTHHKPWT" or
                        "LLADTTHHRPWTILAESTHHKPWTLLAD
                        TTHHRPWTILAESTHHKPWTLLADTTHHRPWT" or
                        "LLADTTHHRPWTGLGDTTHHRPWG"
MOD_RES                 13..1416
                        note = CONT. FROM ABOVE: or
                        "LLADTTHHRPWTGLGDTTHHRPWGLLADTTHHRPWT" or
                        "LLADTTHHRPWTGLGDTTHHRPWGLLADTTHHRPWTGLGDTTHHRPWGLLADTTHHRP
                        WT" or
                        "LLADTTHHRPWTGLGDTTHHRPWGLLADTTHHRPWTGLGDTTHHRPWGLLADTTHHRP
                         WTGLGDTTHHRPWGLLADTTHHRPWT" or
                        "STADTSHHRPSTSGGESTHHRPSTSGGESS
MOD_RES                 13..1416
                        note = CONT. FROM ABOVE: HHKPSTGSGDSSHHRPSGSSGESTHHKPST" or
                        "VGADSTHHR
                        PVTGAADTTHHRPVTAGADTTHHRPVTGGADTTHHRPATGGADTTHHRPGT" or
                        "STADTS
                        HHRPSLLADTTHHRPWTTSGGESTHHRPSVGADSTHHRPVTTSGGESSHHKPSGAADTT
                        HHRP VTTGSGDSSHHRPSGSSGESTHHKPSTGGADTTHHRPAT" or
                        "XXXXXXXXXXX" or
MOD_RES                 13..1416
                        note = CONT. FROM ABOVE: "AAADTTHHRPWT" or
                        "AAADTTHHRPWTAAADTTHHRPWTAA
                        ADTTHHRPWTAAADTTHHRPWTAAADTTHHRPWT" or
                        "LLADAAHHRPWTLLADAAHHRPW
                        TLLADAAHHRPWTLLADAAHHRPWTLLADAAHHRPWT" or
                        "LLADTTAARPWTLLADTTAA
                        RPWTLLADTTAARPWTLLADTTAARPWTLLADTTAARPWT" or
                        "LLADTTHHRPWTLLADT
MOD_RES                 13..1416
                        note = CONT. FROM ABOVE: THHRPWT" or
                        "LLADTTHHRPWTLLADTTHHRPWTLLADTTHH RPWT" or
                        "LLADTTHHRPWTLLADTTHHRPWTLLADTTHHRPWTLLADTTHHRPWTLLADT
                        THHRPWT" or
                        "STSGSTVIGESTHHRPWSLIADSTHHSPWTILAESTHHKPWTILAETTHH
                        RPWSIIGESSHHKPFTGLGDTTHHRPWGVLGDTTHHKPWTIVADSTHHRPWTGQVLPTT
                        TPSS
MOD_RES                 13..1416
                        note = CONT. FROM ABOVE: PSTTSGS" or
                        "LLADTTHHRPWTVIGESTHHRPWSIIGESSHH KPFTGLGDTTHHRPWG" or
                        "VIGESTHHRPWSIIGESSHHKPFTGLGDTTHHRPWGILAE STHHKPWT" and
                        wherein X's respectively = V, L, I, G, S, T or A; I, L, V,
                        Q, T, S, G or A; G, A, V or S; E, D, L or G; S, T, P
MOD_RES                 13..1416
                        note = CONT. FROM ABOVE: T, E or D; T or S; H, T or S; H or
                        T; R, S, K, P or H; P, S, R or K; W, F, S, P, V, A or G;
                        and absent, S, T G, or A
REGION                  1416..1417
                        note = NON_CONS - Residues at these positions can be
                        separated by a linker of unknown length
REGION                  1..1530
                        note = See specification as filed for detailed description
                        of substitutions and preferred embodiments
source                  1..1530
                        mol_type = protein
                        organism = synthetic construct
SEQUENCE: 603
ILAESTHHKP WTXXXXXXXX XXXXXXXXX  XXXXXXXXX  XXXXXXXXX  XXXXXXXXX    60
XXXXXXXXX  XXXXXXXXXX XXXXXXXXX  XXXXXXXXX  XXXXXXXXX  XXXXXXXXX   120
```

```
XXXXXXXXXX XXXXXXXXXX XXXXXXXXXX XXXXXXXXXX XXXXXXXXXX XXXXXXXXXX    180
XXXXXXXXXX XXXXXXXXXX XXXXXXXXXX XXXXXXXXXX XXXXXXXXXX XXXXXXXXXX    240
XXXXXXXXXX XXXXXXXXXX XXXXXXXXXX XXXXXXXXXX XXXXXXXXXX XXXXXXXXXX    300
XXXXXXXXXX XXXXXXXXXX XXXXXXXXXX XXXXXXXXXX XXXXXXXXXX XXXXXXXXXX    360
XXXXXXXXXX XXXXXXXXXX XXXXXXXXXX XXXXXXXXXX XXXXXXXXXX XXXXXXXXXX    420
XXXXXXXXXX XXXXXXXXXX XXXXXXXXXX XXXXXXXXXX XXXXXXXXXX XXXXXXXXXX    480
XXXXXXXXXX XXXXXXXXXX XXXXXXXXXX XXXXXXXXXX XXXXXXXXXX XXXXXXXXXX    540
XXXXXXXXXX XXXXXXXXXX XXXXXXXXXX XXXXXXXXXX XXXXXXXXXX XXXXXXXXXX    600
XXXXXXXXXX XXXXXXXXXX XXXXXXXXXX XXXXXXXXXX XXXXXXXXXX XXXXXXXXXX    660
XXXXXXXXXX XXXXXXXXXX XXXXXXXXXX XXXXXXXXXX XXXXXXXXXX XXXXXXXXXX    720
XXXXXXXXXX XXXXXXXXXX XXXXXXXXXX XXXXXXXXXX XXXXXXXXXX XXXXXXXXXX    780
XXXXXXXXXX XXXXXXXXXX XXXXXXXXXX XXXXXXXXXX XXXXXXXXXX XXXXXXXXXX    840
XXXXXXXXXX XXXXXXXXXX XXXXXXXXXX XXXXXXXXXX XXXXXXXXXX XXXXXXXXXX    900
XXXXXXXXXX XXXXXXXXXX XXXXXXXXXX XXXXXXXXXX XXXXXXXXXX XXXXXXXXXX    960
XXXXXXXXXX XXXXXXXXXX XXXXXXXXXX XXXXXXXXXX XXXXXXXXXX XXXXXXXXXX   1020
XXXXXXXXXX XXXXXXXXXX XXXXXXXXXX XXXXXXXXXX XXXXXXXXXX XXXXXXXXXX   1080
XXXXXXXXXX XXXXXXXXXX XXXXXXXXXX XXXXXXXXXX XXXXXXXXXX XXXXXXXXXX   1140
XXXXXXXXXX XXXXXXXXXX XXXXXXXXXX XXXXXXXXXX XXXXXXXXXX XXXXXXXXXX   1200
XXXXXXXXXX XXXXXXXXXX XXXXXXXXXX XXXXXXXXXX XXXXXXXXXX XXXXXXXXXX   1260
XXXXXXXXXX XXXXXXXXXX XXXXXXXXXX XXXXXXXXXX XXXXXXXXXX XXXXXXXXXX   1320
XXXXXXXXXX XXXXXXXXXX XXXXXXXXXX XXXXXXXXXX XXXXXXXXXX XXXXXXXXXX   1380
XXXXXXXXXX XXXXXXXXXX XXXXXXXXXX XXXXXXQAKH KQRKRLKSSC KRHPLYVDFS   1440
DVGWNDWIVA PPGYHAFYCH GECPFPLADH LNSTNHAIVQ TLVNSVNSKI PKACCVPTEL   1500
SAISMLYLDE NEKVVLKNYQ DMVVEGCGCR                                    1530

SEQ ID NO: 604         moltype = AA   length = 1568
FEATURE                Location/Qualifiers
REGION                 1..1568
                       note = Description of Artificial Sequence: Synthetic
                       polypeptide
MOD_RES                13..1416
                       note = This region may encompass one or more of the
                       following sequences: "LLADTTHHRPWT" or "VIGESTHHRPWS" or
                       "LIADSTHHSPWT" or "ILAESTHHKPWT" or "ILAETTHHRPWS" or
                       "IIGESSHHKPFT" or "GLGDTTHHRPWG" or "VLGDTTHHKPWT" or
                       "IVADSTHHRPWT" or
MOD_RES                13..1416
                       note = CONT. FROM ABOVE: "STADTSHHRPS" or "TSGGESTHHRPS" or
                       "TSGGESSHHKPS" or "TGSGDSSHHRPS" or "GSSGESTHHKPST" or
                       "VGADSTHHRPVT" or "GAADTTHHRPVT" or "AGADTTHHRPVT" or
                       "GGADTTHHRPAT" or "GGADTTHHRPGT" or
                       "LLADTTHHRPWTVIGESTHHRPWS"
MOD_RES                13..1416
                       note = CONT. FROM ABOVE: or
                       "LLADTTHHRPWTVIGESTHHRPWSIIGESSHHKPFT" or
                       "LLADTTHHRPWTVIGESTHHRPWSIIGESSHHKPFTGLGDTTHHRPWGILAESTHHKP
                       WT" or "LLADTTHHRPWTILAESTHHKPWT" or
                       "LLADTTHHRPWTILAESTHHKPWTLLAD
                       TTHHRPWTILAESTHHKPWTLLADTTHHRPWT" or
                       "LLADTTHHRPWTGLGDTTHHRPWG"
MOD_RES                13..1416
                       note = CONT. FROM ABOVE: or
                       "LLADTTHHRPWTGLGDTTHHRPWGLLADTTHHRPWT" or
                       "LLADTTHHRPWTGLGDTTHHRPWGLLADTTHHRPWTGLGDTTHHRPWGLLADTTHHRP
                       WT" or
                       "LLADTTHHRPWTGLGDTTHHRPWGLLADTTHHRPWTGLGDTTHHRPWGLLADTTHHRP
                         WTGLGDTTHHRPWGLLADTTHHRPWT" or
                       "STADTSHHRPSTSGGESTHHRPSTSGGESS
MOD_RES                13..1416
                       note = CONT. FROM ABOVE: HHKPSTGSGDSSHHRPSGSSGESTHHKPST" or
                       "VGADSTHHR
                       PVTGAADTTHHRPVTAGADTTHHRPVTGGADTTHHRPATGGADTTHHRPGT" or
                       "STADTS
                       HHRPSLLADTTHHRPWTTSGGESTHHRPSVGADSTHHRPVTTSGGESSHHKPSGAADTT
                       HHRP VTTGSGDSSHHRPSGSSGESTHHKPSTGGADTTHHRPAT" or
                       "XXXXXXXXXXX" or
MOD_RES                13..1416
                       note = CONT. FROM ABOVE: "AAADTTHHRPWT" or
                       "AAADTTHHRPWTAAADTTHHRPWTAA
                       ADTTHHRPWTAAADTTHHRPWTAAADTTHHRPWT" or
                       "LLADAAHHRPWTLLADAAHHRPW
                       TLLADAAHHRPWTLLADAAHHRPWTLLADAAHHRPWT" or
                       "LLADTTAARPWTLLADTTAA
                       RPWTLLADTTAARPWTLLADTTAARPWTLLADTTAARPWT" or
                       "LLADTTHHRPWTLLADT
MOD_RES                13..1416
                       note = CONT. FROM ABOVE: THHRPWT" or
                       "LLADTTHHRPWTLLADTTHHRPWTLLADTTHH RPWT" or
                       "LLADTTHHRPWTLLADTTHHRPWTLLADTTHHRPWTLLADT
```

-continued

|  |  |
|---|---|
|  | THHRPWT" or<br>"STSGSTVIGESTHHRPWSLIADSTHHSPWTILAESTHHKPWTILAETTHH<br>RPWSIIGESSHHKPFTGLGDTTHHRPWGVLGDTTHHKPWTIVADSTHHRPWTGQVLPTT<br>TPSS |
| MOD_RES | 13..1416<br>note = CONT. FROM ABOVE: PSTTSGS" or<br>"LLADTTHHRPWTVIGESTHHRPWSIIGESSHH KPFTGLGDTTHHRPWG" or<br>"VIGESTHHRPWSIIGESSHHKPFTGLGDTTHHRPWGILAE STHHKPWT" and<br>wherein X's respectively = V, L, I, G, S, T or A; I, L, V,<br>Q, T, S, G or A; G, A, V or S; E, D, L or G; S, T, P |
| MOD_RES | 13..1416<br>note = CONT. FROM ABOVE: T, E or D; T or S; H, T or S; H or<br>T; R, S, K, P or H; P, S, R or K; W, F, S, P, V, A or G;<br>and absent, S, T G, or A |
| REGION | 1..1568<br>note = See specification as filed for detailed description<br>of substitutions and preferred embodiments |
| source | 1..1568<br>mol_type = protein<br>organism = synthetic construct |

SEQUENCE: 604

```
ILAESTHHKP WTXXXXXXXX XXXXXXXXXX XXXXXXXXXX XXXXXXXXXX XXXXXXXXXX    60
XXXXXXXXXX XXXXXXXXXX XXXXXXXXXX XXXXXXXXXX XXXXXXXXXX XXXXXXXXXX   120
XXXXXXXXXX XXXXXXXXXX XXXXXXXXXX XXXXXXXXXX XXXXXXXXXX XXXXXXXXXX   180
XXXXXXXXXX XXXXXXXXXX XXXXXXXXXX XXXXXXXXXX XXXXXXXXXX XXXXXXXXXX   240
XXXXXXXXXX XXXXXXXXXX XXXXXXXXXX XXXXXXXXXX XXXXXXXXXX XXXXXXXXXX   300
XXXXXXXXXX XXXXXXXXXX XXXXXXXXXX XXXXXXXXXX XXXXXXXXXX XXXXXXXXXX   360
XXXXXXXXXX XXXXXXXXXX XXXXXXXXXX XXXXXXXXXX XXXXXXXXXX XXXXXXXXXX   420
XXXXXXXXXX XXXXXXXXXX XXXXXXXXXX XXXXXXXXXX XXXXXXXXXX XXXXXXXXXX   480
XXXXXXXXXX XXXXXXXXXX XXXXXXXXXX XXXXXXXXXX XXXXXXXXXX XXXXXXXXXX   540
XXXXXXXXXX XXXXXXXXXX XXXXXXXXXX XXXXXXXXXX XXXXXXXXXX XXXXXXXXXX   600
XXXXXXXXXX XXXXXXXXXX XXXXXXXXXX XXXXXXXXXX XXXXXXXXXX XXXXXXXXXX   660
XXXXXXXXXX XXXXXXXXXX XXXXXXXXXX XXXXXXXXXX XXXXXXXXXX XXXXXXXXXX   720
XXXXXXXXXX XXXXXXXXXX XXXXXXXXXX XXXXXXXXXX XXXXXXXXXX XXXXXXXXXX   780
XXXXXXXXXX XXXXXXXXXX XXXXXXXXXX XXXXXXXXXX XXXXXXXXXX XXXXXXXXXX   840
XXXXXXXXXX XXXXXXXXXX XXXXXXXXXX XXXXXXXXXX XXXXXXXXXX XXXXXXXXXX   900
XXXXXXXXXX XXXXXXXXXX XXXXXXXXXX XXXXXXXXXX XXXXXXXXXX XXXXXXXXXX   960
XXXXXXXXXX XXXXXXXXXX XXXXXXXXXX XXXXXXXXXX XXXXXXXXXX XXXXXXXXXX  1020
XXXXXXXXXX XXXXXXXXXX XXXXXXXXXX XXXXXXXXXX XXXXXXXXXX XXXXXXXXXX  1080
XXXXXXXXXX XXXXXXXXXX XXXXXXXXXX XXXXXXXXXX XXXXXXXXXX XXXXXXXXXX  1140
XXXXXXXXXX XXXXXXXXXX XXXXXXXXXX XXXXXXXXXX XXXXXXXXXX XXXXXXXXXX  1200
XXXXXXXXXX XXXXXXXXXX XXXXXXXXXX XXXXXXXXXX XXXXXXXXXX XXXXXXXXXX  1260
XXXXXXXXXX XXXXXXXXXX XXXXXXXXXX XXXXXXXXXX XXXXXXXXXX XXXXXXXXXX  1320
XXXXXXXXXX XXXXXXXXXX XXXXXXXXXX XXXXXXXXXX XXXXXXXXXX XXXXXXXXXX  1380
XXXXXXXXXX XXXXXXXXXX XXXXXXXXXX XXXXXXASGA GGSEGGGSEG GTSGATGAGT  1440
STSGGGASTG GGTGQAKHKQ RKRLKSSCKR HPLYVDFSDV GWNDWIVAPP GYHAFYCHGE  1500
CPFPLADHLN STNHAIVQTL VNSVNSKIPK ACCVPTELSA ISMLYLDENE KVVLKNYQDM  1560
VVEGCGCR                                                          1568
```

|  |  |
|---|---|
| SEQ ID NO: 605 | moltype = AA  length = 1530 |
| FEATURE | Location/Qualifiers |
| REGION | 1..1530<br>note = Description of Artificial Sequence: Synthetic<br>polypeptide |
| MOD_RES | 13..1416<br>note = This region may encompass one or more of the<br>following sequences: "LLADTTHHRPWT" or "VIGESTHHRPWS" or<br>"LIADSTHHSPWT" or "ILAESTHHKPWT" or "ILAETTHHRPWS" or<br>"IIGESSHHKPFT" or "GLGDTTHHRPWG" or "VLGDTTHHKPWT" or<br>"IVADSTHHRPWT" or |
| MOD_RES | 13..1416<br>note = CONT. FROM ABOVE: "STADTSHHRPS" or "TSGGESTHHRPS" or<br>"TSGGESSHHKPS" or "TGSGDSSHHRPS" or "GSSGESTHHKPST" or<br>"VGADSTHHRPVT" or "GAADTTHHRPVT" or "AGADTTHHRPVT" or<br>"GGADTTHHRPAT" or "GGADTTHHRPGT" or<br>"LLADTTHHRPWTVIGESTHHRPWS" |
| MOD_RES | 13..1416<br>note = CONT. FROM ABOVE: or<br>"LLADTTHHRPWTVIGESTHHRPWSIIGESSHHKPFT" or<br>"LLADTTHHRPWTVIGESTHHRPWSIIGESSHHKPFTGLGDTTHHRPWGILAESTHHKP<br>WT" or "LLADTTHHRPWTILAESTHHKPWT" or<br>"LLADTTHHRPWTILAESTHHKPWTLLAD<br>TTHHRPWTILAESTHHKPWTLLADTTHHRPWT" or<br>"LLADTTHHRPWTGLGDTTHHRPWG" |
| MOD_RES | 13..1416<br>note = CONT. FROM ABOVE: or<br>"LLADTTHHRPWTGLGDTTHHRPWGLLADTTHHRPWT" or<br>"LLADTTHHRPWTGLGDTTHHRPWGLLADTTHHRPWTGLGDTTHHRPWGLLADTTHHRP<br>WT" or |

```
                            "LLADTTHHRPWTGLGDTTHHRPWGLLADTTHHRPWTGLGDTTHHRPWGLLADTTHHRP
                              WTGLGDTTHHRPWGLLADTTHHRPWT" or
                            "STADTSHHRPSTSGGESTHHRPSTSGGESS
MOD_RES                     13..1416
                            note = CONT. FROM ABOVE: HHKPSTGSGDSSHHRPSGSSGESTHHKPST" or
                            "VGADSTHHR
                            PVTGAADTTHHRPVTAGADTTHHRPVTGGADTTHHRPATGGADTTHHRPGT" or
                            "STADTS
                            HHRPSLLADTTHHRPWTTSGGESTHHRPSVGADSTHHRPVTTSGGESSHHKPSGAADTT
                            HHRP VTTGSGDSSHHRPSGSSGESTHHKPSTGGADTTHHRPAT" or
                            "XXXXXXXXXXXX" or
MOD_RES                     13..1416
                            note = CONT. FROM ABOVE: "AAADTTHHRPWT" or
                            "AAADTTHHRPWTAAADTTHHRPWTAA
                            ADTTHHRPWTAAADTTHHRPWTAAADTTHHRPWT" or
                            "LLADAAHHRPWTLLADAAHHRPW
                            TLLADAAHHRPWTLLADAAHHRPWTLLADAAHHRPWT" or
                            "LLADTTAARPWTLLADTTAA
                            RPWTLLADTTAARPWTLLADTTAARPWTLLADTTAARPWT" or
                            "LLADTTHHRPWTLLADT
MOD_RES                     13..1416
                            note = CONT. FROM ABOVE: THHRPWT" or
                            "LLADTTHHRPWTLLADTTHHRPWTLLADTTHH RPWT" or
                            "LLADTTHHRPWTLLADTTHHRPWTLLADTTHHRPWTLLADTTHHRPWTLLADT
                            THHRPWT" or
                            "STSGSTVIGESTHHRPWSLIADSTHHSPWTILAESTHHKPWTILAETTHH
                            RPWSIIGESSHHKPFTGLGDTTHHRPWGVLGDTTHHKPWTIVADSTHHRPWTGQVLPTT
                            TPSS
MOD_RES                     13..1416
                            note = CONT. FROM ABOVE: PSTTSGS" or
                            "LLADTTHHRPWTVIGESTHHRPWSIIGESSHH KPFTGLGDTTHHRPWG" or
                            "VIGESTHHRPWSIIGESSHHKPFTGLGDTTHHRPWGILAE STHHKPWT" and
                            wherein X's respectively = V, L, I, G, S, T or A; I, L, V,
                            Q, T, S, G or A; G, A, V or S; E, D, L or G; S, T, P
MOD_RES                     13..1416
                            note = CONT. FROM ABOVE: T, E or D; T or S; H, T or S; H or
                            T; R, S, K, P or H; P, S, R or K; W, F, S, P, V, A or G;
                            and absent, S, T G, or A
REGION                      1416..1417
                            note = NON_CONS - Residues at these positions can be
                            separated by a linker of unknown length
REGION                      1..1530
                            note = See specification as filed for detailed description
                            of substitutions and preferred embodiments
source                      1..1530
                            mol_type = protein
                            organism = synthetic construct
SEQUENCE: 605
IIGESSHHKP FTXXXXXXXX XXXXXXXXXX XXXXXXXXXX XXXXXXXXXX XXXXXXXXXX    60
XXXXXXXXXX XXXXXXXXXX XXXXXXXXXX XXXXXXXXXX XXXXXXXXXX XXXXXXXXXX   120
XXXXXXXXXX XXXXXXXXXX XXXXXXXXXX XXXXXXXXXX XXXXXXXXXX XXXXXXXXXX   180
XXXXXXXXXX XXXXXXXXXX XXXXXXXXXX XXXXXXXXXX XXXXXXXXXX XXXXXXXXXX   240
XXXXXXXXXX XXXXXXXXXX XXXXXXXXXX XXXXXXXXXX XXXXXXXXXX XXXXXXXXXX   300
XXXXXXXXXX XXXXXXXXXX XXXXXXXXXX XXXXXXXXXX XXXXXXXXXX XXXXXXXXXX   360
XXXXXXXXXX XXXXXXXXXX XXXXXXXXXX XXXXXXXXXX XXXXXXXXXX XXXXXXXXXX   420
XXXXXXXXXX XXXXXXXXXX XXXXXXXXXX XXXXXXXXXX XXXXXXXXXX XXXXXXXXXX   480
XXXXXXXXXX XXXXXXXXXX XXXXXXXXXX XXXXXXXXXX XXXXXXXXXX XXXXXXXXXX   540
XXXXXXXXXX XXXXXXXXXX XXXXXXXXXX XXXXXXXXXX XXXXXXXXXX XXXXXXXXXX   600
XXXXXXXXXX XXXXXXXXXX XXXXXXXXXX XXXXXXXXXX XXXXXXXXXX XXXXXXXXXX   660
XXXXXXXXXX XXXXXXXXXX XXXXXXXXXX XXXXXXXXXX XXXXXXXXXX XXXXXXXXXX   720
XXXXXXXXXX XXXXXXXXXX XXXXXXXXXX XXXXXXXXXX XXXXXXXXXX XXXXXXXXXX   780
XXXXXXXXXX XXXXXXXXXX XXXXXXXXXX XXXXXXXXXX XXXXXXXXXX XXXXXXXXXX   840
XXXXXXXXXX XXXXXXXXXX XXXXXXXXXX XXXXXXXXXX XXXXXXXXXX XXXXXXXXXX   900
XXXXXXXXXX XXXXXXXXXX XXXXXXXXXX XXXXXXXXXX XXXXXXXXXX XXXXXXXXXX   960
XXXXXXXXXX XXXXXXXXXX XXXXXXXXXX XXXXXXXXXX XXXXXXXXXX XXXXXXXXXX  1020
XXXXXXXXXX XXXXXXXXXX XXXXXXXXXX XXXXXXXXXX XXXXXXXXXX XXXXXXXXXX  1080
XXXXXXXXXX XXXXXXXXXX XXXXXXXXXX XXXXXXXXXX XXXXXXXXXX XXXXXXXXXX  1140
XXXXXXXXXX XXXXXXXXXX XXXXXXXXXX XXXXXXXXXX XXXXXXXXXX XXXXXXXXXX  1200
XXXXXXXXXX XXXXXXXXXX XXXXXXXXXX XXXXXXXXXX XXXXXXXXXX XXXXXXXXXX  1260
XXXXXXXXXX XXXXXXXXXX XXXXXXXXXX XXXXXXXXXX XXXXXXXXXX XXXXXXXXXX  1320
XXXXXXXXXX XXXXXXXXXX XXXXXXXXXX XXXXXXXXXX XXXXXXXXXX XXXXXXXXXX  1380
XXXXXXXXXX XXXXXXXXXX XXXXXXXXXX XXXXXXXQAKH KQRKRLKSSC KRHPLYVDFS  1440
DVGWNDWIVA PPGYHAFYCH GECPFPLADH LNSTNHAIVQ TLVNSVNSKI PKACCVPTEL   1500
SAISMLYLDE NEKVVLKNYQ DMVVEGCGCR                                   1530

SEQ ID NO: 606              moltype = AA   length = 1568
FEATURE                     Location/Qualifiers
REGION                      1..1568
                            note = Description of Artificial Sequence: Synthetic
```

```
                      polypeptide
MOD_RES               13..1416
                      note = This region may encompass one or more of the
                        following sequences: "LLADTTHHRPWT" or "VIGESTHHRPWS" or
                        "LIADSTHHSPWT" or "ILAESTHHKPWT" or "ILAETTHHRPWS" or
                        "IIGESSHHKPFT" or "GLGDTTHHRPWG" or "VLGDTTHHKPWT" or
                        "IVADSTHHRPWT" or
MOD_RES               13..1416
                      note = CONT. FROM ABOVE: "STADTSHHRPS" or "TSGGESTHHRPS" or
                        "TSGGESSHHKPS" or "TGSGDSSHHRPS" or "GSSGESTHHKPST" or
                        "VGADSTHHRPVT" or "GAADTTHHRPVT" or "AGADTTHHRPVT" or
                        "GGADTTHHRPAT" or "GGADTTHHRPGT" or
                        "LLADTTHHRPWTVIGESTHHRPWS"
MOD_RES               13..1416
                      note = CONT. FROM ABOVE: or
                        "LLADTTHHRPWTVIGESTHHRPWSIIGESSHHKPFT" or
                        "LLADTTHHRPWTVIGESTHHRPWSIIGESSHHKPFTGLGDTTHHRPWGILAESTHHKP
                        WT" or "LLADTTHHRPWTILAESTHHKPWT" or
                        "LLADTTHHRPWTILAESTHHKPWTLLAD
                        TTHHRPWTILAESTHHKPWTLLADTTHHRPWT" or
                        "LLADTTHHRPWTGLGDTTHHRPWG"
MOD_RES               13..1416
                      note = CONT. FROM ABOVE: or
                        "LLADTTHHRPWTGLGDTTHHRPWGLLADTTHHRPWT" or
                        "LLADTTHHRPWTGLGDTTHHRPWGLLADTTHHRPWTGLGDTTHHRPWGLLADTTHHRP
                        WT" or
                        "LLADTTHHRPWTGLGDTTHHRPWGLLADTTHHRPWTGLGDTTHHRPWGLLADTTHHRP
                         WTGLGDTTHHRPWGLLADTTHHRPWT" or
                        "STADTSHHRPSTSGGESTHHRPSTSGGESS
MOD_RES               13..1416
                      note = CONT. FROM ABOVE: HHKPSTGSGDSSHHRPSGSSGESTHHKPST" or
                        "VGADSTHHR
                        PVTGAADTTHHRPVTAGADTTHHRPVTGGADTTHHRPATGGADTTHHRPGT" or
                        "STADTS
                        HHRPSLLADTTHHRPWTTSGGESTHHRPSVGADSTHHRPVTTSGGESSHHKPSGAADTT
                        HHRP VTTGSGDSSHHRPSGSSGESTHHKPSTGGADTTHHRPAT" or
                        "XXXXXXXXXXXX" or
MOD_RES               13..1416
                      note = CONT. FROM ABOVE: "AAADTTHHRPWT" or
                        "AAADTTHHRPWTAAADTTHHRPWTAA
                        ADTTHHRPWTAAADTTHHRPWTAAADTTHHRPWT" or
                        "LLADAAHHRPWTLLADAAHHRPW
                        TLLADAAHHRPWTLLADAAHHRPWTLLADAAHHRPWT" or
                        "LLADTTAARPWTLLADTTAA
                        RPWTLLADTTAARPWTLLADTTAARPWTLLADTTAARPWT" or
                        "LLADTTHHRPWTLLADT
MOD_RES               13..1416
                      note = CONT. FROM ABOVE: THHRPWT" or
                        "LLADTTHHRPWTLLADTTHHRPWTLLADTTHH RPWT" or
                        "LLADTTHHRPWTLLADTTHHRPWTLLADTTHHRPWTLLADTTHHRPWTLLADT
                        THHRPWT" or
                        "STSGSTVIGESTHHRPWSLIADSTHHSPWTILAESTHHKPWTILAETTHH
                        RPWSIIGESSHHKPFTGLGDTTHHRPWGVLGDTTHHKPWTIVADSTHHRPWTGQVLPTT
                        TPSS
MOD_RES               13..1416
                      note = CONT. FROM ABOVE: PSTTSGS" or
                        "LLADTTHHRPWTVIGESTHHRPWSIIGESSHH KPFTGLGDTTHHRPWG" or
                        "VIGESTHHRPWSIIGESSHHKPFTGLGDTTHHRPWGILAE STHHKPWT" and
                        wherein X's respectively = V, L, I, G, S, T or A; I, L, V,
                        Q, T, S, G or A; G, A, V or S; E, D, L or G; S, T, P
MOD_RES               13..1416
                      note = CONT. FROM ABOVE: T, E or D; T or S; H, T or S; H or
                        T; R, S, K, P or H; P, S, R or K; W, F, S, P, V, A or G;
                        and absent, S, T G, or A
REGION                1..1568
                      note = See specification as filed for detailed description
                        of substitutions and preferred embodiments
source                1..1568
                      mol_type = protein
                      organism = synthetic construct
SEQUENCE: 606
IIGESSHHKP FTXXXXXXXX XXXXXXXXXX XXXXXXXXXX XXXXXXXXXX XXXXXXXXXX    60
XXXXXXXXXX XXXXXXXXXX XXXXXXXXXX XXXXXXXXXX XXXXXXXXXX XXXXXXXXXX   120
XXXXXXXXXX XXXXXXXXXX XXXXXXXXXX XXXXXXXXXX XXXXXXXXXX XXXXXXXXXX   180
XXXXXXXXXX XXXXXXXXXX XXXXXXXXXX XXXXXXXXXX XXXXXXXXXX XXXXXXXXXX   240
XXXXXXXXXX XXXXXXXXXX XXXXXXXXXX XXXXXXXXXX XXXXXXXXXX XXXXXXXXXX   300
XXXXXXXXXX XXXXXXXXXX XXXXXXXXXX XXXXXXXXXX XXXXXXXXXX XXXXXXXXXX   360
XXXXXXXXXX XXXXXXXXXX XXXXXXXXXX XXXXXXXXXX XXXXXXXXXX XXXXXXXXXX   420
XXXXXXXXXX XXXXXXXXXX XXXXXXXXXX XXXXXXXXXX XXXXXXXXXX XXXXXXXXXX   480
```

```
XXXXXXXXXX XXXXXXXXXX XXXXXXXXXX XXXXXXXXXX XXXXXXXXXX XXXXXXXXXX    540
XXXXXXXXXX XXXXXXXXXX XXXXXXXXXX XXXXXXXXXX XXXXXXXXXX XXXXXXXXXX    600
XXXXXXXXXX XXXXXXXXXX XXXXXXXXXX XXXXXXXXXX XXXXXXXXXX XXXXXXXXXX    660
XXXXXXXXXX XXXXXXXXXX XXXXXXXXXX XXXXXXXXXX XXXXXXXXXX XXXXXXXXXX    720
XXXXXXXXXX XXXXXXXXXX XXXXXXXXXX XXXXXXXXXX XXXXXXXXXX XXXXXXXXXX    780
XXXXXXXXXX XXXXXXXXXX XXXXXXXXXX XXXXXXXXXX XXXXXXXXXX XXXXXXXXXX    840
XXXXXXXXXX XXXXXXXXXX XXXXXXXXXX XXXXXXXXXX XXXXXXXXXX XXXXXXXXXX    900
XXXXXXXXXX XXXXXXXXXX XXXXXXXXXX XXXXXXXXXX XXXXXXXXXX XXXXXXXXXX    960
XXXXXXXXXX XXXXXXXXXX XXXXXXXXXX XXXXXXXXXX XXXXXXXXXX XXXXXXXXXX   1020
XXXXXXXXXX XXXXXXXXXX XXXXXXXXXX XXXXXXXXXX XXXXXXXXXX XXXXXXXXXX   1080
XXXXXXXXXX XXXXXXXXXX XXXXXXXXXX XXXXXXXXXX XXXXXXXXXX XXXXXXXXXX   1140
XXXXXXXXXX XXXXXXXXXX XXXXXXXXXX XXXXXXXXXX XXXXXXXXXX XXXXXXXXXX   1200
XXXXXXXXXX XXXXXXXXXX XXXXXXXXXX XXXXXXXXXX XXXXXXXXXX XXXXXXXXXX   1260
XXXXXXXXXX XXXXXXXXXX XXXXXXXXXX XXXXXXXXXX XXXXXXXXXX XXXXXXXXXX   1320
XXXXXXXXXX XXXXXXXXXX XXXXXXXXXX XXXXXXXXXX XXXXXXXXXX XXXXXXXXXX   1380
XXXXXXXXXX XXXXXXXXXX XXXXXXXXXX XXXXXXASGA GGSEGGGSEG GTSGATGAGT   1440
STSGGGASTG GGTGQAKHKQ RKRLKSSCKR HPLYVDFSDV GWNDWIVAPP GYHAFYCHGE   1500
CPFPLADHLN STNHAIVQTL VNSVNSKIPK ACCVPTELSA ISMLYLDENE KVVLKNYQDM   1560
VVEGCGCR                                                           1568

SEQ ID NO: 607         moltype = AA  length = 1530
FEATURE                Location/Qualifiers
REGION                 1..1530
                       note = Description of Artificial Sequence: Synthetic
                       polypeptide
MOD_RES                13..1416
                       note = This region may encompass one or more of the
                       following sequences: "LLADTTHHRPWT" or "VIGESTHHRPWS" or
                       "LIADSTHHSPWT" or "ILAESTHHKPWT" or "ILAETTHHRPWS" or
                       "IIGESSHHKPFT" or "GLGDTTHHRPWG" or "VLGDTTHHKPWT" or
                       "IVADSTHHRPWT" or
MOD_RES                13..1416
                       note = CONT. FROM ABOVE: "STADTSHHRPS" or "TSGGESTHHRPS" or
                       "TSGGESSHHKPS" or "TGSGDSSHHRPS" or "GSSGESTHHKPST" or
                       "VGADSTHHRPVT" or "GAADTTHHRPVT" or "AGADTTHHRPVT" or
                       "GGADTTHHRPAT" or "GGADTTHHRPGT" or
                       "LLADTTHHRPWTVIGESTHHRPWS"
MOD_RES                13..1416
                       note = CONT. FROM ABOVE: or
                       "LLADTTHHRPWTVIGESTHHRPWSIIGESSHHKPFT" or
                       "LLADTTHHRPWTVIGESTHHRPWSIIGESSHHKPFTGLGDTTHHRPWGILAESTHHKP
                       WT" or "LLADTTHHRPWTILAESTHHKPWT" or
                       "LLADTTHHRPWTILAESTHHKPWTLLAD
                       TTHHRPWTILAESTHHKPWTLLADTTHHRPWT" or
                       "LLADTTHHRPWTGLGDTTHHRPWG"
MOD_RES                13..1416
                       note = CONT. FROM ABOVE: or
                       "LLADTTHHRPWTGLGDTTHHRPWGLLADTTHHRPWT" or
                       "LLADTTHHRPWTGLGDTTHHRPWGLLADTTHHRPWTGLGDTTHHRPWGLLADTTHHRP
                       WT" or
                       "LLADTTHHRPWTGLGDTTHHRPWGLLADTTHHRPWTGLGDTTHHRPWGLLADTTHHRP
                        WTGLGDTTHHRPWGLLADTTHHRPWT" or
                       "STADTSHHRPSTSGGESTHHRPSTSGGESS
MOD_RES                13..1416
                       note = CONT. FROM ABOVE: HHKPSTGSGDSSHHRPSGSSGESTHHKPST" or
                       "VGADSTHHR
                       PVTGAADTTHHRPVTAGADTTHHRPVTGGADTTHHRPATGGADTTHHRPGT" or
                       "STADTS
                       HHRPSLLADTTHHRPWTTSGGESTHHRPSVGADSTHHRPVTTSGGESSHHKPSGAADTT
                       HHRP VTTGSGDSSHHRPSGSSGESTHHKPSTGGADTTHHRPAT" or
                       "XXXXXXXXXXXX" or
MOD_RES                13..1416
                       note = CONT. FROM ABOVE: "AAADTTHHRPWT" or
                       "AAADTTHHRPWTAAADTTHHRPWTAA
                       ADTTHHRPWTAAADTTHHRPWTAAADTTHHRPWT" or
                       "LLADAAHHRPWTLLADAAHHRPW
                       TLLADAAHHRPWTLLADAAHHRPWTLLADAAHHRPWT" or
                       "LLADTTAARPWTLLADTTAA
                       RPWTLLADTTAARPWTLLADTTAARPWTLLADTTAARPWT" or
                       "LLADTTHHRPWTLLADT
MOD_RES                13..1416
                       note = CONT. FROM ABOVE: THHRPWT" or
                       "LLADTTHHRPWTLLADTTHHRPWTLLADTTHH RPWT" or
                       "LLADTTHHRPWTLLADTTHHRPWTLLADTTHHRPWTLLADT
                       THHRPWT" or
                       "STSGSTVIGESTHHRPWSLIADSTHHSPWTILAESTHHKPWTILAETTHH
                       RPWSIIGESSHHKPFTGLGDTTHHRPWGVLGDTTHHKPWTIVADSTHHRPWTGQVLPTT
                       TPSS
MOD_RES                13..1416
```

```
                         note = CONT. FROM ABOVE: PSTTSGS" or
                         "LLADTTHHRPWTVIGESTHHRPWSIIGESSHH KPFTGLGDTTHHRPWG" or
                         "VIGESTHHRPWSIIGESSHHKPFTGLGDTTHHRPWGILAE STHHKPWT" and
                         wherein X's respectively = V, L, I, G, S, T or A; I, L, V,
                         Q, T, S, G or A; G, A, V or S; E, D, L or G; S, T, P
MOD_RES                  13..1416
                         note = CONT. FROM ABOVE: T, E or D; T or S; H, T or S; H or
                         T; R, S, K, P or H; P, S, R or K; W, F, S, P, V, A or G;
                         and absent, S, T G, or A
REGION                   1416..1417
                         note = NON_CONS - Residues at these positions can be
                         separated by a linker of unknown length
REGION                   1..1530
                         note = See specification as filed for detailed description
                         of substitutions and preferred embodiments
source                   1..1530
                         mol_type = protein
                         organism = synthetic construct
SEQUENCE: 607
GLGDTTHHRP WGXXXXXXXX XXXXXXXXXX XXXXXXXXXX XXXXXXXXXX XXXXXXXXXX   60
XXXXXXXXXX XXXXXXXXXX XXXXXXXXXX XXXXXXXXXX XXXXXXXXXX XXXXXXXXXX  120
XXXXXXXXXX XXXXXXXXXX XXXXXXXXXX XXXXXXXXXX XXXXXXXXXX XXXXXXXXXX  180
XXXXXXXXXX XXXXXXXXXX XXXXXXXXXX XXXXXXXXXX XXXXXXXXXX XXXXXXXXXX  240
XXXXXXXXXX XXXXXXXXXX XXXXXXXXXX XXXXXXXXXX XXXXXXXXXX XXXXXXXXXX  300
XXXXXXXXXX XXXXXXXXXX XXXXXXXXXX XXXXXXXXXX XXXXXXXXXX XXXXXXXXXX  360
XXXXXXXXXX XXXXXXXXXX XXXXXXXXXX XXXXXXXXXX XXXXXXXXXX XXXXXXXXXX  420
XXXXXXXXXX XXXXXXXXXX XXXXXXXXXX XXXXXXXXXX XXXXXXXXXX XXXXXXXXXX  480
XXXXXXXXXX XXXXXXXXXX XXXXXXXXXX XXXXXXXXXX XXXXXXXXXX XXXXXXXXXX  540
XXXXXXXXXX XXXXXXXXXX XXXXXXXXXX XXXXXXXXXX XXXXXXXXXX XXXXXXXXXX  600
XXXXXXXXXX XXXXXXXXXX XXXXXXXXXX XXXXXXXXXX XXXXXXXXXX XXXXXXXXXX  660
XXXXXXXXXX XXXXXXXXXX XXXXXXXXXX XXXXXXXXXX XXXXXXXXXX XXXXXXXXXX  720
XXXXXXXXXX XXXXXXXXXX XXXXXXXXXX XXXXXXXXXX XXXXXXXXXX XXXXXXXXXX  780
XXXXXXXXXX XXXXXXXXXX XXXXXXXXXX XXXXXXXXXX XXXXXXXXXX XXXXXXXXXX  840
XXXXXXXXXX XXXXXXXXXX XXXXXXXXXX XXXXXXXXXX XXXXXXXXXX XXXXXXXXXX  900
XXXXXXXXXX XXXXXXXXXX XXXXXXXXXX XXXXXXXXXX XXXXXXXXXX XXXXXXXXXX  960
XXXXXXXXXX XXXXXXXXXX XXXXXXXXXX XXXXXXXXXX XXXXXXXXXX XXXXXXXXXX 1020
XXXXXXXXXX XXXXXXXXXX XXXXXXXXXX XXXXXXXXXX XXXXXXXXXX XXXXXXXXXX 1080
XXXXXXXXXX XXXXXXXXXX XXXXXXXXXX XXXXXXXXXX XXXXXXXXXX XXXXXXXXXX 1140
XXXXXXXXXX XXXXXXXXXX XXXXXXXXXX XXXXXXXXXX XXXXXXXXXX XXXXXXXXXX 1200
XXXXXXXXXX XXXXXXXXXX XXXXXXXXXX XXXXXXXXXX XXXXXXXXXX XXXXXXXXXX 1260
XXXXXXXXXX XXXXXXXXXX XXXXXXXXXX XXXXXXXXXX XXXXXXXXXX XXXXXXXXXX 1320
XXXXXXXXXX XXXXXXXXXX XXXXXXXXXX XXXXXXXXXX XXXXXXXXXX XXXXXXXXXX 1380
XXXXXXXXXX XXXXXXXXXX XXXXXXXXXX XXXXXXQAKH KQRKRLKSSC KRHPLYVDFS 1440
DVGWNDWIVA PPGYHAFYCH GECPFPLADH LNSTNHAIVQ TLVNSVNSKI PKACCVPTEL 1500
SAISMLYLDE NEKVVLKNYQ DMVVEGCGCR                                  1530

SEQ ID NO: 608           moltype = AA   length = 1568
FEATURE                  Location/Qualifiers
REGION                   1..1568
                         note = Description of Artificial Sequence: Synthetic
                         polypeptide
MOD_RES                  13..1416
                         note = This region may encompass one or more of the
                         following sequences: "LLADTTHHRPWT" or "VIGESTHHRPWS" or
                         "LIADSTHHSPWT" or "ILAESTHHKPWT" or "ILAETTHHRPWS" or
                         "IIGESSHHKPFT" or "GLGDTTHHRPWG" or "VLGDTTHHKPWT" or
                         "IVADSTHHRPWT" or
MOD_RES                  13..1416
                         note = CONT. FROM ABOVE: "STADTSHHRPS" or "TSGGESTHHRPS" or
                         "TSGGESSHHKPS" or "TGSGDSSHHRPS" or "GSSGESTHHKPST" or
                         "VGADSTHHRPVT" or "GAADTTHHRPVT" or "AGADTTHHRPVT" or
                         "GGADTTHHRPAT" or "GGADTTHHRPGT" or
                         "LLADTTHHRPWTVIGESTHHRPWS"
MOD_RES                  13..1416
                         note = CONT. FROM ABOVE: or
                         "LLADTTHHRPWTVIGESTHHRPWSIIGESSHHKPFT" or
                         "LLADTTHHRPWTVIGESTHHRPWSIIGESSHHKPFTGLGDTTHHRPWGILAESTHHKP
                         WT" or "LLADTTHHRPWTILAESTHHKPWT" or
                         "LLADTTHHRPWTILAESTHHKPWTLLAD
                         TTHHRPWTILAESTHHKPWTLLADTTHHRPWT" or
                         "LLADTTHHRPWTGLGDTTHHRPWG"
MOD_RES                  13..1416
                         note = CONT. FROM ABOVE: or
                         "LLADTTHHRPWTGLGDTTHHRPWGLLADTTHHRPWT" or
                         "LLADTTHHRPWTGLGDTTHHRPWGLLADTTHHRPWTGLGDTTHHRPWGLLADTTHHRP
                         WT" or
                         "LLADTTHHRPWTGLGDTTHHRPWGLLADTTHHRPWTGLGDTTHHRPWGLLADTTHHRP
                          WTGLGDTTHHRPWGLLADTTHHRPWT" or
                         "STADTSHHRPSTSGGESTHHRPSTSGGESS
```

|  |  |
|---|---|
| MOD_RES | 13..1416<br>note = CONT. FROM ABOVE: HHKPSTGSGDSSHHRPSGSSGESTHHKPST" or<br>"VGADSTHHR<br>PVTGAADTTHHRPVTAGADTTHHRPVTGGADTTHHRPATGGADTTHHRPGT" or<br>"STADTS<br>HHRPSLLADTTHHRPWTTSGGESTHHRPSVGADSTHHRPVTTSGGESSHHKPSGAADTT<br>HHRP VTTGSGDSSHHRPSGSSGESTHHKPSTGGADTTHHRPAT" or<br>"XXXXXXXXXXXX" or |
| MOD_RES | 13..1416<br>note = CONT. FROM ABOVE: "AAADTTHHHRPWT" or<br>"AAADTTHHHRPWTAAADTTHHHRPWTAA<br>ADTTHHHRPWTAAADTTHHHRPWTAAADTTHHHRPWT" or<br>"LLADAAHHRPWTLLADAAHHRPW<br>TLLADAAHHRPWTLLADAAHHRPWTLLADAAHHRPWT" or<br>"LLADTTAARPWTLLADTTAA<br>RPWTLLADTTAARPWTLLADTTAARPWTLLADTTAARPWT" or<br>"LLADTTHHHRPWTLLADT |
| MOD_RES | 13..1416<br>note = CONT. FROM ABOVE: THHRPWT" or<br>"LLADTTHHHRPWTLLADTTHHHRPWTLLADTTHHH RPWT" or<br>"LLADTTHHHRPWTLLADTTHHHRPWTLLADTTHHHRPWTLLADTTHHHRPWTLLADT<br>THHRPWT" or<br>"STSGSTVIGESTHHHRPWSLIADSTHHSPWTILAESTHHKPWTILAETTHH<br>RPWSIIGESSHHKPFTGLGDTTHHHRPWGVLGDTTHHKPWTIVADSTHHRPWTGQVLPTT<br>TPSS |
| MOD_RES | 13..1416<br>note = CONT. FROM ABOVE: PSTTSGS" or<br>"LLADTTHHHRPWTVIGESTHHHRPWSIIGESSHH KPFTGLGDTTHHHRPWG" or<br>"VIGESTHHHRPWSIIGESSHHKPFTGLGDTTHHHRPWGILAE STHHKPWT" and<br>wherein X's respectively = V, L, I, G, S, T or A; I, L, V,<br>Q, T, S, G or A; G, A, V or S; E, D, L or G; S, T, P |
| MOD_RES | 13..1416<br>note = CONT. FROM ABOVE: T, E or D; T or S; H, T or S; H or<br>T; R, S, K, P or H; P, S, R or K; W, F, S, P, V, A or G;<br>and absent, S, T G, or A |
| REGION | 1..1568<br>note = See specification as filed for detailed description<br>of substitutions and preferred embodiments |
| source | 1..1568<br>mol_type = protein<br>organism = synthetic construct |

SEQUENCE: 608
```
GLGDTTHHRP WGXXXXXXXX XXXXXXXXXX XXXXXXXXXX XXXXXXXXXX XXXXXXXXXX   60
XXXXXXXXXX XXXXXXXXXX XXXXXXXXXX XXXXXXXXXX XXXXXXXXXX XXXXXXXXXX  120
XXXXXXXXXX XXXXXXXXXX XXXXXXXXXX XXXXXXXXXX XXXXXXXXXX XXXXXXXXXX  180
XXXXXXXXXX XXXXXXXXXX XXXXXXXXXX XXXXXXXXXX XXXXXXXXXX XXXXXXXXXX  240
XXXXXXXXXX XXXXXXXXXX XXXXXXXXXX XXXXXXXXXX XXXXXXXXXX XXXXXXXXXX  300
XXXXXXXXXX XXXXXXXXXX XXXXXXXXXX XXXXXXXXXX XXXXXXXXXX XXXXXXXXXX  360
XXXXXXXXXX XXXXXXXXXX XXXXXXXXXX XXXXXXXXXX XXXXXXXXXX XXXXXXXXXX  420
XXXXXXXXXX XXXXXXXXXX XXXXXXXXXX XXXXXXXXXX XXXXXXXXXX XXXXXXXXXX  480
XXXXXXXXXX XXXXXXXXXX XXXXXXXXXX XXXXXXXXXX XXXXXXXXXX XXXXXXXXXX  540
XXXXXXXXXX XXXXXXXXXX XXXXXXXXXX XXXXXXXXXX XXXXXXXXXX XXXXXXXXXX  600
XXXXXXXXXX XXXXXXXXXX XXXXXXXXXX XXXXXXXXXX XXXXXXXXXX XXXXXXXXXX  660
XXXXXXXXXX XXXXXXXXXX XXXXXXXXXX XXXXXXXXXX XXXXXXXXXX XXXXXXXXXX  720
XXXXXXXXXX XXXXXXXXXX XXXXXXXXXX XXXXXXXXXX XXXXXXXXXX XXXXXXXXXX  780
XXXXXXXXXX XXXXXXXXXX XXXXXXXXXX XXXXXXXXXX XXXXXXXXXX XXXXXXXXXX  840
XXXXXXXXXX XXXXXXXXXX XXXXXXXXXX XXXXXXXXXX XXXXXXXXXX XXXXXXXXXX  900
XXXXXXXXXX XXXXXXXXXX XXXXXXXXXX XXXXXXXXXX XXXXXXXXXX XXXXXXXXXX  960
XXXXXXXXXX XXXXXXXXXX XXXXXXXXXX XXXXXXXXXX XXXXXXXXXX XXXXXXXXXX 1020
XXXXXXXXXX XXXXXXXXXX XXXXXXXXXX XXXXXXXXXX XXXXXXXXXX XXXXXXXXXX 1080
XXXXXXXXXX XXXXXXXXXX XXXXXXXXXX XXXXXXXXXX XXXXXXXXXX XXXXXXXXXX 1140
XXXXXXXXXX XXXXXXXXXX XXXXXXXXXX XXXXXXXXXX XXXXXXXXXX XXXXXXXXXX 1200
XXXXXXXXXX XXXXXXXXXX XXXXXXXXXX XXXXXXXXXX XXXXXXXXXX XXXXXXXXXX 1260
XXXXXXXXXX XXXXXXXXXX XXXXXXXXXX XXXXXXXXXX XXXXXXXXXX XXXXXXXXXX 1320
XXXXXXXXXX XXXXXXXXXX XXXXXXXXXX XXXXXXXXXX XXXXXXXXXX XXXXXXXXXX 1380
XXXXXXXXXX XXXXXXXXXX XXXXXXXXXX XXXXXXASGA GGSEGGGSEG TSGATGAGT  1440
STSGGGASTG GGTGQAKHKQ RKRLKSSCKR HPLYVDFSDV GWNDWIVAPP GYHAFYCHGE  1500
CPFPLADHLN STNHAIVQTL VNSVNSKIPK ACCVPTELSA ISMLYLDENE KVVLKNYQDM  1560
VVEGCGCR                                                          1568
```

|  |  |
|---|---|
| SEQ ID NO: 609<br>FEATURE<br>REGION | moltype = AA   length = 174<br>Location/Qualifiers<br>1..174<br>note = Description of Artificial Sequence: Synthetic<br>polypeptide |
| MOD_RES | 13..60<br>note = This region may encompass one or more of the<br>following sequences: "VIGESTHHHRPWS" or "ILAESTHHKPWT" or<br>"IIGESSHHKPFT" or "GLGDTTHHHRPWG" |

```
REGION              60..61
                    note = NON_CONS - Residues at these positions can be
                    separated by a linker of unknown length
REGION              1..174
                    note = See specification as filed for detailed description
                    of substitutions and preferred embodiments
source              1..174
                    mol_type = protein
                    organism = synthetic construct
SEQUENCE: 609
LLADTTHHRP WTXXXXXXXX XXXXXXXXX XXXXXXXXX XXXXXXXXX XXXXXXXXX   60
QAKHKQRKRL KSSCKRHPLY VDFSDVGWND WIVAPPGYHA FYCHGECPFP LADHLNSTNH  120
AIVQTLVNSV NSKIPKACCV PTELSAISML YLDENEKVVL KNYQDMVVEG CGCR       174

SEQ ID NO: 610        moltype = AA   length = 212
FEATURE               Location/Qualifiers
REGION                1..212
                      note = Description of Artificial Sequence: Synthetic
                      polypeptide
MOD_RES               13..60
                      note = This region may encompass one or more of the
                      following sequences: "VIGESTHHRPWS" or "ILAESTHHKPWT" or
                      "IIGESSHHKPFT" or "GLGDTTHHRPWG"
REGION                1..212
                      note = See specification as filed for detailed description
                      of substitutions and preferred embodiments
source                1..212
                      mol_type = protein
                      organism = synthetic construct
SEQUENCE: 610
LLADTTHHRP WTXXXXXXXX XXXXXXXXX XXXXXXXXX XXXXXXXXX XXXXXXXXX   60
ASGAGGSEGG GSEGGTSGAT GAGTSTSGGG ASTGGGTGQA KHKQRKRLKS SCKRHPLYVD  120
FSDVGWNDWI VAPPGYHAFY CHGECPFPLA DHLNSTNHAI VQTLVNSVNS KIPKACCVPT  180
ELSAISMLYL DENEKVVLKN YQDMVVEGCG CR                               212

SEQ ID NO: 611        moltype = AA   length = 174
FEATURE               Location/Qualifiers
REGION                1..174
                      note = Description of Artificial Sequence: Synthetic
                      polypeptide
MOD_RES               13..60
                      note = This region may encompass one or more of the
                      following sequences: "LLADTTHHRPWT" or "ILAESTHHKPWT" or
                      "IIGESSHHKPFT" or "GLGDTTHHRPWG"
REGION                60..61
                      note = NON_CONS - Residues at these positions can be
                      separated by a linker of unknown length
REGION                1..174
                      note = See specification as filed for detailed description
                      of substitutions and preferred embodiments
source                1..174
                      mol_type = protein
                      organism = synthetic construct
SEQUENCE: 611
VIGESTHHRP WSXXXXXXXX XXXXXXXXX XXXXXXXXX XXXXXXXXX XXXXXXXXX    60
QAKHKQRKRL KSSCKRHPLY VDFSDVGWND WIVAPPGYHA FYCHGECPFP LADHLNSTNH  120
AIVQTLVNSV NSKIPKACCV PTELSAISML YLDENEKVVL KNYQDMVVEG CGCR       174

SEQ ID NO: 612        moltype = AA   length = 212
FEATURE               Location/Qualifiers
REGION                1..212
                      note = Description of Artificial Sequence: Synthetic
                      polypeptide
MOD_RES               13..60
                      note = This region may encompass one or more of the
                      following sequences: "LLADTTHHRPWT" or "ILAESTHHKPWT" or
                      "IIGESSHHKPFT" or "GLGDTTHHRPWG"
REGION                1..212
                      note = See specification as filed for detailed description
                      of substitutions and preferred embodiments
source                1..212
                      mol_type = protein
                      organism = synthetic construct
SEQUENCE: 612
VIGESTHHRP WSXXXXXXXX XXXXXXXXX XXXXXXXXX XXXXXXXXX XXXXXXXXX    60
ASGAGGSEGG GSEGGTSGAT GAGTSTSGGG ASTGGGTGQA KHKQRKRLKS SCKRHPLYVD  120
FSDVGWNDWI VAPPGYHAFY CHGECPFPLA DHLNSTNHAI VQTLVNSVNS KIPKACCVPT  180
ELSAISMLYL DENEKVVLKN YQDMVVEGCG CR                               212
```

| | |
|---|---|
| SEQ ID NO: 613 | moltype = AA  length = 174 |
| FEATURE | Location/Qualifiers |
| REGION | 1..174 |
| | note = Description of Artificial Sequence: Synthetic polypeptide |
| MOD_RES | 13..60 |
| | note = This region may encompass one or more of the following sequences: "LLADTTHHRPWT" or "VIGESTHHRPWS" or "IIGESSHHKPFT" or "GLGDTTHHRPWG" |
| REGION | 60..61 |
| | note = NON_CONS - Residues at these positions can be separated by a linker of unknown length |
| REGION | 1..174 |
| | note = See specification as filed for detailed description of substitutions and preferred embodiments |
| source | 1..174 |
| | mol_type = protein |
| | organism = synthetic construct |

SEQUENCE: 613
```
ILAESTHHKP WTXXXXXXXX XXXXXXXXXX XXXXXXXXXX XXXXXXXXXX XXXXXXXXXX  60
QAKHKQRKRL KSSCKRHPLY VDFSDVGWND WIVAPPGYHA FYCHGECPFP LADHLNSTNH 120
AIVQTLVNSV NSKIPKACCV PTELSAISML YLDENEKVVL KNYQDMVVEG CGCR       174
```

| | |
|---|---|
| SEQ ID NO: 614 | moltype = AA  length = 212 |
| FEATURE | Location/Qualifiers |
| REGION | 1..212 |
| | note = Description of Artificial Sequence: Synthetic polypeptide |
| MOD_RES | 13..60 |
| | note = This region may encompass one or more of the following sequences: "LLADTTHHRPWT" or "VIGESTHHRPWS" or "IIGESSHHKPFT" or "GLGDTTHHRPWG" |
| REGION | 1..212 |
| | note = See specification as filed for detailed description of substitutions and preferred embodiments |
| source | 1..212 |
| | mol_type = protein |
| | organism = synthetic construct |

SEQUENCE: 614
```
ILAESTHHKP WTXXXXXXXX XXXXXXXXXX XXXXXXXXXX XXXXXXXXXX XXXXXXXXXX  60
ASGAGGSEGG GSEGGTSGAT GAGTSTSGGG ASTGGGTGQA KHKQRKRLKS SCKRHPLYVD 120
FSDVGWNDWI VAPPGYHAFY CHGECPFPLA DHLNSTNHAI VQTLVNSVNS KIPKACCVPT 180
ELSAISMLYL DENEKVVLKN YQDMVVEGCG CR                               212
```

| | |
|---|---|
| SEQ ID NO: 615 | moltype = AA  length = 174 |
| FEATURE | Location/Qualifiers |
| REGION | 1..174 |
| | note = Description of Artificial Sequence: Synthetic polypeptide |
| MOD_RES | 13..60 |
| | note = This region may encompass one or more of the following sequences: "LLADTTHHRPWT" or "ILAESTHHKPWT" or "VIGESTHHRPWS" or "GLGDTTHHRPWG" |
| REGION | 60..61 |
| | note = NON_CONS - Residues at these positions can be separated by a linker of unknown length |
| REGION | 1..174 |
| | note = See specification as filed for detailed description of substitutions and preferred embodiments |
| source | 1..174 |
| | mol_type = protein |
| | organism = synthetic construct |

SEQUENCE: 615
```
IIGESSHHKP FTXXXXXXXX XXXXXXXXXX XXXXXXXXXX XXXXXXXXXX XXXXXXXXXX  60
QAKHKQRKRL KSSCKRHPLY VDFSDVGWND WIVAPPGYHA FYCHGECPFP LADHLNSTNH 120
AIVQTLVNSV NSKIPKACCV PTELSAISML YLDENEKVVL KNYQDMVVEG CGCR       174
```

| | |
|---|---|
| SEQ ID NO: 616 | moltype = AA  length = 212 |
| FEATURE | Location/Qualifiers |
| REGION | 1..212 |
| | note = Description of Artificial Sequence: Synthetic polypeptide |
| MOD_RES | 13..60 |
| | note = This region may encompass one or more of the following sequences: "LLADTTHHRPWT" or "ILAESTHHKPWT" or "VIGESTHHRPWS" or "GLGDTTHHRPWG" |
| REGION | 1..212 |
| | note = See specification as filed for detailed description of substitutions and preferred embodiments |

```
source              1..212
                    mol_type = protein
                    organism = synthetic construct
SEQUENCE: 616
IIGESSHHKP FTXXXXXXXX XXXXXXXXXX XXXXXXXXXX XXXXXXXXXX XXXXXXXXXX    60
ASGAGGSEGG GSEGGTSGAT GAGTSTSGGG ASTGGGTGQA KHKQRKRLKS SCKRHPLYVD   120
FSDVGWNDWI VAPPGYHAFY CHGECPFPLA DHLNSTNHAI VQTLVNSVNS KIPKACCVPT   180
ELSAISMLYL DENEKVVLKN YQDMVVEGCG CR                                 212

SEQ ID NO: 617      moltype = AA   length = 174
FEATURE             Location/Qualifiers
REGION              1..174
                    note = Description of Artificial Sequence: Synthetic
                    polypeptide
MOD_RES             13..60
                    note = This region may encompass one or more of the
                    following sequences: "LLADTTHHRPWT" or "ILAESTHHKPWT" or
                    "IIGESSHHKPFT" or "VIGESTHHRPWS"
REGION              60..61
                    note = NON_CONS - Residues at these positions can be
                    separated by a linker of unknown length
REGION              1..174
                    note = See specification as filed for detailed description
                    of substitutions and preferred embodiments
source              1..174
                    mol_type = protein
                    organism = synthetic construct
SEQUENCE: 617
GLGDTTHHRP WGXXXXXXXX XXXXXXXXXX XXXXXXXXXX XXXXXXXXXX XXXXXXXXXX    60
QAKHKQRKRL KSSCKRHPLY VDFSDVGWND WIVAPPGYHA FYCHGECPFP LADHLNSTNH   120
AIVQTLVNSV NSKIPKACCV PTELSAISML YLDENEKVVL KNYQDMVVEG CGCR         174

SEQ ID NO: 618      moltype = AA   length = 212
FEATURE             Location/Qualifiers
REGION              1..212
                    note = Description of Artificial Sequence: Synthetic
                    polypeptide
MOD_RES             13..60
                    note = This region may encompass one or more of the
                    following sequences: "LLADTTHHRPWT" or "ILAESTHHKPWT" or
                    "IIGESSHHKPFT" or "VIGESTHHRPWS"
REGION              1..212
                    note = See specification as filed for detailed description
                    of substitutions and preferred embodiments
source              1..212
                    mol_type = protein
                    organism = synthetic construct
SEQUENCE: 618
GLGDTTHHRP WGXXXXXXXX XXXXXXXXXX XXXXXXXXXX XXXXXXXXXX XXXXXXXXXX    60
ASGAGGSEGG GSEGGTSGAT GAGTSTSGGG ASTGGGTGQA KHKQRKRLKS SCKRHPLYVD   120
FSDVGWNDWI VAPPGYHAFY CHGECPFPLA DHLNSTNHAI VQTLVNSVNS KIPKACCVPT   180
ELSAISMLYL DENEKVVLKN YQDMVVEGCG CR                                 212

SEQ ID NO: 619      moltype = AA   length = 174
FEATURE             Location/Qualifiers
REGION              1..174
                    note = Description of Artificial Sequence: Synthetic
                    polypeptide
MOD_RES             13..60
                    note = This region may encompass two or more of the
                    following sequences: "VIGESTHHRPWS" or "ILAESTHHKPWT" or
                    "IIGESSHHKPFT" or "GLGDTTHHRPWG"
REGION              60..61
                    note = NON_CONS - Residues at these positions can be
                    separated by a linker of unknown length
REGION              1..174
                    note = See specification as filed for detailed description
                    of substitutions and preferred embodiments
source              1..174
                    mol_type = protein
                    organism = synthetic construct
SEQUENCE: 619
LLADTTHHRP WTXXXXXXXX XXXXXXXXXX XXXXXXXXXX XXXXXXXXXX XXXXXXXXXX    60
QAKHKQRKRL KSSCKRHPLY VDFSDVGWND WIVAPPGYHA FYCHGECPFP LADHLNSTNH   120
AIVQTLVNSV NSKIPKACCV PTELSAISML YLDENEKVVL KNYQDMVVEG CGCR         174

SEQ ID NO: 620      moltype = AA   length = 212
FEATURE             Location/Qualifiers
REGION              1..212
```

```
                          note = Description of Artificial Sequence: Synthetic
                            polypeptide
MOD_RES                   13..60
                          note = This region may encompass two or more of the
                            following sequences: "VIGESTHHRPWS" or "ILAESTHHKPWT" or
                            "IIGESSHHKPFT" or "GLGDTTHHRPWG"
REGION                    1..212
                          note = See specification as filed for detailed description
                            of substitutions and preferred embodiments
source                    1..212
                          mol_type = protein
                          organism = synthetic construct
SEQUENCE: 620
LLADTTHHRP WTXXXXXXXX XXXXXXXXXX XXXXXXXXXX XXXXXXXXXX XXXXXXXXXX   60
ASGAGGSEGG GSEGGTSGAT GAGTSTSGGG ASTGGGTGQA KHKQRKRLKS SCKRHPLYVD  120
FSDVGWNDWI VAPPGYHAFY CHGECPFPLA DHLNSTNHAI VQTLVNSVNS KIPKACCVPT  180
ELSAISMLYL DENEKVVLKN YQDMVVEGCG CR                                212

SEQ ID NO: 621            moltype = AA   length = 174
FEATURE                   Location/Qualifiers
REGION                    1..174
                          note = Description of Artificial Sequence: Synthetic
                            polypeptide
MOD_RES                   13..60
                          note = This region may encompass two or more of the
                            following sequences: "LLADTTHHRPWT" or "ILAESTHHKPWT" or
                            "IIGESSHHKPFT" or "GLGDTTHHRPWG"
REGION                    60..61
                          note = NON_CONS - Residues at these positions can be
                            separated by a linker of unknown length
REGION                    1..174
                          note = See specification as filed for detailed description
                            of substitutions and preferred embodiments
source                    1..174
                          mol_type = protein
                          organism = synthetic construct
SEQUENCE: 621
VIGESTHHRP WSXXXXXXXX XXXXXXXXXX XXXXXXXXXX XXXXXXXXXX XXXXXXXXXX   60
QAKHKQRKRL KSSCKRHPLY VDFSDVGWND WIVAPPGYHA FYCHGECPFP LADHLNSTNH  120
AIVQTLVNSV NSKIPKACCV PTELSAISML YLDENEKVVL KNYQDMVVEG CGCR        174

SEQ ID NO: 622            moltype = AA   length = 212
FEATURE                   Location/Qualifiers
REGION                    1..212
                          note = Description of Artificial Sequence: Synthetic
                            polypeptide
MOD_RES                   13..60
                          note = This region may encompass two or more of the
                            following sequences: "LLADTTHHRPWT" or "ILAESTHHKPWT" or
                            "IIGESSHHKPFT" or "GLGDTTHHRPWG"
REGION                    1..212
                          note = See specification as filed for detailed description
                            of substitutions and preferred embodiments
source                    1..212
                          mol_type = protein
                          organism = synthetic construct
SEQUENCE: 622
VIGESTHHRP WSXXXXXXXX XXXXXXXXXX XXXXXXXXXX XXXXXXXXXX XXXXXXXXXX   60
ASGAGGSEGG GSEGGTSGAT GAGTSTSGGG ASTGGGTGQA KHKQRKRLKS SCKRHPLYVD  120
FSDVGWNDWI VAPPGYHAFY CHGECPFPLA DHLNSTNHAI VQTLVNSVNS KIPKACCVPT  180
ELSAISMLYL DENEKVVLKN YQDMVVEGCG CR                                212

SEQ ID NO: 623            moltype = AA   length = 174
FEATURE                   Location/Qualifiers
REGION                    1..174
                          note = Description of Artificial Sequence: Synthetic
                            polypeptide
MOD_RES                   13..60
                          note = This region may encompass two or more of the
                            following sequences: "LLADTTHHRPWT" or "VIGESTHHRPWS" or
                            "IIGESSHHKPFT" or "GLGDTTHHRPWG"
REGION                    60..61
                          note = NON_CONS - Residues at these positions can be
                            separated by a linker of unknown length
REGION                    1..174
                          note = See specification as filed for detailed description
                            of substitutions and preferred embodiments
source                    1..174
                          mol_type = protein
```

```
                       organism = synthetic construct
SEQUENCE: 623
ILAESTHHKP WTXXXXXXXX XXXXXXXXXX XXXXXXXXXX XXXXXXXXXX XXXXXXXXXX    60
QAKHKQRKRL KSSCKRHPLY VDFSDVGWND WIVAPPGYHA FYCHGECPFP LADHLNSTNH   120
AIVQTLVNSV NSKIPKACCV PTELSAISML YLDENEKVVL KNYQDMVVEG CGCR         174

SEQ ID NO: 624           moltype = AA  length = 212
FEATURE                  Location/Qualifiers
REGION                   1..212
                         note = Description of Artificial Sequence: Synthetic
                           polypeptide
MOD_RES                  13..60
                         note = This region may encompass two or more of the
                           following sequences: "LLADTTHHRPWT" or "VIGESTHHRPWS" or
                           "IIGESSHHKPFT" or "GLGDTTHHRPWG"
REGION                   1..212
                         note = See specification as filed for detailed description
                           of substitutions and preferred embodiments
source                   1..212
                         mol_type = protein
                         organism = synthetic construct
SEQUENCE: 624
ILAESTHHKP WTXXXXXXXX XXXXXXXXXX XXXXXXXXXX XXXXXXXXXX XXXXXXXXXX    60
ASGAGGSEGG GSEGGTSGAT GAGTSTSGGG ASTGGGTGQA KHKQRKRLKS SCKRHPLYVD   120
FSDVGWNDWI VAPPGYHAFY CHGECPFPLA DHLNSTNHAI VQTLVNSVNS KIPKACCVPT   180
ELSAISMLYL DENEKVVLKN YQDMVVEGCG CR                                 212

SEQ ID NO: 625           moltype = AA  length = 174
FEATURE                  Location/Qualifiers
REGION                   1..174
                         note = Description of Artificial Sequence: Synthetic
                           polypeptide
MOD_RES                  13..60
                         note = This region may encompass two or more of the
                           following sequences: "LLADTTHHRPWT" or "ILAESTHHKPWT" or
                           "VIGESTHHRPWS" or "GLGDTTHHRPWG"
REGION                   60..61
                         note = NON_CONS - Residues at these positions can be
                           separated by a linker of unknown length
REGION                   1..174
                         note = See specification as filed for detailed description
                           of substitutions and preferred embodiments
source                   1..174
                         mol_type = protein
                         organism = synthetic construct
SEQUENCE: 625
IIGESSHHKP FTXXXXXXXX XXXXXXXXXX XXXXXXXXXX XXXXXXXXXX XXXXXXXXXX    60
QAKHKQRKRL KSSCKRHPLY VDFSDVGWND WIVAPPGYHA FYCHGECPFP LADHLNSTNH   120
AIVQTLVNSV NSKIPKACCV PTELSAISML YLDENEKVVL KNYQDMVVEG CGCR         174

SEQ ID NO: 626           moltype = AA  length = 212
FEATURE                  Location/Qualifiers
REGION                   1..212
                         note = Description of Artificial Sequence: Synthetic
                           polypeptide
MOD_RES                  13..60
                         note = This region may encompass two or more of the
                           following sequences: "LLADTTHHRPWT" or "ILAESTHHKPWT" or
                           "VIGESTHHRPWS" or "GLGDTTHHRPWG"
REGION                   1..212
                         note = See specification as filed for detailed description
                           of substitutions and preferred embodiments
source                   1..212
                         mol_type = protein
                         organism = synthetic construct
SEQUENCE: 626
IIGESSHHKP FTXXXXXXXX XXXXXXXXXX XXXXXXXXXX XXXXXXXXXX XXXXXXXXXX    60
ASGAGGSEGG GSEGGTSGAT GAGTSTSGGG ASTGGGTGQA KHKQRKRLKS SCKRHPLYVD   120
FSDVGWNDWI VAPPGYHAFY CHGECPFPLA DHLNSTNHAI VQTLVNSVNS KIPKACCVPT   180
ELSAISMLYL DENEKVVLKN YQDMVVEGCG CR                                 212

SEQ ID NO: 627           moltype = AA  length = 174
FEATURE                  Location/Qualifiers
REGION                   1..174
                         note = Description of Artificial Sequence: Synthetic
                           polypeptide
MOD_RES                  13..60
                         note = This region may encompass two or more of the
                           following sequences: "LLADTTHHRPWT" or "ILAESTHHKPWT" or
```

```
                              "IIGESSHHKPFT" or "VIGESTHHRPWS"
REGION                        60..61
                              note = NON_CONS - Residues at these positions can be
                              separated by a linker of unknown length
REGION                        1..174
                              note = See specification as filed for detailed description
                              of substitutions and preferred embodiments
source                        1..174
                              mol_type = protein
                              organism = synthetic construct
SEQUENCE: 627
GLGDTTHHRP WGXXXXXXXX XXXXXXXXX XXXXXXXXX XXXXXXXXX XXXXXXXXX    60
QAKHKQRKRL KSSCKRHPLY VDFSDVGWND WIVAPPGYHA FYCHGECPFP LADHLNSTNH  120
AIVQTLVNSV NSKIPKACCV PTELSAISML YLDENEKVVL KNYQDMVVEG CGCR        174

SEQ ID NO: 628                moltype = AA  length = 212
FEATURE                       Location/Qualifiers
REGION                        1..212
                              note = Description of Artificial Sequence: Synthetic
                              polypeptide
MOD_RES                       13..60
                              note = This region may encompass two or more of the
                              following sequences: "LLADTTHHRPWT" or "ILAESTHHKPWT" or
                              "IIGESSHHKPFT" or "VIGESTHHRPWS"
REGION                        1..212
                              note = See specification as filed for detailed description
                              of substitutions and preferred embodiments
source                        1..212
                              mol_type = protein
                              organism = synthetic construct
SEQUENCE: 628
GLGDTTHHRP WGXXXXXXXX XXXXXXXXX XXXXXXXXX XXXXXXXXX XXXXXXXXX    60
ASGAGGSEGG GSEGGTSGAT GAGTSTSGGG ASTGGGTGQA KHKQRKRLKS SCKRHPLYVD  120
FSDVGWNDWI VAPPGYHAFY CHGECPFPLA DHLNSTNHAI VQTLVNSVNS KIPKACCVPT  180
ELSAISMLYL DENEKVVLKN YQDMVVEGCG CR                                212

SEQ ID NO: 629                moltype = AA  length = 174
FEATURE                       Location/Qualifiers
REGION                        1..174
                              note = Description of Artificial Sequence: Synthetic
                              polypeptide
MOD_RES                       13..60
                              note = This region may encompass three or more of the
                              following sequences: "VIGESTHHRPWS" or "ILAESTHHKPWT" or
                              "IIGESSHHKPFT" or "GLGDTTHHRPWG"
REGION                        60..61
                              note = NON_CONS - Residues at these positions can be
                              separated by a linker of unknown length
REGION                        1..174
                              note = See specification as filed for detailed description
                              of substitutions and preferred embodiments
source                        1..174
                              mol_type = protein
                              organism = synthetic construct
SEQUENCE: 629
LLADTTHHRP WTXXXXXXXX XXXXXXXXX XXXXXXXXX XXXXXXXXX XXXXXXXXX    60
QAKHKQRKRL KSSCKRHPLY VDFSDVGWND WIVAPPGYHA FYCHGECPFP LADHLNSTNH  120
AIVQTLVNSV NSKIPKACCV PTELSAISML YLDENEKVVL KNYQDMVVEG CGCR        174

SEQ ID NO: 630                moltype = AA  length = 212
FEATURE                       Location/Qualifiers
REGION                        1..212
                              note = Description of Artificial Sequence: Synthetic
                              polypeptide
MOD_RES                       13..60
                              note = This region may encompass three or more of the
                              following sequences: "VIGESTHHRPWS" or "ILAESTHHKPWT" or
                              "IIGESSHHKPFT" or "GLGDTTHHRPWG"
REGION                        1..212
                              note = See specification as filed for detailed description
                              of substitutions and preferred embodiments
source                        1..212
                              mol_type = protein
                              organism = synthetic construct
SEQUENCE: 630
LLADTTHHRP WTXXXXXXXX XXXXXXXXX XXXXXXXXX XXXXXXXXX XXXXXXXXX    60
ASGAGGSEGG GSEGGTSGAT GAGTSTSGGG ASTGGGTGQA KHKQRKRLKS SCKRHPLYVD  120
FSDVGWNDWI VAPPGYHAFY CHGECPFPLA DHLNSTNHAI VQTLVNSVNS KIPKACCVPT  180
ELSAISMLYL DENEKVVLKN YQDMVVEGCG CR                                212
```

```
SEQ ID NO: 631          moltype = AA  length = 174
FEATURE                 Location/Qualifiers
REGION                  1..174
                        note = Description of Artificial Sequence: Synthetic
                         polypeptide
MOD_RES                 13..60
                        note = This region may encompass three or more of the
                         following sequences: "LLADTTHHRPWT" or "ILAESTHHKPWT" or
                         "IIGESSHHKPFT" or "GLGDTTHHRPWG"
REGION                  60..61
                        note = NON_CONS - Residues at these positions can be
                         separated by a linker of unknown length
REGION                  1..174
                        note = See specification as filed for detailed description
                         of substitutions and preferred embodiments
source                  1..174
                        mol_type = protein
                        organism = synthetic construct
SEQUENCE: 631
VIGESTHHRP WSXXXXXXXX XXXXXXXXX XXXXXXXXX XXXXXXXXX XXXXXXXXX      60
QAKHKQRKRL KSSCKRHPLY VDFSDVGWND WIVAPPGYHA FYCHGECPFP LADHLNSTNH   120
AIVQTLVNSV NSKIPKACCV PTELSAISML YLDENEKVVL KNYQDMVVEG CGCR         174

SEQ ID NO: 632          moltype = AA  length = 212
FEATURE                 Location/Qualifiers
REGION                  1..212
                        note = Description of Artificial Sequence: Synthetic
                         polypeptide
MOD_RES                 13..60
                        note = This region may encompass three or more of the
                         following sequences: "LLADTTHHRPWT" or "ILAESTHHKPWT" or
                         "IIGESSHHKPFT" or "GLGDTTHHRPWG"
REGION                  1..212
                        note = See specification as filed for detailed description
                         of substitutions and preferred embodiments
source                  1..212
                        mol_type = protein
                        organism = synthetic construct
SEQUENCE: 632
VIGESTHHRP WSXXXXXXXX XXXXXXXXX XXXXXXXXX XXXXXXXXX XXXXXXXXX      60
ASGAGGSEGG GSEGGTSGAT GAGTSTSGGG ASTGGGTGQA KHKQRKRLKS SCKRHPLYVD   120
FSDVGWNDWI VAPPGYHAFY CHGECPFPLA DHLNSTNHAI VQTLVNSVNS KIPKACCVPT   180
ELSAISMLYL DENEKVVLKN YQDMVVEGCG CR                                 212

SEQ ID NO: 633          moltype = AA  length = 174
FEATURE                 Location/Qualifiers
REGION                  1..174
                        note = Description of Artificial Sequence: Synthetic
                         polypeptide
MOD_RES                 13..60
                        note = This region may encompass three or more of the
                         following sequences: "LLADTTHHRPWT" or "VIGESTHHRPWS" or
                         "IIGESSHHKPFT" or "GLGDTTHHRPWG"
REGION                  60..61
                        note = NON_CONS - Residues at these positions can be
                         separated by a linker of unknown length
REGION                  1..174
                        note = See specification as filed for detailed description
                         of substitutions and preferred embodiments
source                  1..174
                        mol_type = protein
                        organism = synthetic construct
SEQUENCE: 633
ILAESTHHKP WTXXXXXXXX XXXXXXXXX XXXXXXXXX XXXXXXXXX XXXXXXXXX      60
QAKHKQRKRL KSSCKRHPLY VDFSDVGWND WIVAPPGYHA FYCHGECPFP LADHLNSTNH   120
AIVQTLVNSV NSKIPKACCV PTELSAISML YLDENEKVVL KNYQDMVVEG CGCR         174

SEQ ID NO: 634          moltype = AA  length = 212
FEATURE                 Location/Qualifiers
REGION                  1..212
                        note = Description of Artificial Sequence: Synthetic
                         polypeptide
MOD_RES                 13..60
                        note = This region may encompass three or more of the
                         following sequences: "LLADTTHHRPWT" or "VIGESTHHRPWS" or
                         "IIGESSHHKPFT" or "GLGDTTHHRPWG"
REGION                  1..212
                        note = See specification as filed for detailed description
```

```
                           of substitutions and preferred embodiments
source                     1..212
                           mol_type = protein
                           organism = synthetic construct
SEQUENCE: 634
ILAESTHHKP WTXXXXXXXX XXXXXXXXXX XXXXXXXXXX XXXXXXXXXX XXXXXXXXXX    60
ASGAGGSEGG GSEGGTSGAT GAGTSTSGGG ASTGGGTGQA KHKQRKRLKS SCKRHPLYVD   120
FSDVGWNDWI VAPPGYHAFY CHGECPFPLA DHLNSTNHAI VQTLVNSVNS KIPKACCVPT   180
ELSAISMLYL DENEKVVLKN YQDMVVEGCG CR                                 212

SEQ ID NO: 635             moltype = AA  length = 174
FEATURE                    Location/Qualifiers
REGION                     1..174
                           note = Description of Artificial Sequence: Synthetic
                           polypeptide
MOD_RES                    13..60
                           note = This region may encompass three or more of the
                           following sequences: "LLADTTHHRPWT" or "ILAESTHHKPWT" or
                           "VIGESTHHRPWS" or "GLGDTTHHRPWG"
REGION                     60..61
                           note = NON_CONS - Residues at these positions can be
                           separated by a linker of unknown length
REGION                     1..174
                           note = See specification as filed for detailed description
                           of substitutions and preferred embodiments
source                     1..174
                           mol_type = protein
                           organism = synthetic construct
SEQUENCE: 635
IIGESSHHKP FTXXXXXXXX XXXXXXXXXX XXXXXXXXXX XXXXXXXXXX XXXXXXXXXX    60
QAKHKQRKRL KSSCKRHPLY VDFSDVGWND WIVAPPGYHA FYCHGECPFP LADHLNSTNH   120
AIVQTLVNSV NSKIPKACCV PTELSAISML YLDENEKVVL KNYQDMVVEG CGCR         174

SEQ ID NO: 636             moltype = AA  length = 212
FEATURE                    Location/Qualifiers
REGION                     1..212
                           note = Description of Artificial Sequence: Synthetic
                           polypeptide
MOD_RES                    13..60
                           note = This region may encompass three or more of the
                           following sequences: "LLADTTHHRPWT" or "ILAESTHHKPWT" or
                           "VIGESTHHRPWS" or "GLGDTTHHRPWG"
REGION                     1..212
                           note = See specification as filed for detailed description
                           of substitutions and preferred embodiments
source                     1..212
                           mol_type = protein
                           organism = synthetic construct
SEQUENCE: 636
IIGESSHHKP FTXXXXXXXX XXXXXXXXXX XXXXXXXXXX XXXXXXXXXX XXXXXXXXXX    60
ASGAGGSEGG GSEGGTSGAT GAGTSTSGGG ASTGGGTGQA KHKQRKRLKS SCKRHPLYVD   120
FSDVGWNDWI VAPPGYHAFY CHGECPFPLA DHLNSTNHAI VQTLVNSVNS KIPKACCVPT   180
ELSAISMLYL DENEKVVLKN YQDMVVEGCG CR                                 212

SEQ ID NO: 637             moltype = AA  length = 174
FEATURE                    Location/Qualifiers
REGION                     1..174
                           note = Description of Artificial Sequence: Synthetic
                           polypeptide
MOD_RES                    13..60
                           note = This region may encompass three or more of the
                           following sequences: "LLADTTHHRPWT" or "ILAESTHHKPWT" or
                           "IIGESSHHKPFT" or "VIGESTHHRPWS"
REGION                     60..61
                           note = NON_CONS - Residues at these positions can be
                           separated by a linker of unknown length
REGION                     1..174
                           note = See specification as filed for detailed description
                           of substitutions and preferred embodiments
source                     1..174
                           mol_type = protein
                           organism = synthetic construct
SEQUENCE: 637
GLGDTTHHRP WGXXXXXXXX XXXXXXXXXX XXXXXXXXXX XXXXXXXXXX XXXXXXXXXX    60
QAKHKQRKRL KSSCKRHPLY VDFSDVGWND WIVAPPGYHA FYCHGECPFP LADHLNSTNH   120
AIVQTLVNSV NSKIPKACCV PTELSAISML YLDENEKVVL KNYQDMVVEG CGCR         174

SEQ ID NO: 638             moltype = AA  length = 212
FEATURE                    Location/Qualifiers
```

```
                           -continued
REGION              1..212
                    note = Description of Artificial Sequence: Synthetic
                     polypeptide
MOD_RES             13..60
                    note = This region may encompass three or more of the
                     following sequences: "LLADTTHHRPWT" or "ILAESTHHKPWT" or
                     "IIGESSHHKPFT" or "VIGESTHHRPWS"
REGION              1..212
                    note = See specification as filed for detailed description
                     of substitutions and preferred embodiments
source              1..212
                    mol_type = protein
                    organism = synthetic construct
SEQUENCE: 638
GLGDTTHHRP WGXXXXXXXX XXXXXXXXXX XXXXXXXXXX XXXXXXXXXX XXXXXXXXXX    60
ASGAGGSEGG GSEGGTSGAT GAGTSTSGGG ASTGGGTGQA KHKQRKRLKS SCKRHPLYVD   120
FSDVGWNDWI VAPPGYHAFY CHGECPFPLA DHLNSTNHAI VQTLVNSVNS KIPKACCVPT   180
ELSAISMLYL DENEKVVLKN YQDMVVEGCG CR                                 212

SEQ ID NO: 639          moltype = AA  length = 126
FEATURE                 Location/Qualifiers
REGION                  1..126
                        note = Description of Artificial Sequence: Synthetic
                         polypeptide
REGION                  12..13
                        note = NON_CONS - Residues at these positions can be
                         separated by a linker of unknown length
source                  1..126
                        mol_type = protein
                        organism = synthetic construct
SEQUENCE: 639
VIGESTHHRP WSQAKHKQRK RLKSSCKRHP LYVDFSDVGW NDWIVAPPGY HAFYCHGECP    60
FPLADHLNST NHAIVQTLVN SVNSKIPKAC CVPTELSAIS MLYLDENEKV VLKNYQDMVV   120
EGCGCR                                                              126

SEQ ID NO: 640          moltype =    length =
SEQUENCE: 640
000

SEQ ID NO: 641          moltype =    length =
SEQUENCE: 641
000

SEQ ID NO: 642          moltype =    length =
SEQUENCE: 642
000

SEQ ID NO: 643          moltype =    length =
SEQUENCE: 643
000

SEQ ID NO: 644          moltype =    length =
SEQUENCE: 644
000

SEQ ID NO: 645          moltype =    length =
SEQUENCE: 645
000

SEQ ID NO: 646          moltype =    length =
SEQUENCE: 646
000

SEQ ID NO: 647          moltype =    length =
SEQUENCE: 647
000

SEQ ID NO: 648          moltype =    length =
SEQUENCE: 648
000

SEQ ID NO: 649          moltype =    length =
SEQUENCE: 649
000

SEQ ID NO: 650          moltype =    length =
SEQUENCE: 650
000
```

| | | |
|---|---|---|
| SEQ ID NO: 651<br>SEQUENCE: 651<br>000 | moltype = | length = |
| SEQ ID NO: 652<br>SEQUENCE: 652<br>000 | moltype = | length = |
| SEQ ID NO: 653<br>SEQUENCE: 653<br>000 | moltype = | length = |
| SEQ ID NO: 654<br>SEQUENCE: 654<br>000 | moltype = | length = |
| SEQ ID NO: 655<br>SEQUENCE: 655<br>000 | moltype = | length = |
| SEQ ID NO: 656<br>SEQUENCE: 656<br>000 | moltype = | length = |
| SEQ ID NO: 657<br>SEQUENCE: 657<br>000 | moltype = | length = |
| SEQ ID NO: 658<br>SEQUENCE: 658<br>000 | moltype = | length = |
| SEQ ID NO: 659<br>SEQUENCE: 659<br>000 | moltype = | length = |
| SEQ ID NO: 660<br>SEQUENCE: 660<br>000 | moltype = | length = |
| SEQ ID NO: 661<br>SEQUENCE: 661<br>000 | moltype = | length = |
| SEQ ID NO: 662<br>SEQUENCE: 662<br>000 | moltype = | length = |
| SEQ ID NO: 663<br>SEQUENCE: 663<br>000 | moltype = | length = |
| SEQ ID NO: 664<br>SEQUENCE: 664<br>000 | moltype = | length = |
| SEQ ID NO: 665<br>SEQUENCE: 665<br>000 | moltype = | length = |
| SEQ ID NO: 666<br>SEQUENCE: 666<br>000 | moltype = | length = |
| SEQ ID NO: 667<br>SEQUENCE: 667<br>000 | moltype = | length = |
| SEQ ID NO: 668<br>SEQUENCE: 668<br>000 | moltype = | length = |
| SEQ ID NO: 669<br>SEQUENCE: 669<br>000 | moltype = | length = |
| SEQ ID NO: 670<br>SEQUENCE: 670<br>000 | moltype = | length = |

| | | |
|---|---|---|
| SEQ ID NO: 671<br>SEQUENCE: 671<br>000 | moltype = | length = |
| SEQ ID NO: 672<br>SEQUENCE: 672<br>000 | moltype = | length = |
| SEQ ID NO: 673<br>SEQUENCE: 673<br>000 | moltype = | length = |
| SEQ ID NO: 674<br>SEQUENCE: 674<br>000 | moltype = | length = |
| SEQ ID NO: 675<br>SEQUENCE: 675<br>000 | moltype = | length = |
| SEQ ID NO: 676<br>SEQUENCE: 676<br>000 | moltype = | length = |
| SEQ ID NO: 677<br>SEQUENCE: 677<br>000 | moltype = | length = |
| SEQ ID NO: 678<br>SEQUENCE: 678<br>000 | moltype = | length = |
| SEQ ID NO: 679<br>SEQUENCE: 679<br>000 | moltype = | length = |
| SEQ ID NO: 680<br>SEQUENCE: 680<br>000 | moltype = | length = |
| SEQ ID NO: 681<br>SEQUENCE: 681<br>000 | moltype = | length = |
| SEQ ID NO: 682<br>SEQUENCE: 682<br>000 | moltype = | length = |
| SEQ ID NO: 683<br>SEQUENCE: 683<br>000 | moltype = | length = |
| SEQ ID NO: 684<br>SEQUENCE: 684<br>000 | moltype = | length = |
| SEQ ID NO: 685<br>SEQUENCE: 685<br>000 | moltype = | length = |
| SEQ ID NO: 686<br>SEQUENCE: 686<br>000 | moltype = | length = |
| SEQ ID NO: 687<br>SEQUENCE: 687<br>000 | moltype = | length = |
| SEQ ID NO: 688<br>SEQUENCE: 688<br>000 | moltype = | length = |
| SEQ ID NO: 689<br>SEQUENCE: 689<br>000 | moltype = | length = |
| SEQ ID NO: 690<br>SEQUENCE: 690 | moltype = | length = |

```
000

SEQ ID NO: 691          moltype =     length =
SEQUENCE: 691
000

SEQ ID NO: 692          moltype =     length =
SEQUENCE: 692
000

SEQ ID NO: 693          moltype =     length =
SEQUENCE: 693
000

SEQ ID NO: 694          moltype =     length =
SEQUENCE: 694
000

SEQ ID NO: 695          moltype =     length =
SEQUENCE: 695
000

SEQ ID NO: 696          moltype =     length =
SEQUENCE: 696
000

SEQ ID NO: 697          moltype =     length =
SEQUENCE: 697
000

SEQ ID NO: 698          moltype =     length =
SEQUENCE: 698
000

SEQ ID NO: 699          moltype =     length =
SEQUENCE: 699
000

SEQ ID NO: 700          moltype =     length =
SEQUENCE: 700
000

SEQ ID NO: 701          moltype = AA   length = 38
FEATURE                 Location/Qualifiers
REGION                  1..38
                        note = Description of Artificial Sequence: Synthetic
                         polypeptide
source                  1..38
                        mol_type = protein
                        organism = synthetic construct
SEQUENCE: 701
ASGAGGSEGG GSEGGTSGAT GAGTSTSGGG ASTGGGTG                                   38

SEQ ID NO: 702          moltype = AA   length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 702
GSEG                                                                         4

SEQ ID NO: 703          moltype = AA   length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 703
SEGG                                                                         4

SEQ ID NO: 704          moltype = AA   length = 5
FEATURE                 Location/Qualifiers
REGION                  1..5
                        note = Description of Artificial Sequence: Synthetic peptide
source                  1..5
                        mol_type = protein
```

```
                        organism = synthetic construct
SEQUENCE: 704
MPIGS                                                                           5

SEQ ID NO: 705          moltype = AA   length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 705
GSGS                                                                            4

SEQ ID NO: 706          moltype = AA   length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 706
GSGSGS                                                                          6

SEQ ID NO: 707          moltype = AA   length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 707
SGSG                                                                            4

SEQ ID NO: 708          moltype = AA   length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 708
SGSGSG                                                                          6

SEQ ID NO: 709          moltype = AA   length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 709
GSSG                                                                            4

SEQ ID NO: 710          moltype = AA   length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 710
GGGGS                                                                           5

SEQ ID NO: 711          moltype = DNA   length = 17
FEATURE                 Location/Qualifiers
misc_feature            1..17
                        note = Description of Artificial Sequence: Synthetic
                         oligonucleotide
source                  1..17
                        mol_type = other DNA
                        organism = synthetic construct
SEQUENCE: 711
aaataaaata cgaaatg                                                              17
```